US012043837B2

(12) United States Patent
Meng

(10) Patent No.: US 12,043,837 B2
(45) **Date of Patent: *Jul. 23, 2024**

(54) METHODS FOR IMPROVING GENOME ENGINEERING AND REGENERATION IN PLANT

(71) Applicant: KWS SAAT SE & Co. KGaA, Einbeck (DE)

(72) Inventor: Ling Meng, St. Louis, MO (US)

(73) Assignee: KWS SAAT SE & Co. KGaA, Einbeck (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/251,633

(22) PCT Filed: Jun. 14, 2019

(86) PCT No.: PCT/EP2019/065645

§ 371 (c)(1),
(2) Date: Dec. 11, 2020

(87) PCT Pub. No.: WO2019/238909

PCT Pub. Date: Dec. 19, 2019

(65) Prior Publication Data

US 2022/0025388 A1 Jan. 27, 2022

Related U.S. Application Data

(60) Provisional application No. 62/685,626, filed on Jun. 15, 2018, provisional application No. 62/728,445, filed on Sep. 7, 2018.

(51) Int. Cl.
*C12N 15/82* (2006.01)
*C07K 14/41* (2006.01)
*C07K 14/415* (2006.01)

(52) U.S. Cl.
CPC ........ *C12N 15/8213* (2013.01); *C07K 14/415* (2013.01); *C12N 15/8207* (2013.01)

(58) Field of Classification Search
CPC .................................................. C12N 15/8213
See application file for complete search history.

(56) References Cited

U.S. PATENT DOCUMENTS

| | | | |
|---|---|---|---|
| 6,528,701 B1 | 3/2003 | Wang et al. | |
| 6,825,397 B1 | 11/2004 | Lowe et al. | |
| 7,763,774 B2 | 7/2010 | Hehl et al. | |
| 7,767,801 B2 | 8/2010 | Hehl et al. | |
| 7,960,612 B2 | 6/2011 | Zhang et al. | |
| 2010/0162427 A1 | 6/2010 | Riechmann et al. | |
| 2011/0165679 A1 | 7/2011 | Gordon-Kamm et al. | |
| 2014/0237681 A1* | 8/2014 | Gordon-Kamm .... | C07K 14/415 800/278 |
| 2017/0121722 A1 | 5/2017 | Anand et al. | |
| 2017/0233756 A1 | 8/2017 | Begemann et al. | |
| 2021/0277407 A1* | 9/2021 | Kong .................. | C12N 15/821 |

FOREIGN PATENT DOCUMENTS

| | | |
|---|---|---|
| CN | 101750487 A | 6/2010 |
| CN | 101849009 A | 9/2010 |
| EP | 2771468 B1 | 2/2015 |
| EP | 3159413 A1 | 4/2017 |
| EP | 3009511 B1 | 5/2017 |
| WO | 94/18313 A1 | 8/1994 |
| WO | 95/09233 A1 | 4/1995 |
| WO | 03/004659 | 1/2003 |
| WO | 03/080809 | 10/2003 |
| WO | 2010/079430 A1 | 7/2010 |
| WO | 2011/072246 | 6/2011 |
| WO | 2011/082310 A2 | 7/2011 |
| WO | 2011/082318 A2 | 7/2011 |
| WO | 2011/146121 A1 | 11/2011 |
| WO | 2011/154393 | 12/2011 |
| WO | 2012/001527 | 1/2012 |
| WO | 2012/093833 | 7/2012 |
| WO | 2012/104729 A1 | 8/2012 |
| WO | 2012/138927 | 10/2012 |
| WO | 2012/138939 A1 | 10/2012 |
| WO | 2013/103369 A1 | 7/2013 |
| WO | 2013/103370 A1 | 7/2013 |
| WO | 2016/021973 A1 | 2/2016 |
| WO | 2016/146552 A1 | 9/2016 |
| WO | 2016184955 A2 | 11/2016 |
| WO | 2016184989 A1 | 11/2016 |
| WO | 2017/074547 A1 | 5/2017 |
| WO | 2018042346 A2 | 3/2018 |
| WO | 2018236548 A1 | 12/2018 |
| WO | 2019122360 A1 | 6/2019 |

(Continued)

OTHER PUBLICATIONS

Nardmann et al (CAT02906, published May 2009) (Year: 2009).*
Milne et al, (An approach to gene-specific transcription inhibition using oligonucleotides complementary to the template strand of the open complex. PNAS. 97:3136-3141, 2000) (Year: 2000).*
Zhang et al (Predicting DNA Hybridization Kinetics from Sequence. Nature Chemistry. 10:91-98, 2018) (Year: 2018).*
Svitashev et al (Genome editing in maize directed by CRISPR-Cas9 ribonucleoprotein complexes, Nature Communications, 1-7, 2016) (Year: 2016).*
Zhang et al (A Two-Step Model for de Novo Activation of Wuschel during Plant Shoot Regeneration. The Plant Cell, vol. 29: 1073-1087, 2017) (Year: 2017).*
Nardmann et al (Accession CAT02906, published 2009). (Year: 2009).*

(Continued)

*Primary Examiner* — Charles Logsdon
*Assistant Examiner* — Wayneshaobin Zhong
(74) *Attorney, Agent, or Firm* — Troutman Pepper Hamilton Sanders LLP

(57) ABSTRACT

This document relates to methods and materials for genome engineering in eukaryotic cells, and particularly to methods for increasing genome engineering (i.e. transformation or genome editing) efficiency via delivery of one or more booster polypeptides, and boost genes, with genome engineering components.

33 Claims, 22 Drawing Sheets

Specification includes a Sequence Listing.

(56) References Cited

FOREIGN PATENT DOCUMENTS

WO 2019238908 A1 12/2019
WO 2019238911 A1 12/2019

OTHER PUBLICATIONS

Kareem et al (Plethora Genes Control Regeneration by a Two-step Mechanism. Curr Biol. 20; 25(8): 1017-1030, 2015) (Year: 2015).*
Helenius et al., "Gene delivery into intact plants using the HellosTM Gene Gun", Plant Molecular Biology Reporter, 2000, vol. 18, No. 3, pp. 287a-287l.
Isalan et al., "A rapid, generally applicable method to engineer zinc fingers illustrated by targeting the HIV-1 promoter", Nature Biotechnology, 2001, vol. 19, No. 7, pp. 656-660.
Liu et al. "Design of polydactyl zinc-finger proteins for unique addressing within complex genomes", Proceedings of the National Academy of Sciences, 1997, vol. 94, No. 11, pp. 5525-5530.
Boch et al., "Breaking the code of DNA binding specificity of TAL-type III effectors", Science, 2009, vol. 326, No. 5959, pp. 1509-1512.
Moscou et al., "A simple cipher governs DNA recognition by TAL effectors", Science, 2009, vol. 326, No. 5959, p. 1501.
Zetsche et al., "Cpf1 Is a Single RNA-Guided Endonuclease of a Class 2 CRISPR-Cas System", Cell, 2015, vol. 163, pp. 759-771.
Makarova et al., "An updated evolutionary classification of CRISPR-Cas systems", Nature Rev. Microbiol., 2015, vol. 13, No. 11, pp. 722-736.
Jinek et al., "A programmable dual-RNA-guided DNA endonuclease in adaptive bacterial immunity", Science, 2012, vol. 337, No. 6096, pp. 816-821.
Burstein et al., "New CRISPR-Cas systems from uncultivated microbes", Nature, 2017, vol. 542, pp. 237-241.
Jore et al., "Structural basis for CRISPR RNA-guided DNA recognition by Cascadek", Nature Structural & Molecular Biology, 2011, vol. 18, No. 5, pp. 529-536.
Gaudelli et al., "Programmable base editing of A• T to G• C in genomic DNA without DNA cleavage", Nature, 2017, vol. 551, No. 7681, p. 464.
Sterner et al., "Acetylation of histones and transcription-related factors", Microbiology and Molecular Biology Reviews, 2000, vol. 64, No. 2, pp. 435-459.
Zhang et al., "Transcription regulation by histone methylation: interplay between different covalent modifications of the core histone tails", Genes & Development, 2001, vol. 15, No. 18, pp. 2343-2360.
Shilatifard, "Chromatin modifications by methylation and ubiquitination: implications in the regulation of gene expression", Annu. Rev. Biochem., 2006, vol. 75, pp. 243-269.
Nowak et al., "Phosphorylation of histone H3: a balancing act between chromosome condensation and transcriptional activation", Trends in Genetics, 2004, vol. 20 , No. 4, pp. 214-220.
Nathan et al., "Histone sumoylation is a negative regulator in *Saccharomyces cerevisiae* and shows dynamic interplay with positive-acting histone modifications", Genes & Development, 2006, vol. 20, No. 8, pp. 966-976.
Hassa et al., "Nuclear ADP-ribosylation reactions in mammalian cells: where are we today and where are we going?", Microbiology and Molecular Biology Reviews, 2006, vol. 70, No. 3, pp. 789-829.
Andrews et al., "Nucleosome structure(s) and stability: Variations on a theme", Annu. Rev. Biophys., 2011, vol. 40, pp. 99-117.
Bannister et al., "Regulation of chromatin by histone modifications", Cell Research, 2011, vol. 21, pp. 381-395.
Zhang et al., "An epigenetic perspective on developmental regulation of seed genes", Molecular Plant, 2009, vol. 2, No. 4, pp. 610-627.
Miguel et al., "An epigenetic view of plant cells cultured in vitro: somaclonal variation and beyond", Journal of Expetimental Botany, 2011, vol. 62, pp. 3713-3725.
Li et al., "The Histone Deacetylase Inhibitor Trichostatin A Promotes Totipotency in the Male Gametophyte", The Plant Cell, 2014, vol. 26, pp. 195-209.
Waki et al., "The *Arabidopsis* RWP-RK protein RKD4 triggers gene expression and pattern formation in early embryogenesis", Current Biology, 2011, vol. 21, No. 15, pp. 1277-1281.
El Ouakfaoui et al., "Control of somatic embryogenesis and embryo development by AP2 transcription factors", Plant Molecular Biology, 2010, vol. 74(4-5), pp. 313-326.
Rice et al., "EMBOSS: The European Molecular Biology Open Software Suite", Trends in Genetics, 2000, vol. 16, No. 6, pp. 276-277.
U.S. Appl. No. 62/609,508, filed Dec. 22, 2017.
International Search Report and Written Opinion Issued in International Application No. PCT/EP2019/065643 dated Oct. 2, 2019.
Svitashev et al., "Genome editing in maize directed by CRISPR-Cas9 ribonucleoprotein complexes", Nature Communications, vol. 7, 2016, p. 13274.
Lowe et al., "Morphogenic Regulators Baby boom and Wuschel Improve Monocot Transformation", The Plant Cell, vol. 28, No. 9, 2016, pp. 1998-2015.
Bouchabke-Coussa et ai., "Wuschel overexpression promotes somatic embryogenesis and induces organogenesis in cotton (*Gossypium hirsutum* L.) tissues cultured in vitro", Plant Cell Reports, 2013, vol. 32, No. 5, pp. 675-686.
International Search Report and Written Opinion issued in International Application No. PCT/EP2019/065645 dated Oct. 7, 2019.
Database EMBL [Online] May 1, 2009 (May 1, 2009), "Ginkgo biloba (maidenhair tree) putative wuschel homeobox protein WUS ID—CAT02906; sv 1.; linear; mRNA; STD; PLN; 786 BP", XP002794173, retrieved from EBI accession No. EMBL:CAT02906 sequence.
Database EMBL [Online] May 1, 2009 (May 1, 2009), "Ginkgo biloba mRNA for putative wuschel homeobox protein WUS (wus gene)", XP002794174, retrieved from EBI accession No. Embl: FM882128 Database accession No. FM882128 sequence.
International Search Report and Written Opinion issued In International Application No. PCT/EP2019/065647 dated Nov. 29, 2019.
International Search Report and Written Opinion issued in International Application No. PCT/IB2020/000063 dated Jun. 16, 2020.
Koszegi et al., "Members of the RKD transcription factor family induce an egg cell-like gene expression program", The Plant Journal, 2011, vol. 67, No. 2, pp. 280-291.
Koi et al., "An Evolutionarily Conserved Plant RKD Factor Controls Germ Ceil Differentiation", Current Biology, 2016, vol. 26, No. 13, pp. 1775-1781.
Zuo et al., "An estrogen receptor-based transactivator XVE mediates highly inducible gene expression in transgenic plants", The Plant Journal, 2000, vol. 24, No. 2, pp. 265-273.
Samalova et al., "p0p6/LhGR: a stringently regulated and highly responsive dexamethasone-inducible gene expression system for tobacco", The Plant Journal, 2005, vol. 41, No. 6, pp. 919-935.
Durr et al., "Highly efficient heritable targeted deletions of gene clusters and non-coding regulatory regions in *Arabidopsis* using CRISPR/Cas9", Scientific Reports, 2018, vol. 8, 4443, 11 pages.
Nardmann et al., "The Shoot Stem Cell Niche in Angiosperms: Expression Patterns of WUS Orthologues in Rice and Maize Imply Major Modifications in the Course of Mono- and Dicot Evolution", Molecular Biology and Evolution, 2006, vol. 23, No. 12, pp. 2492-2504.
Soderlund et al., "Sequencing, Mapping, and Analysis of 27,455 Maize Full-Length cDNAs", PloS Genetics, 2009, vol. 5, Issue 11, e1000740, pp. 1-13.
Lowe et al., "Rapid genotype "independent" *Zea mays* L. (maize) transformation via direct somatic embryogenesis", In Vitro Cellular & Developmental Biology—Plant, 2018, vol. 54(8), pp. 240-252.
Komor et al. Programmable editing of a target base in genomic DNA without double-stranded DNA cleavage. Nature 2016, vol. 533, pp. 420-424.
Zong et al., "Precise base editing in rice, wheat and maize with a Cas9-cytidine deaminase fusion", Nat. Biotechnol., 2017, vol. 35, pp. 438-440.

(56) References Cited

OTHER PUBLICATIONS

Yan et al., "Highly EfficientA• T to G• C Base Editing by Cas9n-Guided tRNA Adenosine Deaminase in Rice", Molecular Plant, Apr. 2, 2018, vol. 11, issue 4, pp. 631-634.
Hua et al., "Precise A• T to G• C Base Editing in the Rice Genome", Molecular Plant, Apr. 2018, vol. 11(4): pp. 327-630.
Anzalone et al., "Search and replace genome editing without double-strand breaks or donor DNA", Nature, Oct. 21, 2019, vol. 576, pp. 149-157.
Smith et al., "Identification of common molecular subsequences" Journal of Molecular Biology, 1981, vol. 147, No. 1, pp. 195-197.
Mayer et al., "Role of Wuschel in regulating stem cell fate in the *Arabidopsis* shoot meristem", Cell, Dec. 11, 1998, vol. 95, pp. 805-815.
Yadav et al., "Wuschel protein movement mediates stem cell homeostasis in the *Arabidopsis* shoot apex", Genes Dev., 2011, vol. 25, pp. 2025-2030.
Laux, et al., "The Wuschel gene is required for shoot and floral meristem integrity in *Arabidopsis*", Development, 1996, vol. 122, pp. 87-96.
Leibfried et al., "Wuschel controls meristem function by direct regulation of cytokinin-inducible response regulators", Nature, Dec. 22, 2005, vol. 438(7071), pp. 1172-1175.
Hofmann, "A Breakthrough in Monocot Transformation Methods", The Plant Cell, Sep. 2016, vol. 28: p. 1989.
Nic-Can et al., "New Insights into Somatic Embryogenesis: Leafy Cotyledon1, Baby Boom1 and Wuschel-Related Homeobox4 Are Epigenetically Regulated in Coffea canephora", PLoS One, Aug. 2013, vol. 8(8), 31 pages, e72160. PMID: 23977240.
Ling Min et al., "Leafy Cotyledon1-Casein Kinase I-TCP15-Phytochrome Interacting Factor4 Network Regulates Somatic Embryogenesis by Regulating Auxin Homeostasis", Plant Physiology, Dec. 2015, vol. 169, pp. 2805-2821.
Cagliari et al., "New insights on the evolution of Leafy cotyledon1 (LEC1) type genes in vascular plants", Genomics, 2014, vol. 103, pp. 380-387.
Kim et al., "The AtGRF family of putative transcription factors is involved in leaf and cotyledon growth in *Arabidopsis*", The Plant Journal, 2003, vol. 36, pp. 94-104.
Choi et al., "Whole Genome Analysis of the OsGRF Gene Family Encoding Plant Specific Putative Transcription Activators in Rice (*Oryza sativa* L.)", Plant Cell Physiol, 2004, vol. 45(7): pp. 897-904.
Ellerström et al., "Etopic Expression of Effector of Transcription perturbs gibberellin-mediated plant developmental proceses", Plant Molecular Biology, 2005, vol. 59: pp. 663-681.
Aida et al., "The Plethora genes mediate patterning of the *Arabidopsis* root stem cell niche", Cell, 2004, vol. 119 pp. 109-120.
Mähönen et al., "Plethora gradient formation mechanism separates auxin responses", Nature, 2014, vol. 515: pp. 125-129.
Santuari et al., "The Plethora Gene Regulatory Network Guides Growth and Cell Differentiation in *Arabidopsis* Roots", The Plant Cell, Dec. 2016, vol. 28: pp. 2937-2951.
Ravi et al., "Haploid plants produced by centromere-mediated genome elimination", Nature, 2010, vol. 464, pp. 615-619.
International Search Report and Written Opinion issued in PCT/EP2021/054805 dated May 21, 2021.
Hortsman et al., 2014, "Antigumenta-Like 5 protiends: hubs in a plethora of networks", Trends in Plant Science, vol. 19, No. 3, pp. 146-157.
Zhang et al., "Chemical probes in plant epigenetics studies", Plant Signaling & Behavoir, 2013, vol. 8, No. 9, e25364.
Nasti et al., 2022, Defining the Parameters to Improve Plant Regeneration with Developmental Regulators, BioRxiv.
Guo et al., 2004, "Protein tolerance to random amino acid change", Proceedings of the Naitonal Academy of Sciences, vol. 101, No. 25, pp. 9205-9210.
Horlbeck et al., 2016, "Nucleosomes impede Cas9 access to DNA in vivo and in vitro", elife, vol. 5, e12677.
Definition of derivative—NCI Dictionary of Cancer Terms—NCI (https://www.cancer.gov/publications/dictionaries/cancer-terms/def/derivative) viewed on Jan. 24, 2023 (Year: 2023).
Variant Definition & Meaning—Merriam-Webster (https://www.meriamp-webster.com/dictionary/variant) viewed on Jan. 24, 2023 (Year: 2023).
Yang et al., "Trichostatin A and 5-azacytidine both cause an increase in global histone H4 acetylation and a decrease in global DNA and H3K9 methylation during mitosis in maize", BMC Plant Biology, 2010, vol. 10, No. 178, 11 pages.
Prasad et al., "Arabidopsis PLETHORA transcription factors control phyllotaxis", Current Biology, 2011, vol. 21, No. 13, pp. 1123-1128.
Purwestri et al., "RWP-PK Domain 3 (OsRKD3) induces somatic embryogenesis in black rice", BMC Plant Biology, 2023, vol. 23, No. 202, 15 pages.
Sprunck et al., "Elucidating small RNA pathways in Arabidopsis thaliana egg cells", BioRxiv, 2019, doi: https://doi.org/10.1101/525956, 39 pages.
Tanaka et al., "The Arabidopsis histone deacetylases HDA6 and HDA19 contribute to the repression of embryonic properities after germination", Plant Physiology, 2008, vol. 146, No. 1, pp. 149-161.
"RWP-RK domain containing protein [Triticum aestivum]", AEB26836.1, GenBank; Aug. 5, 2011.
Li et al., "Analysis of pepper RWP-RK transcription factors", Journal of Anhui Agricultural University, 2018, vol. 45, No. 1, pp. 187-194.
Tsuwamoto et al., "Arabidopsis EMBRYOMAKER encoding an AP2 domain transcription factor plays a key role in developmental change from vegetative to embryonic phase", Plant Molecular Biology, 2010, vol. 73, pp. 481-492.

* cited by examiner

FIG 10
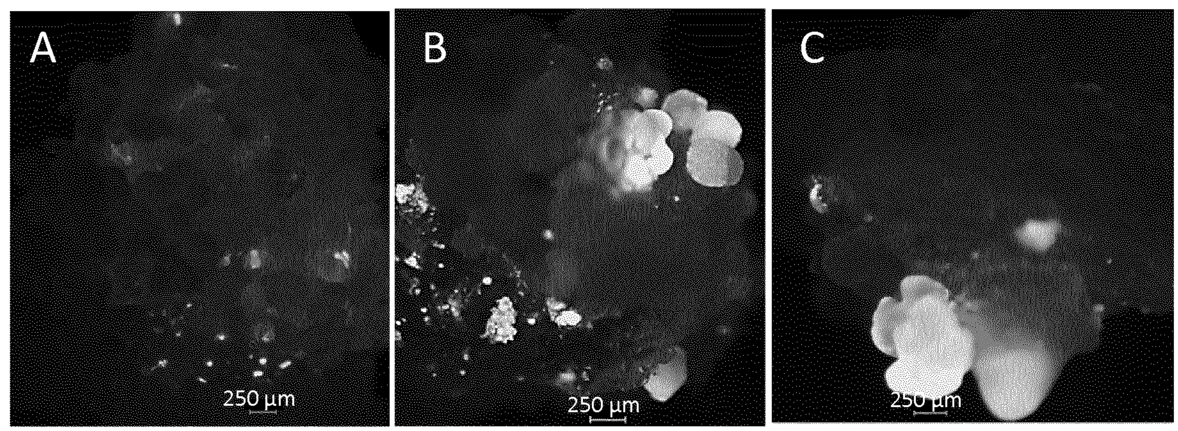
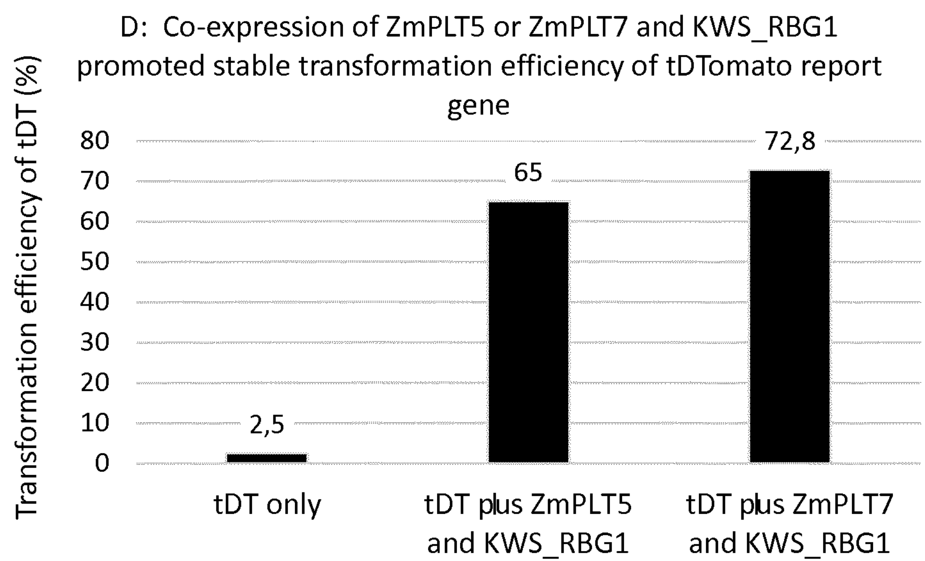

FIG 12
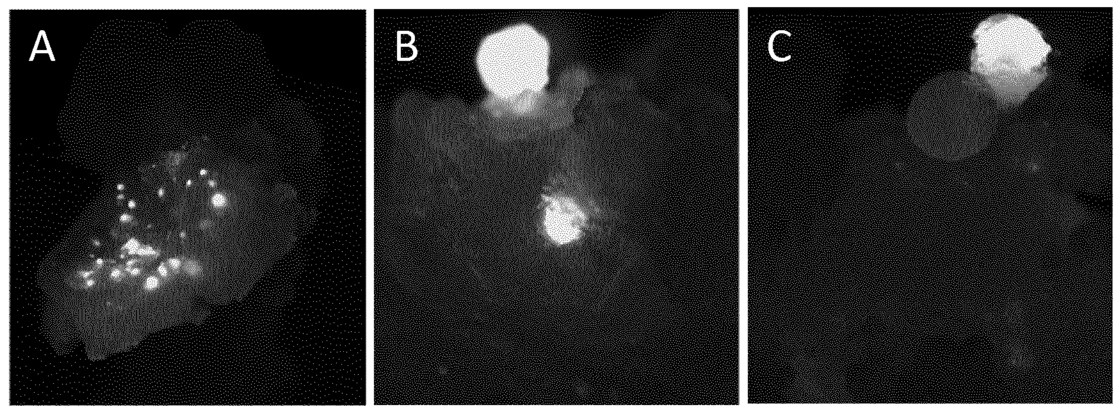
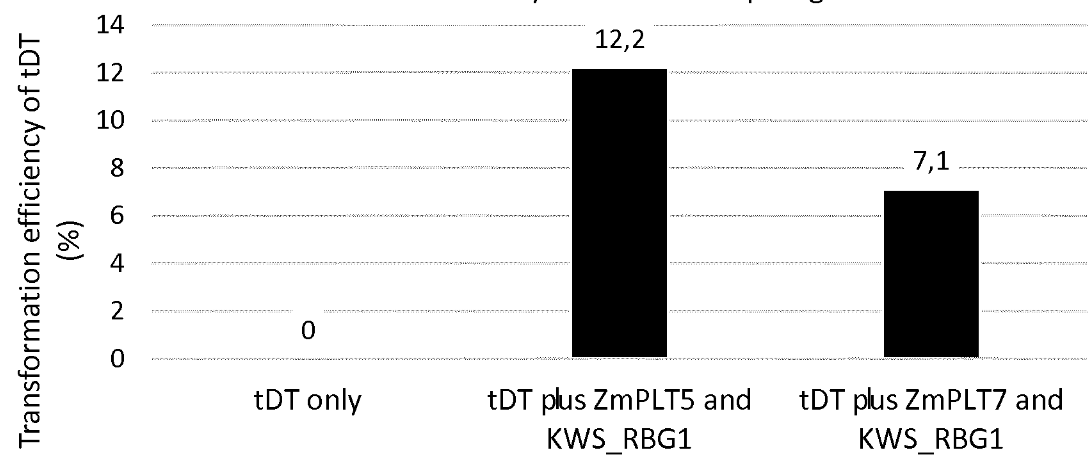

FIG 15
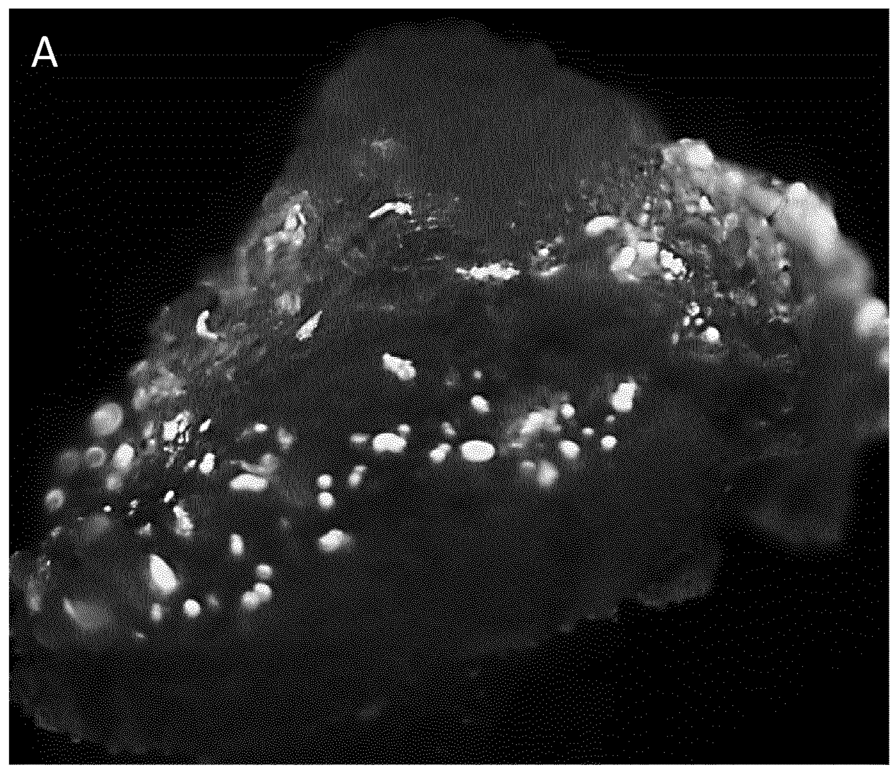
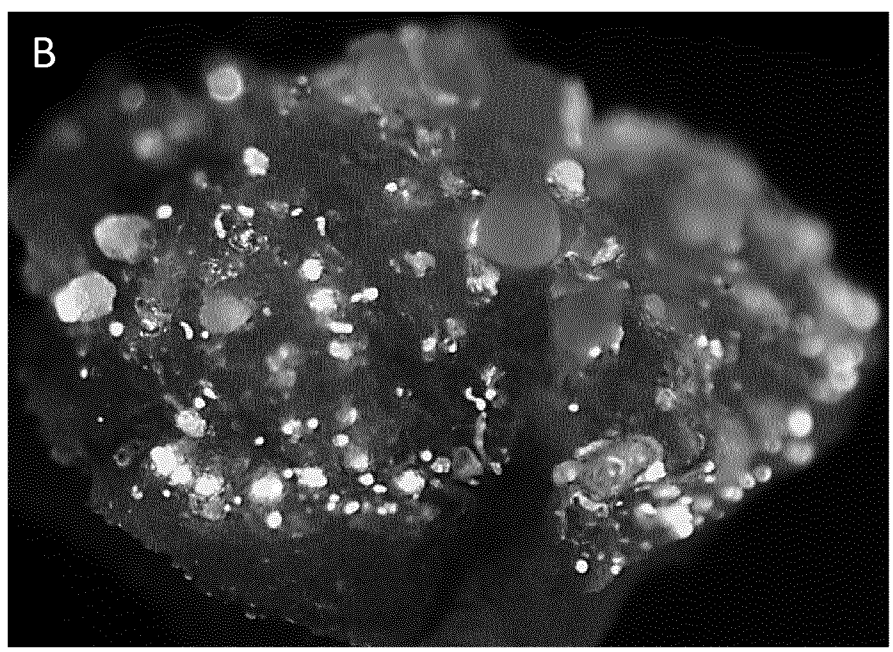

FIG 16
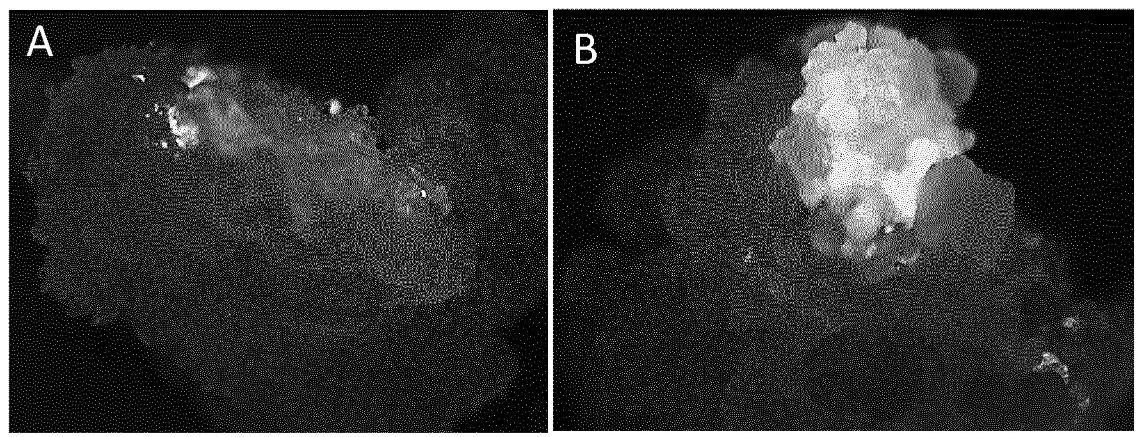
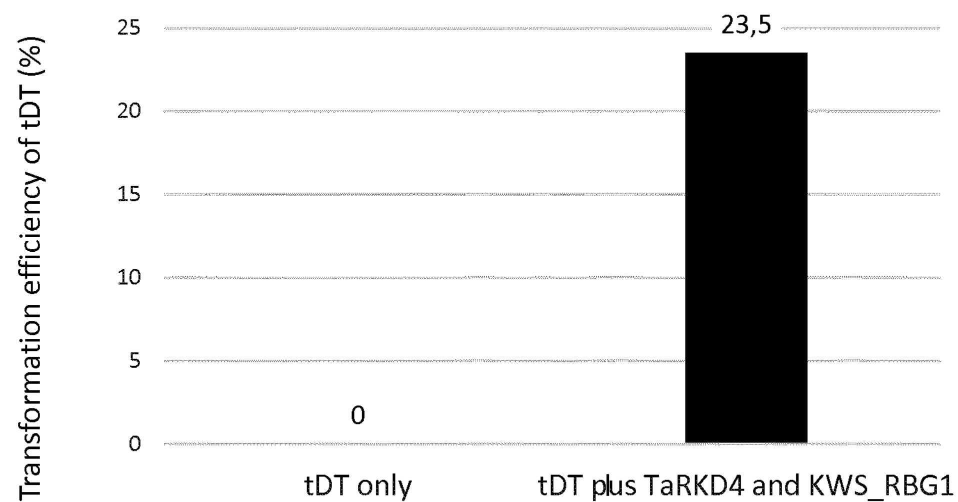

FIG 17
A
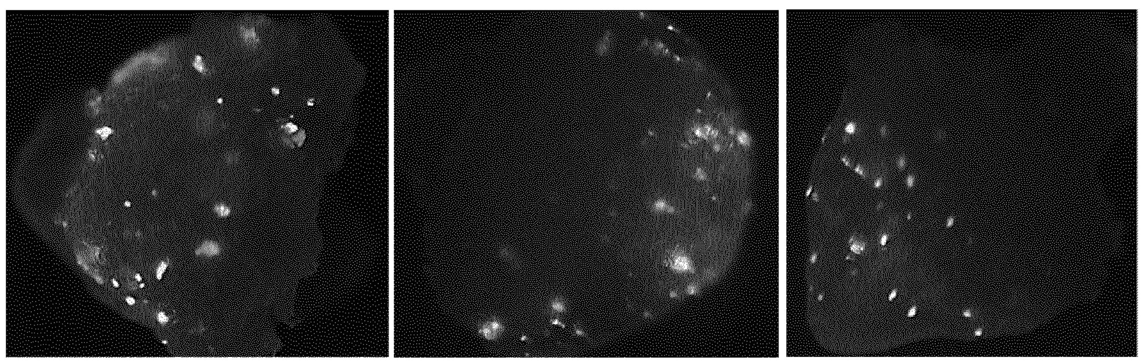
B
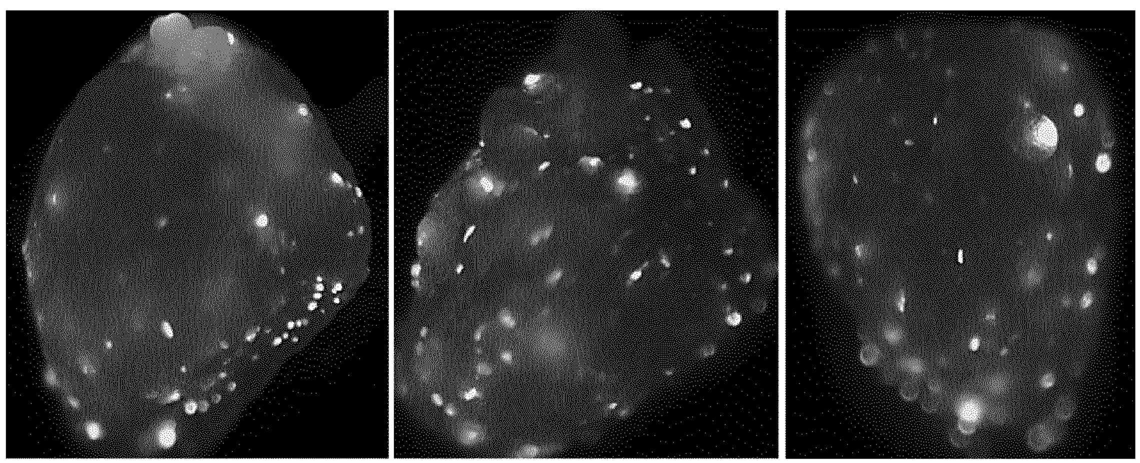

FIG 18
A
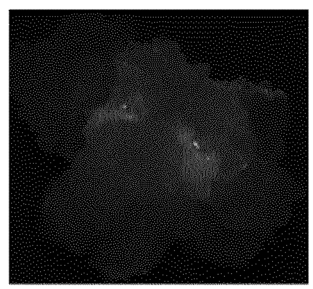
B
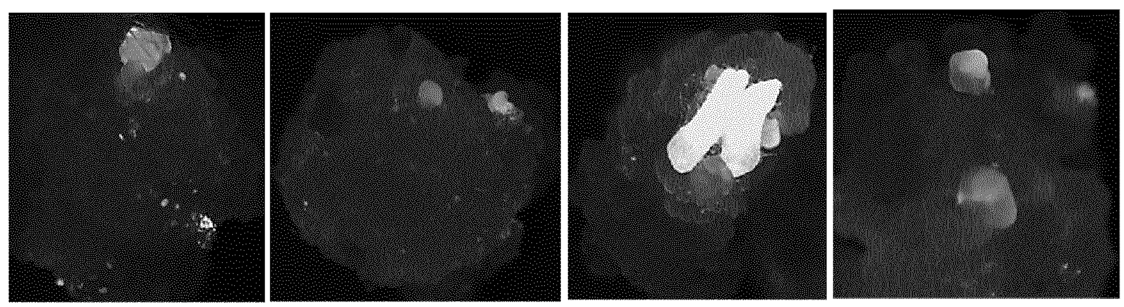
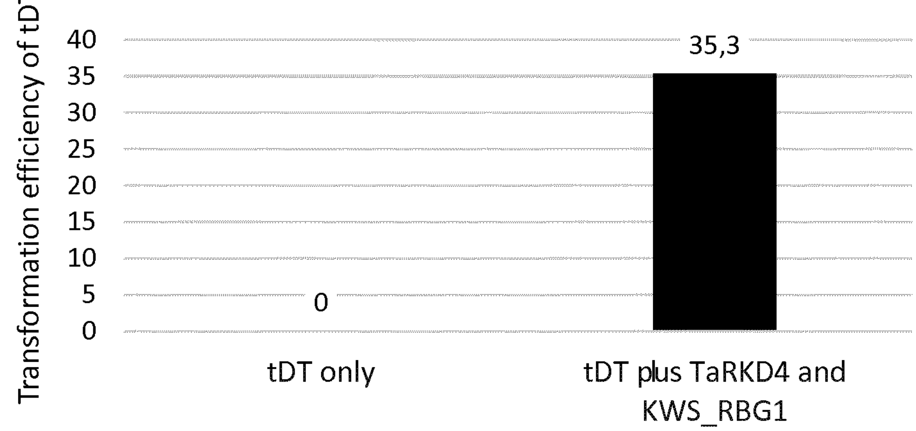

FIG 19
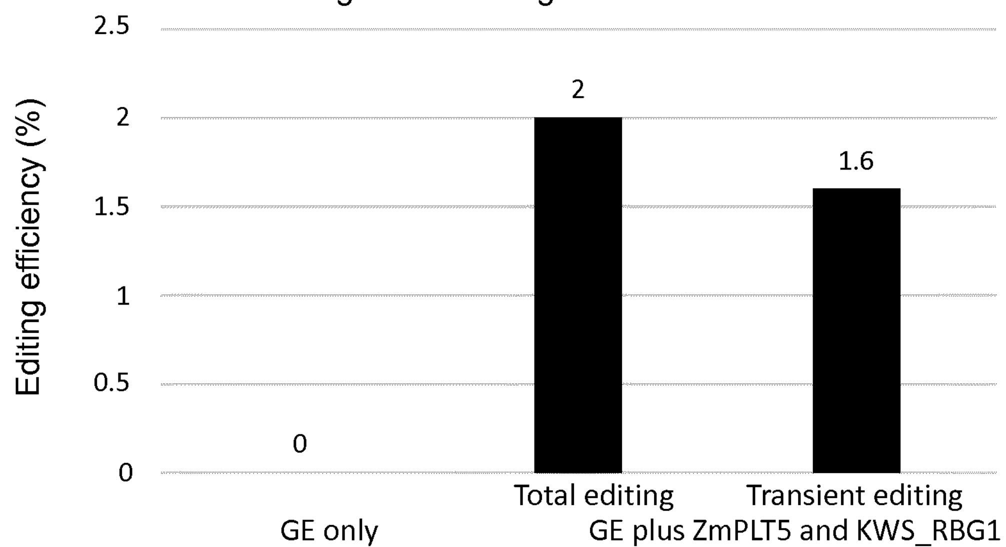
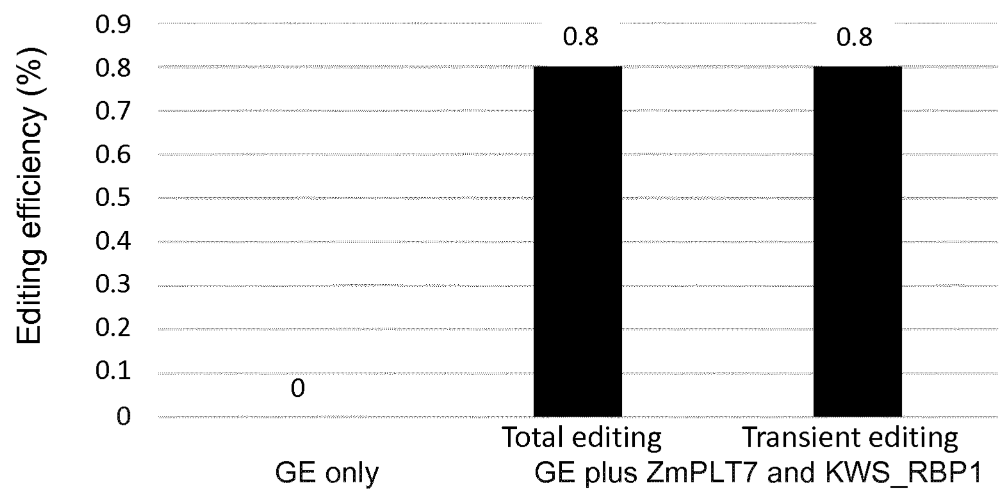

FIG 21

SNP:
G A188
A B73

A

SNP | PAM site | Cleavage site

```
Reference ACGACTTATT ATTTGATTTA CTCGTCACGA TTCCCCTCTC CTGGTCGAAC TTTTCAGGTG GGGAAAGCTG
          ACGACTTATT ATTTGATTTA CTCGTCACGA TTC-----TC CTGGTCGAAC TTTTCAGGTG GGGAAAGCTG
          ACGACTTATT ATTTGATTTA CTCGTCACGA TTC-----TC CTGGTCGAAC TTTTCAGGTG GGGAAAGCTG
          ACGACTTATT ATTTAATTTA CTCGTCACGA TTCCCC--TC CTGGTCGAAC TTTTCAGGTG GGGAAAGCTG
          ACGACTTATT ATTTAATTTA CTCGTCACGA TTCCCC--TC CTGGTCGAAC TTTTCAGGTG GGGAAAGCTG
```

B

SNP | PAM site | Cleavage site

```
Reference CTTATTATTT GATTTACTCG TCACGATTCC CCTCTCCTGG TCGAACTTTT CAGGTGGGGA AAGCTGCTGG
          CTTATTATTT GATTTACTCG TCACGATTCC C------TGG TCGAACTTTT CAGGTGGGGA AAGCTGCTGG
          CTTATTATTT AATTTACTCG TCACGATTCC CC-----TGG TCGAACTTTT CAGGTGGGGA AAGCTGCTGG
```

C

SNP | PAM site | Cleavage site

```
Reference CGACTTATTA TTTGATTTAC TCGTCACGAT TCCCCTCTCC TGGTCGAACT TTTCAGGTGG GGAAAGCTGC
          CGACTTATTA TTTGATTTAC TCGTCACGAT TCCCCTC--- -----GAACT TTTCAGGTGG GGAAAGCTGC
          CGACTTATTA TTTGATTTAC TCGTCACGAT TCCCCTC--- -----GAACT TTTCAGGTGG GGAAAGCTGC
          CGACTTATTA TTTAATTTAC TCGTCACGAT TCCCCTCTCC TGGTCGAACT TTTCAGGTGG GGAAAGCTGC
          CGACTTATTA TTTAATTTAC TCGTCACGAT TCCCCTCTCC TGGTCGAACT TTTCAGGTGG GGAAAGCTGC
```

FIG 24
A
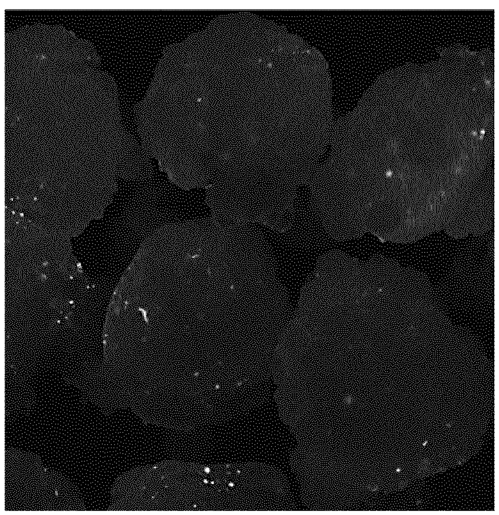
B
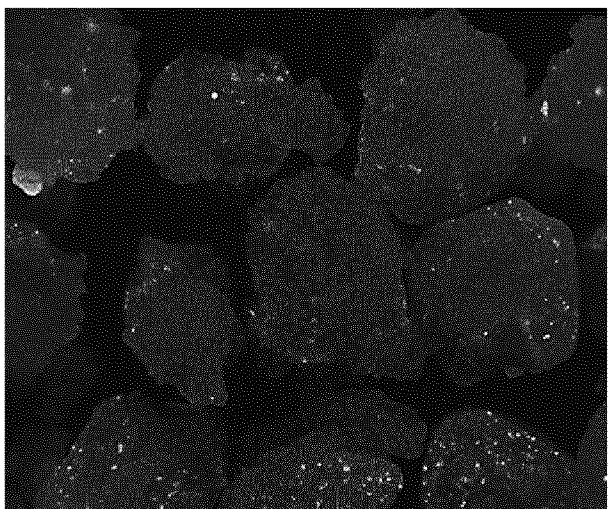
C
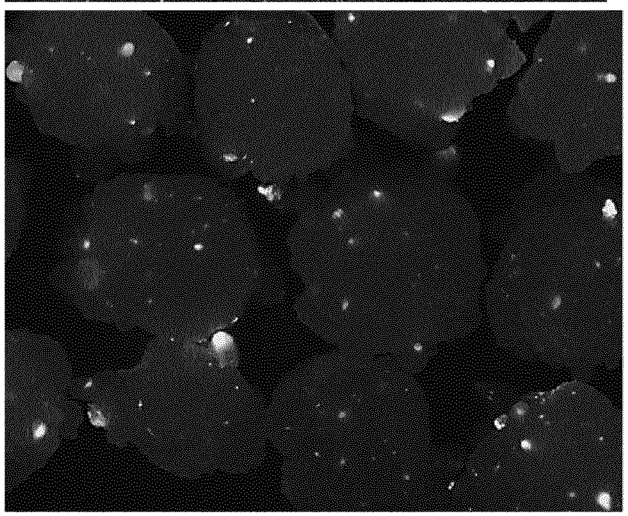

FIG 25
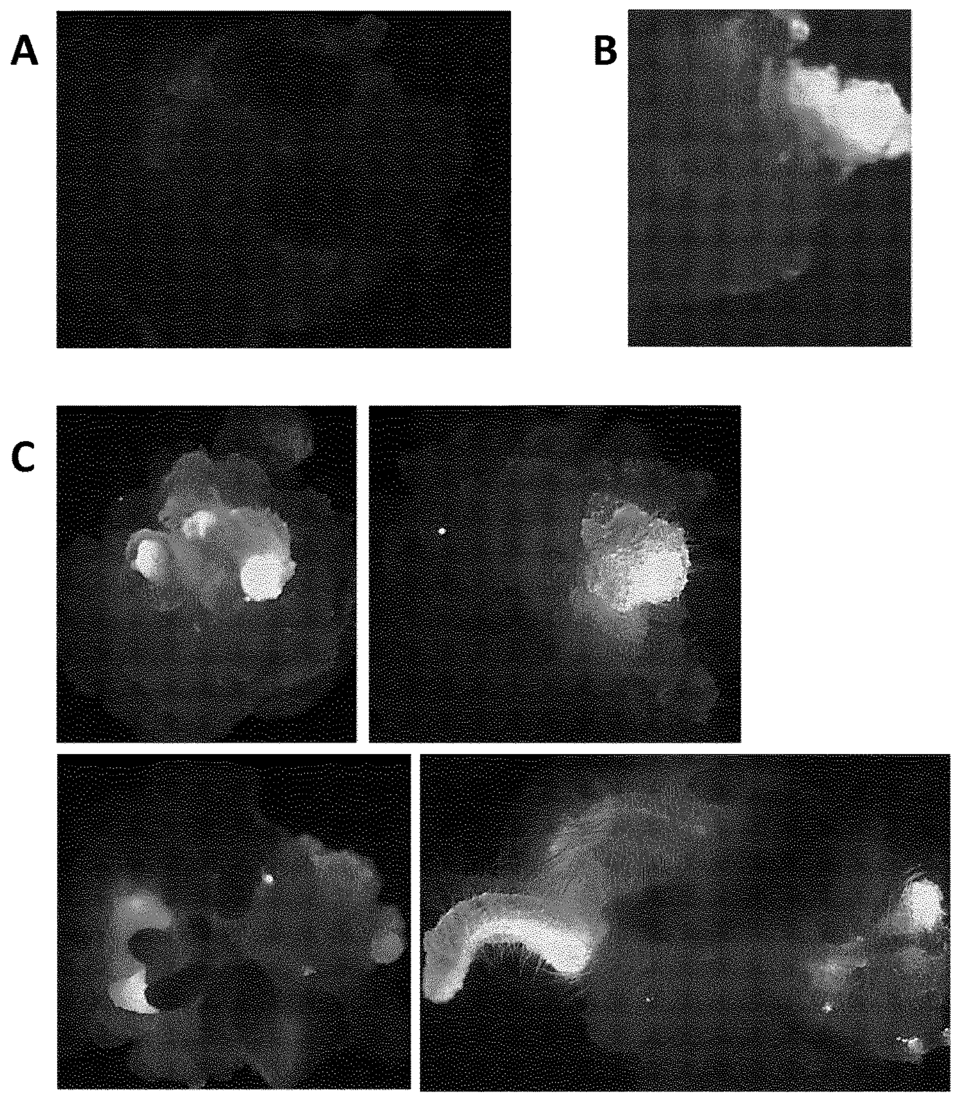
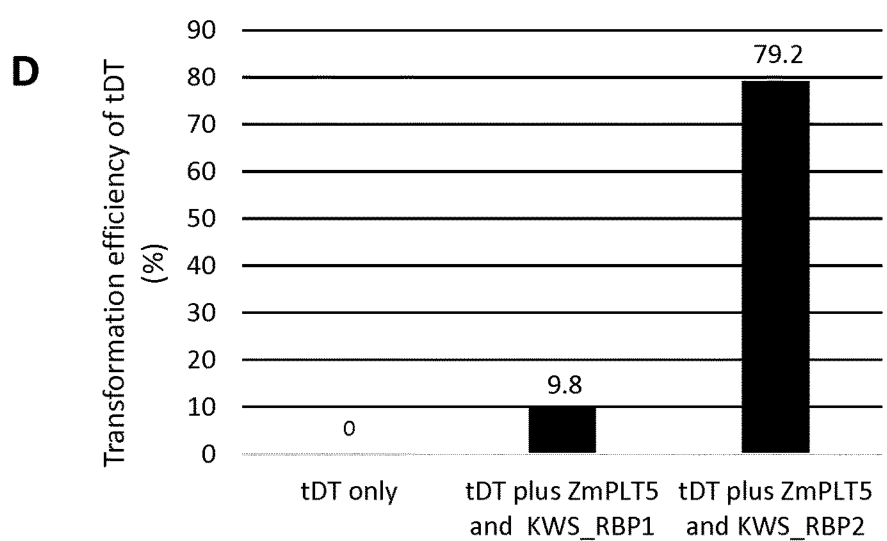

METHODS FOR IMPROVING GENOME ENGINEERING AND REGENERATION IN PLANT

CROSS-REFERENCE TO RELATED APPLICATIONS

This application is a U.S. National Phase of International Patent Application No. PCT/EP2019/065645, filed on Jun. 14, 2019, which claims priority to U.S. application Ser. No. 62/685,626, filed Jun. 15, 2018, and U.S. application Ser. No. 62/728,445, filed Sep. 7, 2018. The entire contents of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 30, 2021, is named 245761_000133_SL.txt and is 210,870 bytes in size.

TECHNICAL FIELD

Described herein are novel regeneration booster genes and polypeptides as well as methods and materials for genome engineering in eukaryotic cells, and particularly methods for increasing genome engineering (i.e., transformation or genome editing) efficiency via delivery of booster polypeptides, and boost genes, with genome engineering components.

BACKGROUND OF THE INVENTION

Traditional breeding has provided domesticated plants and animals, while modern biotechnology, in particular genome engineering, is expanding breeding capability and enabling improvements that are not possible with only traditional crossing of close species. Using biotechnology, various traits, such as high-yield, herbicide tolerance and pest resistance, have been introduced into crops, resulting in dramatic advances in global agriculture and food security. However, the presence of foreign DNA in such products of biotechnology can trigger biosafety and environmental concerns.

By segregating out any integrated DNA, genome-editing technology can be used to generate a site-specific modification of the target genome without the presence of foreign DNA in the end plants. Moreover, by transient expression, genome editing can involve transient editing activity to create site-specific modification without DNA integration at any points of process. The genome-edited plants, especially those derived from the transient activity, would be significantly different from the conventional genome modified plants, and may not be regulated as genetically modified (GM) plants. Genome editing techniques, especially via a transient editing approach, thus can provide a highly accurate, safe and powerful plant breeding and development tool in agriculture.

Genome engineering based on transient activity however faces more challenges. Compared with stable transformation, transient engineering generally results in fewer modified cells. Without an integrated selectable marker, it is highly challenging to identify the engineered cells and achieve homogenous modification in the regenerated plants. These challenges stand in the way of routine implementation of transient gene editing as a breeding tool for plant improvement. Novel methods and materials that enhance genome engineering efficiency are thus highly desirable.

SUMMARY OF THE INVENTION

In one aspect is provided a (regeneration) booster polypeptide comprising an amino acid sequence of SEQ ID NO: 2 or 48, or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2 or 48.

In another aspect is provided a nucleic acid encoding a booster polypeptide comprising an amino acid sequence of SEQ ID NO: 2 or 48, or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2 or 48. In some embodiments, the nucleic acid encoding a booster polypeptide comprising an amino acid sequence of SEQ ID NO: 2 an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2 comprises a coding sequence selected from the group consisting of: (i) a nucleic acid comprising the nucleotide sequence of SEQ ID NO: 1; (ii) a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1; and (iii) a nucleic acid hybridizing with the complementary strand of the nucleic acid as defined in (i) or (ii) under stringent hybridization conditions. In some embodiments, the nucleic acid encoding a booster polypeptide comprising an amino acid sequence of SEQ ID NO: 48 or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 48 comprises a coding sequence selected from the group consisting of: (I) a nucleic acid comprising the nucleotide sequence of SEQ ID NO: 47; (II) a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 47; and (III) a nucleic acid hybridizing with the complementary strand of the nucleic acid as defined in (I) or (II) under stringent hybridization conditions.

In another aspect is provided a recombinant gene comprising a nucleic acid encoding a booster polypeptide comprising an amino acid sequence of SEQ ID NO: 2 or 48, or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2 or 48. In some embodiments, the nucleic acid encoding a booster polypeptide comprising an amino acid sequence of SEQ ID NO: 2 or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2, comprises a coding sequence selected from the group consisting of: (i) a nucleic acid comprising the nucleotide sequence of SEQ ID NO: 1; (ii) a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1; and (iii) a nucleic acid hybridizing with the complementary strand of the nucleic acid as defined in (i) or (ii) under stringent hybridization conditions. In some embodiments, the nucleic acid encoding a booster polypeptide comprising an amino acid sequence of SEQ ID NO: 48 or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 48 comprises a coding sequence selected from the group consisting of: (I) a nucleic acid comprising the nucleotide sequence of SEQ ID NO: 47; (II) a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 47; and (III) a nucleic acid hybridizing with the complementary strand of the nucleic acid as defined in (I) or (II) under stringent hybridization conditions.

In some embodiments, the nucleic acid is operably linked to a heterologous promoter. The heterologous promoter can be a strong constitutive promoter, a tissue-specific promoter, a development-specific promoter, or an inducible promoter.

In another aspect is provided a DNA construct, preferably a vector, comprising any of the above nucleic acids or recombinant genes. In some embodiments, the nucleic acid comprises a coding sequence selected from the group consisting of: (i) a nucleic acid comprising the nucleotide sequence of SEQ ID NO: 1 or 47; (ii) a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1 or 47; and (iii) a nucleic acid hybridizing with the complementary strand of the nucleic acid as defined in (i) or (ii) under stringent hybridization conditions.

In another aspect is provided a plant cell comprising the above booster polypeptides, nucleic acids, recombinant genes or DNA constructs, particularly as transgene or as heterologous polypeptide or heterologous nucleic acid. In some embodiments, the booster polypeptide comprises the amino acid sequence of SEQ ID NO: 2 or 48. In some embodiments, the booster polypeptide comprises the amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2 or 48. In some embodiments, the nucleic acid comprises a coding sequence selected from the group consisting of: (i) a nucleic acid comprising the nucleotide sequence of SEQ ID NO: 1 or 47; (ii) a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1 or 47; and (iii) a nucleic acid hybridizing with the complementary strand of the nucleic acid as defined in (i) or (ii) under stringent hybridization conditions.

Also provided is a plant, a part of the plant, a seed, an embryo or a callus comprising the plant cell.

In another aspect is provided a method for genetic modification in a plant cell. The method comprises: (a) introducing into the plant cell (i) any of the above booster polypeptides, nucleic acids, recombinant genes or DNA constructs; and (ii) a transgene and/or a genome engineering component; (b) optionally, cultivating the plant cell under conditions allowing the synthesis of the booster polypeptide from the nucleic acid, the recombinant gene or the DNA construct; and (c) optionally, cultivating the plant cell under conditions allowing the genetic modification of the genome of said plant cell by integration of the transgene of interest and activity of the genome engineering component in the presence of the booster polypeptide.

In some embodiments, the booster polypeptide is transiently present, transiently active and/or transiently expressed in the plant cell. In some embodiments, the nucleic acid encoding the booster polypeptide is transiently present, transiently active and/or transiently expressed in the plant cell.

In step (i) of the method for genetic modification in a plant cell additionally one or more polypeptides selected from the group consisting of a PLT5 polypeptide, a PLT7 polypeptide, an RKD4 polypeptide, and an RKD2 polypeptide, and/or one or more nucleic acids selected from the group consisting of a nucleic acid encoding a PLT5 polypeptide, a PLT7 polypeptide, an RKD4 polypeptide, and an RKD2 polypeptide, and/or one or more site-directed transcriptional activators suitable to increase transiently the expression of an endogenous PLT5 polypeptide, an endogenous PLT7 polypeptide, an endogenous RKD4 polypeptide, or an endogenous RKD2 polypeptide, and/or a nucleic acid encoding such site-directed transcriptional activator are introduced into the plant cell.

In some embodiments, the PLT5 polypeptide or the PLT7 polypeptide is transiently present, transiently active and/or transiently expressed in the plant cell, or the nucleic acid encoding the PLT5 polypeptide or the PLT7 polypeptide is transiently present, transiently active and/or transiently expressed in the plant cell.

In some embodiments, both the booster polypeptide or the nucleic acid encoding the booster polypeptide, and the PLT5 polypeptide or the nucleic acid encoding the PLT5 polypeptide are introduced or co-delivered into the plant cell, preferably the same plant cell, and optionally transiently co-expressed. In some embodiments, both the booster polypeptide or the nucleic acid encoding the booster polypeptide, and the PLT7 polypeptide or the nucleic acid encoding the PLT7 polypeptide are introduced into the plant cell, and optionally transiently co-expressed.

In some embodiments, the PLT5 polypeptide comprises the amino acid sequence of SEQ ID NO: 4 or 6, or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 4 or 6, or the nucleic acid encoding the PLT5 polypeptide encodes such polypeptides. The PLT7 polypeptide comprises the amino acid sequence of SEQ ID NO: 8 or 10, or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 8 or 10, or the nucleic acid encoding the PLT7 polypeptide encodes such polypeptides. In some embodiments, the RKD4 polypeptide comprises the amino acid sequence of SEQ ID NO: 12, 14 or 16, or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 12, 14 or 16, or the nucleic acid encoding the RKD4 polypeptide encodes such polypeptides. In some embodiments, the RKD2 polypeptide comprises the amino acid sequence of SEQ ID NO: 18, 20 or 22, or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 18, 20 or 22, or the nucleic acid encoding the RKD2 polypeptide encodes such polypeptides.

In some embodiments, the nucleic acid encoding the PLT5 polypeptide comprises a nucleic acid having a coding sequence selected from the group consisting of: (i) a nucleic acid comprising the nucleotide sequence of SEQ ID NO: 3 or 5; (ii) a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 3 or 5; and (iii) a nucleic acid hybridizing with the complementary strand of the nucleic acid as defined in (i) or (ii) under stringent hybridization conditions. In some embodiments, the nucleic acid encoding the PLT7 polypeptide comprises a nucleic acid having a coding sequence selected from the group consisting of: (I) a nucleic acid comprising the nucleotide sequence of SEQ ID NO: 7 or 9; (II) a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 7 or 9; and (III) a nucleic acid hybridizing with the complementary strand of the nucleic acid as defined in (I) or (II) under stringent hybridization conditions. In some embodiments, the nucleic acid encoding the RKD4 polypeptide comprises a nucleic acid having a coding sequence selected from the group consisting of: (1) a nucleic acid comprising the nucleotide sequence of SEQ ID NO: 11, 13, or 15; (2) a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 11, 13, or 15; and (3) a nucleic acid hybridizing with the complementary strand of the nucleic acid as defined in (1) or (2) under stringent hybridization conditions. In some embodiments, the nucleic acid encoding the RKD2 polypeptide comprises a nucleic acid having a coding sequence selected from the group consisting of: a) a nucleic acid comprising the nucleotide sequence of SEQ ID NO: 17, 19, or 21; b) a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 17, 19, or 21; and c) a nucleic acid hybridizing with the complementary strand of the nucleic acid as defined in a) or b) under stringent hybridization conditions.

In some embodiments, the genome engineering component comprises a) an enzyme inducing a double-stranded break (DSB) or a nucleic acid encoding same, and optionally a repair nucleic acid molecule, wherein the DSB-inducing enzyme preferably recognizes a predetermined site in the genome of said cell; b) an enzyme inducing a single-stranded break (SSB) or a nucleic acid encoding same, and optionally a repair nucleic acid molecule, wherein the SSB-inducing enzyme preferably recognizes a predetermined site in the genome of said cell; c) a base editor enzyme, optionally fused to a disarmed DSB- or SSB-inducing enzyme, wherein the base editor enzyme preferably recognizes a predetermined site in the genome of said cell; or d) an enzyme effecting DNA methylation, histone acetylation, histone methylation, histone ubiquitination, histone phosphorylation, histone ribosylation or histone citrullination, optionally fused to a disarmed DSB- or SSB-inducing enzyme, wherein the enzyme preferably recognizes a predetermined site in the genome of said cell.

In some embodiments, the genome engineering component comprising a DSB- or SSB-inducing enzyme or a variant thereof is a CRISPR/Cas endonuclease, a CRISPR/Cas9 endonuclease, a CRISPR/Cpf1 endonuclease, a CRISPR/Csm1 endonuclease, a zinc finger nuclease (ZFN), a homing endonuclease, a meganuclease, or a TAL effector nuclease.

In some embodiments, the activity of the genome engineering component in step (b) comprises inducing one or more double-stranded breaks in the genome of the plant cell, one or more single strand breaks in the genome of the plant cell, one or more base editing events in the genome of the plant cell, or one or more of DNA methylation, histone acetylation, histone methylation, histone ubiquitination, histone phosphorylation, histone sumoylation, histone ribosylation or histone citrullination in the genome of the plant cell.

In some embodiments, the induction of one or more double-stranded breaks or one or more single strand breaks is followed by non-homologous end joining (NHEJ) and/or by homology directed repair of the break(s) though a homologous recombination mechanism (HDR).

In some embodiments, the transgene in step (a) (ii) is selected from the group consisting of a gene encoding resistance or tolerance to abiotic stress, including drought stress, osmotic stress, heat stress, cold stress, oxidative stress, heavy metal stress, nitrogen deficiency, phosphate deficiency, salt stress or waterlogging, herbicide resistance, including resistance to glyphosate, glufosinate/phosphinothricin, hygromycin, protoporphyrinogen oxidase (PPO) inhibitors, ALS inhibitors, and Dicamba, a gene encoding resistance or tolerance to biotic stress, including a viral resistance gene, a fungal resistance gene, a bacterial resistance gene, an insect resistance gene, or a gene encoding a yield related trait, including lodging resistance, flowering time, shattering resistance, seed color, endosperm composition, or nutritional content.

In some embodiments, in step (c) the modification of said genome is selected from i) a replacement of at least one nucleotide; ii) a deletion of at least one nucleotide; iii) an insertion of at least one nucleotide; iv) a change of the DNA methylation; v) a change in histone acetylation, histone methylation, histone ubiquitination, histone phosphorylation, histone sumoylation, histone ribosylation or histone citrullination; or vi) any combination of i)-v).

In some embodiments, the method is effective to promote cell proliferation or cell regeneration, preferably after genetic modification/modification of the genome or is effective to increase the efficiency for regeneration of transgenic, gene edited or base edited plants.

In some embodiments, the method is effective to induce direct or indirect embryogenesis from a single cell, preferably an embryonic cell, a somatic cell or a protoplast, or from a callus cell, preferably after genetic modification/modification of the genome.

In some embodiments, the method is effective to increase the stable transformation efficiency of the transgene into the plant cell or is effective to increase the efficiency for generation of transgenic plants.

In some embodiments, the method is effective to increase the efficiency of the genome engineering component to edit the genome of the plant cell or is effective to increase the efficiency for generation of transgenic, gene edited or base edited plants.

In some embodiments, the method is effective to improve the efficiency of regeneration of plants derived from recalcitrant genotypes, is effective to improve the efficiency of regeneration of plants from non-conventional tissue types, or is effective to accelerate the regeneration process, preferably after genetic modification/modification of the genome.

In some embodiments, the site-directed transcriptional activator, or the nucleic acid encoding the same, comprises at least one recognition domain and at least one activation domain, wherein the site-directed transcriptional activator is configured to increase the expression of an endogenous PLT5 polypeptide, an endogenous PLT7 polypeptide, an endogenous RKD4 polypeptide, or an endogenous RKD2 polypeptide, preferably by binding to a regulation region located at a certain distance in relation to the start codon of the endogenous PLT5 polypeptide, the endogenous PLT7 polypeptide, the endogenous RKD4 polypeptide, or the endogenous RKD2 polypeptide.

In some embodiments, the at least one recognition domain is, or is a fragment of, a molecule selected from the group consisting of at least one TAL effector, at least one disarmed CRISPR/nuclease system, at least one Zinc-finger domain, and at least one disarmed homing endonuclease, or any combination thereof. In some embodiments, the at least one disarmed CRISPR/nuclease system is selected from a CRISPR/dCas9 system, a CRISPR/dCpf1 system, a CRISPR/dCsm1 system, a CRISPR/dCasX system or a CRISPR/dCasY system, or any combination thereof, wherein the at least one disarmed CRISPR/nuclease system comprises at least one guide RNA. In some embodiments, the at least one activation domain is an acidic transcriptional activation domain, preferably, wherein the at least one activation domain is from an TAL effector gene of *Xanthomonas oryzae*, VP16 or tetrameric VP64 from Herpes simplex, VPR, SAM, Scaffold, Suntag, P300, VP160, or any combination thereof.

In another aspect is provided a method for improving the efficiency of plant regeneration or increasing the regeneration ability of a plant cell, the method comprising introducing into the plant cell any of the above booster polypeptides, nucleic acids, recombinant genes or DNA constructs.

In another aspect is provided a genetically modified plant cell obtained or obtainable according to the above methods. Also provided is a plant or a plant part comprising the genetically modified plant cell.

In another aspect is provided a microparticle coated with at least one of the above booster polypeptides, nucleic acids, recombinant genes or DNA constructs. In some embodiments, the microparticle is further coated with a genome engineering component.

In another aspect is provided a kit for the genetic modification of a plant genome by microprojectile bombardment, the kit comprising (I) one or more microparticles, and (II) means for coating the microparticles. In some embodiments, the kit further comprises a means for coating the microparticles with a genome engineering component.

In another aspect is provided a method for producing a genetically modified plant, comprising the steps: (a) genetically modifying a plant cell according to any of the above methods, and (b) regenerating a plant from the modified plant cell of step (a).

In some embodiments, the produced plant does not contain any of the genome engineering component, the boost gene, and the booster polypeptide, co-introduced in step (a).

In another aspect is provided a genetically modified plant or a part thereof obtained or obtainable by the above methods for producing a genetically modified plant, or a progeny plant thereof.

Also provided is a use of the above booster polypeptides, nucleic acids, recombinant gene, DNA construct, microparticle or kit for improving the efficiency of plant regeneration or increasing the regeneration ability of a plant cell.

BRIEF DESCRIPTION OF THE DRAWINGS

FIG. 9A shows bombardment of genome engineering constructs pGEP359 (FIG. 6) and pGEP324 (FIG. 7) only (GE constructs only). FIG. 9B shows co-delivery of ZmPLT5 (FIG. 2) and KWS-RBP1 (FIG. 4) with the GE constructs (GE constructs plus ZmPLT5+KWS-RBP1). FIG. 9C shows co-delivery of ZmPLT7 and KWS-RBP1 with the GE constructs (GE constructs plus ZmPLT7+KWS-RBP1). Images were taken 5 days after bombardment.

FIG. 10 shows transient co-expression of ZmPLT5 and KWS-RBP1 or ZmPLT7 and KWS-RBP1 promotes stable transformation of the co-delivered tDT report gene in maize Hi II embryo. Red fluorescence images show stable tDT expressing structures produced from maize Hi II embryos 12 days after co-bombardment (FIGS. 10A to 10C). FIG. 10A shows bombardment of genome engineering constructs pGEP359 (FIG. 6) and pGEP324 (FIG. 7) only (GE constructs only). FIG. 10B shows co-delivery of ZmPLT5 and KWS-RBP1 with the GE constructs (GE constructs plus ZmPLT5+KWS-RBP1). FIG. 10C shows co-delivery of ZmPLT7 and KWS-RBP1 with the GE constructs (GE constructs plus ZmPLT7+KWS-RBP1). FIG. 10D is a graph showing that co-delivery of ZmPLT5 or ZmPLT7 and KWS- RBP1 increased stable transformation frequency of the tDT report gene. Results were taken 12 days after bombardment.

FIG. 11A shows bombardment of genome engineering constructs pGEP359 (FIG. 6) and pGEP324 (FIG. 7) only (GE constructs only); FIG. 11B shows co-delivery of ZmPLT5 and KWS-RBP1 with the GE constructs (GE constructs plus ZmPLT5+KWS-RBP1); FIG. 11C shows co-delivery of ZmPLT7 and KWS-RBP1 with the GE constructs (GE constructs plus ZmPLT7+KWS-RBP1). Images were taken 7 days after bombardment.

FIG. 12 shows transient co-expression of ZmPLT5 and KWS-RBP1 promotes stable transformation of the co-delivered tDT report gene in maize A188 embryo. Red fluorescence images show stable tDT expressing structures produced from maize A188 embryos 16 days after co-bombardment (A to C). FIG. 12A shows bombardment of genome engineering constructs pGEP359 (FIG. 6) and pGEP324 (FIG. 7) only (GE constructs only); FIG. 12B shows co-delivery of ZmPLT5 and KWS-RBP1 with the GE constructs (GE constructs plus ZmPLT5+KWS-RBP1); FIG. 12C shows co-delivery of ZmPLT7 and KWS-RBP1 with the GE constructs (GE constructs plus ZmPLT7+KWS-RBP1). FIG. 12D shows co-delivery of ZmPLT5 or ZmPLT7 and KWS-RBP1 increased stable transformation frequency of tDT report gene. Results were taken 12 days after bombardment.

FIG. 14A shows a maize WUS2 promoter report construct (FIG. 13; SEQ ID NO: 46) only (pZmWUS2 report only). FIG. 14B shows co-bombardment of the maize WUS promoter report construct and wheat RKD4 construct (FIG. 5) (pZmWUS2 report and TaRKD4). Images were taken 44 hours after bombardment.

FIG. 15 shows transient co-expression of wheat RKD4 (TaRKD4) and KWS-RBP1 promotes embryogenesis in Hi II immature embryos. Images show embryogenic structures induced from maize Hi II embryos 5 days after co-bombardment with the boost gene constructs. FIG. 15A shows bombardment of genome engineering constructs pGEP359 (FIG. 6) and pGEP324 (FIG. 7) only (GE constructs only). FIG. 15B shows co-delivery of TaRKD4 and KWS-RBP1 with the GE constructs (GE constructs plus KWS_RGB1+TaRKD4). Images were taken 5 days after bombardment.

FIG. 16 shows transient co-expression of wheat RKD4 (TaRKD4) and KWS-RBP1 promotes stable transformation of the co-delivered tDT report gene in maize Hi II embryo. Red fluorescence images show stable tDT expressing structures produced from maize Hi II embryos 12 days after co-bombardment (FIGS. 16A to 16C). FIG. 16A shows bombardment of genome engineering constructs pGEP359 (FIG. 6) and pGEP324 (FIG. 7) only (GE constructs only). FIG. 16B shows co-delivery of TaRKD4 and KWS-RBP1 with the GE constructs (GE constructs plus TaRKD4+KWS-RGB1). FIG. 16C shows co-delivery of TaRKD4 and KWS-RBP1 increased stable transformation frequency of tDT report gene in Hi II immature embryos. Results were taken 12 days after bombardment.

FIG. 17 shows that transient co-expression of wheat RKD4 and KWS-RBP1 promotes embryogenesis in A188 immature embryos. Images show embryogenic structures induced from maize Hi II embryos 5 days after co-bombardment with boost gene constructs. FIG. 17A shows bombardment of genome engineering constructs pGEP359 (FIG. 6) and pGEP324 (FIG. 7) only (GE constructs only). FIG. 17B shows co-delivery of TaRKD4 and KWS-RBP1 with the GE constructs (GE constructs plus TaRKD4+KWS-RBP1). Images were taken 5 days after bombardment.

FIG. 18 shows transient co-expression of wheat RKD4 and KWS-RBP1 promotes stable transformation of co-delivered tDT report gene in maize A188 embryo. Red fluorescence images show stable tDT expressing structures produced from maize A188 embryos 14 after co-bombardment (A to C). FIG. 18A shows bombardment of genome engineering constructs pGEP359 (FIG. 6) and pGEP324 (FIG. 7) only (GE constructs only). FIG. 18B shows co-delivery of KWS-RBP1 and TaRKD4 with the GE constructs (GE constructs plus TaRKD4+KWS-RBP1). FIG. 18C shows co-delivery of TaRKD4 and KWS-RBP1 increased stable transformation frequency of tDT report gene in maize A188 immature embryos. Results were taken 14 days after bombardment.

FIG. 19 shows transient co-expression of ZmPLT5 or ZmPLT7 and KWS-RBP1 promotes transient genome editing in maize. The genome editing constructs pGEP359 and pGEP324 were co-bombarded with the boost gene constructs into maize Hi II immature embryos. Editing efficiency is defined as the number of plants with a site-specific modification from 100 plants regenerated. Transient editing is used to describe a site-specific modification that resulted from transient activity of genome editing without an integration of the genetic materials.

FIG. 20 illustrates Droplet Digital PCR results, which demonstrate homogenous genome editing in regenerated plants by transient co-expression of the boost genes and genome editing components without a selection. The site-specific InDel rates of around 50% and 100% indicate a mono-allelic and bi-allelic modification, respectively.

FIG. 21 depicts a multiple sequence alignment of the target region from the edited T0 plants by Sanger sequencing analysis. FIGS. 21A and 21B show bi-allelic events CB0113-T-591 and CB0113-T-632, respectively. FIG. 21C shows mono-allelic event CB0113-T-303. The PAM and expected cleavage site are labeled. A SNP (G from A188 and A from B73 allele) near the PAM site (TTTA) is also marked. The sequencing results confirm the homogenous modification occurred in these T0 plants. Specifically, CB0113-T-591 harbors a biallelic modification of 5 bp and 2 bp deletion from A188 and B73 allele, respectively. CB0113-T-632 contains a biallelic editing of 6 bp and 5 bp deletion from A188 and B73 allele, respectively. CB0113-T-303 has an 8 bp deletion from A188 allele, while the B73 allele is unmodified. CB0113-T-591 and CB0113-T-632 are derived from co-expression of ZmPLT5 and KWS-RBP1, and CB0113-T-303 is from co-expression of ZmPLT7 and KWS-RBP1 with the genome editing constructs. FIG. 21 discloses SEQ ID NOS 51, 52, 52, 53, 53-58, 58, 59, and 59, respectively, in order of appearance.

FIG. 24 shows that co-delivery of ZmPLT5 and KWS_RBG1 or ZmPLT5 and KWS_RBP2 promotes stable transformation efficiency of tDTomato report gene in maize A188. Red fluorescence images show stable tDT expressing structures (bright spots/areas) produced from maize A188 embryos 10 days after co-bombardment (A to C). A: Bombardment of genome engineering (GE) constructs pGEP359 (FIG. 6) and pGEP324 (FIG. 7) only (tDTonly); B: Co-bombardment of the GE constructs with ZmPLT5 and KWS-RBP1 (tDT plus ZmPLT5 and KWS_RBP1); C: Co-bombardment of the GE constructs with ZmPLT5 and KWS-RBP2 (tDT plus ZmPLT5 and KWS_RBP2). Images were taken 10 days after bombardment.

FIG. 25 shows that co-delivery of ZmPLT5 and KWS-RBG1 or ZmPLT5 and KWS_RBP2 promotes stable transformation efficiency of tDTomato report gene in maize A188. Red fluorescence images show stable tDT expressing structures (bright spots/areas) produced from maize A188 embryos 16 days after co-bombardment (A to C). A: Bombardment of genome engineering (GE) constructs pGEP359 (FIG. 6) and pGEP324 (FIG. 7) only (tDTonly); B: Co-bombardment of the GE constructs with ZmPLT5 and KWS-RBP1 (tDT plus ZmPLT5 and KWS_RBP1); C: Co-bombardment of the GE constructs with ZmPLT5 and KWS-RBP2 (tDT plus ZmPLT5 and KWS_RBP2). D: Co-delivery of ZmPLT5 and KWS-RBP1 or ZmPLT5 and KWS-RBP2 increased stable transformation frequency of tDT report gene. Data was recorded 16 days after bombardment. Images were taken 16 days after bombardment.

DETAILED DESCRIPTION

Definitions

Figure 1:
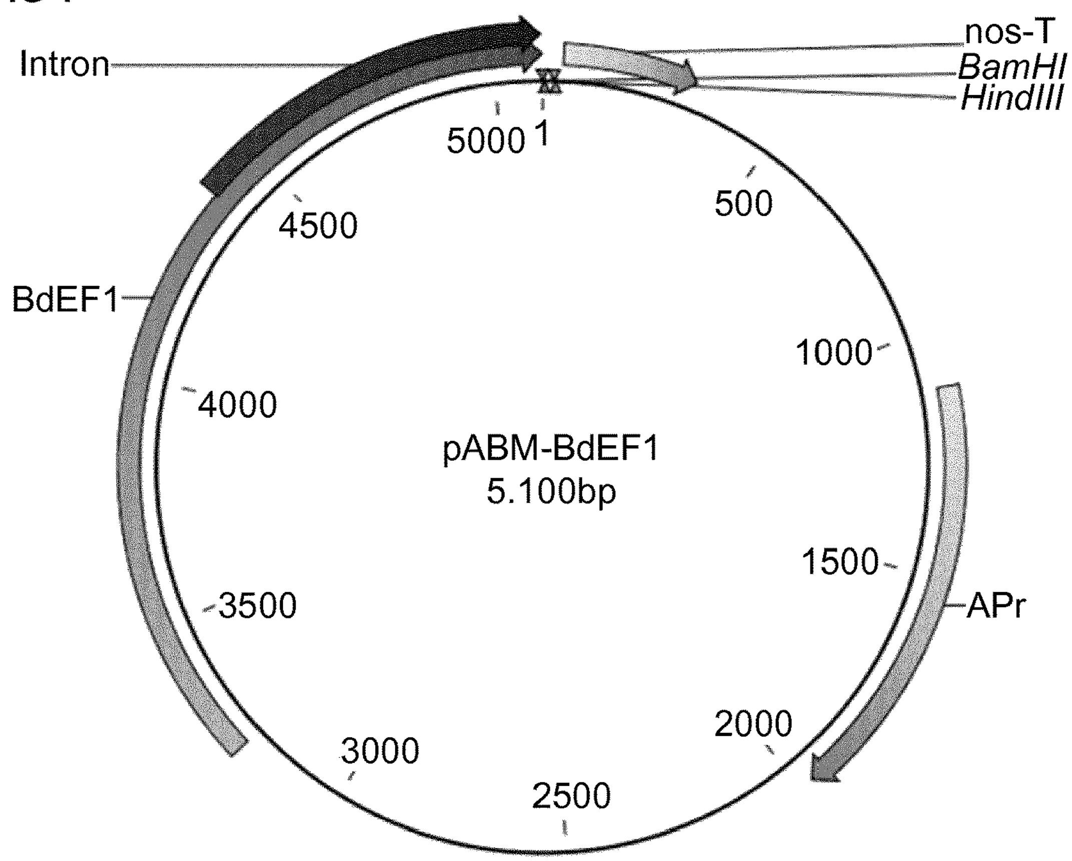
FIG. 1 shows a map of the Boost gene expression vector pABM-BdEF1 (SEQ ID NO: 24). BdEF1 and nos-T define the strong constitutive promoter from *Brachypodium* EF1 gene and nos terminator, respectively. BamHI and HindIII illustrate the cloning sites.
Figure 2:
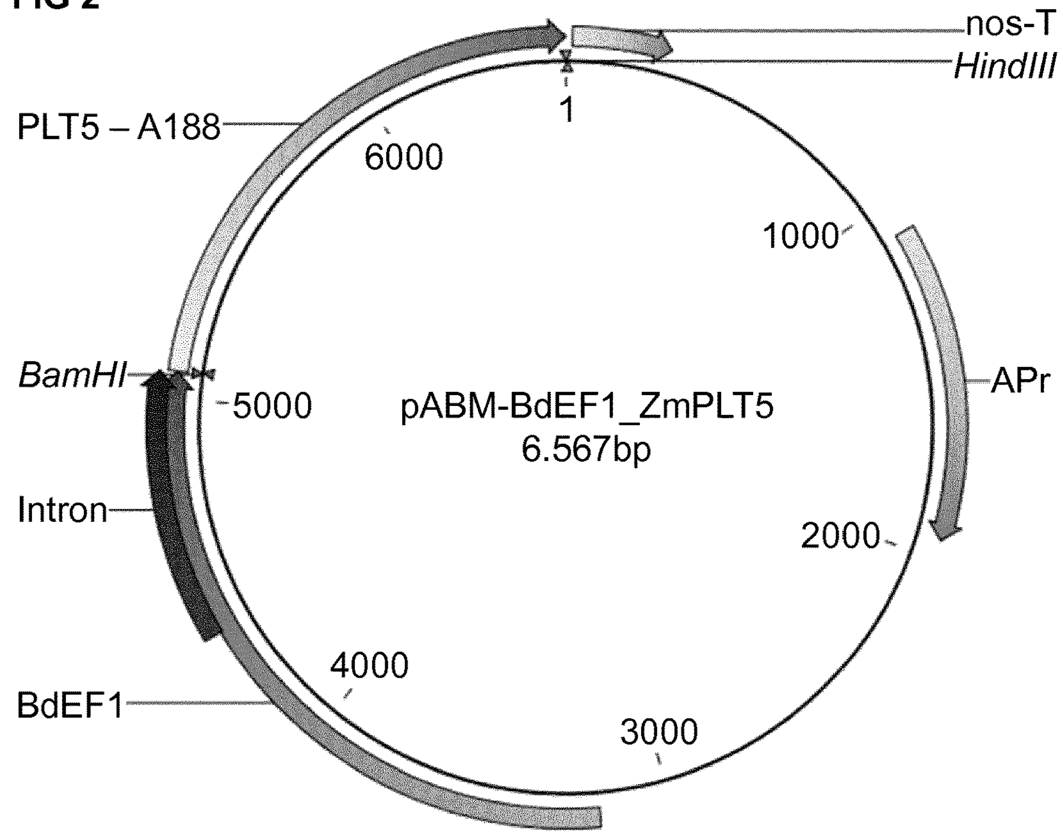
FIG. 2 shows a map of the maize PLT5 expression construct pABM-BdEF1_ZmPLT5 (SEQ ID NO: 25). The maize PLT5 gene (ZmPLT5) is driven by the strong constitutive EF1 promoter from *Brachypodium* (pBdEF1).
Figure 3:
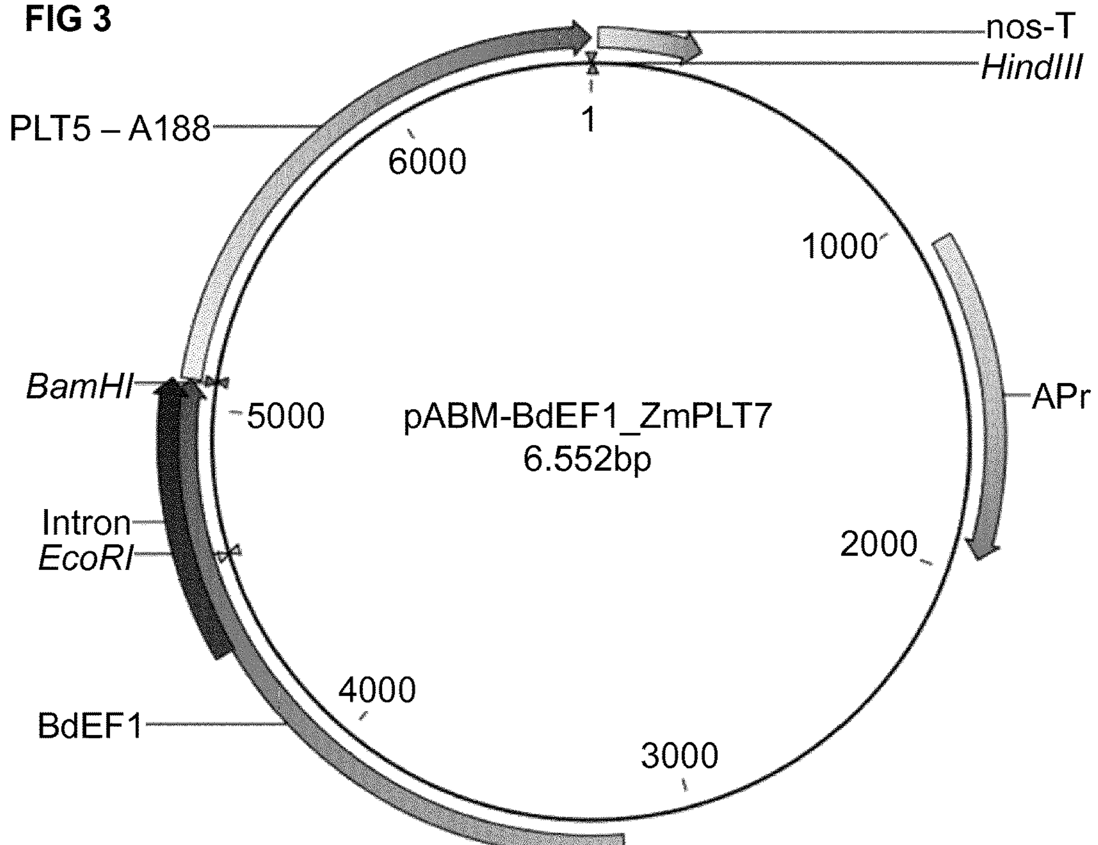
FIG. 3 shows a map of the maize PLT7 expression construct pABM-BdEF1_ZmPLT7 (SEQ ID NO: 26). The maize PLT7 gene (ZmPLT7) is driven by the strong constitutive EF1 promoter from *Brachypodium* (pBdEF1).
Figure 4:
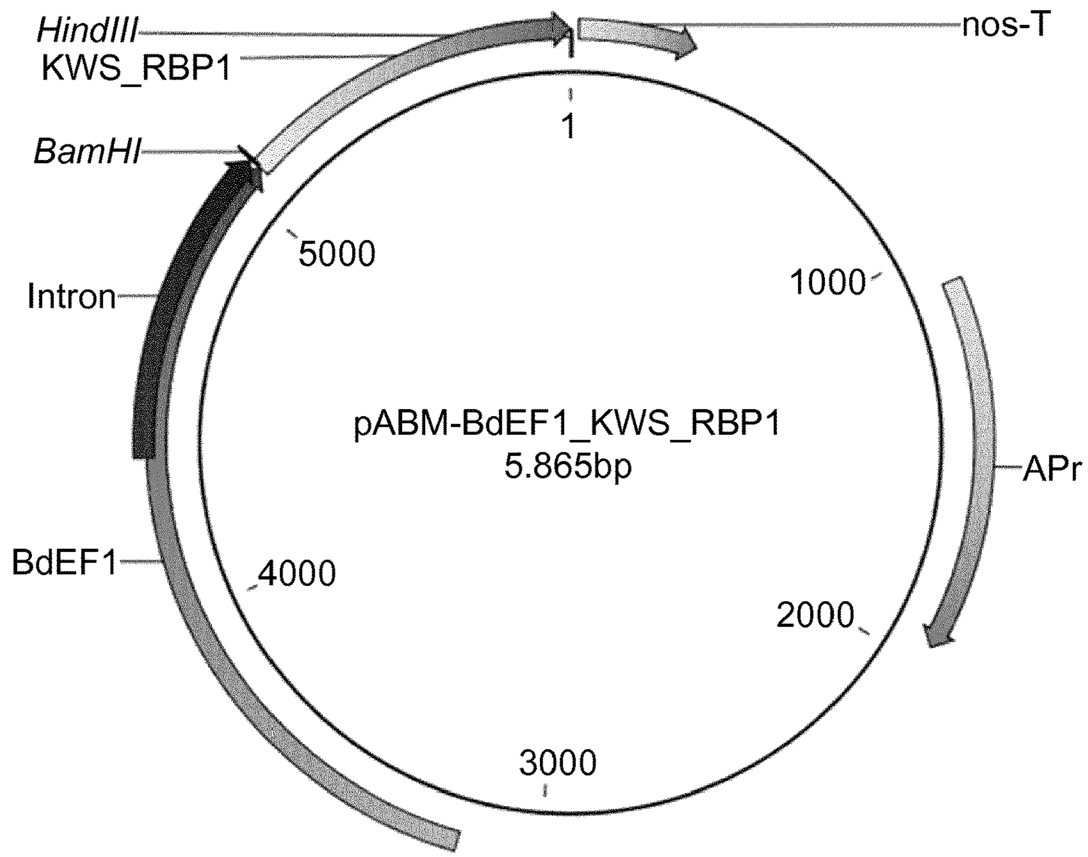
FIG. 4 shows a map of the KWS-RBP1 expression construct pABM-BdEF1-KWS-RBP1 (SEQ ID NO: 27). KWS-RBP1 gene is driven by the strong constitutive EF1 promoter from *Brachypodium* (pBdEF1).
Figure 5:
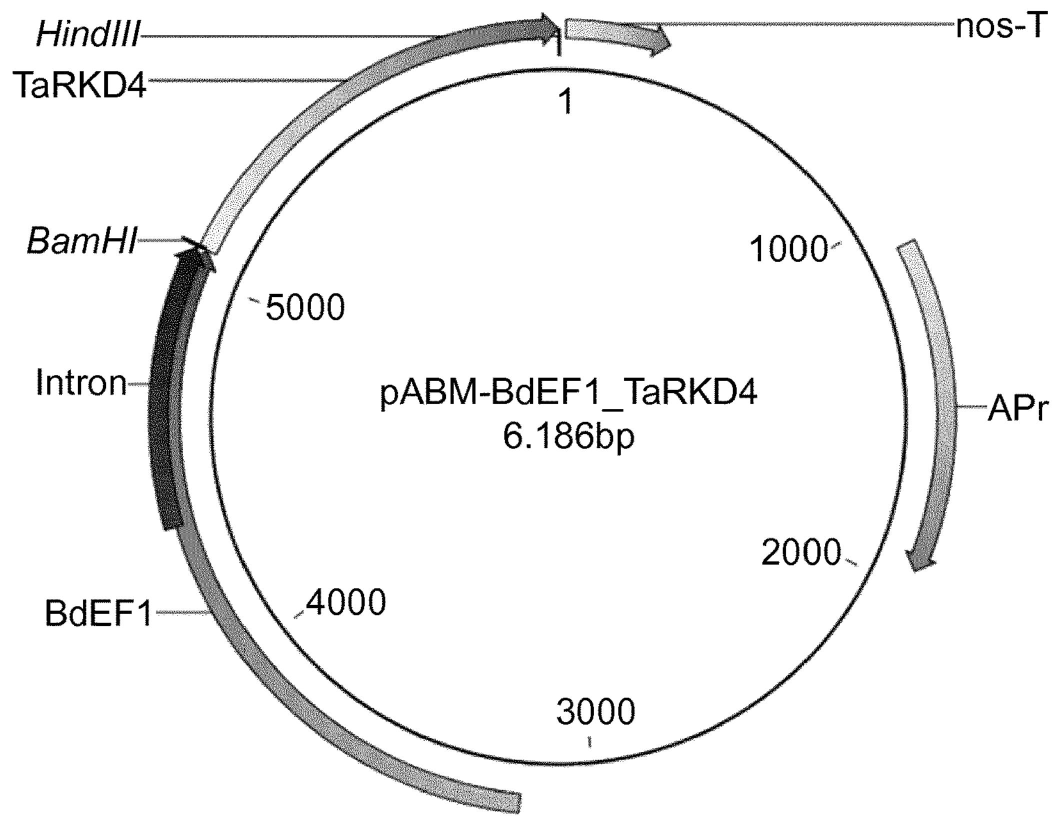
FIG. 5 shows a map of the wheat RKD4 expression construct pABM-BdEF1-TaRKD4 (SEQ ID NO: 28). The wheat RKD4 (TaRKD4 gene is driven by the strong constitutive EF1 promoter from *Brachypodium* (pBdEF1).

Unless defined otherwise, technical and scientific terms used herein have the same meaning as commonly understood by one of ordinary skill in the art to which this invention belongs.

As used in the context of the present application, the term "about" means +/−10% of the recited value, preferably +/−5% of the recited value. For example, about 100 nucleotides (nt) shall be understood as a value between 90 and 110 nt, preferably between 95 and 105 nt.

As used herein, the terms "booster", "booster gene", "booster polypeptide", "boost polypeptide", "boost gene" and "boost factor" refer to a protein/peptide(s) or a (poly) nucleic acid fragment encoding the protein/polypeptide causing improved genome engineering and/or improved plant regeneration of transformed or gene edited plant cells. Such protein/polypeptide may increase the capability or ability of a plant cell, preferably derived from somatic tissue, embryonic tissue, callus tissue or protoplast, to regenerate in an entire plant, preferably a fertile plant. Thereby, they may regulate somatic embryo formation (somatic embryogenesis) and/or they may increase the proliferation rate of plant cells. Exemplary booster polypeptides include, but are not limited to, KWS-RBP1 (e.g., SEQ ID NO: 2) and variants. A variant thereof is for example KWS-RBP2 (SEQ ID NO: 48) which has a sequence identity at amino acid sequence level of 93%. The regeneration of transformed or gene edited plant cells may include the process of somatic embryogenesis, which is an artificial process in which a plant or embryo is derived from a single somatic cell or group of somatic cells. Somatic embryos are formed from plant cells that are not normally involved in the development of embryos, i.e. plant tissue like buds, leaves, shoots etc. Applications of this process may include: clonal propagation of genetically uniform plant material; elimination of viruses; provision of source tissue for genetic transformation; generation of whole plants from single cells, such as protoplasts; development of synthetic seed technology. Cells derived from competent source tissue may be cultured to form a callus. Plant growth regulators like auxins or cytokinins in the tissue culture medium can be manipulated to induce callus formation and subsequently changed to induce embryos to form from the callus. Somatic embryogenesis has been described to occur in two ways: directly or indirectly. Direct embryogenesis occurs when embryos are started directly from explant tissue creating an identical clone. Indirect embryogenesis occurs when explants produced undifferentiated, or partially differentiated, cells (i.e. callus) which then is maintained or differentiated into plant tissues such as leaf, stem, or roots.

The term "transgenic" as used according to the present disclosure refers to a plant, plant cell, tissue, organ or material which comprises a gene or a genetic construct, comprising a "transgene" that has been transferred into the plant, the plant cell, tissue organ or material by natural means or by means of transformation techniques from another organism. The term "transgene" comprises a nucleic acid sequence, including DNA or RNA, or an amino acid sequence, or a combination or mixture thereof. Therefore, the term "transgene" is not restricted to a sequence commonly identified as "gene", i.e. a sequence encoding protein. It can also refer, for example, to a non-protein encoding DNA or RNA sequence. Therefore, the term "transgenic" generally implies that the respective nucleic acid or amino acid sequence is not naturally present in the respective target cell, including a plant, plant cell, tissue, organ or material. The terms "transgene" or "transgenic" as used herein thus refer to a nucleic acid sequence or an amino acid sequence that is taken from the genome of one organism, or produced synthetically, and which is then introduced into another organism, in a transient or a stable way, by artificial techniques of molecular biology, genetics and the like. A "plant material" as used herein refers to any material which can be obtained from a plant during any developmental stage. The plant material can be obtained either in planta or from an in vitro culture of the plant or a plant tissue or organ thereof. The term thus comprises plant cells, tissues and organs as well as developed plant structures as well as sub-cellular components like nucleic acids, polypeptides and all chemical plant substances or metabolites which can be found within a plant cell or compartment and/or which can be produced by the plant, or which can be obtained from an extract of any plant cell, tissue or a plant in any developmental stage. The term also comprises a derivative of the plant material, e.g., a protoplast, derived from at least one plant cell comprised by the plant material. The term therefore also comprises meristematic cells or a meristematic tissue of a plant.

The term of "genome engineering" is used herein, refer to strategies and techniques for the genetic modification of any genetic information or genome of a plant cell, comprising genome transformation, genome editing. As such "genome editing" refers to techniques for the targeted, specific modification of any genetic information or genome of a plant cell. As such, the terms comprise gene editing gene encoding region, but also the editing of regions other than gene encoding regions of a genome. It further comprises the editing or engineering of the nuclear (if present) as well as other genetic information of a plant cell. Furthermore, "genome engineering" also comprises an epigenetic editing or engineering, i.e., the targeted modification of, e.g., methylation, histone modification or of non-coding RNAs possibly causing heritable changes in gene expression.

The term "genome editing" as used herein refers to strategies and techniques for the targeted, specific modification of any genetic information or genome of a plant cell. As such, the terms comprise gene editing, but also the editing of regions other than gene encoding regions of a genome, such as intronic sequences, non-coding RNAs, miRNAs, sequences of regulatory elements like promoter, terminator, transcription activator binding sites, cis or trans acting elements. Additionally, "genome editing" may comprise base editing for targeted replacement of single nucleobases. It can further comprise the editing of the nuclear genome as well as other genetic information of a plant cell, i.e. mitochondrial genome or chloroplast genome as well as miRNA, pre-mRNA or mRNA. Furthermore, "genome editing" may comprise an epigenetic editing or engineering, i.e., the targeted modification of, e.g., DNA methylation or histone modification, such as histone acetylation, histone methylation, histone ubiquitination, histone phosphorylation, histone sumoylation, histone ribosylation or histone citrullination, possibly causing heritable changes in gene expression. "Genome editing" may also comprise an epigenetic editing or engineering of non-coding RNAs possibly causing heritable changes in gene expression.

A "base editor" as used herein refers to a protein or a fragment thereof having the same catalytic activity as the protein it is derived from, which protein or fragment thereof, alone or when provided as molecular complex, referred to as base editing complex herein, has the capacity to mediate a targeted base modification, i.e., the conversion of a base of interest resulting in a point mutation of interest which in turn can result in a targeted mutation, if the base conversion does not cause a silent mutation, but rather a conversion of an amino acid encoded by the codon comprising the position to be converted with the base editor.

As used herein, a "regulatory element" refers to nucleotide sequences which are not part of the protein-encoding nucleotide sequence, but mediate the expression of the protein-encoding nucleotide sequence. Regulatory elements include, for example, promoters, cis-regulatory elements, enhancers, introns or terminators. Depending on the type of regulatory element it is located on the nucleic acid molecule before (i.e., 5' of) or after (i.e., 3' of) the protein-encoding nucleotide sequence. Regulatory elements are functional in a living plant cell. The term "operatively linked" means that a regulatory element is linked in such a way with the protein-encoding nucleotide sequence, i.e., is positioned in such a way relative to the protein-encoding nucleotide sequence on, for example, a nucleic acid molecule that an expression of the protein-encoding nucleotide sequence under the control of the regulatory element can take place in a living cell.

As used herein, "upstream" indicates a location on a nucleic acid molecule which is nearer to the 5' end of said nucleic acid molecule. Likewise, the term "downstream" refers to a location on a nucleic acid molecule which is nearer to the 3' end of said nucleic acid molecule. For avoidance of doubt, nucleic acid molecules and their sequences are typically represented in their 5' to 3' direction (left to right).

As used herein, a "flanking region", is a region of the repair nucleic acid molecule having a nucleotide sequence which is homologous to the nucleotide sequence of the DNA region flanking (i.e. upstream or downstream) of the preselected site.

As used herein, "transient expression" refers to the phenomenon where the transferred protein/polypeptide and nucleic acid fragment encoding the protein/polypeptide is expressed and/or active transiently in the cells, and turned off and/or degraded shortly with the cell growth.

As used herein, a "double-stranded DNA break inducing enzyme", "enzyme inducing a double-stranded break", or "DSBI enzyme" is an enzyme capable of inducing a double-stranded DNA break at a particular nucleotide sequence, called the "recognition site" or "predetermined site". Accordingly, a "single-stranded DNA or RNA break inducing enzyme", "enzyme inducing a single-stranded break", or "SSBI enzyme" is an enzyme capable of inducing a single-stranded DNA or RNA break at a particular nucleotide sequence, called the "recognition site" or "predetermined site".

As used herein, a "repair nucleic acid molecule" is a single-stranded or double-stranded DNA molecule or RNA molecule that is used as a template for modification of the genomic DNA or the RNA at the preselected site in the vicinity of or at the cleavage site. As used herein, "use as a template for modification of the genomic DNA", means that the repair nucleic acid molecule is copied or integrated at the preselected site by homologous recombination between the flanking region(s) and the corresponding homology region(s) in the target genome flanking the preselected site, optionally in combination with non-homologous end-joining (NHEJ) at one of the two end of the repair nucleic acid molecule (e.g. in case there is only one flanking region).

As used herein, "a modification of the genome", means that the genome has changed in at least one nucleotide or by at least one epigenetic editing.

As used herein "a preselected site", "a predetermined site" or "predefined site" indicates a particular nucleotide sequence in the genome (e.g. the nuclear genome or the chloroplast genome) at which location it is desired to insert, replace and/or delete one or more nucleotides.

As used herein, "phytohormone" or "plant growth regulator" refers to any material and chemical, either naturally occurred or synthesized, which promotes plant cell division and/or plant morphogenesis. As used herein, "regeneration" refers to a process, in which single or multiple cells proliferate and develop into tissues, organs, and eventually entire plants.

As used herein, the terms "vector", or "plasmid (vector)" refers to a construct comprising, inter alia, plasmids or (plasmid) vectors, cosmids, artificial yeast- or bacterial artificial chromosomes (YACs and BACs), phagemids, bacterial phage based vectors, an expression cassette, isolated single-stranded or double-stranded nucleic acid sequences, comprising sequences in linear or circular form, or amino acid sequences, viral vectors, including modified viruses, and a combination or a mixture thereof, for introduction or transformation, transfection or transduction into any eukaryotic cell, including a plant, plant cell, tissue, organ or material according to the present disclosure.

"Recombinant" in the context of the recombinant gene can comprise regulatory sequences and/or localization sequences. The recombinant construct or the DNA construct according to the present invention can be integrated into or can be a vector, including a plasmid vector, and/or it can be present isolated from a vector structure, for example, in the form of a single-stranded or double-stranded nucleic acid. After its introduction, e.g. by transformation or transfection by biological or physical means, the recombinant gene or the DNA construct can either persist extrachromosomally, i.e. non integrated into the genome of the target cell, for example in the form of a double-stranded or single-stranded DNA. Alternatively, the recombinant gene or the DNA construct, can be stably integrated into the genome of a target cell, including the nuclear genome or further genetic elements of a target cell, including the genome of plastids like mitochondria or chloroplasts.

Booster Polypeptide and Nucleic Acid Encoding Booster Polypeptide

In one aspect is provided a booster polypeptide comprising an amino acid sequence of SEQ ID NO: 2 or 48 (e.g., KWS-RBP1 or KWS-RBP2), or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2 or 48.

The inventor shows that the booster polypeptides KWS-RBP1 and KWS-RBP2 mediate a strong booster effect alone but also in combination with other booster polypeptides, in particular in the early phase of regeneration after delivery of transgene and/or the genome engineering component. This boost effect does not compromise plant development and regenerated plants show favorable plant growth in the adult stage and are fertile. As such, integration of booster genes or booster polypeptides can be segregated out in the following generation by crossing and selection.

In the various methods disclosed herein, any single booster polypeptide or combination of booster polypeptides can be transiently provided or co-expressed. A booster polypeptide itself may be introduced into the plant cell, or alternatively a polynucleotide encoding for the booster polypeptide may be introduced into the plant cell. With respect to combinations, one of the booster polypeptides can be introduced into the plant cell, along with a nucleotide encoding for another booster polypeptide, or the same booster polypeptide. For example, a booster polypeptide comprising the sequence of SEQ ID NO: 2 can be introduced into a plant cell along with a nucleic acid comprising the nucleotide sequence of SEQ ID NO: 1 (which encodes for the sequence of SEQ ID NO: 2).

```
Sequence of KWS-RBP1 booster polypeptide
                                            (SEQ ID NO: 2)
MESGSGTAAGSGYVYRQPGSTRWNPTAEQLSLLREIYYRNGLRTPTADEI

RQISSKLSRYGKIEGKNVYNWFQNRRAREKRKQRLSTIGCDPALIEMGNV
```

-continued

```
ASLEFGTESALESLSSGPSSELREAPTRKFYEKKTVGENSTIINPVEQNC

TLSCGTSQEFQYAVDSRRVMKAMEEKQATDDEPDGNKWTESNRHVKILQL

FPLHNNEDQTLIKSDKEIYCLGSCEKKMDLSPLGHSGSQRASALDLCLSL

GNESCGLHDN
```

```
Sequence of a nucleic acid encoding the KWS-RBP1
booster polypeptide
                                            (SEQ ID NO: 1)
ATGGAGTCGGGCTCCGGGACGGCTGCTGGCTCTGGCTATGTTTACAGACA

GCCAGGATCAACGCGGTGGAACCCGACAGCTGAACAACTGTCCTTGCTTA

GAGAAATCTACTACCGCAACGGATTGCGGACCCCGACCGCGGACGAAATC

AGACAAATCAGCTCAAAGCTCTCAAGGTACGGAAAAATAGAGGGCAAAAA

CGTTTACAACTGGTTCCAGAATAGACGCGCAAGAGAAAAGCGCAAGCAAC

GGCTCTCTACAATCGGCTGTGATCCAGCACTGATCGAGATGGGGAATGTC

GCTTCACTGGAATTCGGTACTGAGAGCGCCCTGGAATCGCTGTCGTCAGG

ACCATCCTCAGAACTCCGCGAAGCGCCAACGAGAAAATTTTACGAAAAAA

AGACGGTTGGAGAGAACTCAACTATAATAAACCCAGTGGAACAAAACTGT

ACCCTTTCCTGCGGAACGTCCCAAGAGTTCCAGTATGCGGTCGATTCTCG

GCGCGTCATGAAAGCTATGGAGGAAAAGCAGGCGACGGACGATGAACCCG

ACGGAAATAAATGGACTGAGTCAAACAGACACGTCAAGATTCTCCAGCTT

TTCCCGCTCCACAATAACGAGGATCAGACATTGATAAAGAGCGACAAAGA

AATCTATTGTTTGGGCTCGTGCGAGAAGAAAATGGATTTGTCACCGCTGG

GTCATTCAGGCTCTCAGCGCGCTTCGGCCCTTGACTTGTGCCTTTCATTG

GGCAACGAATCTTGTGGGCTGCATGATAATTGA
```

In another example, a booster polypeptide comprising the sequence of SEQ ID NO: 48 can be introduced into a plant cell along with a nucleic acid comprising the nucleotide sequence of SEQ ID NO: 47 (which encodes for the sequence of SEQ ID NO: 48).

```
Sequence of KWS-RBP2 booster polypeptide
                                            (SEQ ID NO: 48)
MESGSGTAAGSGYVYRQSGSTRWNPTAEQLSLLKELYYRNGIRTPSADQI

RQISARLSRYGKIEGKNVFYWFQNHKARERQKKRLSTVGCDPALIEMGNV

ASLEFGTESALESLSSGPSSELREAPTRKFYEKKTVGENSTIINPVEQNC

TLSCGTSQEFQYAVDSRRVMKAMEEKQATDDEPDGNKWTESNRHVKTLPL

FPLHNNEDQTLIKSDKEIYCLGSCEKKMDLSPLGHSGSQRASALDLCLSL

GNESCGLHDN
```

```
Sequence of a nucleic acid encoding the KWS-RBP2
booster bolybebtide
                                            (SEQ ID NO: 47)
ATGGAATCGGGCTCCGGCACGGCGGCAGGGTCTGGTTATGTCTATCGGCA

GAGCGGAAGCACCCGGTGGAATCCAACAGCAGAACAGTTGTCGCTGCTCA

AGGAACTTTATTACCGGAATGGAATTCGGACACCGTCGGCAGATCAAATT

AGGCAAATTTCGGCCCGGCTGTCCAGATACGGCAAAATAGAAGGGAAAAA

CGTCTTTTACTGGTTTCAAAATCATAAAGCACGGGAACGGCAGAAGAAAA

GACTTTCCACGGTCGGCTGCGACCCTGCTCTCATAGAAATGGGTAACGTC
```

-continued

```
GCGAGCTTGGAATTTGGGACCGAAAGCGCTCTTGAATCTCTCAGCTCAGG

CCCGTCCAGCGAGTTGCGCGAGGCTCCTACCCGCAAGTTTTATGAGAAGA

AAACCGTTGGTGAGAACAGCACCATAATCAATCCTGTTGAGCAGAACTGC

ACACTTTCTTGCGGTACTTCGCAGGAATTTCAGTATGCTGTTGATAGCCG

CCGGGTGATGAAGGCAATGGAAGAGAAGCAAGCAACGGATGATGAACCGG

ACGGAAACAAATGGACGGAGTCGAACAGGCATGTGAAGACCCTCCCTCTT

TTCCCCTTGCATAATAATGAAGATCAGACCTTGATCAAGTCGGACAAGGA

AATTTATTGCCTTGGGAGCTGTGAAAAAAAAATGGATCTGTCCCCATTGG

GACACTCGGGCTCTCAGAGGGCGTCGGCACTGGATTTGTGCCTGTCTTTG

GGTAATGAATCTTGTGGCCTCCACGACAATTGA
```

Also provided is a nucleic acid encoding a booster polypeptide comprising an amino acid sequence of SEQ ID NO: 2 or 48. Further provided is a nucleic acid encoding a booster polypeptide comprising an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2 or 48.

The nucleic acid encoding a booster polypeptide comprising an amino acid sequence of SEQ ID NO: 2 or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2, can comprise a nucleic acid comprising the nucleotide sequence of SEQ ID NO: 1. The nucleic acid can comprise a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1. Alternatively, the nucleic acid can hybridize, under stringent hybridization conditions, with the complementary strand of a nucleic acid comprising the nucleotide sequence of SEQ ID NO: 1 or a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1.

The nucleic acid encoding a booster polypeptide comprising an amino acid sequence of SEQ ID NO: 48 or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 48, can also comprise a nucleic acid comprising the nucleotide sequence of SEQ ID NO: 47. The nucleic acid can comprise a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 47. Alternatively, the nucleic acid can hybridize, under stringent hybridization conditions, with the complementary strand of a nucleic acid comprising the nucleotide sequence of SEQ ID NO: 47 or a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 47.

A recombinant gene comprising a nucleic acid encoding a booster polypeptide comprising an amino acid sequence of SEQ ID NO: 2 or 48, or an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2 or 48 is provided. The nucleic acid can be operatively linked to one or more regulatory elements. The regulatory element can be a promoter, a cis-regulatory element, an enhancer, an intron or a terminator. The regulatory element can be 5' to the nucleic acid sequence. The regulatory element can be 3' to the nucleic acid sequence. The nucleic acid can comprise a nucleic acid comprising the nucleotide sequence of SEQ ID NO: 1 or 47. The nucleic acid can comprise a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1 or 47. The nucleic acid can hybridize, under stringent hybridization conditions, with the complementary strand of a nucleic acid comprising the nucleotide sequence of SEQ ID NO: 1 or 47 or a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1 or 47.

In some embodiments, the nucleic acid is operably linked to a heterologous promoter. The heterologous promoter can be a strong constitutive promoter (such as a doubled 35S promoter (d35S)), a tissue-specific promoter, a development-specific promoter, or an inducible promoter. The heterologous promoter can be the promoter from the EF1 gene (such as the *Brachypodium* EF1 gene (pBdEF1, SEQ ID NO: 23), the promoter from a Ubiquitin 1 gene (such as the maize Ubiquitin 1 gene), a WUSCHEL2 promoter (such as the maize WUSHCEL2 promoter (pZmWUS2)). The heterologous promoter can be a ubiquitin promoter described in U.S. Pat. No. 6,528,701, which is incorporated by reference herein. Various tissue-specific promoters that can be used are described in U.S. Pat. Nos. 7,763,774 and 7,767,801, each of which is incorporated by reference herein.

Also provided is a DNA construct, preferably a vector, comprising any of the above nucleic acids or recombinant genes. The nucleic acid can comprise a nucleic acid comprising the nucleotide sequence of SEQ ID NO: 1 or 47. The nucleic acid can comprise a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1 or 47. Alternatively, the nucleic acid can hybridize, under stringent hybridization conditions, with the complementary strand of a nucleic acid comprising the nucleotide sequence of SEQ ID NO: 1 or 47 or a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1 or 47. In some embodiments, the DNA construct is a plasmid.

Plant Cells

In another aspect is provided a plant cell comprising one or more of the booster polypeptide, nucleic acids, recombinant genes and DNA constructs described herein, preferably as transgene(s). In some embodiments, the booster polypeptide comprises the amino acid sequence of SEQ ID NO: 2 or 48. In some embodiments, the booster polypeptide comprises the amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 2 or 48. The nucleic acid can comprise a nucleic acid comprising the nucleotide sequence of SEQ ID NO: 1 or 47. The nucleic acid can comprise a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1 or 47. The nucleic acid can hybridize, under stringent hybridization conditions, with the complementary strand of a nucleic acid comprising the nucleotide sequence of SEQ ID NO: 1 or 47 or a nucleic acid comprising a nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 1 or 47. Also provided is a plant, a part of the plant, a seed, an embryo or callus comprising the plant cell.

Plant cells can be part of or derived from any type of plant material, preferably shoot, hypocotyl, cotyledon, stem, leave, petiole, root, embryo, callus, flower, gametophyte or part thereof or can be a protoplast or derived from a protoplast. It is possible to use isolated plant cells as well as plant material, i.e. whole plants or parts of plants containing the plant cells.

A part of a plant, or parts of plants, may be attached to or separated from a whole intact plant. Such parts of a plant include, but are not limited to, organs, tissues, and cells of a plant, and preferably seeds.

The plant cell, plant part or plant can be from any plant species, whether monocot or dicot. Preferably, plants which may be subject to the methods and uses of the present invention are plants of the genus selected from the group consisting of *Hordeum, Sorghum, Saccharum, Zea, Setaria, Oryza, Triticum, Secale, Triticale, Malus, Brachypodium, Aegilops, Daucus, Beta, Eucalyptus, Nicotiana, Solanum, Coffea, Vitis, Erythrante, Genlisea, Cucumis, Marus, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium*, or *Helianthus*. More preferably, the plant is selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia fournieri, Allium cepa, Allium fistulosum, Allium sativum, Helianthus annuus, Helianthus tuberosus* and/or *Allium tuberosum*. Particularly preferred are *Beta vulgaris, Zea mays, Triticum aestivum, Hordeum vulgare, Secale cereale, Helianthus annuus, Solanum tuberosum, Sorghum bicolor, Brassica rapa, Brassica napus, Brassica juncacea, Brassica oleracea, Raphanus sativus, Oryza sativa, Glycine max*, and/or *Gossypium* sp.

Genetically modified plant cells can be part of a whole plant or part thereof. Thus, the present invention also relates to a plant or plant part comprising the above genetically modified plant cell.

The plant cells into which the genome engineering components have been (co-)introduced are cultured under conditions allowing the genetic modification of the genome of said plant cell by integration of the transgene of interest and activity of the genome engineering components in the presence of the at least one boost factors.

Genetic Modification of a Plant Cell

Also provided is a method for genetic modification in a plant cell. The method comprises introducing into the plant cell (i) any of the booster polypeptides, nucleic acids, recombinant genes or DNA constructs described herein; and (ii) a transgene and/or a genome engineering component. The plant cell may be cultivated under conditions allowing the synthesis of the booster polypeptide from the nucleic acid, the recombinant gene or the DNA construct. The plant cell may be cultivated under conditions allowing the genetic modification of the genome of said plant cell by activity of the genome engineering component in the presence of the booster polypeptide.

The genome engineering component can be introduced as a protein and/or as a nucleic acid encoding the genome engineering component, in particular as DNA such as plasmid DNA, RNA, mRNA or RNP. Genome engineering can be used for the manufacture of transgenic, gene-edited or base-edited plant material.

For plant cells to be modified, transformation methods based on biological approaches may be used, such as *Agrobacterium* transformation or viral vector-mediated plant transformation. A common biological means is transformation with *Agrobacterium* spp. which has been used for decades for a variety of different plant materials. Viral vector mediated plant transformation also can be used to introduce genetic material into a cell of interest. *Agrobacterium*-mediated transformation refers to the method of using *Agrobacterium tumefaciens*, a soil bacterium that works as a natural genetic engineer vector, to deliver foreign DNA into plant cells. *Agrobacterium tumefaciens* can invade plants and transfer foreign DNA in remarkably broad range of plants.

Alternatively, transformation methods based on physical delivery methods may be used, like particle bombardment or microinjection. Particle bombardment includes biolistic transfection or microparticle-mediated gene transfer, which refers to a physical delivery method for transferring a coated microparticle or nanoparticle comprising a nucleic acid or a genetic construct of interest into a target cell or tissue. Physical introduction means are suitable to introduce nucleic acids, i.e., RNA and/or DNA, and proteins. Particle bombardment and microinjection have evolved as prominent techniques for introducing genetic material into a plant cell or tissue of interest. Helenius et al., "Gene delivery into intact plants using the Helios™ Gene Gun", Plant Molecular Biology Reporter, 2000, 18 (3):287-288 discloses a particle bombardment as physical method for introducing material into a plant cell. Thus, there exists a variety of plant transformation methods to introduce genetic material in the form of a genetic construct into a plant cell of interest, comprising biological and physical means known to the skilled person on the field of plant biotechnology and which can be applied to introduce at least one gene encoding at least one wall-associated kinase into at least one cell of at least one of a plant cell, tissue, organ, or whole plant.

The term "particle bombardment" as used herein, also named "biolistic transfection" or "microparticle-mediated gene transfer" refers to a physical delivery method for transferring a coated microparticle or nanoparticle comprising boost genes, booster polypeptides, genome engineering components, and/or transgenes into a target cell or tissue. The micro- or nanoparticle functions as projectile and is fired on the target structure of interest under high pressure using a suitable device, often called gene-gun. The transformation via particle bombardment uses a microprojectile of metal covered with the construct of interest, which is then shot onto the target cells using an equipment known as "gene gun" (Sandford et al. 1987) at high velocity fast enough (~1500 km/h) to penetrate the cell wall of a target tissue, but not harsh enough to cause cell death. For protoplasts, which have their cell wall entirely removed, the conditions are different logically. The precipitated construct on the at least one microprojectile is released into the cell after bombardment. The acceleration of microprojectiles is accomplished by a high voltage electrical discharge or compressed gas (helium). Concerning the metal particles used it is mandatory that they are non-toxic, non-reactive, and that they have a lower diameter than the target cell. The most commonly used are gold or tungsten. There is plenty of information publicly available from the manufacturers and providers of gene-guns and associated system concerning their general use.

In a particularly preferred embodiment of microparticle bombardment, one or more boost genes, booster polypeptides, genome engineering components, and/or transgenes are co-delivered via microcarriers comprising gold particles having a size in a range of 0.4-1.6 micron (μm), preferably 0.4-1.0 μm. In an exemplary process, 10-1000 μg of gold particles, preferably 50-300 μg, are used per one bombardment.

The boost genes, booster polypeptides, genome engineering components, and/or transgenes can be delivered into target cells for example using a Bio-Rad PDS-1000/He particle gun or handheld Helios gene gun system. When a PDS-1000/He particle gun system used, the bombardment rupture pressures are from 450 psi to 2200 psi, preferred from 450-1100 psi, while the rupture pressures are from 100-600 psi for a Helios gene gun system. More than one chemical or construct can be co-delivered with genome engineering components into target cells simultaneously.

The above-described delivery methods for transformation and transfection can be applied to introduce the tools of the present invention simultaneously. Likewise, specific transformation or transfection methods exist for specifically introducing a nucleic acid or an amino acid construct of interest into a plant cell, including electroporation, microinjection, nanoparticles, and cell-penetrating peptides (CPPs). Furthermore, chemical-based transfection methods exist to introduce genetic constructs and/or nucleic acids and/or proteins, comprising inter alia transfection with calcium phosphate, transfection using liposomes, e.g., cationic liposomes, or transfection with cationic polymers, including DEAD-dextran or polyethylenimine, or combinations thereof. The above delivery techniques, alone or in combination, can be used for in vivo (including in planta) or in vitro approaches.

In some embodiments, the genome engineering component comprises:

a) an enzyme inducing a double-stranded break (DSB) or a nucleic acid encoding same, and optionally a repair nucleic acid molecule, wherein the DSB-inducing enzyme optionally recognizes a predetermined site in the genome of said cell;

b) an enzyme inducing a single-stranded break (SSB) or a nucleic acid encoding same, and optionally a repair nucleic acid molecule, wherein the SSB-inducing enzyme optionally recognizes a predetermined site in the genome of said cell;

c) a base editor enzyme, optionally fused to a disarmed DSB- or SSB-inducing enzyme, wherein the base editor enzyme preferably recognizes a predetermined site in the genome of said cell; or d) an enzyme effecting DNA methylation, histone acetylation, histone methylation, histone ubiquitination, histone phosphorylation, histone ribosylation or histone citrullination, optionally fused to a disarmed DSB- or SSB-inducing enzyme, wherein the enzyme preferably recognizes a predetermined site in the genome of said cell.

In order to enable a break at a predetermined target site, the enzymes preferably include a binding/recognition domain and a cleavage domain. Particular enzymes capable of inducing double or single-stranded breaks are nucleases or nickases as well as variants thereof, including such molecules no longer comprising a nuclease or nickase function but rather operating as recognition molecules in combination with another enzyme. In recent years, many suitable nucleases, especially tailored endonucleases have been developed comprising meganucleases, zinc finger nucleases, TALE nucleases, Argonaute nucleases, derived, for example, from *Natronobacterium gregoryi*, and CRISPR nucleases, comprising, for example, Cas9, Cpf1, Csm1, CasX or CasY nucleases as part of the Clustered Regularly Interspaced Short Palindromic Repeats (CRISPR) system. Thus, in a preferred aspect of the invention, the genome engineering component comprises a DSB- or SSB-inducing enzyme or a variant thereof selected from a CRISPR/Cas endonuclease, preferably a CRISPR/Cas9 endonuclease a CRISPR/Cpf1 endonuclease, or a CRISPR/Csm1 endonuclease, a zinc finger nuclease (ZFN), a homing endonuclease, a meganuclease and a TAL effector nuclease.

Rare-cleaving endonucleases are DSBI/SSBI enzymes that have a recognition site of preferably about 14 to 70 consecutive nucleotides, and therefore have a very low frequency of cleaving, even in larger genomes such as most plant genomes. Homing endonucleases, also called meganucleases, constitute a family of such rare-cleaving endonucleases. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrast to the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level. A list of other rare cleaving meganucleases and their respective recognition sites is provided in Table I of WO 03/004659 (pages 17 to 20) (incorporated herein by reference).

Furthermore, methods are available to design custom-tailored rare-cleaving endonucleases that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO 03/080809, WO 94/18313 or WO 95/09233 and in Isalan et al. (2001). A rapid, generally applicable method to engineer zinc fingers illustrated by targeting the HIV-1 promoter. Nature biotechnology, 19(7): 656; Liu et al. (1997). Design of polydactyl zinc-finger proteins for unique addressing within complex genomes. Proceedings of the National Academy of Sciences, 94(11): 5525-5530.

Another example of custom-designed endonucleases includes the TALE nucleases (TALENs), which are based on transcription activator-like effectors (TALEs) from the bacterial genus *Xanthomonas* fused to the catalytic domain of a nuclease (e.g. FokI or a variant thereof). The DNA binding specificity of these TALEs is defined by repeat-variable di-residues (RVDs) of tandem-arranged 34/35-amino acid repeat units, such that one RVD specifically recognizes one nucleotide in the target DNA. The repeat units can be assembled to recognize basically any target sequences and fused to a catalytic domain of a nuclease create sequence specific endonucleases (see e.g. Boch et al. (2009). Breaking the code of DNA binding specificity of TAL-type III effectors. Science, 326(5959), 1509-1512; Moscou & Bogdanove (2009). A simple cipher governs DNA recognition by TAL effectors. *Science,* 326(5959), 1501-1501; and WO 2010/079430, WO 2011/072246, WO 2011/154393, WO 2011/146121, WO 2012/001527, WO 2012/093833, WO 2012/104729, WO 2012/138927, WO 2012/138939). WO 2012/138927 further describes monomeric (compact) TALENs and TALEs with various catalytic domains and combinations thereof.

Recently, a new type of customizable endonuclease system has been described; the so-called CRISPR/Cas system. A CRISPR system in its natural environment describes a molecular complex comprising at least one small and individual non-coding RNA in combination with a Cas nuclease or another CRISPR nuclease like a Cpf1 nuclease or a Csm1 nuclease (Zetsche et al., "Cpf1 Is a Single RNA-Guides Endonuclease of a Class 2 CRISPR-Cas System", Cell, 163, pp. 1-13, October 2015; US 2017/0233756 A1) which can produce a specific DNA double-stranded break. Presently, CRISPR systems are categorized into 2 classes comprising five types of CRISPR systems, the type II system, for instance, using Cas9 as effector and the type V system using Cpf1 as effector molecule (Makarova et al., Nature Rev. Microbiol., 2015). In artificial CRISPR systems, a synthetic non-coding RNA and a CRISPR nuclease and/or optionally a modified CRISPR nuclease, modified to act as nickase or lacking any nuclease function, can be used in combination with at least one synthetic or artificial guide RNA or gRNA combining the function of a crRNA and/or a tracrRNA (Makarova et al., 2015, supra). The immune response mediated by CRISPR/Cas in natural systems requires CRISPR-RNA (crRNA), wherein the maturation of this guiding RNA, which controls the specific activation of the CRISPR nuclease, varies significantly between the various CRISPR systems which have been characterized so far. Firstly, the invading DNA, also known as a spacer, is integrated between two adjacent repeat regions at the proximal end of the CRISPR locus. Type II CRISPR systems code for a Cas9 nuclease as the key enzyme for the interference step, which system contains both a crRNA and also a trans-activating RNA (tracrRNA) as the guide motif. These hybridize and form double-stranded (ds) RNA regions which are recognized by RNAseIII and can be cleaved in order to form mature crRNAs. These then in turn associate with the Cas molecule in order to direct the nuclease specifically to the target nucleic acid region. Recombinant gRNA molecules can comprise both the variable DNA recognition region and also the Cas interaction region and thus can be specifically designed, independently of the specific target nucleic acid and the desired Cas nuclease.

As a further safety mechanism, PAMs (protospacer adjacent motifs) must be present in the target nucleic acid region; these are DNA sequences which follow on directly from the Cas9/RNA complex-recognized DNA. The PAM sequence for the Cas9 from *Streptococcus pyogenes* has been described to be "NGG" or "NAG" (Standard IUPAC nucleotide code) (Jinek et al, "A programmable dual-RNA-guided DNA endonuclease in adaptive bacterial immunity", Science 2012, 337: 816-821). The PAM sequence for Cas9 from *Staphylococcus aureus* is "NNGRRT" or "NNGRR(N)". Further variant CRISPR/Cas9 systems are known. Thus, a *Neisseria meningitidis* Cas9 cleaves at the PAM sequence NNNNGATT. A *Streptococcus thermophilus* Cas9 cleaves at the PAM sequence NNAGAAW. Recently, a further PAM motif NNNNRYAC has been described for a CRISPR system of *Campylobacter* (WO 2016/021973 A1). For Cpf1 nucleases it has been described that the Cpf1-crRNA complex, without a tracrRNA, efficiently recognize and cleave target DNA proceeded by a short T-rich PAM in contrast to the commonly G-rich PAMs recognized by Cas9 systems (Zetsche et al., supra). Furthermore, by using modified CRISPR polypeptides, specific single-stranded breaks can be obtained. The combined use of Cas nickases with various recombinant gRNAs can also induce highly specific DNA double-stranded breaks by means of double DNA nicking. By using two gRNAs, moreover, the specificity of the DNA binding and thus the DNA cleavage can be optimized. Further CRISPR effectors like CasX and CasY effectors originally described for bacteria, are meanwhile available and represent further effectors, which can be used for genome engineering purposes (Burstein et al., "New CRISPR-Cas systems from uncultivated microbes", Nature, 2017, 542, 237-241).

The cleavage site of a DSBI/SSBI enzyme relates to the exact location on the DNA or RNA where the break is induced. The cleavage site may or may not be comprised in (overlap with) the recognition site of the DSBI/SSBI enzyme and hence it is said that the cleavage site of a DSBI/SSBI enzyme is located at or near its recognition site. The recognition site of a DSBI/SSBI enzyme, also sometimes referred to as binding site, is the nucleotide sequence that is (specifically) recognized by the DSBI/SSBI enzyme and determines its binding specificity. For example, a TALEN or ZNF monomer has a recognition site that is determined by their RVD repeats or ZF repeats respectively, whereas its cleavage site is determined by its nuclease domain (e.g. FokI) and is usually located outside the recognition site. In case of dimeric TALENs or ZFNs, the cleavage site is located between the two recognition/binding sites of the respective monomers, this intervening DNA or RNA region where cleavage occurs being referred to as the spacer region.

A person skilled in the art would be able to either choose a DSBI/SSBI enzyme recognizing a certain recognition site and inducing a DSB or SSB at a cleavage site at or in the vicinity of the preselected/predetermined site or engineer such a DSBI/SSBI enzyme. Alternatively, a DSBI/SSBI enzyme recognition site may be introduced into the target genome using any conventional transformation method or by crossing with an organism having a DSBI/SSBI enzyme recognition site in its genome, and any desired nucleic acid may afterwards be introduced at or in the vicinity of the cleavage site of that DSBI/SSBI enzyme.

In various embodiments, in modification of the genome comprises one or more of: i) a replacement of at least one nucleotide; ii) a deletion of at least one nucleotide; iii) an insertion of at least one nucleotide; iv) a change of the DNA methylation; and v) a change in histone acetylation, histone methylation, histone ubiquitination, histone phosphorylation, histone sumoylation, histone ribosylation or histone citrullination.

In some embodiments, the activity of the genome engineering component induces one or more double-stranded breaks in the genome of the plant cell, one or more single strand breaks in the genome of the plant cell, one or more base editing events in the genome of the plant cell, or one or more of DNA methylation, histone acetylation, histone methylation, histone ubiquitination, histone phosphorylation, histone sumoylation, histone ribosylation or histone citrullination in the genome of the plant cell.

In some embodiments, the induction of one or more double-stranded breaks or one or more single strand breaks is followed by non-homologous end joining (NHEJ) and/or by homology directed repair of the break(s) though a homologous recombination mechanism (HDR). NHEJ and HDR are two major and distinct pathways to repair breaks. Homologous recombination requires the presence of a homologous sequence as a template (e.g., repair nucleic acid molecule or "donor") to guide the cellular repair process and the results of the repair are error-free and predictable. In the absence of a template (or repair nucleic acid molecule or "donor") sequence for homologous recombination, the cell typically attempts to repair the break via the process of non-homologous end-joining (NHEJ).

In a particularly preferred aspect of this embodiment, a repair nucleic acid molecule is additionally introduced into the plant cell. The repair nucleic acid molecule is a single-stranded or double-stranded DNA molecule or RNA molecule that is used as a template for modification of the genomic DNA or the RNA at the preselected site in the vicinity of or at the cleavage site. In some embodiments, the repair nucleic acid molecule is used as a template for modification of the genomic DNA, in which the repair nucleic acid molecule is copied or integrated at the preselected site by homologous recombination between the flanking region(s) and the corresponding homology region(s) in the target genome flanking the preselected site, optionally in combination with non-homologous end-joining (NHEJ) at one of the two end of the repair nucleic acid molecule (e.g. in case there is only one flanking region). Integration by homologous recombination allows for precise joining of the repair nucleic acid molecule to the target genome up to the nucleotide level, while NHEJ may result in small insertions/deletions at the junction between the repair nucleic acid molecule and genomic DNA.

In various embodiments of the aspects described herein, a modification of the genome occurs in which the genome has changed by at least one nucleotide. Modification of the genome can occur by insertion of a transgene, preferably an expression cassette comprising a transgene of interest, replacement of at least one nucleotide and/or a deletion of at least one nucleotide and/or an insertion of at least one nucleotide, as long as it results in a total change of at least one nucleotide compared to the nucleotide sequence of the preselected genomic target site before modification, thereby allowing the identification of the modification, e.g., by techniques such as sequencing or PCR analysis and the like, of which the skilled person will be well aware.

Modification of the genome may occur at a preselected site, a predetermined site, or predefined site, i.e., at a particular nucleotide sequence in the genome (e.g. the nuclear genome or the chloroplast genome) at which location it is desired to insert, replace and/or delete one or more nucleotides. For example, the preselected site, predetermined site, or predefined site can be an endogenous locus or a particular nucleotide sequence in or linked to a previously introduced foreign DNA, RNA or transgene. The preselected site can be a particular nucleotide position at (after) which it is intended to make an insertion of one or more nucleotides. The preselected site can also comprise a sequence of one or more nucleotides which are to be exchanged (replaced) or deleted.

In various embodiments, the length and percentage sequence identity of the flanking regions is chosen such as to enable homologous recombination between said flanking regions and their corresponding DNA region upstream or downstream of the preselected site. The DNA region or regions flanking the preselected site having homology to the flanking DNA region or regions of the repair nucleic acid molecule are also referred to as the homology region or regions in the genomic DNA.

To have sufficient homology for recombination, the flanking DNA regions of the repair nucleic acid molecule may vary in length, and should be at least about 10 nt, about 15 nt, about 20 nt, about 25 nt, about 30 nt, about 40 nt or about 50 nt in length. However, the flanking region may be as long as is practically possible (e.g. up to about 100-150 kb such as complete bacterial artificial chromosomes (BACs). Preferably, the flanking region will be about 50 nt to about 2000 nt, e.g. about 100 nt, 200 nt, 500 nt or 1000 nt. Moreover, the regions flanking the DNA of interest need not be identical to the homology regions (the DNA regions flanking the preselected site) and may have between about 80% to about 100% sequence identity, preferably about 95% to about 100% sequence identity with the DNA regions flanking the preselected site. The longer the flanking region, the less stringent the requirement for homology. Furthermore, to achieve exchange of the target DNA sequence at the preselected site without changing the DNA sequence of the adjacent DNA sequences, the flanking DNA sequences should preferably be identical to the upstream and downstream DNA regions flanking the preselected site.

In order to target sequence modification at the preselected site, the flanking regions must be chosen so that 3' end of the upstream flanking region and/or the 5' end of the downstream flanking region align(s) with the ends of the predefined site. As such, the 3' end of the upstream flanking region determines the 5' end of the predefined site, while the 5' end of the downstream flanking region determines the 3' end of the predefined site.

The preselected site is located outside or away from said cleavage (and/or recognition) site, such that the site where it is intended to make the genomic modification (the preselected site) does not comprise the cleavage site and/or recognition site of the DSBI/SSBI enzyme, such that the preselected site does not overlap with the cleavage (and/or recognition) site. Outside/away from in this respect thus means upstream or downstream of the cleavage (and/or recognition) site.

In various embodiments, the at least one base editor according to the present invention is temporarily or permanently linked to at least one site-specific DSBI/SSBI enzyme complex or at least one modified site-specific DSBI/SSBI enzyme complex, or optionally to a component of said at least one site-specific DSBI/SSBI enzyme complex. The linkage can be covalent and/or non-covalent. Any base editor or site-specific DSBI/SSBI enzyme complex, or a catalytically active fragment thereof, or any component of a base editor complex or of a site-specific DSBI/SSBI enzyme complex as disclosed herein can be introduced into a cell as a nucleic acid fragment, the nucleic acid fragment representing or encoding a DNA, RNA or protein effector, or it can be introduced as DNA, RNA and/or protein, or any combination thereof.

The base editor is a protein or a fragment thereof having the capacity to mediate a targeted base modification, i.e., the conversion of a base of interest resulting in a point mutation of interest. Preferably, the at least one base editor in the context of the present invention is temporarily or permanently fused to at least one DSBI/SSBI enzyme, or optionally to a component of at least one DSBI/SSBI. The fusion can be covalent and/or non-covalent. Multiple publications have shown targeted base conversion, primarily cytidine (C) to thymine (T), using a CRISPR/Cas9 nickase or non-functional nuclease linked to a cytidine deaminase domain, Apolipoprotein B mRNA-editing catalytic polypeptide (APOBEC1), e.g., APOBEC derived from rat. The deamination of cytosine (C) is catalyzed by cytidine deaminases and results in uracil (U), which has the base-pairing properties of thymine (T). Most known cytidine deaminases operate on RNA, and the few examples that are known to accept DNA require single-stranded (ss) DNA. Studies on the dCas9-target DNA complex reveal that at least nine nucleotides (nt) of the displaced DNA strand are unpaired upon formation of the Cas9-guide RNA-DNA 'R-loop' complex (Jore et al., Nat. Struct. Mol. Biol., 18, 529-536 (2011)). Indeed, in the structure of the Cas9 R-loop complex, the first 11 nt of the protospacer on the displaced DNA strand are disordered, suggesting that their movement is not highly restricted. It has also been speculated that Cas9 nickase-induced mutations at cytosines in the non-template strand might arise from their accessibility by cellular cytosine deaminase enzymes. It was reasoned that a subset of this stretch of ssDNA in the R-loop might serve as an efficient substrate for a dCas9-tethered cytidine deaminase to effect direct, programmable conversion of C to U in DNA (Komor et al., supra). Recently, Goudelli et al., Programmable base editing of A•T to G•C in genomic DNA without DNA cleavage, *Nature,* 2017, 551(7681), 464, described adenine base editors (ABEs) that mediate the conversion of A•T to G•C in genomic DNA.

Enzymes effecting DNA methylation, as well as histone-modifying enzymes have been identified in the art. Histone posttranslational modifications play significant roles in regulating chromatin structure and gene expression. For example, enzymes for histone acetylation are described in Sterner D. E., Berger S. L. (June 2000): "Acetylation of histones and transcription-related factors", Microbiol. Mol. Biol. Rev. 64 (2): 435-59. Enzymes effecting histone methylation are described in Zhang Y., Reinberg D (2001): "Transcription regulation by histone methylation: interplay between different covalent modifications of the core histone tails", Genes Dev. 15 (18): 2343-60. Histone ubiquitination is described in Shilatifard A (2006): "Chromatin modifications by methylation and ubiquitination: implications in the regulation of gene expression", Annu. Rev. Biochem. 75: 243-69. Enzymes for histone phosphorylation are described in Nowak S. J., Corces V. G. (April 2004): "Phosphorylation of histone H3: a balancing act between chromosome condensation and transcriptional activation", Trends Genet. 20 (4): 214-20. Enzymes for histone sumoylation are described in Nathan D., Ingvarsdottir K., Sterner D. E., et al. (April 2006): "Histone sumoylation is a negative regulator in *Saccharomyces cerevisiae* and shows dynamic interplay with positive-acting histone modifications", Genes Dev. 20 (8): 966-76. Enzymes for histone ribosylation are described in Hassa P. O., Haenni S. S., Elser M., Hottiger M. O. (September 2006): "Nuclear ADP-ribosylation reactions in mammalian cells: where are we today and where are we going?", Microbiol. Mol. Biol. Rev. 70 (3): 789-829. Histone citrullination is catalyzed for example by an enzyme called peptidylarginine deiminase 4 (PAD4, also called PADI4), which converts both histone arginine (Arg) and mono-methyl arginine residues to citrulline.

Enzymes effecting DNA methylation and histone-modifying enzymes may be fused to a disarmed DSB or SSB inducing enzyme, which preferably recognizes a predetermined site in the genome of said cell.

Exemplary Transgenes

In various embodiments of the methods for genetic modification in a plant cell, the transgene may be a gene encoding resistance or tolerance to abiotic stress, including drought stress, osmotic stress, heat stress, cold stress, oxidative stress, heavy metal stress, nitrogen deficiency, phosphate deficiency, salt stress or waterlogging, herbicide resistance, including resistance to glyphosate, glufosinate/phosphinothricin, hygromycin, protoporphyrinogen oxidase (PPO) inhibitors, ALS inhibitors, and Dicamba, a gene encoding resistance or tolerance to biotic stress, including a viral resistance gene, a fungal resistance gene, a bacterial resistance gene, an insect resistance gene, or a gene encoding a yield related trait, including lodging resistance, flowering time, shattering resistance, seed color, endosperm composition, or nutritional content.

In various embodiments of the methods for genetic modification in a plant cell, the method is effective to promote cell proliferation or cell regeneration, or is effective to increase the efficiency for regeneration of transgenic, gene edited or base edited plants The method is effective preferably after genetic modification/modification of the genome. In various embodiments of the methods for genetic modification in a plant cell, the method is effective to induce direct or indirect (somatic) embryogenesis from a single cell, preferably an embryonic cell, a somatic cell or a protoplast, or from a callus cell, or from a callus cell. The method is effective preferably after genetic modification/modification of the genome. In various embodiments, the method is effective to increase the stable transformation efficiency of the transgene into the plant cell or is effective to increase the efficiency for generation of transgenic plants. In various embodiments, the method is effective to increase the efficiency of the genome engineering component to edit the genome of the plant cell or is effective to increase the efficiency for generation of transgenic, gene edited or base edited plants.

In some embodiments, the method is effective to improve the efficiency of regeneration of plants derived from recalcitrant genotypes, is effective to improve the efficiency of regeneration of plants from non-conventional tissue types, or is effective to accelerate the regeneration process, preferably after genetic modification/modification of the genome.

Transient Expression of Booster Polypeptide and Boost Genes

Also provided is a method for transient expression of a booster polypeptide and/or a boost gene in a plant cell. The method comprises introducing into the plant cell (i) a booster polypeptide, nucleic acid, recombinant gene or DNA construct described herein; and (ii) a transgene and/or a genome engineering component.

In some embodiments, one or more of the booster polypeptide and boost genes are transiently co-expressed. The co-expression may be effective to promote cell proliferation. Such co-expression may be effective to promote cell regeneration. The co-expression may be effective to induce embryogenesis from single cells, and thus provide ability to regenerate homogenous plants without selection. The co-expression may improve genome editing efficiency by co-delivery with genome-editing components. Co-expression may comprise transiently co-introducing a boost polypeptide (e.g., KWS-RBP-1) with one or more nucleic acids encoding a boost gene (e.g., PLT5, PLT7, RKD4, and RKD2).

Transient co-delivery of booster polypeptides and/or one or more boost genes may be carried out as described in U.S. Provisional Application No. 62/685,626, incorporated by reference herein in its entirety.

In various embodiments, other boost factors such as chemical HDACi and phytohormones can be delivered, as described in U.S. Provisional Application No. 62/685,626.

In some embodiments, the booster polypeptide is transiently present, transiently active and/or transiently expressed in the plant cell. In some embodiments, the nucleic acid encoding the booster polypeptide is transiently present, transiently active and/or transiently expressed in the plant cell. One or more polypeptides selected from the group consisting of a PLT5 polypeptide, a PLT7 polypeptide, and/or one or more nucleic acids selected from the group consisting of a nucleic acid encoding a PLT5 polypeptide, a PLT7 polypeptide, and an RKD2 polypeptide, and/or one or more site-directed transcriptional activators suitable to increase transiently the expression of an endogenous PLT5 polypeptide, an endogenous PLT7 polypeptide, or an endogenous RKD2 polypeptide, and/or a nucleic acid encoding such site-directed transcriptional activator can also be introduced into the plant cell.

Transient expression can be carried out by transient transformation/transfection of a boost protein/polypeptide or nucleic acid fragment encoding the protein/polypeptide, expressed preferably under a strong constitutive promoter. Transient expression of a nucleic acid encoding a PLT5 polypeptide, a nucleic acid encoding a PLT7 polypeptide, and/or one or more site-directed transcriptional activators suitable to increase transiently the expression of an endogenous PLT5 polypeptide, an endogenous PLT7 polypeptide, can also be realized by stable transformation of a boost gene under the control of a tissue and development specific promoter or an inducible promoter. The boost genes can be expressed and then be active transiently. The boost genes can then be turned off and degraded shortly when plant cell development is changed or the inducing condition(s) are removed. For example, the strong constitutive promoter from *Brachypodium* EF1 gene, pBdEF1 (SEQ ID NO: 23) may be used to drive a boost gene for transient transformation (see, e.g., Example 1).

Transient expression can arise from any of transient transfection, transient transformation, and stable transformation. "Transient transformation" and "transient transfection" comprise the transfer of a foreign material [i.e. a nucleic acid fragment, protein, ribonucleoprotein (RNP), etc.] into host cells resulting in gene expression and/or activity without integration and stable inheritance of the foreign material. The foreign components are not permanently incorporated into the cellular genome, but provide a temporal action resulting in a modification of the genome. A transient transformation event may be unable to be transmitted to next generation, and thus is non-inheritable. "Stable transformation" refers to the event where a transferred nucleic acid fragment is integrated into the genome of a host cell (includes both nuclear and organelle genomes) resulting to stable inheritance of the nucleic acid fragment.

For example, transient expression can be used for transient genome editing. Transient activity and/or transient presence of the genome engineering component in the plant cell can result in introduction of one or more double-stranded breaks in the genome of the plant cell, one or more single-stranded breaks in the genome of the plant cell, one or more base-editing events in the genome of the plant cell, or one or more of DNA methylation, histone acetylation, histone methylation, histone ubiquitination, histone phosphorylation, histone sumoylation, histone ribosylation or histone citrullination in the genome of the plant cell. The resulting modification in the genome of the plant cell can, for example, be selected from a replacement of at least one nucleotide, a deletion of at least one nucleotide, an insertion of at least one nucleotide, a change of DNA methylation, a change in histone acetylation, histone methylation, histone ubiquitination, histone phosphorylation, histone sumoylation, histone ribosylation, or histone citrullination or any combination thereof.

The site-directed transcriptional activator means a synthetic transcription factor described in U.S. Provisional Application No. 62/609,508, incorporated by reference herein. The synthetic transcription factor can comprise at least one recognition domain and at least one gene expression modulation domain, in particular an activation domain, wherein the synthetic transcription factor is configured to modulate the expression of an endogenous gene in the genome of plant or plant cell. Such an endogenous gene is preferably a (native) morphogenic gene which encodes polypeptides involved in plant developmental processes like root formation or shoot formation. In some embodiments, the endogenous morphogenic gene is selected from the group consisting of an endogenous nucleic acid encoding a PLT5 polypeptide, an endogenous nucleic acid encoding a PLT7 polypeptide, an endogenous nucleic acid encoding an RKD4 polypeptide, or an endogenous nucleic acid encoding an RKD2 polypeptide. In some embodiments, the at least one recognition domain is, or is a fragment of, a molecule selected from the group consisting of at least one TAL effector, at least one disarmed CRISPR/nuclease system, at least one Zinc-finger domain, and at least one disarmed homing endonuclease, or any combination thereof.

In some embodiments, the at least one disarmed CRISPR/nuclease system is a CRISPR/dCas9 system, a CRISPR/dCpf1 system, a CRISPR/dCsm1 system, a CRISPR/dCasX system or a CRISPR/dCasY system, or any combination thereof, and wherein the at least one disarmed CRISPR/nuclease system comprises at least one guide RNA.

In some embodiments, the at least one activation domain is selected from the group consisting of an acidic transcriptional activation domain, preferably, wherein the at least one activation domain is from a TAL effector gene of *Xanthomonas oryzae*, VP16 or tetrameric VP64 from Herpes simplex, VPR, SAM, Scaffold, Suntag, P300, VP160, or any combination thereof. In some embodiments, the activation domain is VP64.

In some embodiments, the synthetic transcription factor is configured to modulate expression, preferably transcription, of the morphogenic gene by binding to a regulation region located at a certain distance in relation to the start codon. In preferred embodiments, the synthetic transcription factor is configured to increase expression, preferably transcription, of the morphogenic gene by binding to a regulation region located at a certain distance in relation to the start codon.

In some embodiments, the site-directed transcriptional activator/synthetic transcription factor, or the nucleic acid encoding the same, comprises at least one recognition domain and at least one activation domain, wherein the site-directed transcriptional activator is configured to increase the expression of an endogenous PLT5 polypeptide, an endogenous PLT7 polypeptide, an endogenous RKD4 polypeptide, or an endogenous RKD2 polypeptide, preferably by binding to a regulation region located at a certain distance in relation to the start codon of the endogenous PLT5 polypeptide, the endogenous PLT7 polypeptide, the endogenous RKD4 polypeptide, or the endogenous RKD2 polypeptide.

The "regulation region" as used herein refer to the binding site of at least one recognition domain to a target sequence in the genome at or near a morphogenic gene. There may be two discrete regulation regions, or there may be overlapping regulation regions, depending on the nature of the at least one activation domain and the at least one recognition domain as further disclosed herein, which different domains of the synthetic transcription factor can be assembled in a modular manner.

In certain embodiments, the at least one recognition domain may target at least one sequence (recognition site) relative to the start codon of a gene of interest, which sequence may be at least 1.000 bp upstream (−) or downstream (+), −700 bp to +700 bp, −550 bp to +500 bp, or −550 bp to +425 bp relative to of the start codon of a gene of interest. Promoter-near recognizing recognition domains might be preferable in certain embodiments, whereas it represents an advantage of the specific synthetic transcription factors that the targeting range of the synthetic transcription factors is highly expanded over conventional or naturally occurring transcription factors. As the recognition and/or the activation domains can be specifically designed and constructed to specifically identify and target hot-spots of modulation.

In certain embodiments, the at least one recognition site may be −169 bp to −4 bp, −101 bp to −48 bp, −104 to −42 bp, or −175 to +450 bp (upstream (−) or downstream (+), respectively) relative to the start codon of a gene of interest to provide an optimum sterical binding environment allowing the best modulation, preferably transcriptional activation, activity. In particular for CRISPR-based synthetic transcription factors acting together with a guide RNA as recognition moiety, the binding site can also reside in within the coding region of a gene of interest (downstream of the start codon of a gene of interest).

In further embodiments, the recognition domain of the synthetic transcription factor can bind to the 5' and/or 3' untranslated region (UTR) of a gene of interest. In embodiments, where different recognition domains are employed, the at least two recognition domains can bind to different target regions of a morphogenic gene, including 5' and/or 3'UTRs, but they can also bind outside the gene region, but still in a certain distance of at most 1 to 1.500 bps thereto. One preferred region, where a recognition domain can bind, resides about −4 bp to about −300, preferably about −40 bp to about −170 bp upstream of the start codon of a morphogenic gene of interest. Furthermore, the length of a recognition domain and thus the corresponding recognition site in a genome of interest may thus vary depending on the synthetic transcription factor and the nature of the recognition domain applied. Based on the molecular characteristics of the at least one recognition domain, this will also determine the length of the corresponding at least one recognition site. For example, where individual zinc finger may be from about 8 bp to about 20 bp, wherein arrays of between three to six zinc finger motifs may be preferred, individual TALE recognition sites may be from about 11 to about 30 bp, or more. Recognition sites of gRNAs of a CRISPR-based synthetic transcription factor comprise the targeting or "spacer" sequence of a gRNA hybridizing to a genomic region of interest, whereas the gRNA comprises further domains, including a domain interacting with a disarmed CRISPR effector. The recognition site of a synthetic transcription factor based on a disarmed CRISPR effector will comprise a PAM motif, as the PAM sequence is necessary for target binding of any CRISPR effector and the exact sequence is dependent upon the species of the CRISPR effector, i.e., a disarmed CRISPR effector.

Introduction of Boost Genes and Boost Polypeptides

The boosters and/or genome engineering components can be introduced as a protein/polypeptide or as a nucleic acid encoding the protein/polypeptide, in particular as protein/polypeptide, or DNA such as plasmid DNA, RNA, mRNA or RNP.

The boosters may be co-delivered with one or more genome engineering components. As used herein, "co-delivery" or "co-deliver" and "co-introduction" or "co-introduce" are used interchangeably. In terms of the present invention, "co-introducing" refers to the process, in which at least two different components are delivered into the same plant cell concurrently. Thus, the genome engineering components and boost factors are introduced together into the same plant cell. Preferably, both types of components, booster and genes of interest, are introduced via separate constructs. Co-introduction into the plant cell can be conducted by particle bombardment, microinjection, agrobacterium-mediated transformation, electroporation, electrofusion, agroinfiltration or vacuum infiltration.

Regeneration Boost Genes

It is believed that transformed cells are less regenerable than wild type cells. Transformed cells are susceptible to programmed cell death due to presence of foreign DNA inside of the cells. Stresses arising from delivery (e.g. bombardment damage) may trigger a cell death as well. Therefore, promoting cell division is essential for the regeneration of the modified cells. Further, genome engineering efficiency is controlled largely by host cell statuses. Cells undergoing rapid cell-division, like those in plant meristem, are the most suitable recipients for genome engineering. Promoting cell division will probably increase DNA integration or modification during DNA replication and division process, and thus increase genome engineering efficiency.

The boost genes and booster polypeptides according to the invention, KWS-RBP1 (SEQ ID NO: 2) and KWS-RBP2 (SEQ ID NO: 48) are man-made and have been designed to improve the activity of the genome engineering component. When a booster polypeptide is introduced into a plant cell along with a transgene, the booster polypeptide can increase expression of the transgene and polypeptides encoded by the transgene. When the booster polypeptide is introduced into a plant cell along with a genome engineering component and the transgene, the activity of the genome engineering component may be increased. Such increase may result in more efficient integration of the transgene into the genome of the plant cell. One or more boost genes can be co-expressed with the booster polypeptide. One or more boost genes can be co-transfected with the booster polypeptide.

Such additional boost genes are selected based on their functions involved in promoting cell division and plant morphogenesis. Each of the candidate genes are cloned and driven by a strong constitutive promoter, and evaluated by transient expression in corn cells without a selection. Examples for boost genes are PLT5 (PLETHORA5; SEQ ID NOs: 4 and 6), PLT7 (PLETHORA7; SEQ ID NOs: 8, 10) and RKD2 (SEQ ID NOs: 18, 20 and 22).

PLT (PLETHORA), also called AIL (AINTEGUMENT-LIKE) genes, are members of the AP2 family of transcriptional regulators. Members of the AP2 family of transcription factors play important roles in cell proliferation and embryogenesis in plants (El Ouakfaoui, S., Schnell, J., Abdeen, A., Colville, A., Labbé, H., Han, S., Baum, B., Laberge, S., Miki, B (2010) Control of somatic embryogenesis and embryo development by AP2 transcription factors. *PLANT MOLECULAR BIOLOGY* 74(4-5):313-326). PLT genes are expressed mainly in developing tissues of shoots and roots, and are required for stem cell homeostasis, cell division and regeneration, and for patterning of organ primordia.

PLT family comprises an AP2 subclade of six members. Four PLT members, PLT1/AIL3 PLT2/AIL4, PLT3/AIL6, and BBM/PLT4/AIL2, are expressed partly overlap in root apical meristem (RAM) and required for the expression of QC (quiescent center) markers at the correct position within the stem cell niche. These genes function redundantly to maintain cell division and prevent cell differentiation in root apical meristem.

Three PLT genes, PLT3/AIL6, PLT5/AIL5, and PLT7/AIL7, are expressed in shoot apical meristem (SAM), where they function redundantly in the positioning and outgrowth of lateral organs. PLT3, PLT5, and PLT7, regulate de novo shoot regeneration in *Arabidopsis* by controlling two distinct developmental events. PLT3, PLT5, and PLT7 required to maintain high levels of PIN1 expression at the periphery of the meristem and modulate local auxin production in the central region of the SAM which underlies phyllotactic transitions. Cumulative loss of function of these three genes causes the intermediate cell mass, callus, to be incompetent to form shoot progenitors, whereas induction of PLT5 or PLT7 can render shoot regeneration in a hormone-independent manner. PLT3, PLT5, PLT7 regulate and require the shoot-promoting factor CUP-SHAPED COTYLEDON2 (CUC2) to complete the shoot-formation program. PLT3, PLT5, and PLT7, are also expressed in lateral root founder cells, where they redundantly activate the expression of PLT1 and PLT2, and consequently regulate lateral root formation.

The additional boost genes can be from any number of plants known in the art. Such plants include, but are not limited to, *Zea mays, Arabidopsis thaliana*, and *Triticum aestivum*. In some embodiments, the boost gene is *Zea mays* PLT5. In some embodiments, the boost gene is *Arabidopsis thaliana* PLT5. In some embodiments, the boost gene is *Zea mays* PLT7. In some embodiments, the boost gene is *Arabidopsis thaliana* PLT7. In some embodiments, the boost gene is *Triticum aestivum* RKD4. In some embodiments, the boost gene is *Arabidopsis thaliana* RKD4. In some embodiments, the boost gene is *Zea mays* RKD4. In some embodiments, the boost gene is *Triticum aestivum* RKD2. In some embodiments, the boost gene is *Arabidopsis thaliana* RKD2. In some embodiments, the boost gene is *Zea mays* RKD2.

In some embodiments, both the booster polypeptide according to the invention and the PLT5 polypeptide (encoded by the PLT5 boost gene) are introduced into the plant cell, and optionally transiently co-expressed. In some embodiments, both the booster polypeptide according to the invention and the PLT7 polypeptide (encoded by the PLT7 boost gene) are introduced into the plant cell, and optionally transiently co-expressed.

The polypeptide encoded by the PLT5 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 4. The polypeptide encoded by the PLT5 boost gene may comprise the sequence of SEQ ID NO: 4. The polypeptide encoded by the PLT5 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 6. The polypeptide encoded by the PLT5 boost gene may comprise the sequence of SEQ ID NO: 6.

The polypeptide encoded by the *Zea mays* PLT5 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 4. The polypeptide encoded by the *Zea mays* PLT5 boost gene may comprise the sequence of SEQ ID NO: 4.

The polypeptide encoded by the *Arabidopsis thaliana* PLT5 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 6. The polypeptide encoded by the *Arabidopsis thaliana* PLT5 boost gene may comprise the sequence of SEQ ID NO: 6.

The polypeptide encoded by the PLT7 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 8. The polypeptide encoded by the PLT7 boost gene may comprise the sequence of SEQ ID NO: 8. The PLT7 polypeptide may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 10. The polypeptide encoded by the PLT7 boost gene may comprise the sequence of SEQ ID NO: 10.

The polypeptide encoded by the *Zea mays* PLT7 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 8. The polypeptide encoded by the *Zea mays* PLT7 boost gene may comprise the sequence of SEQ ID NO: 8.

The polypeptide encoded by the *Arabidopsis thaliana* PLT7 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO:

10. The polypeptide encoded by the *Arabidopsis thaliana* PLT7 boost gene may comprise the sequence of SEQ ID NO: 10.

The polypeptide encoded by the RKD4 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 12. The polypeptide encoded by the RKD4 boost gene may comprise the sequence of SEQ ID NO: 12. The polypeptide encoded by the RKD4 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 14. The polypeptide encoded by the RKD4 boost gene may comprise the sequence of SEQ ID NO: 14. The polypeptide encoded by the RKD4 boost gene may comprise an amino acid sequence at least 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 16. The polypeptide encoded by the RKD4 boost gene may comprise the sequence of SEQ ID NO: 16.

The polypeptide encoded by the *Triticum aestivum* RKD4 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 12. The polypeptide encoded by the *Triticum aestivum* RKD4 boost gene may comprise the sequence of SEQ ID NO: 12.

The polypeptide encoded by the *Arabidopsis thaliana* RKD4 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 14. The polypeptide encoded by the *Arabidopsis thaliana* RKD4 boost gene may comprise the sequence of SEQ ID NO: 14.

The polypeptide encoded by the *Zea mays* RKD4 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 16. The polypeptide encoded by the *Zea mays* RKD4 boost gene may comprise the sequence of SEQ ID NO: 16.

The polypeptide encoded by the RKD2 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 18. The polypeptide encoded by the RKD2 boost gene may comprise the sequence of SEQ ID NO: 18. The polypeptide encoded by the RKD2 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 20. The polypeptide encoded by the RKD2 boost gene may comprise the sequence of SEQ ID NO: 20. The polypeptide encoded by the RKD2 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 22. The polypeptide encoded by the RKD2 boost gene may comprise the sequence of SEQ ID NO: 22.

The polypeptide encoded by the *Triticum aestivum* RKD2 boost gene may comprise an amino acid sequence at least 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 18. The polypeptide encoded by the *Triticum aestivum* RKD2 boost gene may comprise the sequence of SEQ ID NO: 18.

The polypeptide encoded by the *Arabidopsis thaliana* RKD2 boost gene may comprise an amino acid sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 20. The polypeptide encoded by the *Arabidopsis thaliana* RKD2 boost gene may comprise the sequence of SEQ ID NO: 20.

The polypeptide encoded by the *Zea mays* RKD2 boost gene may comprise an amino acid sequence at least 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 22. The polypeptide encoded by the *Zea mays* RKD2 boost gene may comprise the sequence of SEQ ID NO: 22.

In some embodiments, the nucleic acid encoding the PLT5 polypeptide comprises a nucleic acid comprising the nucleotide sequence of SEQ ID NO: 3 or 5. In some embodiments, the nucleic acid encoding the PLT5 polypeptide comprises a nucleic acid comprising the nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 3 or 5. In some embodiments, the nucleic acid encoding the PLT5 polypeptide comprises a nucleic acid hybridizing with the complementary strand of a nucleic acid comprising the nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 3 or 5, or a nucleic acid comprising the nucleotide sequence of SEQ ID NO: 3 or 5.

In some embodiments, the nucleic acid encoding the PLT7 polypeptide comprises a nucleic acid comprising the nucleotide sequence of SEQ ID NO: 7 or 9. In some embodiments, the nucleic acid encoding the PLT7 polypeptide comprises a nucleic acid comprising the nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 7 or 9. In some embodiments, the nucleic acid encoding the PLT7 polypeptide comprises a nucleic acid hybridizing with the complementary strand of a nucleic acid comprising the nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 7 or 9, or a nucleic acid comprising the nucleotide sequence of SEQ ID NO: 7 or 9.

In some embodiments, the nucleic acid encoding the RKD4 polypeptide comprises a nucleic acid comprising the nucleotide sequence of SEQ ID NO: 11, 13, or 15. In some embodiments, the nucleic acid encoding the RKD4 polypeptide comprises a nucleic acid comprising the nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 11, 13, or 15. In some embodiments, the nucleic acid encoding the RKD4 polypeptide comprises a nucleic acid hybridizing with the complementary strand of a nucleic acid comprising the nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 11, 13, or 15, or a nucleic acid comprising the nucleotide sequence of SEQ ID NO: 11, 13, or 15.

In some embodiments, the nucleic acid encoding the RKD2 polypeptide comprises a nucleic acid comprising the nucleotide sequence of SEQ ID NO: 17, 19, or 21. In some embodiments, the nucleic acid encoding the RKD2 polypeptide comprises a nucleic acid comprising the nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 17, 19, or 21. In some embodiments, the nucleic acid encoding the RKD2 polypeptide comprises a nucleic acid hybridizing with the complementary strand of a nucleic acid comprising the nucleotide sequence at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO: 17, 19, or 21, or a nucleic acid comprising the nucleotide sequence of SEQ ID NO: 17, 19, or 21.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as program NEEDLE as implemented in the European Molecular Biology Open Software Suite (EMBOSS), e.g. version 6.3.1.2 (*Trends in Genetics* 16 (6), 276 (2000)), with its default parameter, e.g. for proteins matrix=EBLOSUM62, gapopen=10.0 and gapextend=0.5.

As used herein, the term "hybridize(s)(ing)" refers to the formation of a hybrid between two nucleic acid molecules via base-pairing of complementary nucleotides. The term "hybridize(s)(ing) under stringent conditions" means hybridization under specific conditions. An example of such conditions includes conditions under which a substantially complementary strand, namely a strand composed of a nucleotide sequence having at least 80% complementarity, hybridizes to a given strand, while a less complementary strand does not hybridize. Alternatively, such conditions refer to specific hybridizing conditions of sodium salt concentration, temperature and washing conditions. As an example, highly stringent conditions comprise incubation at 42° C., 50% formamide, 5×SSC (150 mM NaCl, 15 mM trisodium citrate), 50 mM sodium phosphate, 5×Denhardt's solution, 10×dextran sulfate, 20 mg/ml sheared salmon sperm DNA and washing in 0.2×SSC at about 65° C. (SSC stands for 0.15 M sodium chloride and 0.015 M trisodium citrate buffer). Alternatively, highly stringent conditions may mean hybridization at 68° C. in 0.25 M sodium phosphate, pH 7.2, 7% SDDS, 1 mM EDTA and 1% BSA for 16 hours and washing twice with 2×SSC and 0.1% SDDS at 68° C. Further alternatively, highly stringent hybridisation conditions are, for example: Hybridizing in 4×SSC at 65° C. and then multiple washing in 0.1×SSC at 65° C. for a total of approximately 1 hour, or hybridizing at 68° C. in 0.25 M sodium phosphate, pH 7.2, 7% SDS, 1 mM EDTA and 1% BSA for 16 hours and subsequent washing twice with 2×SSC and 0.1% SDS at 68° C.

Epigenetically-Regulating Chemicals

An epigenetically regulating chemical, e.g., protein deacetylase inhibitor (ii.1), can be co-introduced with the genome engineering component. Exemplary epigenetically regulating chemicals for use according to the invention include, but are not limited to, histone deacetylase inhibitors (HDACis) such as trichostatin A (TSA), and DNA methyltransferase inhibitors.

It is assumed that the co-delivered epigenetically regulating chemicals (ii.1) (in particular HDACis) relax plant chromatin structure, promote the DNA accessibility to the genome engineering components in the bombarded cells, thus consequently promote genome engineering (i.e. transformation and genome editing) efficiencies. The reason for this assumption is: The basic structural and functional unit of genetic material is the nucleosome, in which negatively charged DNA is wrapped around a positively charged histone octamer and associated linker histones. Nucleosome units further fold and pack into chromatin (Andrews, A. J., and Luger, K. (2011). Nucleosome structure(s) and stability: Variations on a theme. Annu. Rev. Biophys. 40: 99-117). DNA accessibility largely depends on compactness of the nucleosomes and chromatins. Chromatin-remodeling enzymes dynamically modify lysine or other amino acids of histones, which cause changes in their charges and interactions with DNA and other proteins, and result in chromatin folding or unfolding (Bannister A. J., Kouzarides T. (2011) Regulation of chromatin by histone modifications. Cell Res 21: 381-95). By adding or removing an acetyl group, acetylation and deacetylation of the lysine residue in histone proteins are often involved in the reversible modulation of chromatin structure in eukaryotes, and mediate chromatin accessibility and the regulation of gene expression. Histone deacetylases (HDAC) are enzymes that remove acetyl groups from lysine resides on the N-terminal tail of histones, which makes the histone more positively charged, and therefore allows the histone wrap DNA more tightly. Inhibition of HDACs might help chromatin unfolding and enable the DNA to be more accessible.

Chromatin remodeling and other epigenetic modifications surely play an important role in regulating cell totipotency and regeneration (Zhang, H., and Ogas, J. (2009). An epigenetic perspective on developmental regulation of seed genes. Mol. Plant 2: 610-627). Inhibition of histone deacetylase (HDAC) activities have been shown associated with plant regeneration and microspore embryogenesis (Miguel, C., and Marum, L., 2011. An epigenetic view of plant cells cultured in vitro: somaclonal variation and beyond. *J. Exp. Bot.* 62:3713-3725., Li Hui et al. (2014) The Histone Deacetylase Inhibitor Trichostatin A Promotes Totipotency in the Male Gametophyte Plant Cell, 26: 195-209). Inhibition of HDAC activity or downstream HDAC-mediated pathways plays a major role in the initiation of stress-induced haploid embryogenesis. One such HDACi is trichostatin A (TSA). It has been shown that TSA induces massive embryogenic cell proliferation in the male gametophyte of *B. napus*. TSA treatment leads to a high frequency of sporophytic cell division in cultured microspores and pollen.

Various methods may be used to increase further the genome engineering efficiency in presence of one or more epigenetically regulating chemicals, e.g. protein deacetylase inhibitors, in particular HDACi. Such an HDACi may be trichostatin A (TSA), N-Hydroxy-7-(4-dimethylaminobenzoyl)-aminoheptanamide (M344), suberoylanilide hydroxamic acid (SAHA), or others. These HDACis are selected from hydroxamic acid (HA)-based chemicals, which target to zinc dependent HDACs.

Phytohormones

In various embodiments, one or more phytohormones, such as auxins and cytokinins like 2,4-D, 6-Benzylaminopurine (6-BA) and Zeatin, are co-delivered with one or more of a boost gene, a booster polypeptide, a genome engineering component, and a transgene.

Plant somatic cells are capable to resume cell division and regenerate into an entire plant in in-vitro culture through somatic embryogenesis or organogenesis, which largely depends on phytohormones, such as auxins and cytokinins. In the present invention it was found, that phytohormones promote cell proliferation, increase the sensitivity of the plant cells to genome engineering, and thus improve genome engineering (i.e. transformation and genome editing) efficiency.

One of auxins is 2,4-Dichlorophenoxyacetic acid (2,4-D), which is nearly indispensable for somatic embryogenesis and cell regeneration in monocot plants, e.g. maize and wheat. Meanwhile, cytokinins e.g. 6 benzylaminopurine (6-BA) or Zeatin, are essential for plant organogenesis, and shoot meristem initiation and development. The methods to improve genome engineering efficiency may include co-delivery of one or more of phytohormones (2,4-D, 6-BA, Zeatin, etc.) with the genome engineering component.

A genome engineering component and at least one of the epigenetically-regulating chemicals and phytohormones can be co-introduced into one plant cell.

As used herein, "co-delivery" or "co-deliver" and "co-introduction" or "co-introduce" are used interchangeably. In terms of the present invention, "co-introducing" refers to the process, in which at least two different components are delivered into the same plant cell concurrently. Thus, the genome engineering component and at least one of the epigenetically-regulating chemicals and phytohormones may be introduced together into the same plant cell.

Co-introduction into the plant cell can be conducted by particle bombardment, microinjection, agrobacterium-mediated transformation, electroporation, agroinfiltration or vacuum infiltration. According to the invention, methods based on physical delivery like particle bombardment, microinjection, electroporation, nanoparticles, and cell-penetrating peptides (CPPs) are particularly preferred for co-introducing boost genes, booster polypeptides, genome engineering components, and/or transgenes. Particularly preferred is the co-introduction via particle bombardment.

Regeneration of a Plant Cell into a Whole Plant

According to another aspect of the present invention, the genetically modified plant cells can be regenerated into a whole (fertile) plant. Thus, in a preferred aspect of the invention, the genetic modification of a plant cell is followed by a step of regenerating a plant. Accordingly, the present invention provides a method for producing a genetically modified plant comprising the steps:

a) genetically modifying a plant cell according to any of the above methods for genetic modification in a plant cell, and b) regenerating a plant from the modified plant cell of step a), Single or multiple cells proliferate and develop into tissues, organs, and eventually entire plants. In some embodiments, the produced plant does not contain any of the genome engineering components, boost genes, and booster polypeptides introduced, or co-introduced in step a). Step b) of regenerating a plant can for example comprise culturing the genetically modified plant cell from step a) on a regeneration medium.

The efficiency of plant regeneration or of increasing the regeneration ability of a plant cell can be improved by introducing into the plant cell any of the booster polypeptides, boost genes, nucleic acids, recombinant genes and DNA constructs described herein.

Production of a Genetically Modified Plant

The present invention also provides a genetically modified plant obtained or obtainable by the above methods for producing a genetically modified plant or a progeny plant thereof. The genetically modified plant may comprise any of the genetically modified plant cells described herein.

In various embodiments, the produced plant does not contain any of the genome engineering components, boost genes, and booster polypeptides introduced or co-introduced into a plant cell used to generate the produced plant.

The present invention also provides a plant or a seed derived from the above-described genetically modified cells without a conventional selection. As used herein, "conventional selection" refers to any processes to select and purify the transformed cells from wild-type cells by using an integrated selection marker, e.g. antibiotic (e.g. kanamycin, hygromycin), or herbicide (e.g. phosphinothricin, glyphosate) resistance gene. Without a conventional selection, such a plant or seed may not have any of the genome engineering components integrated, and thus leads to transgene-free genetic modified plants.

The genetic modification can be a permanent and heritable change in the genome of the plant cell. Plant tissue culture and genome engineering can be carried out using currently available methods, comprising of microparticle bombardment, *Agrobacterium* transformation, electroporation, etc. Transformation and transgene expression may be monitored by use of a visible report gene, for example, the red fluorescent tDTomato gene (tDT) that encodes an exceptionally bright red fluorescent protein with excitation maximum at 554 nm and emission maximum at 581 nm. The genome editing efficiency can be analyzed for instance by next generation sequencing (NGS), qPCR, marker capillary electrophoresis analysis, and Droplet Digital PCR. Site-specific modification was further conformed by Sanger sequencing.

Cultivation Step

The plant cell into which boost genes, booster polypeptides, genome engineering components, and/or transgenes have been introduced, or co-introduced, can be cultivated under conditions allowing the genetic modification of the genome of said plant cell by activity of the genome engineering component in the presence of one or more of a boost gene, a booster polypeptide, and one or more transgenes.

As used herein, "genetic modification of the genome" includes any type of manipulation such that endogenous nucleotides have been altered to include a mutation, such as a deletion, an insertion, a transition, a transversion, or a combination thereof. For instance, an endogenous coding region could be deleted. Such mutations may result in a polypeptide having a different amino acid sequence than was encoded by the endogenous polynucleotide. Another example of a genetic modification is an alteration in the regulatory sequence, such as a promoter, to result in increased or decreased expression of an operably linked endogenous coding region.

Conditions that are "suitable" for a genetic modification of the plant genome to occur, such as cleavage of a polynucleotide, or "suitable" conditions are conditions that do not prevent such events from occurring. Thus, these conditions permit, enhance, facilitate, and/or are conducive to the event. Depending on the respective genome engineering component (i), these conditions may differ.

In the method of the present invention, the plant cell is preferably transiently transformed with the genome engineering component (i) and the at least one compound (ii). As used herein, "transient transformation" refers to the transfer of a foreign material [i.e. a nucleic acid fragment, protein, ribonucleoprotein (RNP), etc.] into host cells resulting in gene expression and/or activity without integration and stable inheritance of the foreign material. Thus, the genome engineering component (i) is transiently active and/or transiently present in the plant cell. The genome engineering component is not permanently incorporated into the cellular genome, but provides a temporal action resulting in a modification of the genome. For example, transient activity and/or transient presence of the genome engineering component in the plant cell can result in introducing one or more double-stranded breaks in the genome of the plant cell, one or more single-stranded breaks in the genome of the plant cell, one or more base-editing events in the genome of the plant cell, or one or more of DNA methylation, histone acetylation, histone methylation, histone ubiquitination, histone phosphorylation, histone sumoylation, histone ribosylation or histone citrullination in the genome of the plant cell.

The introduction of one or more double-stranded breaks or one or more single-stranded breaks is preferably followed by non-homologous end joining (NHEJ) and/or by homology directed repair (HDR) of the break(s) through a homologous recombination mechanism.

The resulting modification in the genome of the plant cell can, for example, be selected from an insertion of a transgene, preferably an expression cassette comprising a transgene of interest, a replacement of at least one nucleotide, a deletion of at least one nucleotide, an insertion of at least one nucleotide, a change of DNA methylation, a change in histone acetylation, histone methylation, histone ubiquitination, histone phosphorylation, histone sumoylation, histone ribosylation, or histone citrullination or any combination thereof. According to a particularly preferred aspect of the invention, no exogenous genetic material related to the applied gene editing machinery/systems is stably integrated into the genome of the plant cell.

The genetic modification can be a permanent and heritable change in the genome of the plant cell.

Optional Pre-Treatment

In various embodiments, pre-treatment of plant materials with one or more chemicals described in U.S. Provisional Application No. 62/685,626, incorporated herein by reference, can be included. Thus, the methods for genetic modification in a plant cell may further comprise a step of pretreatment of the plant cell, said pretreatment comprising culturing the plant cell or plant material comprising same in a medium containing (1) an epigenetically regulating chemical or an active derivative thereof, in particular the histone deacetylase inhibitor (HDACi) or the DNA methyltransferase inhibitor, or (2) a phytohormone or an active derivative thereof, or any combination thereof.

After the pretreatment step, the treated plant cells may be taken from the medium containing at least one of compounds (1) and (2) and used for co-introduction.

Exemplary, as for the histone deacetylase inhibitor TSA, the duration of the HDACis pre-treatment is from 10 minutes to 2 days, preferred 2.0 to 24 hours. TSA concentration for a pre-treatment is 1.0 nM to 1000 nM, preferred 10 nM to 100 nM. Hereafter the treated plant materials are transferred to HDACi-free medium and used for TSA co-introduction immediately (a prolonged TSA pre-treatment may cause non-selectively enhancement of cell regeneration, which may increase difficult in retrieving the bombarded and modified cells).

Similar conditions of pre-treatment can be applied for all types of compounds (1) and (2). Plant tissue culture and genome engineering can be carried out using currently available methods. Transient transformation and transgene expression may be monitored by use of the red fluorescent report gene tdTomato, which encodes an exceptionally bright red fluorescent protein with excitation maximum at 554 nm and emission maximum at 581 nm, or the green fluorescent report gene mNeonGreen, which encodes the brightest monomeric green or yellow fluorescent protein with excitation maximum at 506 nm and emission maximum at 517 nm. The genome editing efficiency can be analyzed for instance by next generation sequencing (NGS).

Microparticles

In another aspect is provided a microparticle coated with at least one of the above booster polypeptides, nucleic acids, recombinant genes or DNA constructs. In some embodiments, the microparticle is further coated with a genome engineering component.

In another aspect is provided a kit for the genetic modification of a plant genome by microprojectile bombardment, comprising (I) one or more microparticles, and (II) means for coating the microparticles.

In some embodiments, the kit further comprises a means for coating the microparticles with a genome engineering component.

In various embodiments, the microparticle is coated with at least (i) a booster polypeptide, or a nucleic acid encoding the booster polypeptide;

(ii) a transgene; and/or a genome engineering component.

In a particularly preferred embodiment of microparticle bombardment, the boost polypeptide and/or one or more boost genes can be co-delivered with the genome engineering components via microcarriers comprising gold particles having a size in a range of 0.4-1.6 micron (μm), preferably 0.4-1.0 μm. In an exemplary process, 10 ng-10 μg of DNA, preferably 50-1000 ng of DNA, coated onto 10-1000 μg of gold particles, preferably 50-300 μg, are used per one bombardment. Up to 10 bombardments (shots), preferred 1-4 shots, per one sample plate can be used for the delivery of foreign molecules into plant cells.

Boost factors (e.g., boost polypeptides or polynucleotides encoding such boost polypeptides) and genome engineering components can be delivered into target cells for example using a Bio-Rad PDS-1000/He particle gun or handheld Helios gene gun system. When a PDS-1000/He particle gun system used, the bombardment rupture pressures are from 450 psi to 2200 psi, preferably from 450 psi to 1100 psi, while the rupture pressures are from 100 psi to 600 psi for a Helios gene gun system. More than one chemical or construct can be co-delivered with genome engineering components into target cells simultaneously.

The microparticle coating can further comprise one or more coating layers. For example, a microparticle may contain a first coating layer comprising a boost factor and a second coating layer comprising the genome engineering component and the transgene. Alternatively, a microparticle may contain a coating layer comprising a boost factor and either the transgene or the genome engineering component.

Further, the invention provides a kit for the genetic modification of a plant genome by microprojectile bombardment, comprising (I) above one or more microparticles, and (II) means for coating the microparticles with at least a genome engineering component and (1) an epigenetically regulating chemical, e.g. a DNA methyltransferase inhibitor or a protein deacetylase inhibitor or an active derivative thereof, in particular a histone deacetylase inhibitor (HDACi), and/or (2) a phytohormone or an active derivative thereof.

Another aspect of the present invention is the use of a microparticle as described above for the biolistic transformation of a plant cell.

Subject matter of the present invention are also the plant cells that are obtained or obtainable by the methods described above. Accordingly, one embodiment of the invention is a genetically modified plant cell obtained or obtainable by the above method for genetic modification in a plant cell. The genetic modification in these plant cells compared to the original plant cells may, for example, include an insertion of a transgene, preferably an expression cassette comprising a transgene of interest, a replacement of at least one nucleotide, a deletion of at least one nucleotide, an insertion of at least one nucleotide, a change of DNA methylation, a change in histone acetylation, histone methylation, histone ubiquitination, histone phosphorylation, histone sumoylation, histone ribosylation, or histone citrullination or any combination thereof. Preferably, the genetically modified plant cell does not comprise any exogenous genetic materials stably integrated into the genome of the plant cell.

Genetically modified plant cells can be part of a whole plant or part thereof. Thus, the present invention also relates to a plant or plant part comprising the above genetically modified plant cell.

According to another aspect of the present invention, the genetically modified plant cells can be regenerated into a whole (fertile) plant. Thus, in a preferred aspect of the invention, the genetic modification of a plant cell is followed by a step of regenerating a plant. Accordingly, the present invention provides a method for producing a genetically modified plant comprising the steps:

a) genetically modifying a plant cell according to the above method for genetic modification in a plant cell, and b) regenerating a plant from the modified plant cell of step a).

Step b) of regenerating a plant can for example comprise culturing the genetically modified plant cell from step a) on a regeneration medium.

Regeneration techniques rely on manipulation of certain phytohormones in a tissue culture growth medium, occasionally relying on a biocide and/or herbicide marker that can been introduced. Regeneration can be obtained from plant somatic cells, callus cells or embryonic cells and protoplasts derived from different explants, e.g. callus, immature or mature embryos, leaves, shoot, roots, flowers, microspores, embryonic tissue, meristematic tissues, organs, or any parts thereof. Such regeneration techniques are described generally in Klee (1987) Ann. Rev. of Plant Phys. 38:467486. Plant regeneration from cultured protoplasts is described in Evans et al., Protoplasts Isolation and Culture, Handbook of Plant Cell Culture, pp. 124-176, Macmillan Publishing Company, New York, 1983; and Binding, Regeneration of Plants, Plant Protoplasts, pp. 21-73, CRC Press, Boca Raton, 1985. To obtain whole plants from transformed or gene edited cells, the cells can be grown under controlled environmental conditions in a series of media containing nutrients and hormones, a process known as tissue culture. Once whole plants are generated and produce seed, evaluation of the progeny begins.

The present invention also provides a genetically modified plant obtained or obtainable by the above method for producing a genetically modified plant or a progeny plant thereof.

Further subject matter of the present invention is a plant cell or a seed derived from the above genetically modified plant.

Further subject matter of the present invention is a plant, plant cell or a seed derived from the above genetically modified cell without a marker gene-based selection. As used herein, "marker gene-based selection" refers to any processes to select, identify and/or purify the modified cells, in particular the transformed, gene edited or base edited cells, from wild-type cells by using an integrated selection marker (gene), e.g. antibiotic resistance gene (e.g. kanamycin resistance gene, hygromycin resistance gene), or herbicide resistance gene (e.g. phosphinothricin resistance gene, glyphosate resistance gene). Without such selection, such a plant, plant cell or seed may not have any of the genome engineering components integrated, which may yield (i) transgene-free genetic modified plants or (ii) modified plants which have integrated solely the transgene of interest.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Cray, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Sequences

| SEQ ID NO: | Description |
|---|---|
| 1 | cDNA of KWS-RBP1 |
| 2 | protein of KWS-RBP1 |
| 3 | cDNA of ZmPLT5 |
| 4 | protein of ZmPLT5 |
| 5 | cDNA of AtPLT5 |
| 6 | protein of AtPLT5 |
| 7 | cDNA of ZmPLT7 (genotype A188) |
| 8 | protein of ZmPLT7 (genotype A188) |
| 9 | cDNA of AtPLT7 |
| 10 | protein of AtPLT7 |
| 11 | cDNA of TaRKD4 |
| 12 | protein of TaRKD4 |
| 13 | cDNA of AtRKD4 |
| 14 | protein of AtRKD4 |

-continued

| Sequences | |
|---|---|
| SEQ ID NO: | Description |
| 15 | cDNA of ZmRKD4 |
| 16 | protein of ZmRKD4 |
| 17 | cDNA of TaRKD2 |
| 18 | protein of TaRKD2 |
| 19 | cDNA of AtRKD2 |
| 20 | protein of AtRKD2 |
| 21 | cDNA of ZmRKD2 |
| 22 | protein of ZmRKD2 |
| 23 | promoter of BdEF1 |
| 24 | pABM-BdEF1 |
| 25 | pABM-BdEF1_ZmPLT5 |
| 26 | pABM-BdEF1_ZmPLT7 |
| 27 | pABM-BdEF1_KWS-RBP1 |
| 28 | pABM-BdEF1_TaRKD4 |
| 29 | PGEP359 |
| 30 | pGEP324 |
| 31 | pAMK-BdEF_ZmWUS2 |
| 32 | BdEF1::ZmPLT5_expression_cassette |
| 33 | BdEF1::ZmPLT7_expression_cassette |
| 34 | BdEF1::KWS-RBP1_expression_cassette |
| 35 | BdEF1::TaRKD4_expression_cassette |
| 36 | BdEF1::ZmWUS2_expression_cassette |
| 37 | pUbi::LpCpf1_expression_cassette |
| 38 | pUbi::crRNA5_expression_cassette |
| 39 | cDNA of LbCpf1 |
| 40 | protein of LbCpf1 |
| 41 | crRNA5_target_HMG13 |
| 42 | crRNA5_target_sequence |
| 43 | pAMK-ZmWUS2-tDT-nosT |
| 44 | cDNA of ZmPLT7 (genotype B73) |
| 45 | protein of ZmPLT7 (genotype B73) |
| 46 | pZmWUS2::tDT-nosT expression cassette |
| 47 | cDNA of KWS-RBP2 |
| 48 | protein of KWS-RBP2 |
| 49 | pABM-BdEF1_KWS-RBP2 |
| 50 | BdEF1::KWS-RBP2_expression_cassette |

All patents, patent applications, and publications or public disclosures (including publications on internet) referred to or cited herein are incorporated by reference in their entirety.

EXAMPLES

The present invention is further illustrated by the following examples. However, it is to be understood that the invention is not limited to such examples. The use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1. Transient Co-Expression of Boost Genes and Genes of Interest (GOI) by Co-Bombardment Gene Cloning and Construct Preparation Maize PLT5 (ZmPLT5) and PLT7 (ZmPLT7) genes were cloned by RT-PCR using total RNA isolated from maize A188 immature embryos. Wheat RKD4 and KWS-RBP1 genes were maize-codon optimized from its protein sequence, and synthesized by Integrated DNA Technologies (IDT, San Diego, Calif., USA). The boost gene fragments are cloned into expression vector pABM-BdEF1 (FIG. 1) at the cloning site of BamHI and HindIII, and expressed under the control of a BdEF1 promoter (pBdFE1) and a nos terminator (nos-T). pBdFE1 is a strong constitutive promoter from *Brachypodium*. The sequencing-confirmed construct maps are shown in FIGS. 2-5.

Preparing Maize Immature Embryo for Bombardment

At 9-12 days post pollination, maize ears (i.e. A188 or Hi II) with immature embryos having a size of 0.8 to 1.8 mm, preferably 1.0-1.5 mm, were harvested. The ears were sterilized with 70% ethanol for 10-15 minutes. After brief air drying in a laminar hood, the top ~⅓ of the kernels were removed from the ears with a shark scalpel, and the immature embryos were pulled out of the kernels carefully with a spatula. The fresh isolated embryos were placed onto the bombardment target area in an osmotic medium plate (see below) with scutellum-side up. The plates were wrapped with parafilm and incubated at 25° C. in the dark for 4 hours before bombardment.

Particle Co-Bombardment

Figure 6:
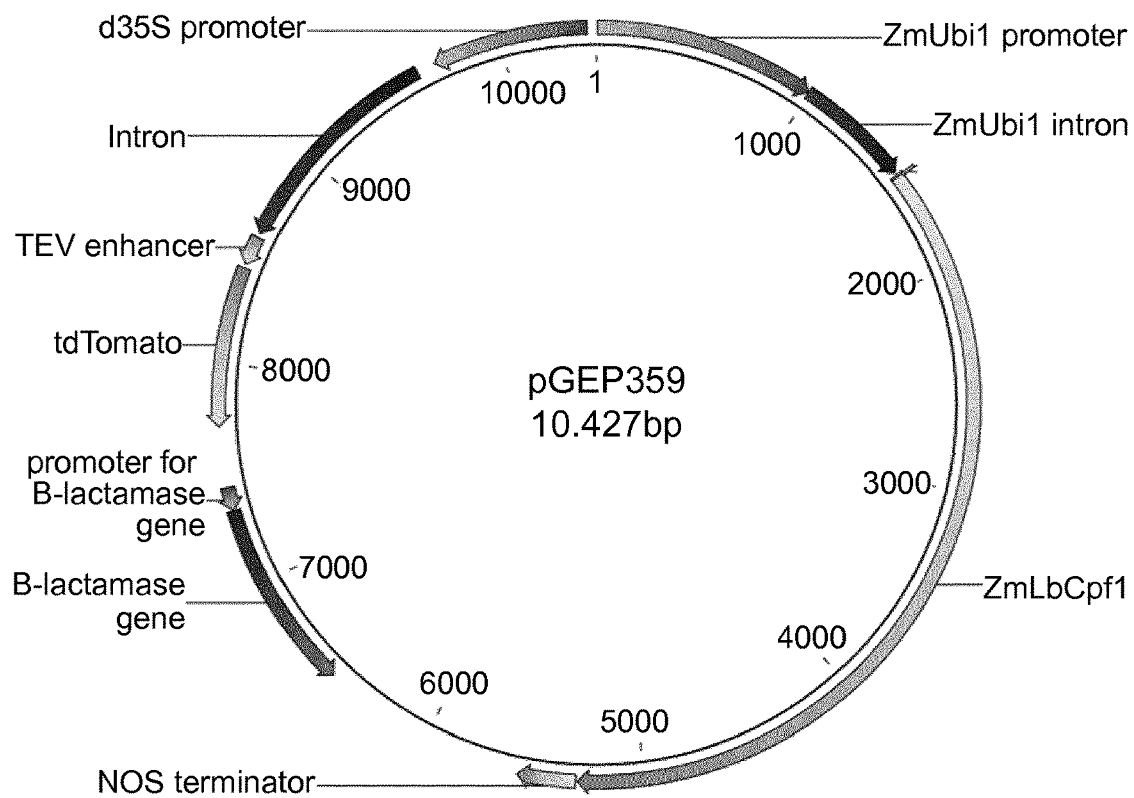
FIG. 6 shows a map of the genome editing CRISPR Cpf1 expression construct pGEP359 (SEQ ID NO: 29). tDTomato defines tdTomato gene (tDT). ZmLpCpf1 defines the maize codon-optimized CDS of the Lachnospiraceae bacterium CRISPR/Cpf1 (LbCpf1) gene.
Figure 7:
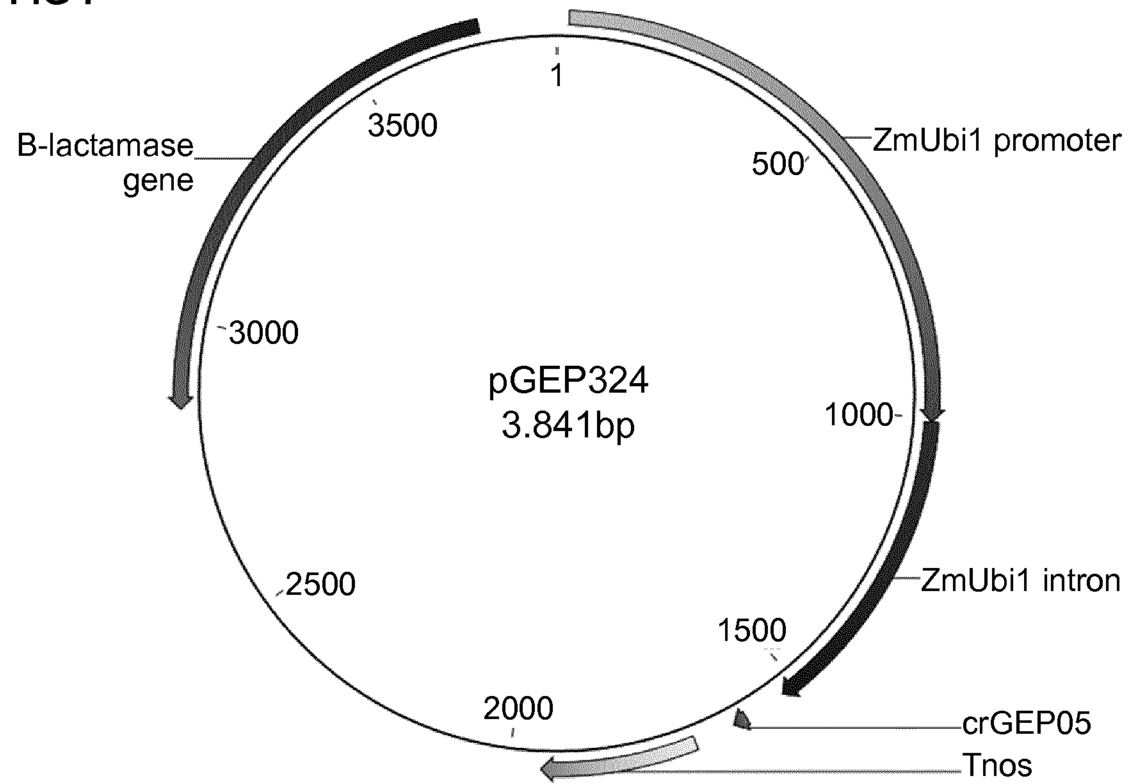
FIG. 7 shows a map of the genome editing CRISPR RNA construct pGEP324 (SEQ ID NO: 30). crGEP05 defines the crRNA5 that targets to maize HMG13 gene. ZmUbi1 defines the promoter and intron from maize Ubiquitin 1 gene. Tnos defines the nos terminator.

A particle bombardment gun and gold particles having a size of 0.4 or 0.6 microns (μm) were used to deliver DNA into the scutellum cells of maize immature embryos. The boost gene plasmids were premixed with genes of interest (GOI), e.g., genome editing constructs pGEP359 that harbor CRISPR nuclease Cpf1 and a tDT report gene (FIG. 6), and pGEP324 that contains the CRISPR guide RNA crRNA5 target to maize HMG13 (FIG. 7). For 10 shots, 1 mg of gold particle in 50% (v/v) glycerol (100 μg of gold particles per shot) in a total volume of 100 microliter (μl) was pipetted into a clear low-retention microcentrifuge tube. The mixture was sonicated for 15 seconds to suspend the gold particles. While vortexing at a low speed, the following were added, in order, to each 100 μl of gold particles: (a) up to 10 μl of DNA (1.0-10.0 μg total DNA of pre-mixed, 100-1000 ng per each shot), (b) 100 μl of 2.5 M $CaCl_2$ (pre-cold on ice), and (c) 40 μl of 0.1 M cold spermidine.

The lid was closed and the tube vortexed for 2-30 minutes at 0-10° C., and the DNA-coated gold particles were spun down. After washing in 500 μl of 100% ethanol two times, the pellet was resuspended in 120 μl of 100% ethanol. While vortexing at a low speed, 10 μl of co-coated gold particles were pipetted with a wide open 20 μl tip from the tube onto the center of the macrocarrier evenly. Since the particles tend to form clumps at this point, the gold particles were placed onto the macrocarriers as soon as possible, followed by air drying. Bombardment was conducted using a Bio-Rad PDS-1000/He particle gun. The bombardment conditions were: 28 mm/Hg vacuum, 450 or 650 psi rupture disc, 6 mm gap distance, the specimen platform is in the second position from the bottom in the chamber at a distance of 60 mm, three shots per sample (maize immature embryos) plate.

Post Bombardment Observation and Embryo Culture

Figure 8:
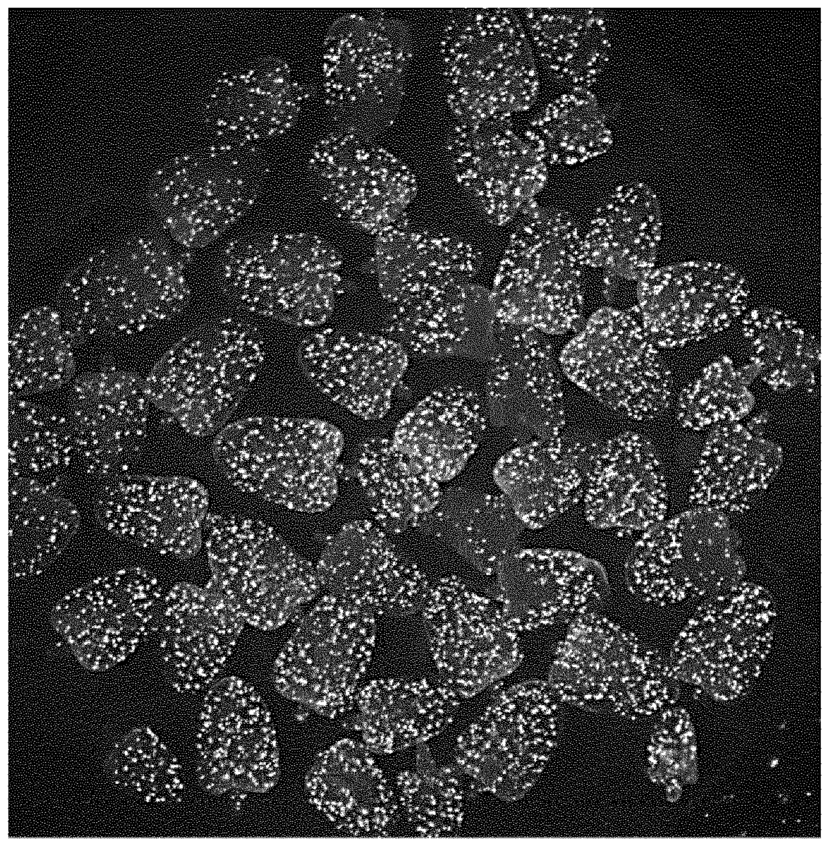
FIG. 8 shows a Fluorescent image of A188 immature embryos 18 hours after co-bombardment of ZmPLT5 (FIG. 2) with pGEP359 (FIG. 6) and pGEP324 (FIG. 7) plasmids. Images were taken 18 hours after bombardment.

After bombardment, the embryos remained on the osmotic medium for another 16 hours. Transient transformation was examined using a fluorescence microscope for the tDT expression at excitation maximum 554 nm and emission maximum 581 nm 16-20 hours after bombardment. The embryos with dense fluorescent signals under a fluorescence microscope (FIG. 8) were selected and transferred from N6OSM onto a N6-5Ag plate (~15 embryos per plate) with scutellum-face-up for callus induction (see below).

Osmotic medium: N6 salt, N6 vitamin, 1.0 mg/L of 2, 4-D, 100 mg/L of Casein, 0.7 g/L of L-proline, 0.2 M Mannitol (36.4 g/L), 0.2 M sorbitol (36.4 g/L), 20 g/L sucrose, 15 g/L of Bactoagar, pH 5.8.

N6-5Ag: N6 salt, N6 vitamin, 1.0 mg/L of 2, 4-D, 100 mg/L of Casein, 2.9 g/L of L-proline, 20 g/L sucrose, 5 g/L of glucose, 5 mg/L of AgNO3, 8 g/L of Bacto-agar, pH 5.8.

Example 2. Transient Co-Expression of ZmPLT5 or ZmPLT7 Gene and KWS-RBP1 Promotes Early Embryogenesis and Regeneration in Maize Hi II Immature Embryo Transient co-delivery, embryo preparation and culturing are described above in Example 1. For each bombardment, four premixed DNA plasmids were coated onto 100 μg of gold particles having a size of 0.4 μm, and co-introduced into the scutellum cell of Hi II immature embryos at 650 psi rupture pressure. Four plasmids were premixed as follows for one bombardment:

100 ng of boost ZmPLT5 or ZmPLT7 (FIG. 2 and FIG. 3)
200 ng of KWS-RBP1 (FIG. 4)
100 ng of pGEP359 (FIG. 6)
150 ng of pGEP324 (FIG. 7)

The embryos with dense fluorescent signals under a fluorescence microscope (FIG. 8) were selected and transferred from N6OSM onto N6-5Ag for embryonic callus induction. The selected embryos were cultured in a N6-5Ag plate with the scutellum-face-up (roughly 15 embryos per plate) at 27° C. in dark for 14 in dark. Embryogenic callus induction was monitored by observation under a dissection microscope. Specifically, the boost effect on cell division and regeneration was measured by its capability to induce embryo formation 5-7 days after bombardment by visual observation under a fluorescence microscope.

Figure 9:
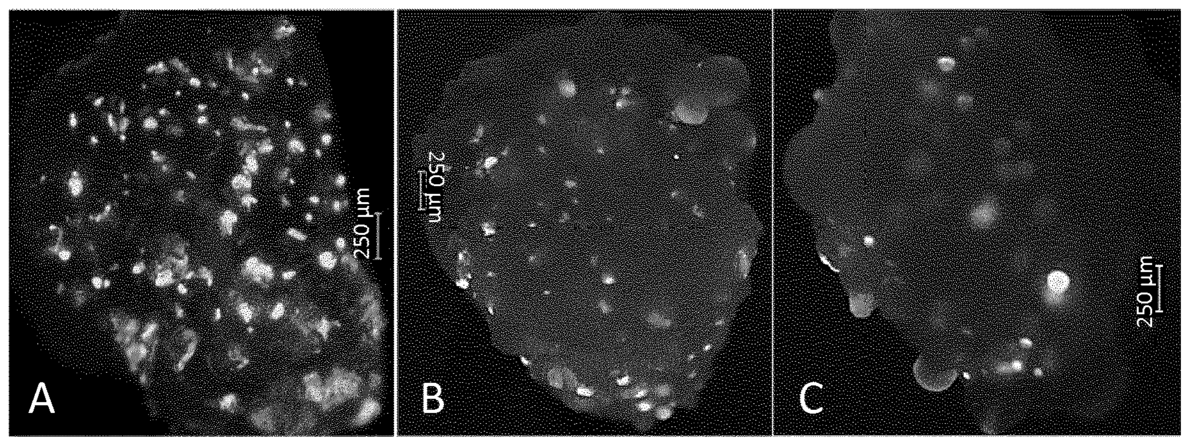
FIG. 9 shows transient co-expression of ZmPLT5 and KWS-RBP1 or ZmPLT7 and KWS-RBP1 promoting embryogenesis in Hi II immature embryos. Images show embryogenic structures induced from maize Hi II embryos 5 days after co-bombardment with boost gene constructs.

FIG. 9 shows that co-expression of ZmPLT5 (FIG. 9B) or ZmPLT7 (FIG. 9C) and KWS-RBP1 by microprojectile bombardment significantly promotes embryogenic callus induction in maize Hi II immature embryos. Compared to the image in FIG. 9A from the bombardment without a booster, the images in FIG. 9B and FIG. 9C show multiple embryonic structure formed and emerging 5 days after the particle bombardment.

Example 3. Transient Co-Expression of ZmPLT5 or ZmPLT7 and KWS-RBP1 Improves Stable Transformation of a Co-Delivered Report Gene in Maize Hi Immature Embryo Maize embryo preparation, transient bombardment, and embryonic callus induction are described in Examples 1 and 2. The embryos were cultured in N6-5Ag medium at 27° C. in the dark for 14 days. tDT fluorescence was used to monitor embryogenic callus induction and stable transformation by observation under a fluorescent microscope. Specifically, the boost effect was measured by its capability to increase transformation frequency (TF) of the tDT report gene 12 days after bombardment without a selection.

The strong and uniformed tDT fluorescent signals from the emerging embryonic structures in FIG. 10 indicated integration and stable transformation of tDT gene. Stable transformation frequency is defined as the number of embryos with at least one stable tDT fluorescent structures induced from 100 embryos initially used. Stable transformation frequency was measured 12 days after bombardment.

Transient co-expression of ZmPLT5 and KWS-RBP1 genes led to a 65% transformation frequency of the tDT gene (26-fold increase compared to the control without a booster), while the co-delivery of tDT with ZmPLT7 and KWS-RBP1 gave a 72.8% transformation frequency of the tDT gene (over 29-fold increase compared to the control) (FIG. 10D). The results from FIG. 10 suggest that transient co-expression of (i) ZmPLT5 or ZmPLT7 and (ii) KWS-RBP1 promote stable transformation frequency in maize Hi II immature embryos.

Stable transformation occurs at the single cell level, in which initially transferred DNA integrated into the genome of a host cell. To recover a homogenous transgenic plant, a few rounds of selection were needed to identify and purify the cells with the stable DNA integration. Without a booster, a stable transformation took a few weeks to develop (depending on the speed of cell proliferation), e.g. 4-8 weeks in maize. Compared to traditional transformation without a booster, the stable transformation shown in FIG. 10 was achieved only 12 days after bombardment with boost genes. Therefore, transient co-expression of ZmPLT5 or ZmPLT7 and KWS-RBP1 genes reduced the time needed for generating a stable transformation, and result in fast and highly efficient transformation in maize.

Figure 11:
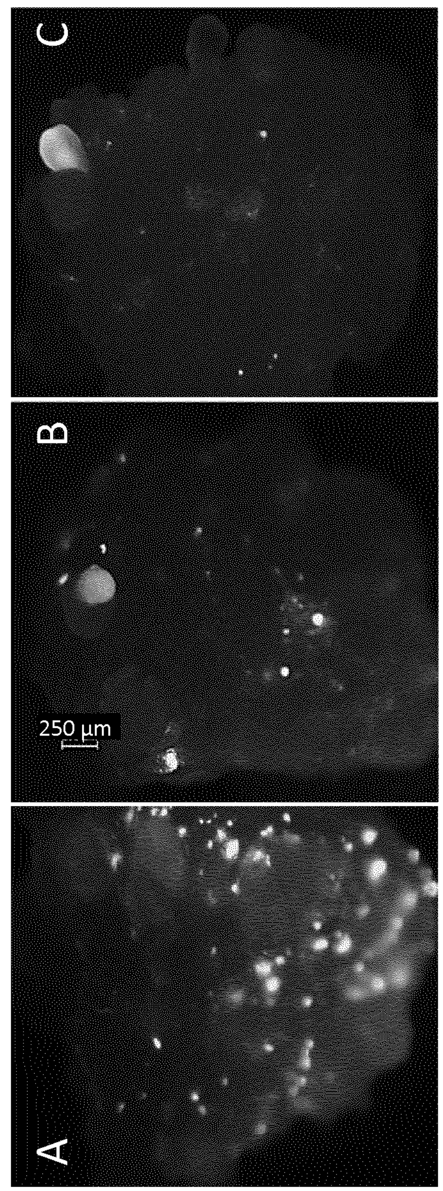
FIG. 11 shows transient co-expression of ZmPLT5 and KWS-RBP1 or ZmPLT7 and KWS-RBP1 promotes embryogenesis in A188 immature embryos. Images show embryogenic structures induced from maize A188 embryos 7 days after co-bombardment with boost gene constructs.

Example 4.1 Transient Co-Expression of ZmPLT5 or ZmPLT7 Gene and KWS-RBP1 Promotes Early Embryogenesis and Regeneration in Maize A188 Immature Embryo The experimental procedure was carried out as described in Example 2. The results were recorded seven days after bombardment. The results are shown in FIG. 11, which demonstrates that transient co-expression of ZmPLT5 (FIG. 11B) or ZmPLT7 (FIG. 11C) and KWS-RBP1 by microprojectile bombardment significantly promotes embryogenic structure induction in maize A188 immature embryos. Compared to the image in FIG. 11A without a booster, the images in FIG. 11B and FIG. 11C show multiple embryonic structures were formed. The structures emerged seven days after the particle bombardment.

Figure 23:
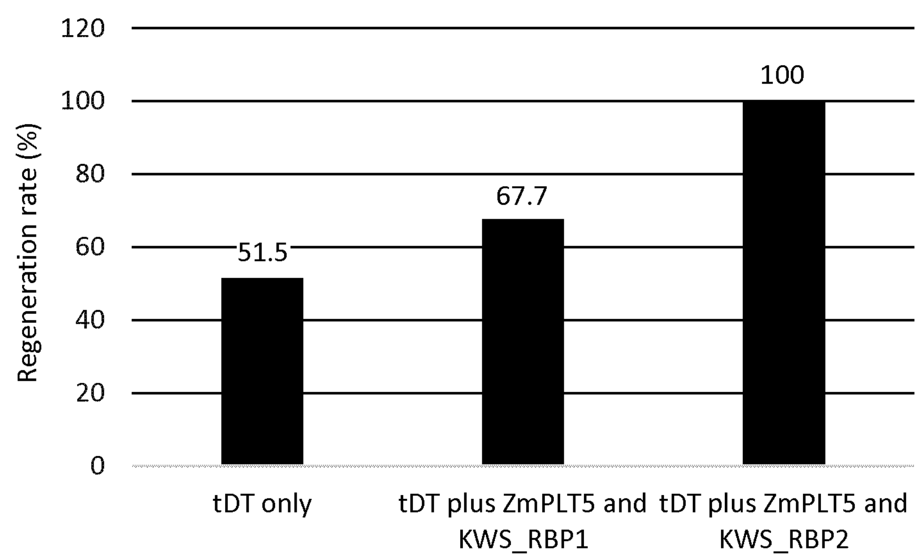
FIG. 23 illustrates that co-delivery of ZmPLT5 and KWS-RBG1 or ZmPLT5 and KWS-RBP2 promotes regeneration rate in maize A188. Maize immature embryos were bombarded with genome engineering constructs pGEP359 (FIG. 6) and pGEP324 (FIG. 7) only (tDTonly) or co-bombarded with ZmPLT5 and KWS_RBP1 (tDT plus ZmPLT5 and KWS_RBP1) or with ZmPLT5 and KWS_RBP2 (tDT plus ZmPLT5 and KWS_RBP2).

Example 4.2 Transient Co-Expression of ZmPLT5 Gene and KWS-RBP2 Promotes Early Embryogenesis and Regeneration in Maize A188 Immature Embryo The experimental procedure was carried out as described in Example 2. The results were recorded ten days after bombardment. The results are shown in FIG. 23, which demonstrates that transient co-expression of ZmPLT5 and KWS-RBP2 by microprojectile bombardment significantly promotes embryogenic structure induction in maize A188 immature embryos. The regeneration rate (in %) after co-expression of ZmPLT5 gene and KWS-RBP2 is even higher than the rate observed after co-expression of ZmPLT5 gene and KWS-RBP1. Regeneration rate is defined as the number of embryos giving at least one plant regenerated from 100 embryos initially used. Data was record 10 days after bombardment.

Example 5.1 Transient Co-Expression of ZmPLT5 or ZmPLT7 Gene and KWS-RBP1 Promotes Early Stable Transformation of a Co-Delivered Report Gene in Maize A188 Immature Embryo The experimental procedure was carried out as described in Example 3. The results were recorded 16 days after bombardment. The strong and uniformed tDT fluorescent signals from the emerging embryonic structures in FIGS. 12B and 12C indicate integration and stable transformation of tDT gene. Compared to the image in FIG. 12A, the red fluorescence images in FIGS. 12B and 12C illustrate that co-expression of ZmPLT5 (FIG. 12B) or ZmPLT7 (FIG. 12C) with KWS-RBP1 significantly improves stable transformation of the report gene in maize A188 immature embryos.

After 16 days from bombardment of A188 immature embryos without selection, no stable transformation was observed from the control without a booster. Compared to the control, co-bombardment of the tDT construct with ZmPLT5 and KWS-RBP1 led to 12.2% of the transformation frequency, while co-bombardment with ZmPLT7 and KWS-RBP1 gave 7.1% of transformation frequency of tDT report (FIG. 12D) 16 days after bombardment in maize A188.

Example 5.2 Transient Co-Expression of ZmPLT5 and KWS-RBP2 Promotes Early Stable Transformation of a Co-Delivered Report Gene in Maize A188 Immature Embryo The experimental procedure was carried out as described in Example 3. The results were recorded 10 days after bombardment. The strong and uniformed tDT fluorescent signals from the emerging embryonic structures in FIGS. 24B and 24C indicate integration and stable transformation of tDT gene. Compared to the image in FIG. 24A, the red fluorescence images in FIGS. 24B and 24C illustrate that co-expression of ZmPLT5 with KWS-RBP1 and ZmPLT5 with KWS-RBP2 significantly improves stable transformation of the report gene in maize A188 immature embryos.

After 16 days from bombardment of A188 immature embryos without selection, no stable transformation was observed from the control without a booster (tDT only; FIG. 25A). Compared to the control, co-bombardment of the tDT construct with ZmPLT5 and KWS-RBP1 (FIG. 25B) led to 9.8% of the transformation frequency, while co-bombardment with ZmPLT5 and KWS-RBP2 (FIG. 25C) gave 79.2% of transformation frequency of tDT report (FIG. 25D) 16 days after bombardment in maize A188.

Example 6. Wheat RKD4 Activates Maize WUSCHEL (WUS) Expression

Figure 13:
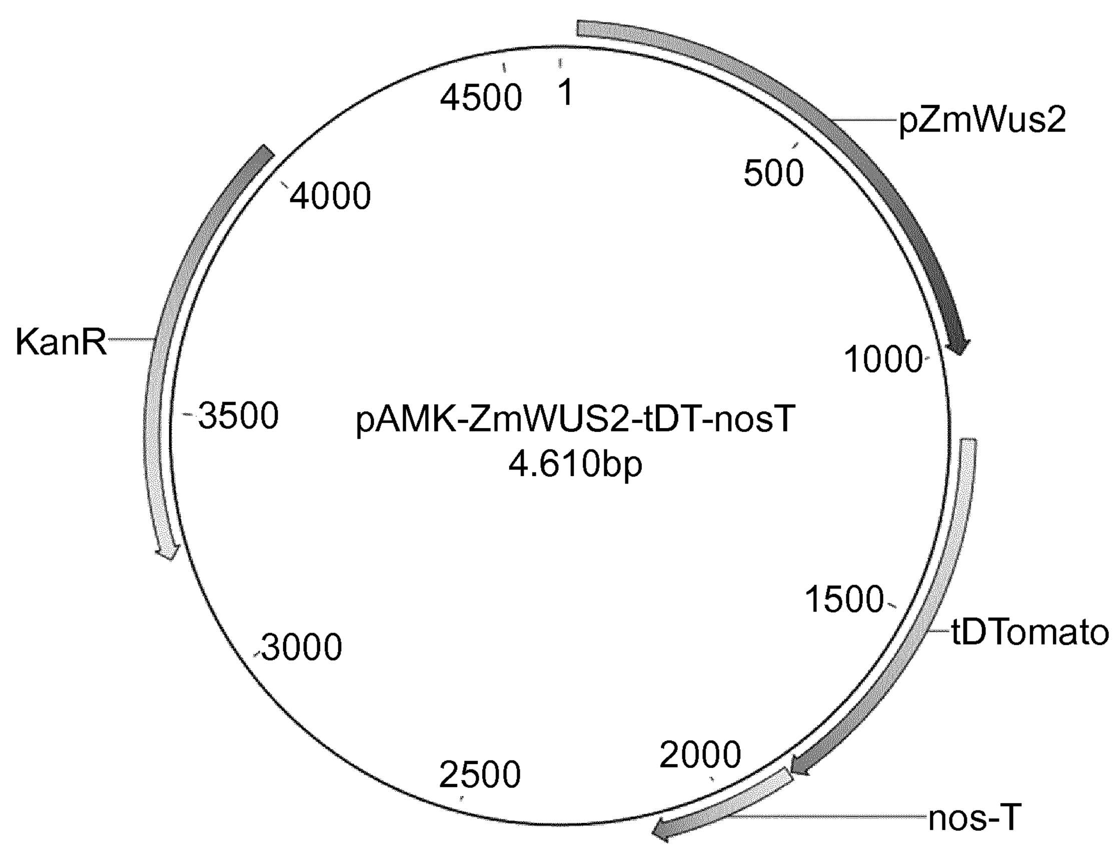
FIG. 13 shows a map of the maize WUS2 (ZmWUS2) promoter report construct pAMK-ZmWUS2-tDT-nosT (SEQ ID NO: 43). tDTomato define the fluorescence tDT report gene, which is driven by maize WUSCHEL2 promoter (pZmWUS2).

Homeobox domain transcriptional factor WUSCHEL (WUS) plays an important role in establishing and maintaining of shoot meristem. To identify boost factors that promote endogenous WUS2 expression, the maize WUSCHEL 2 promoter report construct (pAMK-ZmWUS2-tDT-noT) (SEQ ID NO: 43; FIG. 13) was used to illustrate maize WUS2 promoter activity. The maize WUS2 promoter (pZmWUS2) drove expression of the tDT report gene in this report construct (FIG. 13). The WUS2 promoter report construct was co-bombarded with boost factors individually in maize immature embryos and leaf segments.

Fresh leaf segments of 1-2 cm in length were prepared from the in vitro-cultured maize A188 seedling of 10-14 days old, and placed on the Osmotic medium with abaxial side up for 4 hours. For co-bombardment, two plasmids (100 ng of ZmWUS2 promoter report (FIG. 13) and 100 ng of boost construct, e.g. TaRKD4 (FIG. 5)) were premixed and coated onto 100 μg of gold particles size 0.4 μm. Immature embryo preparation, bombardment, and post-bombardment culturing were carried out as described in Example 1 and Example 2. Red fluorescence showing tDT expression was monitored using a fluorescent microscope started at 16 hours after bombardment.

WUS is transcribed specifically in the organization center (OC) of plant shoot apical meristem (SAM) and controls stem cell identity in the SAM.

Figure 14:
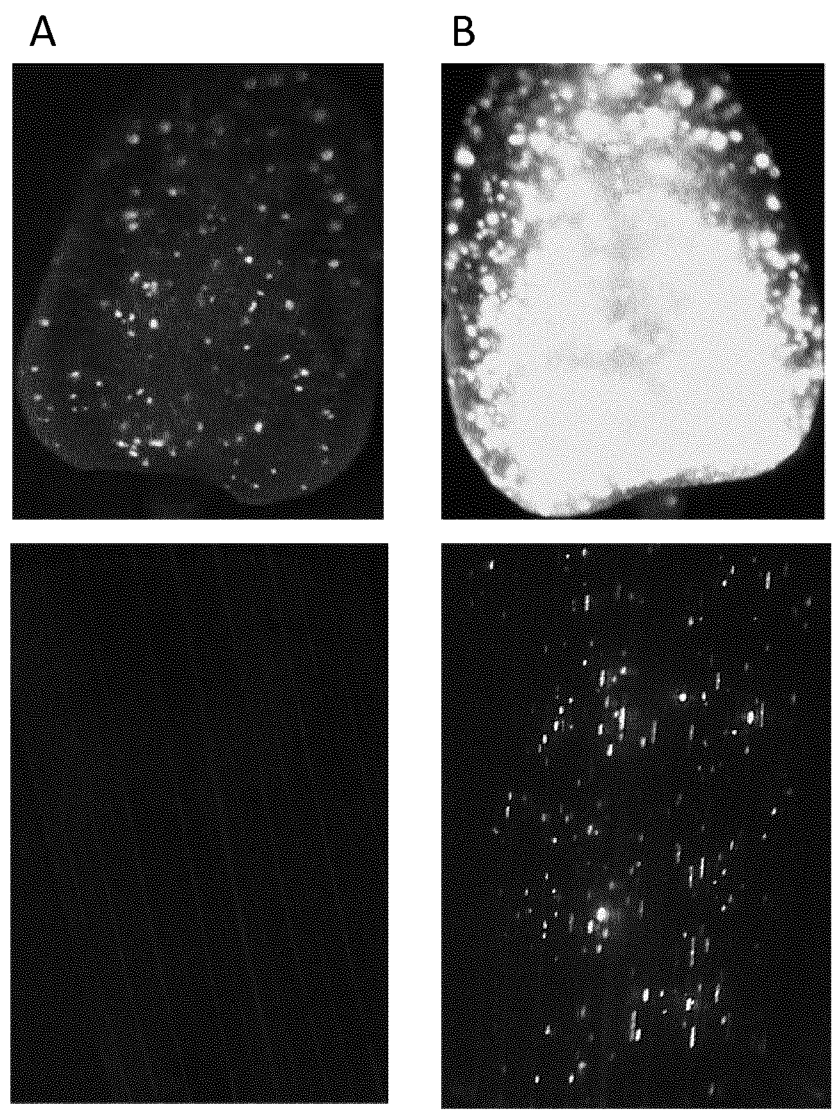
FIG. 14 shows that wheat TaRKD4 gene activates maize WUS2 promoter by transient co-bombardment in maize immature embryos IE (top panel) and leaves (bottom panel).

Bombardment with the ZmWUS2 promoter report only (pZmWUS2 report only) did not result in any tDT fluorescent signals from the bombarded leaf samples at any time during the after-bombardment culture (16 hours to 7 days). However, when co-bombarded with wheat RKD4 construct (FIG. 5), the tDT signal was detected in the leaf segments around 36 hours after bombardment, and peaked around 44 hours after bombardment (the bottom panel in FIG. 14B). Compared to the control bombardment with the WUS promoter reporter only, in which only weak tDT signals were noticed from the immature embryos (the top panel in FIG. 14A), extremely strong red fluorescent signals were observed from the embryos co-bombarded with the WUS promoter reporter and wheat RKD4 construct (the top panel in FIG. 14B). These results suggest wheat RKD4 strongly activate maize WUS2 genes. Images were taken 44 hours after bombardment.

Example 7. Transient Co-Expression of TaRKD4 and KWS-RBP1 Promotes Early Embryogenesis from Maize Hi II Immature Embryo FIG. 15 shows that co-expression of wheat RKD4 (FIG. 5) and KWS-RBP1 (FIG. 4) by microprojectile bombardment significantly promotes embryogenic structure induction in maize Hi II immature embryos. The experiment was conducted as described in Example 2, with results recorded 5 days after bombardment. Compared to the image in FIG. 15A without a booster, the images in FIG. 15B show multiple embryonic structure were formed and emerging 5 days after the particle bombardment. Images were taken 5 days after the particle bombardment.

Example 8. Transient Co-Expression of TaRKD4 and KWS-RBP1 Promotes Early Stable Transformation of a Co-Delivered Report Gene from Maize Hi II Immature Embryo The experiment was conducted as described in Example 3, with results recorded 12 days after bombardment.

The strong and uniformed tDT fluorescent signals from the emerging embryonic structures in FIG. 16B indicate integration and stable transformation of tDT gene. Compared to the image in FIG. 16A, the red fluorescence images in FIG. 16B illustrate that co-delivery of TaRKD4 and KWS-RBP1 significantly improves stable transformation of the report gene in maize Hi II immature embryos.

12 days after bombardment of Hi II immature embryos without a selection, no stable transformation was observed from the control bombardment without a booster. Compared to the control, co-bombardment of the tDT construct with TaPLT4 and KWS-RBP1 led to 23.5% of the transformation frequency of the tDT report (FIG. 16C).

Example 9. Transient Co-Expression of TaRKD4 and KWS-RBP1 Promotes Early Embryogenesis from Maize A188 Immature Embryo The experiment was conducted as described in Example 3, with results recorded 5 days after bombardment. FIG. 17 shows that co-delivery of TaRKD4 (FIG. 5) and KWS-RBP1 (FIG. 4) by microprojectile bombardment significantly promotes embryogenic structure induction in maize A188 immature embryos. Compared to the image in FIG. 17A without a booster, the images in FIG. 17B show multiple embryonic structure were formed and emerged 5 days after the particle bombardment. Images were taken 5 days after the particle bombardment.

Example 10. Transient Co-Expression of TaRKD4 and KWS-RBP1 Promotes Early Stable Transformation of a Co-Delivered Report Gene from Maize A188 Immature Embryo The experiment was conducted as described in Example 3, with results recorded 14 days after bombardment. Strong and uniform tDT fluorescent signals from the emerging embryonic structures in FIG. 18B indicate integration and stable transformation of the tDT gene. Compared to the image in FIG. 18A, the red fluorescence images in FIG. 18B illustrate that co-delivery of TaRKD4 and KWS-RBP1 significantly improves stable transformation of the report gene in maize A188 immature embryos.

No stable tDT fluorescent structure was observed from the control bombardment without a booster at 14 days after bombardment of A188 immature embryos without a selection. Compared to the control, co-bombardment of the tDT construct with TaRKD4 and KWS-RBP1 led to 35.5% of the transformation frequency of tDT report from A188 immature embryo (FIG. 18C).

Example 11. Co-Expression of the Boost Genes with Genome Editing Components Promotes Transient Genome Editing in Maize For embryo preparation, bombardment, and post-bombardment embryo culture, the procedures described in Example 1 and Example 2 were carried out. After callus induction in N6-5Ag medium for 14 days (Hi II) or 18 days (A188), the fast-growing embryogenic calluses from the bombarded scutellum surface of the embryos were picked and transferred onto MRM1 medium (see below) for embryo maturation. After about two weeks of culturing in MRM1 medium at 25° C. in the dark, mature embryos were moved onto MSO medium (see below) for embryo germination in phytotray in light at 25° C. After about 10 days of culturing in MSO medium, the regenerated plantlets were ready for molecular analysis and were transferred to soil. An approximately 5 mm leaf tip from all the leaves of a regenerated plantlet were collected for DNA extraction. The site-specific genome modification from the regenerated plants was screened by Taqman qPCR, marker capillary electrophoresis, and confirmed by Digital PCR, next generation sequencing (NGS), and Sanger sequencing. DNA integration was examined by qPCR.

Without a booster, genome editing using the Cpf1 (pGEP359) and crRNA5 (pGEP324) did not result in any detectable editing event by transient expression with a selection (GE only) (FIG. 19). However, with co-expression with ZmPLT5 and KWS-RBP1 (GE plus ZmPLT5 and KWS-RBP1), 1% of transient genome editing efficiency was achieved (FIG. 19A), and 0.8% transient genome editing efficiency was also obtained when co-expressed with ZmPLT7 and KWS-RBP1 (GE plus ZmPLT5 and KWS-RBP1) (FIG. 19B). These results suggest the booster ZmPLT5, ZmPLT7, and KWS-RBP1 improve transient genome editing.

Media

MRM1: MS Salts+MS vitamins+100 mg/L of myoinositol+6% sucrose+9 g/L of Bactoagar, pH 5.8

MS0: MS Salts+MS vitamins+2 g/L of myoinositol+2% sucrose+8 g/L of Bactoagar, pH 5.8

Figure 20A:
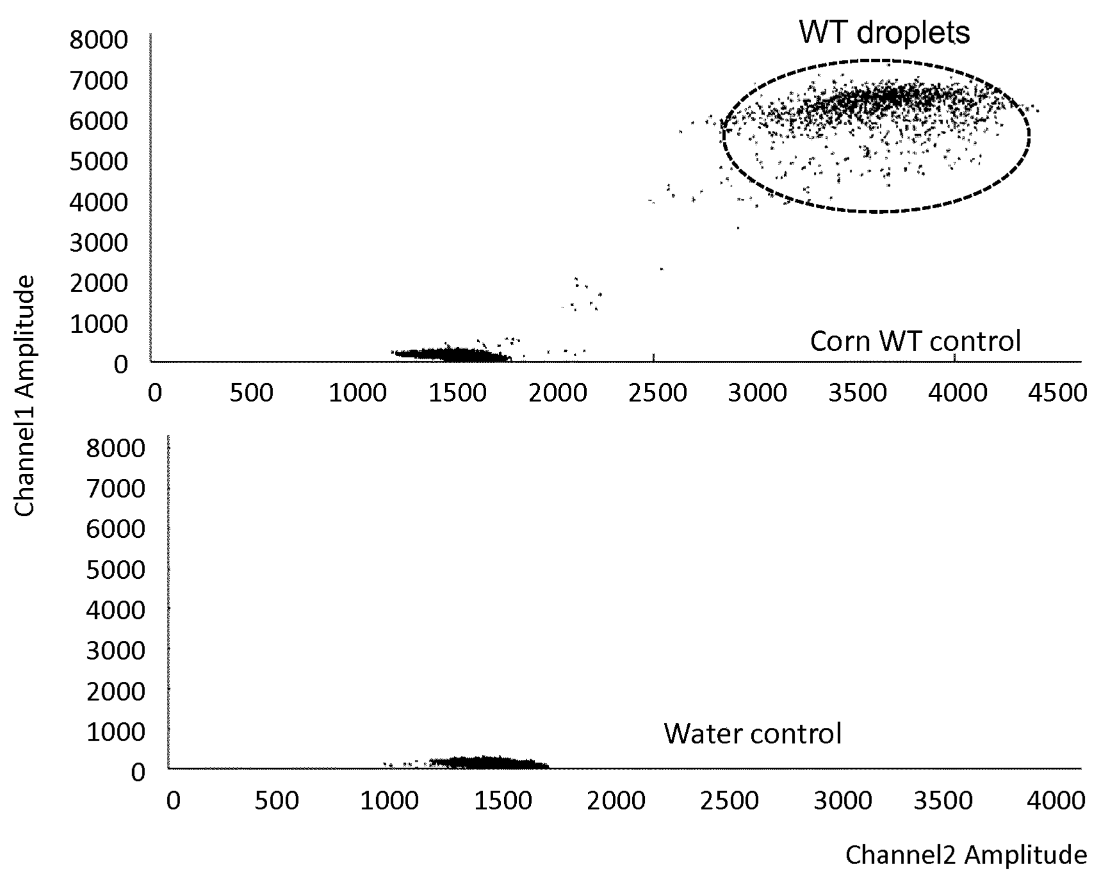
FIG. 20A shows negative control results from Droplet Digital PCR using water (bottom) or the wild type DNA (WT droplets).
Figure 20B:
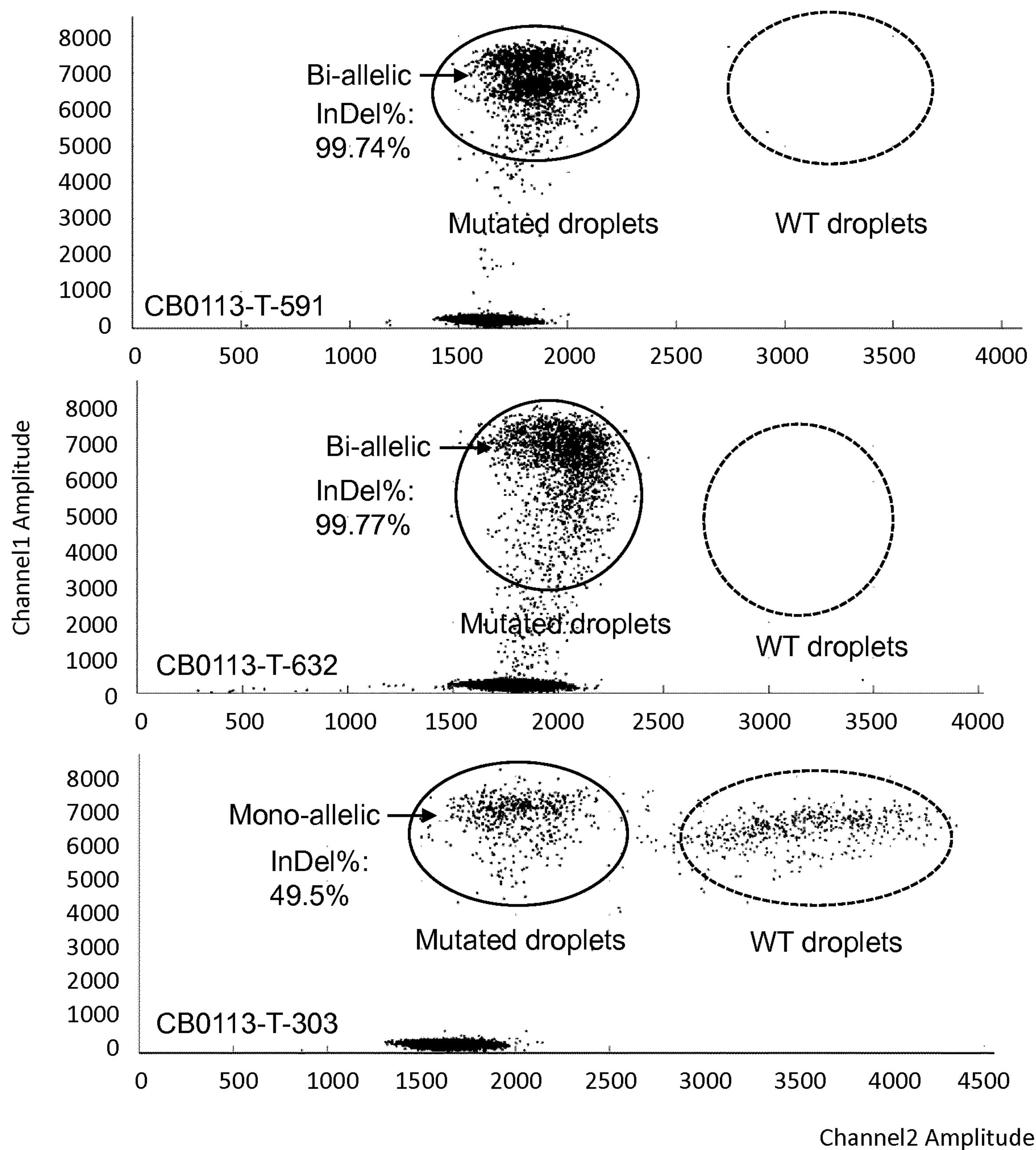
FIG. 20B shows Droplet Digital PCR results from the edited T0 plants derived from transient co-expression of boosters and genome editing components. The top and middle graphs show a near 100% InDel rate from two edited T0 plants, indicating homogenous bi-allelic modification, while the bottom graph illustrates a homogenous mono-allelic edited event.
Figure 22:
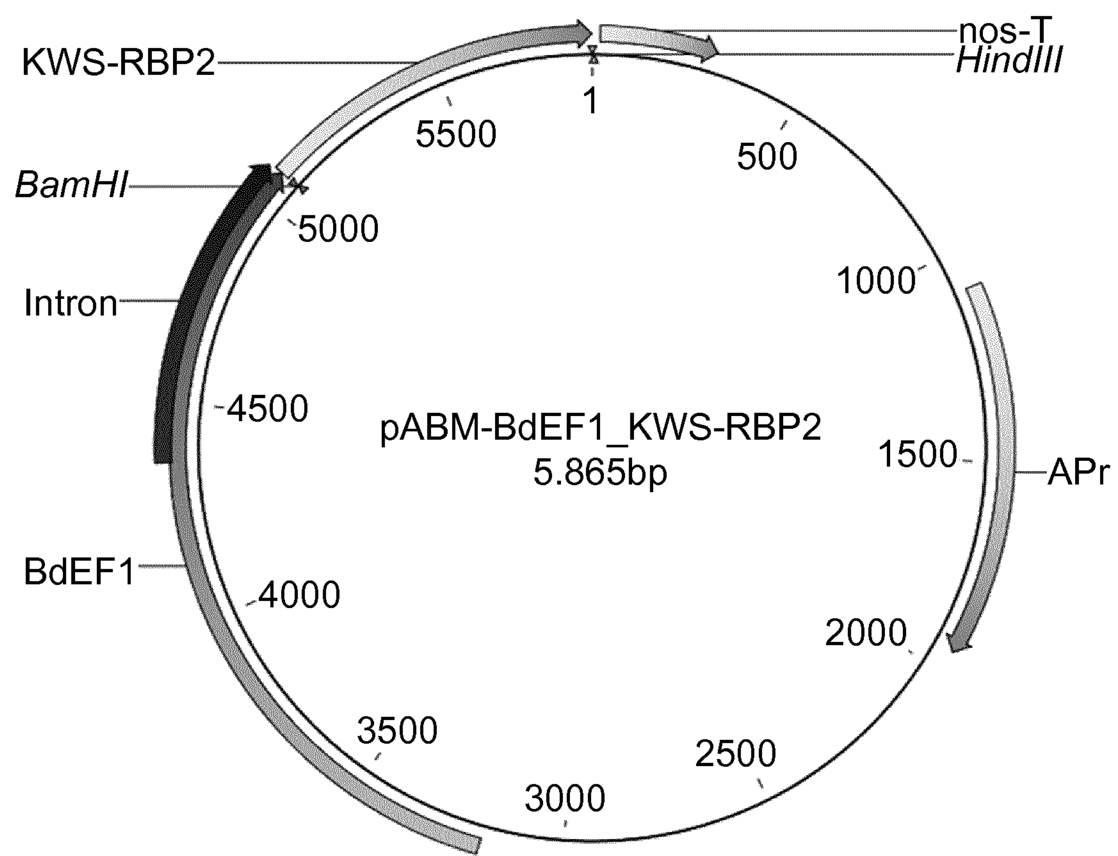
FIG. 22 shows KWS-RBP2 expression construct (pABM-BdEF1_KWS_RBP2) map. KWS-RBP2 gene was maize-codon optimized from its protein sequence and synthesized by Integrated DNA Technologies (IDT, San Diego, Calif., USA), and cloned into expression vector pABM-BdEF1 (FIG. 1) at the cloning site of BamHI and HindIII. pKWS-RBP2 gene is driven by the strong constitutive EF1 promoter from *Brachypodium* (pBdEF1).

Example 12. Homogenously Edited Plants can be Recovered by Transient Co-Expression of Genome Editing Components with the Boost Genes in Maize Droplet Digital PCR (ddPCR) was performed with transient co-expression of the boost genes and genome editing components without a selection. The site-specific InDel rates around 50% and 100% indicate a mono-allelic and bi-allelic modification, respectively. The data in FIG. 20A are results from a negative control with Droplet Digital PCR using water (bottom) or the wild type DNA (WT droplets). FIG. 20B shows the results from Droplet Digital PCR performed on edited T0 plants derived from transient co-expression of boosters and genome editing components. The top and middle graphs show a near 100% InDel rate from two edited T0 plants, indicating homogenous bi-allelic modification, while the bottom graph illustrates a homogenous mono-allelic edited event.

Without wishing to be bound by theory, genetic modification occurs at single cell level. To recover a homogenously modified plant, a selection is normally required to isolate the cells with a modification and remove wild-type cells. A conventional selection generally involves using an integrated selection marker, e.g. antibiotic (e.g. kanamycin, hygromycin), or herbicide (e.g. phosphinothricin, glyphosate) resistance gene. Without an integrated selection marker as the case in transient genome editing, regenerated plants will most likely be chimeric.

In contrast, the Droplet Digital PCR (ddPCR) results shown in FIG. 20 suggest that homogenous genome editing can be achieved by transient co-expression of genome editing components with the boost genes without a selection. An around 50% or 100% InDel rate from all the edited plants indicate a homogenous mono-allelic or bi-allelic modification. Sanger sequencing results further confirm the ddPCR results (FIG. 21). These results suggest that transient co-expression with the boost genes can lead to plant regeneration from single cell.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A booster polypeptide comprising an amino acid sequence of SEQ ID NO: 2 or 48, or an amino acid sequence at least 93% identical to SEQ ID NO: 2 or 48.

2. A nucleic acid encoding said booster polypeptide of claim 1.

3. A nucleic acid of claim 2, wherein the nucleic acid encoding the booster polypeptide comprising an amino acid sequence of SEQ ID NO: 2, or an amino acid sequence at least 93% identical to SEQ ID NO: 2, comprises a coding sequence selected from the group consisting of:

(i) a nucleic acid comprising the nucleotide sequence of SEQ ID NO: 1; and (ii) a nucleic acid comprising a nucleotide sequence at least 93% identical to SEQ ID NO: 1; and wherein the nucleic acid encoding the booster polypeptide comprising an amino acid sequence of SEQ ID NO: 48, or an amino acid sequence at least 93% identical to SEQ ID NO: 48, comprises a coding sequence selected from the group consisting of:

(I) a nucleic acid comprising the nucleotide sequence of SEQ ID NO: 47; and (II) a nucleic acid comprising a nucleotide sequence at least 93% identical to SEQ ID NO: 47.

4. A recombinant gene comprising the nucleic acid of claim 2.

5. The recombinant gene of claim 4, wherein the nucleic acid is operably linked to a heterologous promoter.

6. The recombinant gene of claim 5, wherein the heterologous promoter is a strong constitutive promoter, a tissue-specific promoter, a development-specific promoter, or an inducible promoter.

7. A DNA construct comprising the nucleic acid of claim 2.

8. A plant cell comprising the booster polypeptide of claim 1.

9. A plant, a part thereof, a seed, an embryo or a callus comprising the cell of claim 8.

10. A method for genetic modification in a plant cell, the method comprising (a) introducing into the plant cell (i) a booster polypeptide comprising an amino acid sequence of SEQ ID NO: 2 or 48, or an amino acid sequence at least 93% identical to SEQ ID NO: 2 or 48; and (ii) a transgene of interest and/or a genome engineering component;

(b) optionally, cultivating the plant cell under conditions allowing the synthesis of the booster polypeptide from the nucleic acid, the recombinant gene or the DNA construct; and (c) optionally, cultivating the plant cell under conditions allowing the genetic modification of the genome of said plant cell by integration of the transgene of interest and activity of the genome engineering component in the presence of the booster polypeptide.

11. The method of claim 10, wherein the booster polypeptide is transiently present, transiently active and/or transiently expressed in the plant cell, or wherein the nucleic acid encoding the booster polypeptide is transiently present, transiently active and/or transiently expressed in the plant cell.

12. The method of claim 10, wherein in step (i) additionally one or more polypeptides selected from the group consisting of (i) a PLETHORA 5 (PLT5) polypeptide, a PLETHORA 7 (PLT7) polypeptide, an RWP-RK4 domain-containing (RKD4) polypeptide, and an RWP-RK2 domain-containing (RKD2) polypeptide, and/or (ii) one or more nucleic acids selected from the group consisting of a nucleic acid encoding a PLT5 polypeptide, a PLT7 polypeptide, an RKD4 polypeptide, and an RKD2 polypeptide, and/or (iii) one or more site-directed transcriptional activators suitable to increase transiently the expression of an endogenous PLT5 polypeptide, an endogenous PLT7 polypeptide, an endogenous RKD4 polypeptide, or an endogenous RKD2 polypeptide, and/or (iv) a nucleic acid encoding such site-directed transcriptional activator are introduced into the plant cell.

13. The method of claim 12, wherein the PLT5 polypeptide or the PLT7 polypeptide is transiently present, transiently active and/or transiently expressed in the plant cell, or wherein the nucleic acid encoding the PLT5 polypeptide or the PLT7 polypeptide is transiently present, transiently active and/or transiently expressed in the plant cell.

14. The method of claim 12, wherein both the booster polypeptide or the nucleic acid encoding the booster polypeptide, and the PLT5 polypeptide or the nucleic acid encoding the PLT5 polypeptide are introduced into the plant cell, and optionally transiently co-expressed; and/or wherein both the booster polypeptide or the nucleic acid encoding the booster polypeptide, and the PLT7 polypeptide or the nucleic acid encoding the PLT5 polypeptide are introduced into the plant cell, and optionally transiently co-expressed.

15. The method of claim 12, wherein the PLT5 polypeptide comprises the amino acid sequence of SEQ ID NO: 4 or 6, or an amino acid sequence at least 95% identical to SEQ ID NO: 4 or 6; or wherein the nucleic acid encoding the PLT5 polypeptide encodes the amino acid sequence of SEQ ID NO: 4 or 6, or an amino acid sequence at least 95% identical to SEQ ID NO: 4 or 6; or wherein the PLT7 polypeptide comprises the amino acid sequence of SEQ ID NO: 8 or 10, or an amino acid sequence at least 95% identical to SEQ ID NO: 8 or 10; or wherein the nucleic acid encoding the PLT7 polypeptide encodes the amino acid sequence of SEQ ID NO: 8 or 10, or an amino acid sequence at least 95% identical to SEQ ID NO: 8 or 10; or wherein the RKD4 polypeptide comprises the amino acid sequence of SEQ ID NO: 12, 14 or 16, or an amino acid sequence at least 95% identical to SEQ ID NO: 12, 14 or 16; or wherein the nucleic acid encoding the RKD4 polypeptide encodes the amino acid sequence of SEQ ID NO: 12, 14 or 16, or an amino acid sequence at least 95% identical to SEQ ID NO: 12, 14 or 16; or wherein the RKD2 polypeptide comprises the amino acid sequence of SEQ ID NO: 18, 20 or 22, or an amino acid sequence at least 95% identical to SEQ ID NO: 18, 20 or 22; or wherein the nucleic acid encoding the RKD2 polypeptide encodes the amino acid sequence of SEQ ID NO: 18, 20 or 22, or an amino acid sequence at least 95% identical to SEQ ID NO: 18, 20 or 22.

16. The method of claim 12, wherein nucleic acid encoding the PLT5 polypeptide comprises a nucleic acid having a coding sequence selected from the group consisting of:

(i) a nucleic acid comprising the nucleotide sequence of SEQ ID NO: 3 or 5; and (ii) a nucleic acid comprising a nucleotide sequence at least 95% identical to SEQ ID NO: 3 or 5;

wherein the nucleic acid encoding the PLT7 polypeptide comprises a nucleic acid having a coding sequence selected from the group consisting of:

(I) a nucleic acid comprising the nucleotide sequence of SEQ ID NO: 7 or 9; and (II) a nucleic acid comprising a nucleotide sequence at least 95% identical to SEQ ID NO: 7 or 9;

wherein the nucleic acid encoding the RKD4 polypeptide comprises a nucleic acid having a coding sequence selected from the group consisting of:

(1) a nucleic acid comprising the nucleotide sequence of SEQ ID NO: 11, 13, or 15; and (2) a nucleic acid comprising a nucleotide sequence at least 95% identical to SEQ ID NO: 11, 13, or 15;

wherein the nucleic acid encoding the RKD2 polypeptide comprises a nucleic acid having a coding sequence selected from the group consisting of:

a) a nucleic acid comprising the nucleotide sequence of SEQ ID NO: 17, 19, or 21; and b) a nucleic acid comprising a nucleotide sequence at least 95% identical to SEQ ID NO: 17, 19, or 21.

17. The method of claim 10, wherein the genome engineering component comprises a) an enzyme inducing a double-stranded break (DSB) or a nucleic acid encoding same, and optionally a repair nucleic acid molecule, wherein the DSB-inducing enzyme preferably recognizes a predetermined site in the genome of said cell;

b) an enzyme inducing a single-stranded break (SSB) or a nucleic acid encoding same, and optionally a repair nucleic acid molecule, wherein the SSB-inducing enzyme preferably recognizes a predetermined site in the genome of said cell;

c) a base editor enzyme, optionally fused to a disarmed DSB- or SSB-inducing enzyme, wherein the base editor enzyme preferably recognizes a predetermined site in the genome of said cell; or d) an enzyme effecting DNA methylation, histone acetylation, histone methylation, histone ubiquitination, histone phosphorylation, histone ribosylation or histone citrullination, optionally fused to a disarmed DSB- or SSB-inducing enzyme, wherein the enzyme preferably recognizes a predetermined site in the genome of said cell.

18. The method of claim 10, wherein the genome engineering component comprising a DSB- or SSB-inducing enzyme or a variant thereof is a CRISPR/Cas endonuclease, a CRISPR/Cas9 endonuclease, a CRISPR/Cpf1 endonuclease, a CRISPR/Csm1 endonuclease, a zinc finger nuclease (ZFN), a homing endonuclease, a meganuclease, or a TAL effector nuclease.

19. The method of claim 10, wherein the activity of the genome engineering component in step (c) comprises inducing one or more double-stranded breaks in the genome of the plant cell, one or more single strand breaks in the genome of the plant cell, one or more base editing events in the genome of the plant cell, or one or more of DNA methylation, histone acetylation, histone methylation, histone ubiquitination, histone phosphorylation, histone sumoylation, histone ribosylation or histone citrullination in the genome of the plant cell.

20. The method of claim 19, wherein the induction of one or more double-stranded breaks or one or more single strand breaks is followed by non-homologous end joining (NHEJ) and/or by homology directed repair of the break(s) though a homologous recombination mechanism (HDR).

21. The method of claim 10, wherein the transgene in step (a) (ii) is selected from the group consisting of a gene encoding resistance to abiotic stress, a gene encoding tolerance to abiotic stress, a gene encoding resistance to biotic stress, a gene encoding tolerance to biotic, and a gene encoding a yield related trait.

22. The method of claim 10, wherein in step (c) the modification of said genome is selected from i) a replacement of at least one nucleotide;

ii) a deletion of at least one nucleotide;

iii) an insertion of at least one nucleotide;

iv) a change of the DNA methylation;

v) a change in histone acetylation, histone methylation, histone ubiquitination, histone phosphorylation, histone sumoylation, histone ribosylation or histone citrullination; and vi) any combination of i)-v).

23. The method of claim 10, wherein the method is effective to promote cell proliferation or cell regeneration preferably after genetic modification.

24. The method of claim 10, wherein the method is effective to induce embryogenesis from a single cell preferably after genetic modification.

25. The method of claim 10, wherein the method is effective to increase the stable transformation efficiency of the transgene into the plant cell.

26. The method of claim 10, wherein the method is effective to increase the efficiency of the genome engineering component to edit the genome of the plant cell.

27. The method of claim 12, wherein the site-directed transcriptional activator, or the nucleic acid encoding the same, comprising at least one recognition domain and at least one activation domain, wherein the site-directed transcriptional activator is configured to increase the expression of an endogenous PLT5 polypeptide, an endogenous PLT7 polypeptide, an endogenous RKD4 polypeptide, or an endogenous RKD2 polypeptide, by binding to a regulation region located at a certain distance in relation to the start codon of the endogenous PLT5 polypeptide, the endogenous PLT7 polypeptide, the endogenous RKD4 polypeptide, or the endogenous RKD2 polypeptide.

28. The method of claim 27, wherein the at least one recognition domain is, or is a fragment, of a molecule selected from the group consisting of at least one TAL effector, at least one disarmed CRISPR/nuclease system, at least one Zinc-finger domain, and at least one disarmed homing endonuclease, or any combination thereof.

29. The method of claim 28, wherein the at least one disarmed CRISPR/nuclease system is selected from a CRISPR/dCas9 system, a CRISPR/dCpf1 system, a CRISPR/dCsm1 system, a CRISPR/dCasX system or a CRISPR/dCasY system, or any combination thereof, wherein the at least one disarmed CRISPR/nuclease system comprises at least one guide RNA.

30. The method of claim 27, wherein the at least one activation domain is an acidic transcriptional activation domain.

31. A method for improving the efficiency of plant regeneration or increasing the regeneration ability of a plant cell comprising introducing into the plant cell a booster polypeptide comprising an amino acid sequence of SEQ ID NO: 2 or 48, or an amino acid sequence at least 93% identical to SEQ ID NO: 2 or 48.

32. The method of claim 10, further comprising regenerating a plant from the modified plant cell of step (a).

33. The method of claim 32, wherein the produced plant does not contain any of the genome engineering components, boost genes, and booster polypeptides introduced in step (a) of claim 10.

* * * * *

SEQUENCE LISTING

```
<160> NUMBER OF SEQ ID NOS: 59

<210> SEQ ID NO 1
<211> LENGTH: 783
<212> TYPE: DNA
<213> ORGANISM: Artificial Sequence
```

<220> FEATURE:
<223> OTHER INFORMATION: Description of Artificial Sequence: Synthetic polynucleotide
<220> FEATURE:
<223> OTHER INFORMATION: coding sequence of KWS_RBP1

<400> SEQUENCE: 1

```
atggagtcgg gctccgggac ggctgctggc tctggctatg tttacagaca gccaggatca     60

acgcggtgga acccgacagc tgaacaactg tccttgctta gagaaatcta ctaccgcaac    120

ggattgcgga ccccgaccgc ggacgaaatc agacaaatca gctcaaagct ctcaaggtac    180

ggaaaaatag agggcaaaaa cgtttacaac tggttccaga atagacgcgc aagagaaaag    240

cgcaagcaac ggctctctac aatcggctgt gatccagcac tgatcgagat ggggaatgtc    300

gcttcactgg aattcggtac tgagagcgcc ctggaatcgc tgtcgtcagg accatcctca    360

gaactccgcg aagcgccaac gagaaaattt tacgaaaaaa agacggttgg agagaactca    420

actataataa acccagtgga acaaaactgt accctttcct gcggaacgtc ccaagagttc    480

cagtatgcgg tcgattctcg gcgcgtcatg aaagctatgg aggaaaagca ggcgacggac    540

gatgaacccg acggaaataa atggactgag tcaaacagac acgtcaagat tctccagctt    600

ttcccgctcc acaataacga ggatcagaca ttgataaaga gcgacaaaga aatctattgt    660

ttgggctcgt gcgagaagaa aatggatttg tcaccgctgg gtcattcagg ctctcagcgc    720

gcttcggccc ttgacttgtg cctttcattg ggcaacgaat cttgtgggct gcatgataat    780

tga                                                                  783
```

<210> SEQ ID NO 2
<211> LENGTH: 260
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: protein of KWS_RBP1

<400> SEQUENCE: 2

```
Met Glu Ser Gly Ser Gly Thr Ala Ala Gly Ser Gly Tyr Val Tyr Arg
1               5                   10                  15

Gln Pro Gly Ser Thr Arg Trp Asn Pro Thr Ala Glu Gln Leu Ser Leu
            20                  25                  30

Leu Arg Glu Ile Tyr Tyr Arg Asn Gly Leu Arg Thr Pro Thr Ala Asp
        35                  40                  45

Glu Ile Arg Gln Ile Ser Ser Lys Leu Ser Arg Tyr Gly Lys Ile Glu
    50                  55                  60

Gly Lys Asn Val Tyr Asn Trp Phe Gln Asn Arg Arg Ala Arg Glu Lys
65                  70                  75                  80

Arg Lys Gln Arg Leu Ser Thr Ile Gly Cys Asp Pro Ala Leu Ile Glu
                85                  90                  95

Met Gly Asn Val Ala Ser Leu Glu Phe Gly Thr Glu Ser Ala Leu Glu
            100                 105                 110

Ser Leu Ser Ser Gly Pro Ser Ser Glu Leu Arg Glu Ala Pro Thr Arg
        115                 120                 125

Lys Phe Tyr Glu Lys Lys Thr Val Gly Glu Asn Ser Thr Ile Ile Asn
    130                 135                 140

Pro Val Glu Gln Asn Cys Thr Leu Ser Cys Gly Thr Ser Gln Glu Phe
145                 150                 155                 160
```

```
Gln Tyr Ala Val Asp Ser Arg Arg Val Met Lys Ala Met Glu Glu Lys
                165                 170                 175

Gln Ala Thr Asp Asp Glu Pro Asp Gly Asn Lys Trp Thr Glu Ser Asn
            180                 185                 190

Arg His Val Lys Ile Leu Gln Leu Phe Pro Leu His Asn Asn Glu Asp
        195                 200                 205

Gln Thr Leu Ile Lys Ser Asp Lys Glu Ile Tyr Cys Leu Gly Ser Cys
    210                 215                 220

Glu Lys Lys Met Asp Leu Ser Pro Leu Gly His Ser Gly Ser Gln Arg
225                 230                 235                 240

Ala Ser Ala Leu Asp Leu Cys Leu Ser Leu Gly Asn Glu Ser Cys Gly
                245                 250                 255

Leu His Asp Asn
            260


<210> SEQ ID NO 3
<211> LENGTH: 1485
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of PLT5

<400> SEQUENCE: 3

atggacacct cgcaccacta tcatccatgg ctcaacttct ccctcgccca ccactgtgac     60

ctcgaggagg aggagagggg cgcggccgcc gagctggccg cgatagccgg cgccgcgccg    120

ccgccgaagc tggaggactt cctcggcgga ggcgtcgcca ccggtggtcc ggaggcggtg    180

gcgcccgcgg agatgtacga ctcggacctc aagttcatag ccgccgccgg gttccttggc    240

ggctcggcgg cggcggcggc gacgtcgccg ctgtcctccc tcgaccaggc cggttccaag    300

ctggccttgc ctgcggcggc ggctgctccg gcgccggagc agaggaaggc cgtcgactcc    360

tttgggcagc gcacgtccat ctaccgcggc gtcacacggc accggtggac tggcaggtac    420

gaggcacatc tgtgggacaa cagctgccga cgcgaagggc agagccgcaa gggccgccaa    480

gtatatttgg gtggctatga taaggaggag aaggctgcca gggcgtatga tcttgcagct    540

ttgaagtact ggggttctag caccaccacc aactttccgg ttgctgagta tgagaaggag    600

gtcgaggaga tgaagaacat gacgcgacaa gagtttgttg cttcccttcg aaggaagagc    660

agtggattct ctcggggtgc ttccatctac agaggtgtaa ccagacatca ccagcatgga    720

cggtggcagg cgaggatcgg aagggtggcc ggtaacaagg acctctacct tgggacgttc    780

agcaccgagg aggaagctgc agaggcctac gacatagcgg ccatcaagtt cagaggcctg    840

aacgccgtca caaacttcga gatcagccgg tacaacgtgg agaccataat gagcagcaac    900

cttccagtcg cgagcatgtc gtcgtcgtcg gcggcggcgg cgggtggccg gagcagcaag    960

gcgctggagt cccctccgtc cggctcgctt gacggcggcg gcggcatgcc agtcgtcgaa   1020

ggcagcacgg caccgccgct gttcattccg gtgaagtacg accagcagca gcaggagtac   1080

ctgtcgatgc tcgcgttgca gcaccaccac cagcagcaac aagcagggaa cctgttgcag   1140

gggccgctag tagggttcgg cggcctctac tcctccgggg tgaacctgga tttcgccaac   1200

tcccacggca cggcggctcc gtcgtcgatg gcccaccact gctacgccaa tggcaccgcg   1260

tccgcctcgc atgagcacca gcaccagcac cagatgcagc agggcggcga gaacgagacg   1320

cagccgcagc cgcagcagag ctccagcagc tgctcctccc tgccattcgc caccccggtc   1380
```

gctttcaatg ggtcctatga aagctccatc acggcggcag gcccctttgg atactcctac 1440
ccaaatgtgg cagcctttca gacgccgatc tatggaatgg aatga 1485

<210> SEQ ID NO 4
<211> LENGTH: 492
<212> TYPE: PRT
<213> ORGANISM: Zea mays

<400> SEQUENCE: 4

```
Met Asp Thr Ser His His Tyr His Pro Trp Leu Asn Phe Ser Leu Ala
1               5                   10                  15

His His Cys Asp Leu Glu Glu Glu Glu Arg Gly Ala Ala Ala Glu Leu
            20                  25                  30

Ala Ala Ile Ala Gly Ala Ala Pro Pro Pro Lys Leu Glu Asp Phe Leu
        35                  40                  45

Gly Gly Gly Val Ala Thr Gly Gly Pro Glu Ala Val Ala Pro Ala Glu
    50                  55                  60

Met Tyr Asp Ser Asp Leu Lys Phe Ile Ala Ala Ala Gly Phe Leu Gly
65                  70                  75                  80

Gly Ser Ala Ala Ala Ala Ala Thr Ser Pro Leu Ser Ser Leu Asp Gln
                85                  90                  95

Ala Gly Ser Lys Leu Ala Leu Pro Ala Ala Ala Ala Ala Pro Ala Pro
            100                 105                 110

Glu Gln Arg Lys Ala Val Asp Ser Phe Gly Gln Arg Thr Ser Ile Tyr
        115                 120                 125

Arg Gly Val Thr Arg His Arg Trp Thr Gly Arg Tyr Glu Ala His Leu
    130                 135                 140

Trp Asp Asn Ser Cys Arg Arg Glu Gly Gln Ser Arg Lys Gly Arg Gln
145                 150                 155                 160

Glu Ser Glu Gly Gly Tyr Asp Lys Glu Glu Lys Ala Ala Arg Ala Tyr
                165                 170                 175

Asp Leu Ala Ala Leu Lys Tyr Trp Gly Ser Ser Thr Thr Thr Asn Phe
            180                 185                 190

Pro Val Ala Glu Tyr Glu Lys Glu Val Glu Glu Met Lys Asn Met Thr
        195                 200                 205

Arg Gln Glu Phe Val Ala Ser Leu Arg Arg Lys Ser Ser Gly Phe Ser
    210                 215                 220

Arg Gly Ala Ser Ile Tyr Arg Gly Val Thr Arg His His Gln His Gly
225                 230                 235                 240

Arg Trp Gln Ala Arg Ile Gly Arg Val Ala Gly Asn Lys Asp Leu Tyr
                245                 250                 255

Leu Gly Thr Phe Ser Thr Glu Glu Glu Ala Ala Glu Ala Tyr Asp Ile
            260                 265                 270

Ala Ala Ile Lys Phe Arg Gly Leu Asn Ala Val Thr Asn Phe Glu Ile
        275                 280                 285

Ser Arg Tyr Asn Val Glu Thr Ile Met Ser Ser Asn Leu Pro Val Ala
    290                 295                 300

Ser Met Ser Ser Ser Ala Ala Ala Ala Ala Gly Gly Arg Ser Ser Lys
305                 310                 315                 320

Ala Leu Glu Ser Pro Pro Ser Gly Ser Leu Asp Gly Gly Gly Gly Met
                325                 330                 335

Pro Val Val Glu Ala Ser Thr Ala Pro Pro Leu Phe Ile Pro Val Lys
            340                 345                 350
```

```
Tyr Asp Gln Gln Gln Gln Glu Tyr Leu Ser Met Leu Ala Leu Gln Gln
        355                 360                 365

His His Gln Gln Gln Gln Ala Gly Asn Leu Leu Gln Gly Pro Leu Val
    370                 375                 380

Gly Phe Gly Gly Leu Tyr Ser Ser Gly Val Asn Leu Asp Phe Ala Asn
385                 390                 395                 400

Ser His Gly Thr Ala Ala Pro Ser Ser Met Ala His His Cys Tyr Ala
                405                 410                 415

Asn Gly Thr Ala Ser Ala Ser His Glu His Gln His Gln Met Gln Gln
            420                 425                 430

Gly Gly Glu Asn Glu Thr Gln Pro Gln Pro Gln Gln Ser Ser Ser Ser
        435                 440                 445

Cys Ser Ser Leu Pro Phe Ala Thr Pro Val Ala Phe Asn Gly Ser Tyr
    450                 455                 460

Glu Ser Ser Ile Thr Ala Ala Gly Pro Phe Gly Tyr Ser Tyr Pro Asn
465                 470                 475                 480

Val Ala Ala Phe Gln Thr Pro Ile Tyr Gly Met Glu
                485                 490
```

```
<210> SEQ ID NO 5
<211> LENGTH: 1677
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of AtPLT5

<400> SEQUENCE: 5

atgaagaaca ataacaacaa atcttcttct tcttctagct atgattcttc tttgtctcct      60

tcttcttcat cctcctccca ccagaactgg ctctctttct ctctctccaa caataacaac     120

aacttcaatt cttcctcaaa ccctaatctc acttcctcca catcagatca tcatcatcct     180

caccccttctc acctctctct ctttcaagct ttctccactt ctccagtcga acggcaagat     240

gggtcaccgg gagtttcacc cagcgatgcc acggcggttc tttccgtata ccccggcggt     300

cctaaacttg agaacttcct cggcggagga gcctcaacga cgacaacaag accaatgcaa     360

caagtgcaat ctcttggcgg cgttgtcttc tcttccgacc tacagccacc gcttcatcct     420

ccgtccgccg ccgagatcta cgactctgag ctcaagtcaa tagccgctag cttcctagga     480

aactactccg gtggacactc gtcggaggtc tctagcgtac ataaacaaca accgaatcct     540

ctagctgtct cagaggcttc gcctactccg aagaagaacg tagagagttt tggacaacgt     600

acctcgattt atagaggagt cacaagacat agatggactg gaagatacga agctcatcta     660

tgggataata gttgccgaag agaaggccaa agcagaaaag gaagacaagt ttatttaggt     720

ggttatgata aggaagataa agcagctaga gcttacgacc ttgcagctct taagtattgg     780

ggtcctacaa ctacgactaa tttcccgata tcaaattacg aatctgaact tgaagaaatg     840

aaacacatga ctcgacaaga gttcgttgct tctttaagac ggaaaagcag tggattctct     900

aggggtgcct ccatgtacag aggcgtcact agacatcatc agcatggtcg atggcaggca     960

cgaattggaa gagttgcagg caacaaagac ctttatcttg gcacatttag cactcaagag    1020

gaagctgcag aagcttatga tatagcagcg atcaaattcc gcggtctaaa tgcagtcacc    1080

aatttcgaca tcagtcgata tgatgtcaaa tcaattgcta gctgtaatct ccctgtgggt    1140

ggactaatgc ctaaaccttc tccagcaacc gcagcggctg acaaaaccgt tgatctttct    1200
```

```
ccatccgact ctccatctct aaccacaccg tccctcacgt tcaatgtggc aacaccggtc   1260

aatgaccatg gaggaacttt ttaccacact ggtataccaa tcaaaccaga cccggctgat   1320

cattattggt ccaacatctt tggattccag gcaaacccga aagcagaaat gcgaccatta   1380

gcaaactttg ggtcggatct tcataaccct tctcctggtt atgctataat gccggtaatg   1440

caggaaggtg aaaacaactt tggtggtagt tttgttgggt ctgatgggta taacaatcat   1500

tccgctgcat cgaacccggt ctcagcaatt ccgctgtcct cgacaactac aatgagtaac   1560

ggtaacgaag ggtatggtgg aaacataaac tggattaata acaacatttc aagttcttac   1620

caaactgcaa aatcaaatct ctctgttttg cacacaccgg tttttgggtt ggaatga      1677
```

```
<210> SEQ ID NO 6
<211> LENGTH: 558
<212> TYPE: PRT
<213> ORGANISM: Zea mays

<400> SEQUENCE: 6

Met Lys Asn Asn Asn Asn Lys Ser Ser Ser Ser Ser Ser Tyr Asp Ser
1               5                   10                  15

Ser Leu Ser Pro Ser Ser Ser Ser Ser Ser His Gln Asn Trp Leu Ser
            20                  25                  30

Phe Ser Leu Ser Asn Asn Asn Asn Asn Phe Asn Ser Ser Ser Asn Pro
        35                  40                  45

Asn Leu Thr Ser Ser Thr Ser Asp His His His Pro His Pro Ser His
    50                  55                  60

Leu Ser Leu Phe Gln Ala Phe Ser Thr Ser Pro Val Glu Arg Gln Asp
65                  70                  75                  80

Gly Ser Pro Gly Val Ser Pro Ser Asp Ala Thr Ala Val Leu Ser Val
                85                  90                  95

Tyr Pro Gly Gly Pro Lys Leu Glu Asn Phe Leu Gly Gly Gly Ala Ser
            100                 105                 110

Thr Thr Thr Thr Arg Pro Met Gln Gln Val Gln Ser Leu Gly Gly Val
        115                 120                 125

Val Phe Ser Ser Asp Leu Gln Pro Pro Leu His Pro Pro Ser Ala Ala
    130                 135                 140

Glu Ile Tyr Asp Ser Glu Leu Lys Ser Ile Ala Ala Ser Phe Leu Gly
145                 150                 155                 160

Asn Tyr Ser Gly Gly His Ser Ser Glu Val Ser Ser Val His Lys Gln
                165                 170                 175

Gln Pro Asn Pro Leu Ala Val Ser Glu Ala Ser Pro Thr Pro Lys Lys
            180                 185                 190

Asn Val Glu Ser Phe Gly Gln Arg Thr Ser Ile Tyr Arg Gly Val Thr
        195                 200                 205

Arg His Arg Trp Thr Gly Arg Tyr Glu Ala His Leu Trp Asp Asn Ser
    210                 215                 220

Cys Arg Arg Glu Gly Gln Ser Arg Lys Gly Arg Gln Val Tyr Leu Gly
225                 230                 235                 240

Gly Tyr Asp Lys Glu Asp Lys Ala Ala Arg Ala Tyr Asp Leu Ala Ala
                245                 250                 255

Leu Lys Tyr Trp Gly Pro Thr Thr Thr Thr Asn Phe Pro Ile Ser Asn
            260                 265                 270

Tyr Glu Ser Glu Leu Glu Glu Met Lys His Met Thr Arg Gln Glu Phe
        275                 280                 285
```

```
Val Ala Ser Leu Arg Arg Lys Ser Ser Gly Phe Ser Arg Gly Ala Ser
    290                 295                 300

Met Tyr Arg Gly Val Thr Arg His His Gln His Gly Arg Trp Gln Ala
305                 310                 315                 320

Arg Ile Gly Arg Val Ala Gly Asn Lys Asp Leu Tyr Leu Gly Thr Phe
                325                 330                 335

Ser Thr Gln Glu Glu Ala Ala Glu Ala Tyr Asp Ile Ala Ala Ile Lys
            340                 345                 350

Phe Arg Gly Leu Asn Ala Val Thr Asn Phe Asp Ile Ser Arg Tyr Asp
        355                 360                 365

Val Lys Ser Ile Ala Ser Cys Asn Leu Pro Val Gly Gly Leu Met Pro
    370                 375                 380

Lys Pro Ser Pro Ala Thr Ala Ala Ala Asp Lys Thr Val Asp Leu Ser
385                 390                 395                 400

Pro Ser Asp Ser Pro Ser Leu Thr Thr Pro Ser Leu Thr Phe Asn Val
                405                 410                 415

Ala Thr Pro Val Asn Asp His Gly Gly Thr Phe Tyr His Thr Gly Ile
            420                 425                 430

Pro Ile Lys Pro Asp Pro Ala Asp His Tyr Trp Ser Asn Ile Phe Gly
        435                 440                 445

Phe Gln Ala Asn Pro Lys Ala Glu Met Arg Pro Leu Ala Asn Phe Gly
    450                 455                 460

Ser Asp Leu His Asn Pro Ser Pro Gly Tyr Ala Ile Met Pro Val Met
465                 470                 475                 480

Gln Glu Gly Glu Asn Asn Phe Gly Gly Ser Phe Val Gly Ser Asp Gly
                485                 490                 495

Tyr Asn Asn His Ser Ala Ala Ser Asn Pro Val Ser Ala Ile Pro Leu
            500                 505                 510

Ser Ser Thr Thr Thr Met Ser Asn Gly Asn Glu Gly Tyr Gly Gly Asn
        515                 520                 525

Ile Asn Trp Ile Asn Asn Asn Ile Ser Ser Ser Tyr Gln Thr Ala Lys
    530                 535                 540

Ser Asn Leu Ser Val Leu His Thr Pro Val Phe Gly Leu Glu
545                 550                 555
```

<210> SEQ ID NO 7
<211> LENGTH: 1470
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of ZmPLT7

<400> SEQUENCE: 7

```
atggacatgg acatgagctc agcttatccc caccattggc tctccttctc cctctccaac     60

aactaccacc atggcctact cgaggccttc tctaactcct ccggtactcc tcttggagac    120

gagccgggcg cagtggagga gtccccgagg acggtggagg acttcctcgg cggcgtcggt    180

ggcgccggcg ccccgccgca gccggcggct gctgcagatc aggatcacca gcttgtgtgc    240

ggcgagctgg gcagcatcac agccaggttc ttgcgccact acccggcggc gccagctggg    300

acgacggtgg agaaccccgg cgcggtgacc gtggcggcca tgtcgtcgac ggacgtggcg    360

ggggcggagt ccgaccaggc gaggcggccc gccgagacgt tcggccagcg cacatccatc    420

taccgtggcg tcaccaggca ccggtggaca gggagatatg aggcgcactt gtgggacaac    480
```

```
agctgccgcc gggagggcca aagccgcaaa ggacgccaag tctacctagg aggctatgac    540

aaggaggaga aggcggctag agcttacgac ctcgccgcgc tcaagtactg gggcctaca    600

accacgacca acttcccggt gtccaactac gagaaggagc tggaggagat gaagtccatg    660

acgcggcagg agttcatcgc gtcgttgcgc aggaagagca gcggcttctc acgaggcgcc    720

tccatctaca gaggagtcac aaggcatcat cagcacggcc ggtggcaggc gaggatcggc    780

agggtggccg gaaacaagga cctgtacttg ggcactttca gtactcagga agaggcggcg    840

gaggcgtacg acatcgctgc gatcaagttc cgcgggctca acgccgtcac caacttcgac    900

atgagccgct acgacgtgga gagcatcctc agcagcgacc tccccgtcgg gggcggagcc    960

accgggcgcg ccgccaagtt cccgttggac tcgctgcagc cggggagcgc tgctgcgatg   1020

atgctcgccg ggctgctgc cgcttcgcag gccaccatgc cgccgtccga gaaggactac   1080

tggtctctgc tcgccctgca ctaccagcag cagcaggagc aggagcggca gttcccggct   1140

tctgcttacg aggcttacgg ctccggcggc gtgaacgtgg acttcacgat gggcaccagt   1200

agcggcaaca acaacaacaa caccggcagc ggcgtcatgt ggggcgccac cactggtgca   1260

gtagtagtgg gacagcaaga cagcagcggc aagcagggca acggctatgc cagcaacatt   1320

ccttatgctg ctgctgctgc tatggtttct ggatctgctg gctacgaggg ctccaccggc   1380

gacaatggaa cctgggttac tacgactatt accagcagca acaccggcac ggctccccac   1440

tactacaact atctcttcgg gatggagtag                                    1470
```

<210> SEQ ID NO 8
<211> LENGTH: 489
<212> TYPE: PRT
<213> ORGANISM: Zea mays

<400> SEQUENCE: 8

```
Met Asp Met Asp Met Ser Ser Ala Tyr Pro His His Trp Leu Ser Phe
1               5                   10                  15

Ser Leu Ser Asn Asn Tyr His His Gly Leu Leu Glu Ala Phe Ser Asn
            20                  25                  30

Ser Ser Gly Thr Pro Leu Gly Asp Glu Pro Gly Ala Val Glu Glu Ser
        35                  40                  45

Pro Arg Thr Val Glu Asp Phe Leu Gly Gly Val Gly Gly Ala Gly Ala
    50                  55                  60

Pro Pro Gln Pro Ala Ala Ala Ala Asp Gln Asp His Gln Leu Val Cys
65                  70                  75                  80

Gly Glu Leu Gly Ser Ile Thr Ala Arg Phe Leu Arg His Tyr Pro Ala
                85                  90                  95

Ala Pro Ala Gly Thr Thr Val Glu Asn Pro Gly Ala Val Thr Val Ala
            100                 105                 110

Ala Met Ser Ser Thr Asp Val Ala Gly Ala Glu Ser Asp Gln Ala Arg
        115                 120                 125

Arg Pro Ala Glu Thr Phe Gly Gln Arg Thr Ser Ile Tyr Arg Gly Val
    130                 135                 140

Thr Arg His Arg Trp Thr Gly Arg Tyr Glu Ala His Leu Trp Asp Asn
145                 150                 155                 160

Ser Cys Arg Arg Glu Gly Gln Ser Arg Lys Gly Arg Gln Val Tyr Leu
                165                 170                 175

Gly Gly Tyr Asp Lys Glu Glu Lys Ala Ala Arg Ala Tyr Asp Leu Ala
            180                 185                 190
```

```
Ala Leu Lys Tyr Trp Gly Pro Thr Thr Thr Thr Asn Phe Pro Val Ser
        195                 200                 205

Asn Tyr Glu Lys Glu Leu Glu Glu Met Lys Ser Met Thr Arg Gln Glu
    210                 215                 220

Phe Ile Ala Ser Leu Arg Arg Lys Ser Ser Gly Phe Ser Arg Gly Ala
225                 230                 235                 240

Ser Ile Tyr Arg Gly Val Thr Arg His His Gln His Gly Arg Trp Gln
                245                 250                 255

Ala Arg Ile Gly Arg Val Ala Gly Asn Lys Asp Leu Tyr Leu Gly Thr
            260                 265                 270

Phe Ser Thr Gln Glu Glu Ala Ala Glu Ala Tyr Asp Ile Ala Ala Ile
        275                 280                 285

Lys Phe Arg Gly Leu Asn Ala Val Thr Asn Phe Asp Met Ser Arg Tyr
    290                 295                 300

Asp Val Glu Ser Ile Leu Ser Ser Asp Leu Pro Val Gly Gly Gly Ala
305                 310                 315                 320

Thr Gly Arg Ala Ala Lys Phe Pro Leu Asp Ser Leu Gln Pro Gly Ser
                325                 330                 335

Ala Ala Ala Met Met Leu Ala Gly Ala Ala Ala Ala Ser Gln Ala Thr
            340                 345                 350

Met Pro Pro Ser Glu Lys Asp Tyr Trp Ser Leu Leu Ala Leu His Tyr
        355                 360                 365

Gln Gln Gln Gln Glu Gln Glu Arg Gln Phe Pro Ala Ser Ala Tyr Glu
    370                 375                 380

Ala Tyr Gly Ser Gly Gly Val Asn Val Asp Phe Thr Met Gly Thr Ser
385                 390                 395                 400

Ser Gly Asn Asn Asn Asn Asn Thr Gly Ser Gly Val Met Trp Gly Ala
                405                 410                 415

Thr Thr Gly Ala Val Val Val Gly Gln Gln Asp Ser Ser Gly Lys Gln
            420                 425                 430

Gly Asn Gly Tyr Ala Ser Asn Ile Pro Tyr Ala Ala Ala Ala Ala Met
        435                 440                 445

Val Ser Gly Ser Ala Gly Tyr Glu Gly Ser Thr Gly Asp Asn Gly Thr
    450                 455                 460

Trp Val Thr Thr Thr Ile Thr Ser Ser Asn Thr Gly Thr Ala Pro His
465                 470                 475                 480

Tyr Tyr Asn Tyr Leu Phe Gly Met Glu
                485
```

<210> SEQ ID NO 9
<211> LENGTH: 1497
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of AtPLT7

<400> SEQUENCE: 9

```
atggctcctc caatgacgaa ttgcttaacg ttttctctgt caccaatgga gatgttgaaa     60

tcaactgatc agtctcactt ctcttcttct tacgacgatt cttctactcc ttatctcatc    120

gataacttct atgctttcaa agaagaagct gagatagaag ctgctgctgc ttcaatggcg    180

gattcaacaa ccttatctac ttttttcgat cattctcaga ctcagattcc aaagctggaa    240

gatttcctcg gtgattcctt tgtccgttac tctgataacc aaacagagac ccaagactct    300
```

```
tcttctctca ctccattcta cgatccacgt caccgcaccg ttgccgaagg agttacaggg    360

ttcttctctg atcatcatca gccagatttc aagacgataa actcgggacc agaaatcttc    420

gatgactcaa caacttccaa catcggtggt actcatctct ccagtcacgt ggtggagtca    480

tcaacgacgg cgaagttagg gtttaacggt gattgcacca ccaccggagg agttttgtct    540

ctaggggtta acaacacatc agatcaacct ttgagctgta acaatggcga gagaggtgga    600

aacagtaaca agaagaaaac agtttctaag aaggaaacat cagatgattc aaagaagaag    660

attgtcgaaa cattgggaca aagaacttca atttatcgtg gagtcacccg acatagatgg    720

actggaagat acgaagcgca tctatgggat aacagctgta ggagggaagg tcaagccaga    780

aaaggacgtc aagtgtactt aggtggatat gacaaggaag atagagcagc tagagcctat    840

gacttggcag ctttaaaata ctggggttct actgctacta caaattttcc ggtctcgagt    900

tattcaaaag aacttgagga aatgaatcac atgaccaagc aagagtttat tgcatctctt    960

aggaggaaaa gtagcggttt ttcgagagga gcttcaatat atagaggtgt cacaaggcat   1020

catcaacaag gtcgctggca agcaagaatc ggccgtgtcg caggaaacaa agatctttac   1080

ctcggaacct ttgcaaccga agaggaagca gcagaggctt atgacattgc agccataaag   1140

ttcagaggaa tcaacgcagt aactaacttt gagatgaaca ggtatgacat tgaagctgtc   1200

atgaatagtt ctttacctgt aggaggagca gctgcgaaac gccacaaact caaactcgct   1260

cttgaatctc cttcttcatc atcctctgac cataacctcc aacaacaaca gttgcttccg   1320

tcctcttctc cctcggatca aaaccctaac tcaatcccat gtggcattcc atttgagcct   1380

tcagttctct attaccacca gaacttcttt cagcattatc ctttggtctc tgactctaca   1440

attcaagctc ctatgaacca agctgagttt ttcttgtggc ctaaccagtc ttactaa      1497
```

```
<210> SEQ ID NO 10
<211> LENGTH: 498
<212> TYPE: PRT
<213> ORGANISM: Zea mays

<400> SEQUENCE: 10

Met Ala Pro Pro Met Thr Asn Cys Leu Thr Phe Ser Leu Ser Pro Met
1               5                   10                  15

Glu Met Leu Lys Ser Thr Asp Gln Ser His Phe Ser Ser Ser Tyr Asp
            20                  25                  30

Asp Ser Ser Thr Pro Tyr Leu Ile Asp Asn Phe Tyr Ala Phe Lys Glu
        35                  40                  45

Glu Ala Glu Ile Glu Ala Ala Ala Ser Met Ala Asp Ser Thr Thr
    50                  55                  60

Leu Ser Thr Phe Phe Asp His Ser Gln Thr Gln Ile Pro Lys Leu Glu
65                  70                  75                  80

Asp Phe Leu Gly Asp Ser Phe Val Arg Tyr Ser Asp Asn Gln Thr Glu
                85                  90                  95

Thr Gln Asp Ser Ser Ser Leu Thr Pro Phe Tyr Asp Pro Arg His Arg
            100                 105                 110

Thr Val Ala Glu Gly Val Thr Gly Phe Phe Ser Asp His His Gln Pro
        115                 120                 125

Asp Phe Lys Thr Ile Asn Ser Gly Pro Glu Ile Phe Asp Asp Ser Thr
    130                 135                 140

Thr Ser Asn Ile Gly Gly Thr His Leu Ser Ser His Val Val Glu Ser
145                 150                 155                 160
```

```
Ser Thr Thr Ala Lys Leu Gly Phe Asn Gly Asp Cys Thr Thr Thr Gly
                165                 170                 175

Gly Val Leu Ser Leu Gly Val Asn Asn Thr Ser Asp Gln Pro Leu Ser
            180                 185                 190

Cys Asn Asn Gly Glu Arg Gly Gly Asn Ser Asn Lys Lys Lys Thr Val
        195                 200                 205

Ser Lys Lys Glu Thr Ser Asp Asp Ser Lys Lys Lys Ile Val Glu Thr
    210                 215                 220

Leu Gly Gln Arg Thr Ser Ile Tyr Arg Gly Val Thr Arg His Arg Trp
225                 230                 235                 240

Thr Gly Arg Tyr Glu Ala His Leu Trp Asp Asn Ser Cys Arg Arg Glu
                245                 250                 255

Gly Gln Ala Arg Lys Gly Arg Gln Val Tyr Leu Gly Gly Tyr Asp Lys
            260                 265                 270

Glu Asp Arg Ala Ala Arg Ala Tyr Asp Leu Ala Ala Leu Lys Tyr Trp
        275                 280                 285

Gly Ser Thr Ala Thr Thr Asn Phe Pro Val Ser Ser Tyr Ser Lys Glu
    290                 295                 300

Leu Glu Glu Met Asn His Met Thr Lys Gln Glu Phe Ile Ala Ser Leu
305                 310                 315                 320

Arg Arg Lys Ser Ser Gly Phe Ser Arg Gly Ala Ser Ile Tyr Arg Gly
                325                 330                 335

Val Thr Arg His His Gln Gln Gly Arg Trp Gln Ala Arg Ile Gly Arg
            340                 345                 350

Val Ala Gly Asn Lys Asp Leu Tyr Leu Gly Thr Phe Ala Thr Glu Glu
        355                 360                 365

Glu Ala Ala Glu Ala Tyr Asp Ile Ala Ala Ile Lys Phe Arg Gly Ile
    370                 375                 380

Asn Ala Val Thr Asn Phe Glu Met Asn Arg Tyr Asp Ile Glu Ala Val
385                 390                 395                 400

Met Asn Ser Ser Leu Pro Val Gly Gly Ala Ala Ala Lys Arg His Lys
                405                 410                 415

Leu Lys Leu Ala Leu Glu Ser Pro Ser Ser Ser Ser Ser Asp His Asn
            420                 425                 430

Leu Gln Gln Gln Gln Leu Leu Pro Ser Ser Ser Pro Ser Asp Gln Asn
        435                 440                 445

Pro Asn Ser Ile Pro Cys Gly Ile Pro Phe Glu Pro Ser Val Leu Tyr
    450                 455                 460

Tyr His Gln Asn Phe Phe Gln His Tyr Pro Leu Val Ser Asp Ser Thr
465                 470                 475                 480

Ile Gln Ala Pro Met Asn Gln Ala Glu Phe Phe Leu Trp Pro Asn Gln
                485                 490                 495

Ser Tyr
```

<210> SEQ ID NO 11
<211> LENGTH: 1104
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of TaRKD4

<400> SEQUENCE: 11

```
atggagatgc aacaacaata cttcgggggg gacggcgatg cggactggtt ccatcaactc      60
```

```
gcattgcttc ccccacttcc aatctcatcg tctctccccc cactcccgat gtcagagggc    120

tcatgtctcc ctatggcagc agcagctgca gctgcactcc cccttggcga ttgctcgagc    180

gccctcatga tacgccctga ggaacagatg tcttgccttc caatgaaccc ctctccagcg    240

gtcgtcgacg atgtctactc ttcctacgca ccgaacaatg tcgacgtgtt gccgccattc    300

ccggcaggac ttgacgacgc tctgttgatg gagtcttttt ctgacatcga cctcgaggag    360

tttgctgacg catttggcca caagatcaag acagaacccc tcgacgatgc catggtcccc    420

gcggaccacg acttcgcggc tcaagcccaa caggcctgcc ctgtggtcat catgaatcag    480

caacaactca acgcacccag agacgtgcgc ctgctcattg acccggatga tgatgacagc    540

accgtggtgg ccgggggcta tgaagctgca gcggtggggt gcgccgagca gaaacaggtc    600

aggccagcac cacgtagggt gagaaagagc tcaggcggcg caagaccagc cgcgggagga    660

aagtccctcg atcacatcgg attcgaggaa ctcaggacct atttctatat gccaatcacc    720

aaggcagcga gggaaatgaa cgtggggctg acagtcctga agaagagatg ccgggaactg    780

ggggtggcgc gctggccaca cagaaagatg aagtctctga gaagcctgat cctcaacatt    840

caggagatgg ggaagggcgc aacatctccc gcagccgtgc aggggggaact tgaagcgctt   900

gagaggtatt gcgccattat ggaggagaac ccggctatag agctcaccga gcaaacgaag    960

aagctcaggc aggcttgttt caaagagaat tataagcggc gtagagccgc cgcttctgtt   1020

aatcttctcg atcactgcta taacgatctg gcatctcatg agcagcaaat gcctctccca   1080

caaatgggat tctttggatt ttag                                           1104
```

<210> SEQ ID NO 12
<211> LENGTH: 367
<212> TYPE: PRT
<213> ORGANISM: Triticum aestivum

<400> SEQUENCE: 12

```
Met Glu Met Gln Gln Gln Tyr Phe Gly Gly Asp Gly Asp Ala Asp Trp
1               5                   10                  15

Phe His Gln Leu Ala Leu Leu Pro Pro Leu Pro Ile Ser Ser Ser Leu
            20                  25                  30

Pro Pro Leu Pro Met Ser Glu Gly Ser Cys Leu Pro Met Ala Ala Ala
        35                  40                  45

Ala Ala Ala Ala Leu Pro Leu Gly Asp Cys Ser Ser Ala Leu Met Ile
    50                  55                  60

Arg Pro Glu Glu Gln Met Ser Cys Leu Pro Met Asn Pro Ser Pro Ala
65                  70                  75                  80

Val Val Asp Asp Val Tyr Ser Ser Tyr Ala Pro Asn Asn Val Asp Val
                85                  90                  95

Leu Pro Pro Phe Pro Ala Gly Leu Asp Asp Ala Leu Leu Met Glu Ser
            100                 105                 110

Phe Ser Asp Ile Asp Leu Glu Glu Phe Ala Asp Ala Phe Gly His Lys
        115                 120                 125

Ile Lys Thr Glu Pro Leu Asp Asp Ala Met Val Pro Ala Asp His Asp
    130                 135                 140

Phe Ala Ala Gln Ala Gln Gln Ala Cys Pro Val Val Ile Met Asn Gln
145                 150                 155                 160

Gln Gln Leu Asn Ala Pro Arg Asp Val Arg Leu Leu Ile Asp Pro Asp
                165                 170                 175

Asp Asp Asp Ser Thr Val Val Ala Gly Gly Tyr Glu Ala Ala Ala Val
```

```
            180                 185                 190

Gly Cys Ala Glu Gln Lys Gln Val Arg Pro Ala Pro Arg Arg Val Arg
        195                 200                 205

Lys Ser Ser Gly Gly Ala Arg Pro Ala Ala Gly Gly Lys Ser Leu Asp
    210                 215                 220

His Ile Gly Phe Glu Glu Leu Arg Thr Tyr Phe Tyr Met Pro Ile Thr
225                 230                 235                 240

Lys Ala Ala Arg Glu Met Asn Val Gly Leu Thr Val Leu Lys Lys Arg
                245                 250                 255

Cys Arg Glu Leu Gly Val Ala Arg Trp Pro His Arg Lys Met Lys Ser
            260                 265                 270

Leu Arg Ser Leu Ile Leu Asn Ile Gln Glu Met Gly Lys Gly Ala Thr
        275                 280                 285

Ser Pro Ala Ala Val Gln Gly Glu Leu Glu Ala Leu Glu Arg Tyr Cys
    290                 295                 300

Ala Ile Met Glu Glu Asn Pro Ala Ile Glu Leu Thr Glu Gln Thr Lys
305                 310                 315                 320

Lys Leu Arg Gln Ala Cys Phe Lys Glu Asn Tyr Lys Arg Arg Arg Ala
                325                 330                 335

Ala Ala Ser Val Asn Leu Leu Asp His Cys Tyr Asn Asp Leu Ala Ser
            340                 345                 350

His Glu Gln Gln Met Pro Leu Pro Gln Met Gly Phe Phe Gly Phe
        355                 360                 365


<210> SEQ ID NO 13
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of AtRKD4

<400> SEQUENCE: 13

atggctgatc acacaaccaa agaacagaag tcattctcat tcctagctca ttctccatcc      60

tttgatcaca gctccttaag ttatccttta ttcgactggg aagaagatct tcttgctctc     120

caagaaaact ctggctctca agcatttcct tttactacaa cttctctgcc tttacctgat     180

cttgaaccct tgtctgaaga tgtactcaat tcatacagct ctgcgtcatg gaacgaaaca     240

gagcaaaaca gaggagatgg cgcttcatcg gagaagaaga gggaaaatgg aacagtgaaa     300

gagacaacta agaagaggaa aatcaatgag agacacagag aacatagcgt gagaatcatc     360

agcgatatta ctacctacac aactagttca gctccaacga cattgtcaaa ggaaactgtc     420

tctcgctact tctacatgcc cataactcag gctgcaatag cacttaacgt tggtttaact     480

ctactaaaaa ggagatgtcg cgaattgggt attcgccgat ggcctcatcg taaacttatg     540

agcttaaaca ctttgatcag taacgtcaag gagctgcaga agatggaagg cgaagagaat     600

gcagaaaaac tgcaggacgc gttggagatg cttgagaagg agaagaggac aattgaggat     660

ttgccggatt tggagtttaa ggacaagaca aagaggctaa gacaagcttg tttcaaggct     720

aaccacaaga ggaagaagaa gagaagtctc aagtccgatc agtctcaagt accctcgtgt     780

tcaagcagcg gatcagttcc tagtgatgag tcggttgatg aagcaggaat ggagagtgat     840

gaagaaatga agtatctctt gtgtggtttc tcaagtgaat ttactagtgg tttgtga        897
```

```
<210> SEQ ID NO 14
<211> LENGTH: 298
<212> TYPE: PRT
<213> ORGANISM: Arabidopsis thaliana

<400> SEQUENCE: 14

Met Ala Asp His Thr Thr Lys Glu Gln Lys Ser Phe Ser Phe Leu Ala
1               5                   10                  15

His Ser Pro Ser Phe Asp His Ser Ser Leu Ser Tyr Pro Leu Phe Asp
            20                  25                  30

Trp Glu Glu Asp Leu Leu Ala Leu Gln Glu Asn Ser Gly Ser Gln Ala
        35                  40                  45

Phe Pro Phe Thr Thr Thr Ser Leu Pro Leu Pro Asp Leu Glu Pro Leu
    50                  55                  60

Ser Glu Asp Val Leu Asn Ser Tyr Ser Ser Ala Ser Trp Asn Glu Thr
65                  70                  75                  80

Glu Gln Asn Arg Gly Asp Gly Ala Ser Ser Glu Lys Lys Arg Glu Asn
                85                  90                  95

Gly Thr Val Lys Glu Thr Thr Lys Lys Arg Lys Ile Asn Glu Arg His
            100                 105                 110

Arg Glu His Ser Val Arg Ile Ile Ser Asp Ile Thr Thr Tyr Thr Thr
        115                 120                 125

Ser Ser Ala Pro Thr Thr Leu Ser Lys Glu Thr Val Ser Arg Tyr Phe
    130                 135                 140

Tyr Met Pro Ile Thr Gln Ala Ala Ile Ala Leu Asn Val Gly Leu Thr
145                 150                 155                 160

Leu Leu Lys Arg Arg Cys Arg Glu Leu Gly Ile Arg Arg Trp Pro His
                165                 170                 175

Arg Lys Leu Met Ser Leu Asn Thr Leu Ile Ser Asn Val Lys Glu Leu
            180                 185                 190

Gln Lys Met Glu Gly Glu Glu Asn Ala Glu Lys Leu Gln Asp Ala Leu
        195                 200                 205

Glu Met Leu Glu Lys Glu Lys Arg Thr Ile Glu Asp Leu Pro Asp Leu
    210                 215                 220

Glu Phe Lys Asp Lys Thr Lys Arg Leu Arg Gln Ala Cys Phe Lys Ala
225                 230                 235                 240

Asn His Lys Arg Lys Lys Lys Arg Ser Leu Lys Ser Asp Gln Ser Gln
                245                 250                 255

Val Pro Ser Cys Ser Ser Ser Gly Ser Val Pro Ser Asp Glu Ser Val
            260                 265                 270

Asp Glu Ala Gly Met Glu Ser Asp Glu Glu Met Lys Tyr Leu Leu Cys
        275                 280                 285

Gly Phe Ser Ser Glu Phe Thr Ser Gly Leu
    290                 295


<210> SEQ ID NO 15
<211> LENGTH: 1185
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of ZmRKD4

<400> SEQUENCE: 15

atggcgatgg tgccatgcgg cgatgacacc gactggtgcc acgtgctgga caacttcaac     60
```

```
ctgttgctgt gttcgtcgtc ctgctcgccg aatgctatgg ccaacagagc ggaagactgt    120

ctgccgatat ctgctgctcc acccggaccc ggccatcatc agagctgctg caaaaacgaa    180

gtcgtcctcg aagcctcttg tgatggcgcg tttgctgcag ccgactgctt gtcttcggct    240

ctgacgaacc tgcagaggga ggacgacagt ttctatttgc ccatgtactc tgcgccaccc    300

gcagtcggcg atgagtactt ctccgatcta ctcgcgcccg atgccgacgg cattgacgag    360

gcgctcctga tgccgttcag cgacatcgat cttcaggtct tcgacagtga cgacgagcac    420

aggcctcctg tcgaccaaat ggttaatatg atcccgccgg cggttcttca tcatccctcc    480

accgccggga cgcaaaatgg aggtgccgtt catgctcatc agaaggccat ggcggtcatc    540

gatgactcct gtttccgacg aggagccagt ggtgtcgaga tggccgtcgt caggcatcat    600

ggtgagcctc gtcaaggaag ctcttccgtg gcgccagtgc cgccaccgtc actgccgggg    660

acgcgtgcaa ggaggagcga cggccgatca gctcgggcgg ggaagacgac gaagctggac    720

tacatcggct tcgacgagct gcggaagtac ttctgcatgc ccatcaccag ggcggcgagg    780

gagatgaacg tcgggctcac cgtgctcaag aagcgctgcc gcgagctcgg cgtggcgcgg    840

tggcctcacc ggaagatgaa gagcctcaag tccctcatgg ccaacgtcca ggaaatgggg    900

aacgtcatgt cctcggtggc tgtgcagcag gagcttgcgg cgctcgagac gtactgcacg    960

ctcatggagg acaatccctg gatcgagctc acggacagga ccaagaagct gcgccaggcg   1020

tgcttcaagg agaggtacaa gcgtaggagg gcggccgaag tcaacgtcat ggatatggat   1080

cgcatctact gctttggcca gcatcaccac cagcagctgc tgcctccgac gacaagcagt   1140

tctgacgacc gccatggcca gtgcagccgt tcctttggct actga                   1185
```

<210> SEQ ID NO 16
<211> LENGTH: 394
<212> TYPE: PRT
<213> ORGANISM: Zea mays

<400> SEQUENCE: 16

```
Met Ala Met Val Pro Cys Gly Asp Asp Thr Asp Trp Cys His Val Leu
1               5                   10                  15

Asp Asn Phe Asn Leu Leu Leu Cys Ser Ser Ser Cys Ser Pro Asn Ala
            20                  25                  30

Met Ala Asn Arg Ala Glu Asp Cys Leu Pro Ile Ser Ala Ala Pro Pro
        35                  40                  45

Gly Pro Gly His His Gln Ser Cys Cys Lys Asn Glu Val Val Leu Glu
    50                  55                  60

Ala Ser Cys Asp Gly Ala Phe Ala Ala Ala Asp Cys Leu Ser Ser Ala
65                  70                  75                  80

Leu Thr Asn Leu Gln Arg Glu Asp Asp Ser Phe Tyr Leu Pro Met Tyr
                85                  90                  95

Ser Ala Pro Pro Ala Val Gly Asp Glu Tyr Phe Ser Asp Leu Leu Ala
            100                 105                 110

Pro Asp Ala Asp Gly Ile Asp Glu Ala Leu Leu Met Pro Phe Ser Asp
        115                 120                 125

Ile Asp Leu Gln Val Phe Asp Ser Asp Asp Glu His Arg Pro Pro Val
    130                 135                 140

Asp Gln Met Val Asn Met Ile Pro Pro Ala Val Leu His His Pro Ser
145                 150                 155                 160

Thr Ala Gly Thr Gln Asn Gly Gly Ala Val His Ala His Gln Lys Ala
                165                 170                 175
```

```
Met Ala Val Ile Asp Asp Ser Cys Phe Arg Arg Gly Ala Ser Gly Val
            180                 185                 190

Glu Met Ala Val Val Arg His His Gly Glu Pro Arg Gln Gly Ser Ser
        195                 200                 205

Ser Val Ala Pro Val Pro Pro Pro Ser Leu Pro Gly Thr Arg Ala Arg
    210                 215                 220

Arg Ser Asp Gly Arg Ser Ala Arg Ala Gly Lys Thr Thr Lys Leu Asp
225                 230                 235                 240

Tyr Ile Gly Phe Asp Glu Leu Arg Lys Tyr Phe Cys Met Pro Ile Thr
                245                 250                 255

Arg Ala Ala Arg Glu Met Asn Val Gly Leu Thr Val Leu Lys Lys Arg
            260                 265                 270

Cys Arg Glu Leu Gly Val Ala Arg Trp Pro His Arg Lys Met Lys Ser
        275                 280                 285

Leu Lys Ser Leu Met Ala Asn Val Gln Glu Met Gly Asn Val Met Ser
    290                 295                 300

Ser Val Ala Val Gln Gln Glu Leu Ala Ala Leu Glu Thr Tyr Cys Thr
305                 310                 315                 320

Leu Met Glu Asp Asn Pro Trp Ile Glu Leu Thr Asp Arg Thr Lys Lys
                325                 330                 335

Leu Arg Gln Ala Cys Phe Lys Glu Arg Tyr Lys Arg Arg Arg Ala Ala
            340                 345                 350

Glu Val Asn Val Met Asp Met Asp Arg Ile Tyr Cys Phe Gly Gln His
        355                 360                 365

His His Gln Gln Leu Leu Pro Pro Thr Thr Ser Ser Ser Asp Asp Arg
    370                 375                 380

His Gly Gln Cys Ser Arg Ser Phe Gly Tyr
385                 390
```

```
<210> SEQ ID NO 17
<211> LENGTH: 1125
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of TaRKD2

<400> SEQUENCE: 17

atggagatgc agcagtactt cggcggctgc ggcgatggcg atgctgactg gttccatcag      60

ctcgccttgc tcccgccttt gccggtctct tcgtctctgc cgcctctccc catgagcgag     120

ggcagctgct tacctatggc cgccgccgcc ccaacgcttc ctcttgggga ttgctcatca     180

gctctcatga ttaggccgga agaacagatg ggctgcctgc agatgatacc tccacaggct     240

gttgccgatg atgagtacag cagctacgcc accaacaatg tcgacgtcct cccgccgttt     300

cctgcaggtc tcgatgatcc cacggcaggc ctcgacgacg cgctgctcat ggagtccttc     360

agagacatcg acctggagga gttcgccgac gccgtcggcc ccaagattaa gaccgagcct     420

ctcgacgacg ccatggtgcc ggcggatcac gatttcgcgg cgcaagtgca acaggcgcgc     480

cccgtggtga tcatgaacca gcagcagctg aatgcgccac acggcgtgcg cctgctcaat     540

gatcccgacg acgatgactc agctgtcgtc gccgggggct atgaggcggc ggccgttggg     600

tgcgctgagc agaagcgggt gaggccggcg ccacgtcgtg tgcggaagag cagcggtggg     660

tcacgccctg ccgccggtgg gaaaagcctc gatcacatag ggtttgagga gctgcgtacg     720
```

```
tatttctaca tgcctatcac caaggcggcg cgggagatga acgtcggtct caccgtgctc    780

aagaagcgct gccgtgagct cggtgtcgcc cgttggcctc accggaagat gaagagcctc    840

aggtctctca tccttaacat ccaggacatg ggaagggcg ccacgtcgcc ggcggcggtg    900

caaggggagc tggaggcgct tgagaggtat tgtgccataa tggaggagaa cccggcgatc    960

gagctgacgg agcagaccaa gaagctgagg caggcctgct ttaaggagaa ctacaagagg   1020

aggagagcgg cggcctccgt caacttgctc gagcattgct acaacgactt gggcagtcat   1080

gagcagcaga tgccattgcc acagatgggt ttctttgggt tctaa                  1125
```

<210> SEQ ID NO 18
<211> LENGTH: 374
<212> TYPE: PRT
<213> ORGANISM: Triticum aestivum

<400> SEQUENCE: 18

```
Met Glu Met Gln Gln Tyr Phe Gly Gly Cys Gly Asp Gly Asp Ala Asp
1               5                   10                  15

Trp Phe His Gln Leu Ala Leu Leu Pro Pro Leu Pro Val Ser Ser Ser
            20                  25                  30

Leu Pro Pro Leu Pro Met Ser Glu Gly Ser Cys Leu Pro Met Ala Ala
        35                  40                  45

Ala Ala Pro Thr Leu Pro Leu Gly Asp Cys Ser Ser Ala Leu Met Ile
    50                  55                  60

Arg Pro Glu Glu Gln Met Gly Cys Leu Gln Met Ile Pro Pro Gln Ala
65                  70                  75                  80

Val Ala Asp Asp Glu Tyr Ser Ser Tyr Ala Thr Asn Asn Val Asp Val
                85                  90                  95

Leu Pro Pro Phe Pro Ala Gly Leu Asp Asp Pro Thr Ala Gly Leu Asp
            100                 105                 110

Asp Ala Leu Leu Met Glu Ser Phe Arg Asp Ile Asp Leu Glu Glu Phe
        115                 120                 125

Ala Asp Ala Val Gly Pro Lys Ile Lys Thr Glu Pro Leu Asp Asp Ala
    130                 135                 140

Met Val Pro Ala Asp His Asp Phe Ala Ala Gln Val Gln Gln Ala Arg
145                 150                 155                 160

Pro Val Val Ile Met Asn Gln Gln Gln Leu Asn Ala Pro His Gly Val
                165                 170                 175

Arg Leu Leu Asn Asp Pro Asp Asp Asp Asp Ser Ala Val Val Ala Gly
            180                 185                 190

Gly Tyr Glu Ala Ala Ala Val Gly Cys Ala Glu Gln Lys Arg Val Arg
        195                 200                 205

Pro Ala Pro Arg Arg Val Arg Lys Ser Ser Gly Gly Ser Arg Pro Ala
    210                 215                 220

Ala Gly Gly Lys Ser Leu Asp His Ile Gly Phe Glu Glu Leu Arg Thr
225                 230                 235                 240

Tyr Phe Tyr Met Pro Ile Thr Lys Ala Ala Arg Glu Met Asn Val Gly
                245                 250                 255

Leu Thr Val Leu Lys Lys Arg Cys Arg Glu Leu Gly Val Ala Arg Trp
            260                 265                 270

Pro His Arg Lys Met Lys Ser Leu Arg Ser Leu Ile Leu Asn Ile Gln
        275                 280                 285

Asp Met Gly Lys Gly Ala Thr Ser Pro Ala Ala Val Gln Gly Glu Leu
    290                 295                 300
```

```
Glu Ala Leu Glu Arg Tyr Cys Ala Ile Met Glu Glu Asn Pro Ala Ile
305                 310                 315                 320

Glu Leu Thr Glu Gln Thr Lys Lys Leu Arg Gln Ala Cys Phe Lys Glu
                325                 330                 335

Asn Tyr Lys Arg Arg Arg Ala Ala Ala Ser Val Asn Leu Leu Glu His
            340                 345                 350

Cys Tyr Asn Asp Leu Gly Ser His Glu Gln Gln Met Pro Leu Pro Gln
        355                 360                 365

Met Gly Phe Phe Gly Phe
    370


<210> SEQ ID NO 19
<211> LENGTH: 771
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA of AtRKD2

<400> SEQUENCE: 19

atgagttcgt caaaacattc ctctgttttt aactattctg ctctgtttct atcactgttt      60

cttcaacaaa tggatcagaa ctctcttcat catctcgatt ctccaaaaat cgaaaacgag     120

tatgaaccag attcgttata cgacatgtta gataagttgc ctccgcttga ttctctccta     180

gatatggaag atttgaaacc aaatgcaggg ttgcactttc agttccatta caatagcttt     240

gaagatttct tcgaaaacat tgaagtggat aacacaattc catctgatat tcacttgttg     300

acacaagagc cctacttctc aagtgactcc tcttcctctt caccattggc tatccaaaac     360

gacggtctca tttccaacgt gaaagttgaa aaggtaacag ttaagaagaa gaggaacctt     420

aagaaaaaga ggcaagacaa attggagatg tctgagatca aacaattttt cgataggccg     480

atcatgaaag cggctaaaga actgaacgtg ggactcactg tgttgaagaa gcgatgcagg     540

gaattaggaa tttaccggtg gcctcaccgg aagctcaaga gtctaaactc tcttataaag     600

aatctcaaga atgttggaat ggaagaggaa gtgaagaact tggaggaaca taggtttctt     660

attgaacaag aacctgatgc agaactcagt gatggaacca agaagctaag gcaagcttgt     720

ttcaaagcca attataagag aagaaaatca cttggtgatg attattattg a              771


<210> SEQ ID NO 20
<211> LENGTH: 256
<212> TYPE: PRT
<213> ORGANISM: Arabidopsis thaliana

<400> SEQUENCE: 20

Met Ser Ser Ser Lys His Ser Ser Val Phe Asn Tyr Ser Ala Leu Phe
1               5                   10                  15

Leu Ser Leu Phe Leu Gln Gln Met Asp Gln Asn Ser Leu His His Leu
            20                  25                  30

Asp Ser Pro Lys Ile Glu Asn Glu Tyr Glu Pro Asp Ser Leu Tyr Asp
        35                  40                  45

Met Leu Asp Lys Leu Pro Pro Leu Asp Ser Leu Leu Asp Met Glu Asp
    50                  55                  60

Leu Lys Pro Asn Ala Gly Leu His Phe Gln Phe His Tyr Asn Ser Phe
65                  70                  75                  80

Glu Asp Phe Phe Glu Asn Ile Glu Val Asp Asn Thr Ile Pro Ser Asp
                85                  90                  95
```

```
Ile His Leu Leu Thr Gln Glu Pro Tyr Phe Ser Ser Asp Ser Ser Ser
            100                 105                 110

Ser Ser Pro Leu Ala Ile Gln Asn Asp Gly Leu Ile Ser Asn Val Lys
        115                 120                 125

Val Glu Lys Val Thr Val Lys Lys Lys Arg Asn Leu Lys Lys Lys Arg
    130                 135                 140

Gln Asp Lys Leu Glu Met Ser Glu Ile Lys Gln Phe Phe Asp Arg Pro
145                 150                 155                 160

Ile Met Lys Ala Ala Lys Glu Leu Asn Val Gly Leu Thr Val Leu Lys
                165                 170                 175

Lys Arg Cys Arg Glu Leu Gly Ile Tyr Arg Trp Pro His Arg Lys Leu
            180                 185                 190

Lys Ser Leu Asn Ser Leu Ile Lys Asn Leu Lys Asn Val Gly Met Glu
        195                 200                 205

Glu Glu Val Lys Asn Leu Glu Glu His Arg Phe Leu Ile Glu Gln Glu
    210                 215                 220

Pro Asp Ala Glu Leu Ser Asp Gly Thr Lys Lys Leu Arg Gln Ala Cys
225                 230                 235                 240

Phe Lys Ala Asn Tyr Lys Arg Arg Lys Ser Leu Gly Asp Asp Tyr Tyr
                245                 250                 255
```

<210> SEQ ID NO 21
<211> LENGTH: 936
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of ZmRKD2

<400> SEQUENCE: 21

```
atgacgggcc tcgacgaggc gctcatgctg ccgttcaccg acatcgatct tgaggccttc     60

gacaacgccg aagagcaaaa gcctcctgtc gaccaaatgg ttatgatgcc gccgacggtt    120

gaacaccccg ccgccgccgg gacgcgagcc ccaatcatca ttgatggtac ggcgaccgtt    180

ggccaaaatg taggtggtgg tgtcgtccac gctcatcaga aggcggccat gacgaccata    240

gaggactcca gctgcttccg acgaggagcc agctgtgtcg acgacgacat ggccgtcgtc    300

attcaccatg tcgagcgtcg tcgtcaagca ggctctaccg ccgtggcgct attgccgccg    360

ccgcagccgt cactgccgcg gccgcgtgca agggcgagcg gcggcgcggg cgagcggtca    420

gctccggcgg ccgccgggaa gacgaggatg gaccacatcg gcttcgacga gctgcgcaag    480

tacttctaca tgcccatcac cagggcggcc agggagatga acgtggggct caccgtgctc    540

aagaagcgct gccgcgagct cggcgtggcg cggtggcctc accggaagat gaagagcctc    600

aagtccctca tggccaacgt acaggaaatg ggaacggca tgtcgccggt ggctgtgcag     660

catgagcttg cggcgctgga gacgtactgc gcgctcatgg aggagaaccc atggatcgag    720

ctcacggacc ggacgaagag gctgcggcag gcctgcttca aggagagcta caagcggagg    780

aaggcggccg caggcaacgc tatcgagacg gatcacattg tctacagctt tggacagcat    840

cgtcgttaca agcagcagct gctgcctccg ccaactgcgg gtagtaccag tgctgacgac    900

cgccatggcc agagcagccg tttcttttgc tactga                              936
```

<210> SEQ ID NO 22
<211> LENGTH: 311

<212> TYPE: PRT
<213> ORGANISM: Zea mays

<400> SEQUENCE: 22

```
Met Thr Gly Leu Asp Glu Ala Leu Met Leu Pro Phe Thr Asp Ile Asp
1               5                   10                  15

Leu Glu Ala Phe Asp Asn Ala Glu Glu Gln Lys Pro Pro Val Asp Gln
            20                  25                  30

Met Val Met Met Pro Pro Thr Val Glu His Pro Ala Ala Ala Gly Thr
        35                  40                  45

Arg Ala Pro Ile Ile Ile Asp Gly Thr Ala Thr Val Gly Gln Asn Val
    50                  55                  60

Gly Gly Gly Val Val His Ala His Gln Lys Ala Ala Met Thr Thr Ile
65                  70                  75                  80

Glu Asp Ser Ser Cys Phe Arg Arg Gly Ala Ser Cys Val Asp Asp Asp
                85                  90                  95

Met Ala Val Val Ile His His Val Glu Arg Arg Arg Gln Ala Gly Ser
            100                 105                 110

Thr Ala Val Ala Leu Leu Pro Pro Pro Gln Pro Ser Leu Pro Arg Pro
        115                 120                 125

Arg Ala Arg Ala Ser Gly Gly Ala Gly Glu Arg Ser Ala Pro Ala Ala
    130                 135                 140

Ala Gly Lys Thr Arg Met Asp His Ile Gly Phe Asp Glu Leu Arg Lys
145                 150                 155                 160

Tyr Phe Tyr Met Pro Ile Thr Arg Ala Ala Arg Glu Met Asn Val Gly
                165                 170                 175

Leu Thr Val Leu Lys Lys Arg Cys Arg Glu Leu Gly Val Ala Arg Trp
            180                 185                 190

Pro His Arg Lys Met Lys Ser Leu Lys Ser Leu Met Ala Asn Val Gln
        195                 200                 205

Glu Met Gly Asn Gly Met Ser Pro Val Ala Val Gln His Glu Leu Ala
    210                 215                 220

Ala Leu Glu Thr Tyr Cys Ala Leu Met Glu Glu Asn Pro Trp Ile Glu
225                 230                 235                 240

Leu Thr Asp Arg Thr Lys Arg Leu Arg Gln Ala Cys Phe Lys Glu Ser
                245                 250                 255

Tyr Lys Arg Arg Lys Ala Ala Ala Gly Asn Ala Ile Glu Thr Asp His
            260                 265                 270

Ile Val Tyr Ser Phe Gly Gln His Arg Arg Tyr Lys Gln Gln Leu Leu
        275                 280                 285

Pro Pro Pro Thr Ala Gly Ser Thr Ser Ala Asp Asp Arg His Gly Gln
    290                 295                 300

Ser Ser Arg Phe Phe Cys Tyr
305                 310
```

<210> SEQ ID NO 23
<211> LENGTH: 1883
<212> TYPE: DNA
<213> ORGANISM: Brachypodium distachyon

<400> SEQUENCE: 23

```
cttcaccgcc attgcaaaaa ttgtcaataa atatttagag tgggtggcat cagaaaaaca      60

tctctagtgg actctcttcc tatcatagct actcgggctg tagatagaac gagggcacaa     120

gagttgggtg gcgtaggttt actcgtgacc tcaactcttt tggctgtgtc ttacgtctaa     180
```

```
gatgggtttg gcatgtgaga aacataggtc taagcaattc atgttagggc tgttgcattg    240
ttgttgcatc aaccaaatgt ccagatagca gttcatgcta catctagttg aaaaccctca    300
tcattaggcg gaacatgtgt tctttttttag catagtcaaa gtcagattgc ggcactcgct    360
catccacgga aagaattttc cctgtgcagg catctcgatc aaaagacgca aattaatttt    420
tgaatagcga tataacaata tctaattaac gtttcttgtt ttctgcgaaa tgtctttcat    480
cataaaatga gtcatctcga tgagcccaag tgacatagcc caacacccca ccccaccaat    540
aaaagtgaag aaaacatgtt gggaaaacta taccaagtaa aatacgagtt gttctaaaga    600
aaaagtaaag tacgagttag atcgcaccct gtcctggagt gtggcttgat gatccaactc    660
ctagcattgt atccctgttt ttggatgatg taactattat ttacaatgaa taaagaggtg    720
ttttactagt aaaaaaatct tgaggggagg agaaaataat ggaggtcttt tttcaaaccg    780
atggactatt atttttagtg aaagagaata atattattgg aaaaattatt ctatccactt    840
attttatatt ggcagaatac aaagaatggt ggggtccacg cggaacttgc ggcccccgaa    900
acctatcgag ggcgcggtac ccaagcaagg aacggaggaa acttgcgggg cccgaaacct    960
agtgataaaa ggcatatcat ccacacgatg aagatctgac ggaccatatc tcccaccacg   1020
gaaagccatc agacgaggat cagacggcca ggaaggaacc ctagcgcccg ccggtgccaa   1080
tataaagcgc cactctctct cgtcttaagc cccagcctct ccattcccct ctccctctcg   1140
ccgccgccgt ctccttctcc tactcccttc gaggtgtgtt gttcatccgt cccgaatcca   1200
tccatcccct cttcagatgt gttgttcatg gctctaatag ctctagatct gcttgtttgt   1260
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttattt cttcgcgagg   1440
gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag ttt                                            1883
```

<210> SEQ ID NO 24
<211> LENGTH: 5100
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pABM-BdEF1

<400> SEQUENCE: 24

```
gatcccccgg gctgcaggaa ttcaagctta cgcgtgtcga ctcgaatttc cccgatcgtt     60
caaacatttg gcaataaagt ttcttaagat tgaatcctgt tgccggtctt gcgatgatta    120
tcatataatt tctgttgaat tacgttaagc atgtaataat taacatgtaa tgcatgacgt    180
tatttatgag atgggttttt atgattagag tcccgcaatt atacatttaa tacgcgatag    240
```

-continued

```
aaaacaaaat atagcgcgca aactaggata aattatcgcg cgcggtgtca tctatgttac    300
tagatcgctc gacgcggccg ccatggccag atcgtaccca attcgcccta tagtgagtcg    360
tattacaatt cactggccgt cgttttacaa cgtcgtgact gggaaaaccc tggcgttacc    420
caacttaatc gccttgcagc acatccccct ttcgccagct ggcgtaatag cgaagaggcc    480
cgcaccgatc gcccttccca acagttgcgc agcctgaatg gcgaatggaa attgtaagcg    540
ttaatatttt gttaaaattc gcgttaaatt tttgttaaat cagctcattt tttaaccaat    600
aggccgaaat cggcaaaatc ccttataaat caaaagaata gaccgagata gggttgagtg    660
ttgttccagt ttggaacaag agtccactat taaagaacgt ggactccaac gtcaaagggc    720
gaaaaaccgt ctatcagggc gatggcccac tacgtgaacc atcaccctaa tcaagttttt    780
tggggtcgag gtgccgtaaa gcactaaatc ggaaccctaa agggagcccc cgatttagag    840
cttgacgggg aaagccggcg aacgtggcga gaaaggaagg gaagaaagcg aaaggagcgg    900
gcgctagggc gctggcaagt gtagcggtca cgctgcgcgt aaccaccaca cccgccgcgc    960
ttaatgcgcc gctacagggc gcgtcaggtg gcacttttcg gggaaatgtg cgcggaaccc   1020
ctatttgttt atttttctaa atacattcaa atatgtatcc gctcatgaga caataaccct   1080
gataaatgct tcaataatat tgaaaaagga agagtatgag tattcaacat ttccgtgtcg   1140
cccttattcc cttttttgcg gcattttgcc ttcctgtttt tgctcaccca gaaacgctgg   1200
tgaaagtaaa agatgctgaa gatcagttgg gtgcacgagt gggttacatc gaactggatc   1260
tcaacagcgg taagatcctt gagagttttc gccccgaaga acgttttcca atgatgagca   1320
cttttaaagt tctgctatgt ggcgcggtat tatcccgtat tgacgccggg caagagcaac   1380
tcggtcgccg catacactat tctcagaatg acttggttga gtactcacca gtcacagaaa   1440
agcatcttac ggatggcatg acagtaagag aattatgcag tgctgccata accatgagtg   1500
ataacactgc ggccaactta cttctgacaa cgatcggagg accgaaggag ctaaccgctt   1560
ttttgcacaa catgggggat catgtaactc gccttgatcg ttgggaaccg gagctgaatg   1620
aagccatacc aaacgacgag cgtgacacca cgatgcctgt agcaatggca acaacgttgc   1680
gcaaactatt aactggcgaa ctacttactc tagcttcccg gcaacaatta atagactgga   1740
tggaggcgga taaagttgca ggaccacttc tgcgctcggc ccttccggct ggctggttta   1800
ttgctgataa atctggagcc ggtgagcgtg ggtctcgcgg tatcattgca gcactggggc   1860
cagatggtaa gccctcccgt atcgtagtta tctacacgac ggggagtcag gcaactatgg   1920
atgaacgaaa tagacagatc gctgagatag gtgcctcact gattaagcat tggtaactgt   1980
cagaccaagt ttactcatat atactttaga ttgatttaaa acttcatttt taatttaaaa   2040
ggatctaggt gaagatcctt tttgataatc tcatgaccaa aatcccttaa cgtgagtttt   2100
cgttccactg agcgtcagac cccgtagaaa agatcaaagg atcttcttga gatccttttt   2160
ttctgcgcgt aatctgctgc ttgcaaacaa aaaaaccacc gctaccagcg gtggtttgtt   2220
tgccggatca agagctacca actctttttc cgaaggtaac tggcttcagc agagcgcaga   2280
taccaaatac tgtccttcta gtgtagccgt agttaggcca ccacttcaag aactctgtag   2340
caccgcctac atacctcgct ctgctaatcc tgttaccagt ggctgctgcc agtggcgata   2400
agtcgtgtct taccgggttg gactcaagac gatagttacc ggataaggcg cagcggtcgg   2460
gctgaacggg gggttcgtgc acacagccca gcttggagcg aacgacctac accgaactga   2520
gatacctaca gcgtgagcta tgagaaagcg ccacgcttcc cgaagggaga aaggcggaca   2580
ggtatccggt aagcggcagg gtcggaacag gagagcgcac gagggagctt ccagggggaa   2640
```

```
acgcctggta tctttatagt cctgtcgggt ttcgccacct ctgacttgag cgtcgatttt   2700
tgtgatgctc gtcagggggg cggagcctat ggaaaaacgc cagcaacgcg gcctttttac   2760
ggttcctggc cttttgctgg ccttttgctc acatgttctt tcctgcgtta tcccctgatt   2820
ctgtggataa ccgtattacc gcctttgagt gagctgatac cgctcgccgc agccgaacga   2880
ccgagcgcag cgagtcagtg agcgaggaag cggaagagcg cccaatacgc aaaccgcctc   2940
tccccgcgcg ttggccgatt cattaatgca gctggcacga caggtttccc gactggaaag   3000
cgggcagtga gcgcaacgca attaatgtga gttagctcac tcattaggca ccccaggctt   3060
tacactttat gcttccggct cgtatgttgt gtggaattgt gagcggataa caatttcaca   3120
caggaaacag ctatgaccat gattacgcca agctcgaaat taaccctcac taaagggaac   3180
aaaagctgga ctagaggccc ttaaggcctt actagacttc accgccattg caaaaattgt   3240
caataaatat ttagagtggg tggcatcaga aaaacatctc tagtggactc tcttcctatc   3300
atagctactc gggctgtaga tagaacgagg gcacaagagt tgggtggcgt aggtttactc   3360
gtgacctcaa ctcttttggc tgtgtcttac gtctaagatg ggtttggcat gtgagaaaca   3420
taggtctaag caattcatgt tagggctgtt gcattgttgt tgcatcaacc aaatgtccag   3480
atagcagttc atgctacatc tagttgaaaa ccctcatcat taggcggaac atgtgttctt   3540
ttttagcata gtcaaagtca gattgcggca ctcgctcatc cacggaaaga attttccctg   3600
tgcaggcatc tcgatcaaaa gacgcaaatt aatttttgaa tagcgatata acaatatcta   3660
attaacgttt cttgttttct gcgaaatgtc tttcatcata aaatgagtca tctcgatgag   3720
cccaagtgac atagcccaac accccacccc accaataaaa gtgaagaaaa catgttggga   3780
aaactatacc aagtaaaata cgagttgttc taaagaaaaa gtaaagtacg agttagatcg   3840
caccctgtcc tggagtgtgg cttgatgatc caactcctag cattgtatcc ctgtttttgg   3900
atgatgtaac tattatttac aatgaataaa gaggtgtttt actagtaaaa aaatcttgag   3960
gggaggagaa aataatggag gtcttttttc aaaccgatgg actattattt ttagtgaaag   4020
agaataatat tattggaaaa attattctat ccacttattt tatattggca gaatacaaag   4080
aatggtgggg tccacgcgga acttgcggcc cccgaaacct atcgagggcg cggtacccaa   4140
gcaaggaacg gaggaaactt gcggggcccg aaacctagtg ataaaaggca tatcatccac   4200
acgatgaaga tctgacggac catatctccc accacggaaa gccatcagac gaggatcaga   4260
cggccaggaa ggaaccctag cgcccgccgg tgccaatata aagcgccact ctctctcgtc   4320
ttaagcccca gcctctccat tcccctctcc ctctcgccgc cgccgtctcc ttctcctact   4380
cccttcgagg tgtgttgttc atccgtcccg aatccatcca tcccctcttc agatgtgttg   4440
ttcatggctc taatagctct agatctgctt gtttgtgttg tttagctcta gatctactcg   4500
cgcgcgcttc tctctcgatc tcctgtagaa caattttggt tggtttttttg tgcatatcca   4560
tggtaatttt gtctgcaata tggaggaggc tttctaagct cctacgtagc atcgatcttt   4620
agaattccct cggtttctgt ttatttcttc gcgagggctc tctgttatct gtaggagtag   4680
ctgtaagcgc ggttcgttac ggattaatcg tcatgcttag ttgaacctat cggtcgaagg   4740
atttgtgtgg gttgtcgtgt agaattgaca ccatctactt actgtactga tatgccgatc   4800
tgtaggatac tcttcattac ttttgtttac tgctagttgt ggtgtagatt tagcattctc   4860
aaacccatgc tgtagcgttt ctaatattgt tacatagatc taccggtgcc tgttaattgt   4920
attcgatcgg gcgtttctac atctgtccgc ccacctagtt ttatatgtgg taatcaaaat   4980
```

```
tgcgttgact tcgtgatgct gtctgtgtac tgtttttaat cgctcttact tagatgatca   5040

acatggtgat ggttacgatt tactgttttc taatccctgt tacttcgatg ctgcagtttg   5100
```

```
<210> SEQ ID NO 25
<211> LENGTH: 6567
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pABM-BdEF1_ZmPLT5

<400> SEQUENCE: 25

agcttacgcg tgtcgactcg aatttccccg atcgttcaaa catttggcaa taaagtttct     60

taagattgaa tcctgttgcc ggtcttgcga tgattatcat ataatttctg ttgaattacg    120

ttaagcatgt aataattaac atgtaatgca tgacgttatt tatgagatgg gtttttatga    180

ttagagtccc gcaattatac atttaatacg cgatagaaaa caaaatatag cgcgcaaact    240

aggataaatt atcgcgcgcg gtgtcatcta tgttactaga tcgctcgacg cggccgccat    300

ggccagatcg tacccaattc gccctatagt gagtcgtatt acaattcact ggccgtcgtt    360

ttacaacgtc gtgactggga aaaccctggc gttacccaac ttaatcgcct tgcagcacat    420

ccccctttcg ccagctggcg taatagcgaa gaggcccgca ccgatcgccc ttcccaacag    480

ttgcgcagcc tgaatggcga atggaaattg taagcgttaa tattttgtta aaattcgcgt    540

taaatttttg ttaaatcagc tcatttttta accaataggc cgaaatcggc aaaatccctt    600

ataaatcaaa agaatagacc gagatagggt tgagtgttgt tccagtttgg aacaagagtc    660

cactattaaa gaacgtggac tccaacgtca aagggcgaaa aaccgtctat cagggcgatg    720

gcccactacg tgaaccatca ccctaatcaa gttttttggg gtcgaggtgc cgtaaagcac    780

taaatcggaa ccctaaaggg agcccccgat ttagagcttg acggggaaag ccggcgaacg    840

tggcgagaaa ggaagggaag aaagcgaaag gagcgggcgc tagggcgctg gcaagtgtag    900

cggtcacgct gcgcgtaacc accacacccg ccgcgcttaa tgcgccgcta cagggcgcgt    960

caggtggcac ttttcgggga aatgtgcgcg gaacccctat ttgtttattt ttctaaatac   1020

attcaaatat gtatccgctc atgagacaat aaccctgata aatgcttcaa taatattgaa   1080

aaaggaagag tatgagtatt caacatttcc gtgtcgccct tattcccttt tttgcggcat   1140

tttgccttcc tgtttttgct cacccagaaa cgctggtgaa agtaaaagat gctgaagatc   1200

agttgggtgc acgagtgggt tacatcgaac tggatctcaa cagcggtaag atccttgaga   1260

gttttcgccc cgaagaacgt tttccaatga tgagcacttt taaagttctg ctatgtggcg   1320

cggtattatc ccgtattgac gccgggcaag agcaactcgg tcgccgcata cactattctc   1380

agaatgactt ggttgagtac tcaccagtca cagaaaagca tcttacggat ggcatgacag   1440

taagagaatt atgcagtgct gccataacca tgagtgataa cactgcggcc aacttacttc   1500

tgacaacgat cggaggaccg aaggagctaa ccgctttttt gcacaacatg ggggatcatg   1560

taactcgcct tgatcgttgg gaaccggagc tgaatgaagc cataccaaac gacgagcgtg   1620

acaccacgat gcctgtagca atggcaacaa cgttgcgcaa actattaact ggcgaactac   1680

ttactctagc ttcccggcaa caattaatag actggatgga ggcggataaa gttgcaggac   1740

cacttctgcg ctcggccctt ccggctggct ggtttattgc tgataaatct ggagccggtg   1800

agcgtgggtc tcgcggtatc attgcagcac tggggccaga tggtaagccc tcccgtatcg   1860
```

```
tagttatcta cacgacgggg agtcaggcaa ctatggatga acgaaataga cagatcgctg   1920
agataggtgc ctcactgatt aagcattggt aactgtcaga ccaagtttac tcatatatac   1980
tttagattga tttaaaactt catttttaat ttaaaaggat ctaggtgaag atcctttttg   2040
ataatctcat gaccaaaatc ccttaacgtg agttttcgtt ccactgagcg tcagaccccg   2100
tagaaaagat caaaggatct tcttgagatc cttttttct gcgcgtaatc tgctgcttgc    2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca ggggggcgga   2700
gcctatggaa aaacgccagc aacgcggcct ttttacggtt cctggccttt tgctggcctt   2760
ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
caccccacca ataaaagtga agaaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgttttacta gtaaaaaaat cttgagggga ggagaaaata atggaggtct   3960
tttttcaaac cgatggacta ttatttttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
```

```
cgccggtgcc aatataaagc gccactctct ctcgtcttaa gccccagcct ctccattccc   4320
ctctccctct cgccgccgcc gtctccttct cctactccct tcgaggtgtg ttgttcatcc   4380
gtcccgaatc catccatccc ctcttcagat gtgttgttca tggctctaat agctctagat   4440
ctgcttgttt gtgttgttta gctctagatc tactcgcgcg cgcttctctc tcgatctcct   4500
gtagaacaat tttggttggt tttttgtgca tatccatggt aattttgtct gcaatatgga   4560
ggaggctttc taagctccta cgtagcatcg atctttagaa ttccctcggt ttctgtttat   4620
ttcttcgcga gggctctctg ttatctgtag gagtagctgt aagcgcggtt cgttacggat   4680
taatcgtcat gcttagttga acctatcggt cgaaggattt gtgtgggttg tcgtgtagaa   4740
ttgacaccat ctacttactg tactgatatg ccgatctgta ggatactctt cattactttt   4800
gtttactgct agttgtggtg tagatttagc attctcaaac ccatgctgta gcgtttctaa   4860
tattgttaca tagatctacc ggtgcctgtt aattgtattc gatcgggcgt ttctacatct   4920
gtccgcccac ctagttttat atgtggtaat caaaattgcg ttgacttcgt gatgctgtct   4980
gtgtactgtt tttaatcgct cttacttaga tgatcaacat ggtgatggtt acgatttact   5040
gttttctaat ccctgttact tcgatgctgc agtttggatc catggacacc tcgcaccact   5100
atcatccatg gctcaacttc tccctcgccc accactgtga cctcgaggag gaggagaggg   5160
gcgcggccgc cgagctggcc gcgatagccg gcgccgcgcc gccgccgaag ctggaggact   5220
tcctcggcgg aggcgtcgcc accggtggtc cggaggcggt ggcgcccgcg gagatgtacg   5280
actcggacct caagttcata gccgccgccg ggttccttgg cggctcggcg gcggcggcgg   5340
cgacgtcgcc gctgtcctcc ctcgaccagg ccggttccaa gctggccttg cctgcggcgg   5400
cggctgctcc ggcgccggag cagaggaagg ccgtcgactc ctttgggcag cgcacgtcca   5460
tctaccgcgg cgtcacacgg caccggtgga ctggcaggta cgaggcacat ctgtgggaca   5520
acagctgccg acgcgaaggg cagagccgca agggccgcca agtatatttg ggtggctatg   5580
ataaggagga gaaggctgcc agggcgtatg atcttgcagc tttgaagtac tggggttcta   5640
gcaccaccac caactttccg gttgctgagt atgagaagga ggtcgaggag atgaagaaca   5700
tgacgcgaca agagtttgtt gcttcccttc gaaggaagag cagtggattc tctcggggtg   5760
cttccatcta cagaggtgta accagacatc accagcatgg acggtggcag gcgaggatcg   5820
gaagggtggc cggtaacaag gacctctacc ttgggacgtt cagcaccgag gaggaagctg   5880
cagaggccta cgacatagcg gccatcaagt tcagaggcct gaacgccgtc acaaacttcg   5940
agatcagccg gtacaacgtg gagaccataa tgagcagcaa ccttccagtc gcgagcatgt   6000
cgtcgtcgtc ggcggcggcg gcgggtggcc ggagcagcaa ggcgctggag tcccctccgt   6060
ccggctcgct tgacggcggc ggcggcatgc cagtcgtcga aggcagcacg gcaccgccgc   6120
tgttcattcc ggtgaagtac gaccagcagc agcaggagta cctgtcgatg ctcgcgttgc   6180
agcaccacca ccagcagcaa caagcaggga acctgttgca ggggccgcta gtagggttcg   6240
gcggcctcta ctcctccggg gtgaacctgg atttcgccaa ctcccacggc acggcggctc   6300
cgtcgtcgat ggcccaccac tgctacgcca atggcaccgc gtccgcctcg catgagcacc   6360
agcaccagca ccagatgcag cagggcggcg agaacgagac gcagccgcag ccgcagcaga   6420
gctccagcag ctgctcctcc ctgccattcg ccaccccggt cgctttcaat gggtcctatg   6480
aaagctccat cacggcggca ggcccctttg gatactccta cccaaatgtg gcagcctttc   6540
agacgccgat ctatggaatg gaatgaa                                        6567
```

<210> SEQ ID NO 26
<211> LENGTH: 6552
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pABM-BdEF1_ZmPLT7

<400> SEQUENCE: 26

```
agcttacgcg tgtcgactcg aatttccccg atcgttcaaa catttggcaa taaagtttct     60
taagattgaa tcctgttgcc ggtcttgcga tgattatcat ataatttctg ttgaattacg    120
ttaagcatgt aataattaac atgtaatgca tgacgttatt tatgagatgg gtttttatga    180
ttagagtccc gcaattatac atttaatacg cgatagaaaa caaaatatag cgcgcaaact    240
aggataaatt atcgcgcgcg gtgtcatcta tgttactaga tcgctcgacg cggccgccat    300
ggccagatcg tacccaattc gccctatagt gagtcgtatt acaattcact ggccgtcgtt    360
ttacaacgtc gtgactggga aaaccctggc gttacccaac ttaatcgcct tgcagcacat    420
ccccctttcg ccagctggcg taatagcgaa gaggcccgca ccgatcgccc ttcccaacag    480
ttgcgcagcc tgaatggcga atggaaattg taagcgttaa tattttgtta aaattcgcgt    540
taaatttttg ttaaatcagc tcatttttta accaataggc cgaaatcggc aaaatccctt    600
ataaatcaaa agaatagacc gagatagggt tgagtgttgt tccagtttgg aacaagagtc    660
cactattaaa gaacgtggac tccaacgtca aagggcgaaa aaccgtctat cagggcgatg    720
gcccactacg tgaaccatca ccctaatcaa gttttttggg gtcgaggtgc cgtaaagcac    780
taaatcggaa ccctaaaggg agcccccgat ttagagcttg acggggaaag ccggcgaacg    840
tggcgagaaa ggaagggaag aaagcgaaag gagcgggcgc tagggcgctg gcaagtgtag    900
cggtcacgct gcgcgtaacc accacacccg ccgcgcttaa tgcgccgcta cagggcgcgt    960
caggtggcac ttttcgggga aatgtgcgcg gaacccctat ttgtttattt ttctaaatac   1020
attcaaatat gtatccgctc atgagacaat aaccctgata aatgcttcaa taatattgaa   1080
aaaggaagag tatgagtatt caacatttcc gtgtcgccct tattcccttt tttgcggcat   1140
tttgccttcc tgtttttgct cacccagaaa cgctggtgaa agtaaaagat gctgaagatc   1200
agttgggtgc acgagtgggt tacatcgaac tggatctcaa cagcggtaag atccttgaga   1260
gttttcgccc cgaagaacgt tttccaatga tgagcacttt taaagttctg ctatgtggcg   1320
cggtattatc ccgtattgac gccgggcaag agcaactcgg tcgccgcata cactattctc   1380
agaatgactt ggttgagtac tcaccagtca cagaaaagca tcttacggat ggcatgacag   1440
taagagaatt atgcagtgct gccataacca tgagtgataa cactgcggcc aacttacttc   1500
tgacaacgat cggaggaccg aaggagctaa ccgctttttt gcacaacatg ggggatcatg   1560
taactcgcct tgatcgttgg gaaccggagc tgaatgaagc cataccaaac gacgagcgtg   1620
acaccacgat gcctgtagca atggcaacaa cgttgcgcaa actattaact ggcgaactac   1680
ttactctagc ttcccggcaa caattaatag actggatgga ggcggataaa gttgcaggac   1740
cacttctgcg ctcggccctt ccggctggct ggtttattgc tgataaatct ggagccggtg   1800
agcgtgggtc tcgcggtatc attgcagcac tggggccaga tggtaagccc tcccgtatcg   1860
tagttatcta cacgacgggg agtcaggcaa ctatggatga acgaaataga cagatcgctg   1920
agataggtgc ctcactgatt aagcattggt aactgtcaga ccaagtttac tcatatatac   1980
```

```
tttagattga tttaaaactt catttttaat ttaaaaggat ctaggtgaag atcctttttg   2040
ataatctcat gaccaaaatc ccttaacgtg agttttcgtt ccactgagcg tcagaccccg   2100
tagaaaagat caaaggatct tcttgagatc ctttttttct gcgcgtaatc tgctgcttgc   2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca ggggggcgga   2700
gcctatggaa aaacgccagc aacgcggcct ttttacggtt cctggccttt tgctggcctt   2760
ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
caccccacca ataaaagtga agaaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgttttacta gtaaaaaaat cttgagggga ggagaaaata atggaggtct   3960
tttttcaaac cgatggacta ttatttttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
cgccggtgcc aatataaagc gccactctct ctcgtcttaa gccccagcct ctccattccc   4320
ctctccctct cgccgccgcc gtctccttct cctactccct tcgaggtgtg ttgttcatcc   4380
```

```
gtcccgaatc catccatccc ctcttcagat gtgttgttca tggctctaat agctctagat   4440
ctgcttgttt gtgttgttta gctctagatc tactcgcgcg cgcttctctc tcgatctcct   4500
gtagaacaat tttggttggt tttttgtgca tatccatggt aattttgtct gcaatatgga   4560
ggaggctttc taagctccta cgtagcatcg atctttagaa ttccctcggt ttctgtttat   4620
ttcttcgcga gggctctctg ttatctgtag gagtagctgt aagcgcggtt cgttacggat   4680
taatcgtcat gcttagttga acctatcggt cgaaggattt gtgtgggttg tcgtgtagaa   4740
ttgacaccat ctacttactg tactgatatg ccgatctgta ggatactctt cattactttt   4800
gtttactgct agttgtggtg tagatttagc attctcaaac ccatgctgta gcgtttctaa   4860
tattgttaca tagatctacc ggtgcctgtt aattgtattc gatcgggcgt ttctacatct   4920
gtccgcccac ctagttttat atgtggtaat caaaattgcg ttgacttcgt gatgctgtct   4980
gtgtactgtt tttaatcgct cttacttaga tgatcaacat ggtgatggtt acgatttact   5040
gttttctaat ccctgttact tcgatgctgc agtttggatc catggacatg gacatgagct   5100
cagcttatcc ccaccattgg ctctccttct ccctctccaa caactaccac catggcctac   5160
tcgaggcctt ctctaactcc tccggtactc ctcttggaga cgagccgggc gcagtggagg   5220
agtccccgag gacggtggag gacttcctcg gcggcgtcgg tggcgccggc gccccgccgc   5280
agccggcggc tgctgcagat caggatcacc agcttgtgtg cggcgagctg ggcagcatca   5340
cagccaggtt cttgcgccac tacccggcgg cgccagctgg gacgacggtg gagaaccccg   5400
gcgcggtgac cgtggcggcc atgtcgtcga cggacgtggc gggggcggag tccgaccagg   5460
cgaggcggcc cgccgagacg ttcggccagc gcacatccat ctaccgtggc gtcaccaggc   5520
accggtggac agggagatat gaggcgcact tgtgggacaa cagctgccgc cgggagggcc   5580
aaagccgcaa aggacgccaa gtctacctag gaggctatga caaggaggag aaggcggcta   5640
gagcttacga cctcgccgcg ctcaagtact gggggcctac aaccacgacc aacttcccgg   5700
tgtccaacta cgagaaggag ctggaggaga tgaagtccat gacgcggcag gagttcatcg   5760
cgtcgttgcg caggaagagc agcggcttct cacgaggcgc ctccatctac agaggagtca   5820
caaggcatca tcagcacggc cggtggcagg cgaggatcgg cagggtggcc ggaaacaagg   5880
acctgtactt gggcactttc agtactcagg aagaggcggc ggaggcgtac gacatcgctg   5940
cgatcaagtt ccgcgggctc aacgccgtca ccaacttcga catgagccgc tacgacgtgg   6000
agagcatcct cagcagcgac ctccccgtcg gggcggagc caccgggcgc gccgccaagt   6060
tcccgttgga ctcgctgcag ccggggagcg ctgctgcgat gatgctcgcc ggggctgctg   6120
ccgcttcgca ggccaccatg ccgccgtccg agaaggacta ctggtctctg ctcgccctgc   6180
actaccagca gcagcaggag caggagcggc agttcccggc ttctgcttac gaggcttacg   6240
gctccggcgg cgtgaacgtg gacttcacga tgggcaccag tagcggcaac aacaacaaca   6300
acaccggcag cggcgtcatg tggggcgcca ccactggtgc agtagtagtg ggacagcaag   6360
acagcagcgg caagcagggc aacggctatg ccagcaacat tccttatgct gctgctgctg   6420
ctatggtttc tggatctgct ggctacgagg gctccaccgg cgacaatgga acctgggtta   6480
ctacgactat taccagcagc aacaccggca cggctcccca ctactacaac tatctcttcg   6540
ggatggagta ga                                                       6552
```

<210> SEQ ID NO 27
<211> LENGTH: 5865
<212> TYPE: DNA

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pABM-BdEF1_KWS_RBP1

<400> SEQUENCE: 27

```
agcttacgcg tgtcgactcg aatttccccg atcgttcaaa catttggcaa taaagtttct     60

taagattgaa tcctgttgcc ggtcttgcga tgattatcat ataatttctg ttgaattacg    120

ttaagcatgt aataattaac atgtaatgca tgacgttatt tatgagatgg gtttttatga    180

ttagagtccc gcaattatac atttaatacg cgatagaaaa caaaatatag cgcgcaaact    240

aggataaatt atcgcgcgcg gtgtcatcta tgttactaga tcgctcgacg cggccgccat    300

ggccagatcg tacccaattc gccctatagt gagtcgtatt acaattcact ggccgtcgtt    360

ttacaacgtc gtgactggga aaaccctggc gttacccaac ttaatcgcct tgcagcacat    420

ccccctttcg ccagctggcg taatagcgaa gaggcccgca ccgatcgccc ttcccaacag    480

ttgcgcagcc tgaatggcga atggaaattg taagcgttaa tattttgtta aaattcgcgt    540

taaatttttg ttaaatcagc tcatttttta accaataggc cgaaatcggc aaaatccctt    600

ataaatcaaa agaatagacc gagatagggt tgagtgttgt tccagtttgg aacaagagtc    660

cactattaaa gaacgtggac tccaacgtca aagggcgaaa aaccgtctat cagggcgatg    720

gcccactacg tgaaccatca ccctaatcaa gttttttggg gtcgaggtgc cgtaaagcac    780

taaatcggaa ccctaaaggg agcccccgat ttagagcttg acggggaaag ccggcgaacg    840

tggcgagaaa ggaagggaag aaagcgaaag gagcgggcgc tagggcgctg gcaagtgtag    900

cggtcacgct gcgcgtaacc accacacccg ccgcgcttaa tgcgccgcta cagggcgcgt    960

caggtggcac ttttcgggga aatgtgcgcg gaacccctat ttgtttattt ttctaaatac   1020

attcaaatat gtatccgctc atgagacaat aaccctgata aatgcttcaa taatattgaa   1080

aaaggaagag tatgagtatt caacatttcc gtgtcgccct tattcccttt tttgcggcat   1140

tttgccttcc tgtttttgct cacccagaaa cgctggtgaa agtaaaagat gctgaagatc   1200

agttgggtgc acgagtgggt tacatcgaac tggatctcaa cagcggtaag atccttgaga   1260

gttttcgccc cgaagaacgt tttccaatga tgagcacttt taaagttctg ctatgtggcg   1320

cggtattatc ccgtattgac gccgggcaag agcaactcgg tcgccgcata cactattctc   1380

agaatgactt ggttgagtac tcaccagtca cagaaaagca tcttacggat ggcatgacag   1440

taagagaatt atgcagtgct gccataacca tgagtgataa cactgcggcc aacttacttc   1500

tgacaacgat cggaggaccg aaggagctaa ccgctttttt gcacaacatg ggggatcatg   1560

taactcgcct tgatcgttgg gaaccggagc tgaatgaagc cataccaaac gacgagcgtg   1620

acaccacgat gcctgtagca atggcaacaa cgttgcgcaa actattaact ggcgaactac   1680

ttactctagc ttcccggcaa caattaatag actggatgga ggcggataaa gttgcaggac   1740

cacttctgcg ctcggccctt ccggctggct ggtttattgc tgataaatct ggagccggtg   1800

agcgtgggtc tcgcggtatc attgcagcac tggggccaga tggtaagccc tcccgtatcg   1860

tagttatcta cacgacgggg agtcaggcaa ctatggatga acgaaataga cagatcgctg   1920

agataggtgc ctcactgatt aagcattggt aactgtcaga ccaagtttac tcatatatac   1980

tttagattga tttaaaactt catttttaat ttaaaaggat ctaggtgaag atcctttttg   2040

ataatctcat gaccaaaatc ccttaacgtg agttttcgtt ccactgagcg tcagaccccg   2100
```

```
tagaaaagat caaaggatct tcttgagatc ctttttttct gcgcgtaatc tgctgcttgc   2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca ggggggcgga   2700
gcctatggaa aaacgccagc aacgcggcct ttttacggtt cctggccttt tgctggcctt   2760
ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
caccccacca ataaaagtga agaaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgttttacta gtaaaaaaat cttgagggga ggagaaaata atggaggtct   3960
tttttcaaac cgatggacta ttatttttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
cgccggtgcc aatataaagc gccactctct ctcgtcttaa gccccagcct ctccattccc   4320
ctctccctct cgccgccgcc gtctccttct cctactccct tcgaggtgtg ttgttcatcc   4380
gtcccgaatc catccatccc ctcttcagat gtgttgttca tggctctaat agctctagat   4440
ctgcttgttt gtgttgttta gctctagatc tactcgcgcg cgcttctctc tcgatctcct   4500
```

```
gtagaacaat tttggttggt tttttgtgca tatccatggt aattttgtct gcaatatgga   4560
ggaggctttc taagctccta cgtagcatcg atctttagaa ttccctcggt ttctgtttat   4620
ttcttcgcga gggctctctg ttatctgtag gagtagctgt aagcgcggtt cgttacggat   4680
taatcgtcat gcttagttga acctatcggt cgaaggattt gtgtgggttg tcgtgtagaa   4740
ttgacaccat ctacttactg tactgatatg ccgatctgta ggatactctt cattactttt   4800
gtttactgct agttgtggtg tagatttagc attctcaaac ccatgctgta gcgtttctaa   4860
tattgttaca tagatctacc ggtgcctgtt aattgtattc gatcgggcgt ttctacatct   4920
gtccgcccac ctagttttat atgtggtaat caaaattgcg ttgacttcgt gatgctgtct   4980
gtgtactgtt tttaatcgct cttacttaga tgatcaacat ggtgatggtt acgatttact   5040
gttttctaat ccctgttact tcgatgctgc agtttggatc catggagtcg ggctccggga   5100
cggctgctgg ctctggctat gtttacagac agccaggatc aacgcggtgg aacccgacag   5160
ctgaacaact gtccttgctt agagaaatct actaccgcaa cggattgcgg accccgaccg   5220
cggacgaaat cagacaaatc agctcaaagc tctcaaggta cggaaaaata gagggcaaaa   5280
acgtttacaa ctggttccag aatagacgcg caagagaaaa gcgcaagcaa cggctctcta   5340
caatcggctg tgatccagca ctgatcgaga tggggaatgt cgcttcactg gaattcggta   5400
ctgagagcgc cctggaatcg ctgtcgtcag gaccatcctc agaactccgc gaagcgccaa   5460
cgagaaaatt ttacgaaaaa aagacggttg gagagaactc aactataata aacccagtgg   5520
aacaaaactg taccctttcc tgcggaacgt cccaagagtt ccagtatgcg gtcgattctc   5580
ggcgcgtcat gaaagctatg gaggaaaagc aggcgacgga cgatgaaccc gacggaaata   5640
aatggactga gtcaaacaga cacgtcaaga ttctccagct tttcccgctc cacaataacg   5700
aggatcagac attgataaag agcgacaaag aaatctattg tttgggctcg tgcgagaaga   5760
aaatggattt gtcaccgctg ggtcattcag gctctcagcg cgcttcggcc cttgacttgt   5820
gcctttcatt gggcaacgaa tcttgtgggc tgcatgataa ttgaa                   5865
```

<210> SEQ ID NO 28
<211> LENGTH: 6186
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pABM-BdEF1_TaRKD4

<400> SEQUENCE: 28

```
agcttacgcg tgtcgactcg aatttccccg atcgttcaaa catttggcaa taaagtttct     60
taagattgaa tcctgttgcc ggtcttgcga tgattatcat ataatttctg ttgaattacg    120
ttaagcatgt aataattaac atgtaatgca tgacgttatt tatgagatgg gtttttatga    180
ttagagtccc gcaattatac atttaatacg cgatagaaaa caaaatatag cgcgcaaact    240
aggataaatt atcgcgcgcg gtgtcatcta tgttactaga tcgctcgacg cggccgccat    300
ggccagatcg tacccaattc gccctatagt gagtcgtatt acaattcact ggccgtcgtt    360
ttacaacgtc gtgactggga aaaccctggc gttacccaac ttaatcgcct tgcagcacat    420
ccccctttcg ccagctggcg taatagcgaa gaggcccgca ccgatcgccc ttcccaacag    480
ttgcgcagcc tgaatggcga atggaaattg taagcgttaa tattttgtta aaattcgcgt    540
taaatttttg ttaaatcagc tcatttttta accaataggc cgaaatcggc aaaatccctt    600
```

```
ataaatcaaa agaatagacc gagatagggt tgagtgttgt tccagtttgg aacaagagtc    660
cactattaaa gaacgtggac tccaacgtca aagggcgaaa aaccgtctat cagggcgatg    720
gcccactacg tgaaccatca ccctaatcaa gttttttggg gtcgaggtgc cgtaaagcac    780
taaatcggaa ccctaaaggg agcccccgat ttagagcttg acggggaaag ccggcgaacg    840
tggcgagaaa ggaagggaag aaagcgaaag gagcgggcgc tagggcgctg gcaagtgtag    900
cggtcacgct gcgcgtaacc accacacccg ccgcgcttaa tgcgccgcta cagggcgcgt    960
caggtggcac ttttcgggga aatgtgcgcg gaacccctat ttgtttattt ttctaaatac   1020
attcaaatat gtatccgctc atgagacaat aaccctgata aatgcttcaa taatattgaa   1080
aaaggaagag tatgagtatt caacatttcc gtgtcgccct tattcccttt tttgcggcat   1140
tttgccttcc tgtttttgct cacccagaaa cgctggtgaa agtaaaagat gctgaagatc   1200
agttgggtgc acgagtgggt tacatcgaac tggatctcaa cagcggtaag atccttgaga   1260
gttttcgccc cgaagaacgt tttccaatga tgagcacttt taaagttctg ctatgtggcg   1320
cggtattatc ccgtattgac gccgggcaag agcaactcgg tcgccgcata cactattctc   1380
agaatgactt ggttgagtac tcaccagtca cagaaaagca tcttacggat ggcatgacag   1440
taagagaatt atgcagtgct gccataacca tgagtgataa cactgcggcc aacttacttc   1500
tgacaacgat cggaggaccg aaggagctaa ccgctttttt gcacaacatg ggggatcatg   1560
taactcgcct tgatcgttgg gaaccggagc tgaatgaagc cataccaaac gacgagcgtg   1620
acaccacgat gcctgtagca atggcaacaa cgttgcgcaa actattaact ggcgaactac   1680
ttactctagc ttcccggcaa caattaatag actggatgga ggcggataaa gttgcaggac   1740
cacttctgcg ctcggccctt ccggctggct ggtttattgc tgataaatct ggagccggtg   1800
agcgtgggtc tcgcggtatc attgcagcac tggggccaga tggtaagccc tcccgtatcg   1860
tagttatcta cacgacgggg agtcaggcaa ctatggatga acgaaataga cagatcgctg   1920
agataggtgc ctcactgatt aagcattggt aactgtcaga ccaagtttac tcatatatac   1980
tttagattga tttaaaactt catttttaat ttaaaaggat ctaggtgaag atcctttttg   2040
ataatctcat gaccaaaatc ccttaacgtg agttttcgtt ccactgagcg tcagaccccg   2100
tagaaaagat caaaggatct tcttgagatc ctttttttct gcgcgtaatc tgctgcttgc   2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca ggggggcgga   2700
gcctatggaa aaacgccagc aacgcggcct ttttacggtt cctggccttt tgctggcctt   2760
ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
```

```
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
caccccacca ataaaagtga agaaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgttttacta gtaaaaaaat cttgagggga ggagaaaata atggaggtct   3960
tttttcaaac cgatggacta ttatttttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
cgccggtgcc aatataaagc gccactctct ctcgtcttaa gccccagcct ctccattccc   4320
ctctccctct cgccgccgcc gtctccttct cctactccct tcgaggtgtg ttgttcatcc   4380
gtcccgaatc catccatccc ctcttcagat gtgttgttca tggctctaat agctctagat   4440
ctgcttgttt gtgttgttta gctctagatc tactcgcgcg cgcttctctc tcgatctcct   4500
gtagaacaat tttggttggt tttttgtgca tatccatggt aattttgtct gcaatatgga   4560
ggaggctttc taagctccta cgtagcatcg atctttagaa ttccctcggt ttctgtttat   4620
ttcttcgcga gggctctctg ttatctgtag gagtagctgt aagcgcggtt cgttacggat   4680
taatcgtcat gcttagttga acctatcggt cgaaggattt gtgtgggttg tcgtgtagaa   4740
ttgacaccat ctacttactg tactgatatg ccgatctgta ggatactctt cattactttt   4800
gtttactgct agttgtggtg tagatttagc attctcaaac ccatgctgta gcgtttctaa   4860
tattgttaca tagatctacc ggtgcctgtt aattgtattc gatcgggcgt ttctacatct   4920
gtccgcccac ctagttttat atgtggtaat caaaattgcg ttgacttcgt gatgctgtct   4980
gtgtactgtt tttaatcgct cttacttaga tgatcaacat ggtgatggtt acgatttact   5040
gttttctaat ccctgttact tcgatgctgc agtttggatc catggagatg caacaacaat   5100
acttcggggg ggacggcgat gcggactggt tccatcaact cgcattgctt cccccacttc   5160
caatctcatc gtctctcccc ccactcccga tgtcagaggg ctcatgtctc cctatggcag   5220
cagcagctgc agctgcactc ccccttggcg attgctcgag cgccctcatg atacgccctg   5280
aggaacagat gtcttgcctt ccaatgaacc cctctccagc ggtcgtcgac gatgtctact   5340
```

```
cttcctacgc accgaacaat gtcgacgtgt tgccgccatt cccggcagga cttgacgacg   5400

ctctgttgat ggagtctttt tctgacatcg acctcgagga gtttgctgac gcatttggcc   5460

acaagatcaa gacagaaccc ctcgacgatg ccatggtccc cgcggaccac gacttcgcgg   5520

ctcaagccca acaggcctgc cctgtggtca tcatgaatca gcaacaactc aacgcaccca   5580

gagacgtgcg cctgctcatt gacccggatg atgatgacag caccgtggtg gccgggggct   5640

atgaagctgc agcggtgggg tgcgccgagc agaaacaggt caggccagca ccacgtaggg   5700

tgagaaagag ctcaggcggc gcaagaccag ccgcgggagg aaagtccctc gatcacatcg   5760

gattcgagga actcaggacc tatttctata tgccaatcac caaggcagcg agggaaatga   5820

acgtggggct gacagtcctg aagaagagat gccgggaact gggggtggcg cgctggccac   5880

acagaaagat gaagtctctg agaagcctga tcctcaacat tcaggagatg ggaagggcg    5940

caacatctcc cgcagccgtg caggggggaac ttgaagcgct tgagaggtat tgcgccatta   6000

tggaggagaa cccggctata gagctcaccg agcaaacgaa gaagctcagg caggcttgtt   6060

tcaaagagaa ttataagcgg cgtagagccg ccgcttctgt taatcttctc gatcactgct   6120

ataacgatct ggcatctcat gagcagcaaa tgcctctccc acaaatggga ttctttggat   6180

tttaga                                                              6186
```

```
<210> SEQ ID NO 29
<211> LENGTH: 10427
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pGEP359

<400> SEQUENCE: 29
```

```
actgctgcag tgcagcgtga cccggtcgtg cccctctcta gagataatga gcattgcatg     60

tctaagttat aaaaaattac cacatatttt ttttgtcaca cttgtttgaa gtgcagttta    120

tctatcttta tacatatatt taaactttac tctacgaata atataatcta tagtactaca    180

ataatatcag tgttttagag aatcatataa atgaacagtt agacatggtc taaaggacaa    240

ttgagtattt tgacaacagg actctacagt tttatctttt tagtgtgcat gtgttctcct    300

tttttttgc aaatagcttc acctatataa tacttcatcc attttattag tacatccatt     360

tagggtttag ggttaatggt tttatagac taattttttt agtacatcta ttttattcta     420

ttttagcctc taaattaaga aaactaaaac tctattttag tttttttatt taataattta    480

gatataaaat agaataaaat aaagtgacta aaaattaaac aaatacctt taagaaatta     540

aaaaaactaa ggaaacattt ttcttgtttc gagtagataa tgccagcctg ttaaacgccg    600

tcgatcgacg agtctaacgg acaccaacca gcgaaccagc agcgtcgcgt cgggccaagc    660

gaagcagacg gcacggcatc tctgtcgctg cctctggacc cctctcgaga gttccgctcc    720

accgttggac ttgctccgct gtcggcatcc agaaattgcg tggcggagcg gcagacgtga    780

gccggcacgg caggcggcct cctcctcctc tcacggcacc ggcagctacg gggattcct     840

ttcccaccgc tccttcgctt tcccttcctc gcccgccgta ataaatagac acccctcca     900

caccctcttt ccccaacctc gtgttgttcg gagcgcacac acacacaacc agatctcccc    960

caaatccacc cgtcggcacc tccgcttcaa ggtacgccgc tcgtcctccc cccccccccc   1020

tctctacctt ctctagatcg gcgttccggt ccatggttag ggcccggtag ttctacttct   1080
```

-continued gttcatgttt gtgttagatc cgtgtttgtg ttagatccgt gctgctagcg ttcgtacacg 1140
gatgcgacct gtacgtcaga cacgttctga ttgctaactt gccagtgttt ctctttgggg 1200
aatcctggga tggctctagc cgttccgcag acgggatcga tctaggatag gtatacatgt 1260
tgatgtgggt tttactgatg catatacatg atggcatatg cagcatctat tcatatgctc 1320
taaccttgag tacctatcta ttataataaa caagtatgtt ttataattat tttgatcttg 1380
atatacttgg atgatggcat atgcagcagc tatatgtgga tttttttagc cctgccttca 1440
tacgctattt atttgcttgg tactgtttct tttgtcgatg ctcaccctgt tgtttggtgt 1500
tacttctgca ggtcgaagct tgaagcaaac atggcatcta gcatggcacc aaagaaaaaa 1560
aggaaagttt ccaaacttga aaaatttaca aactgctact ccctttccaa gacgcttagg 1620
tttaaagcga tccccgttgg caagacccaa gagaatatcg ataacaaaag acttctggtc 1680
gaagatgaaa aaagggccga agactacaag gggtcaaga agttgctcga tcgctattat 1740
ctttccttta tcaacgatgt gcttcattca atcaaactga agaacttgaa taactacatt 1800
agccttttca gaaagaaaac gaggactgaa aaggagaaca aggaacttga gaatcttgaa 1860
ataaaccttc gcaaagaaat tgcaaaagcc ttcaagggga acgaaggata taaatctctt 1920
ttcaaaaaag acattataga aacaattttg cctgagtttc ttgacgacaa ggatgaaatt 1980
gcgctcgtca atagctttaa cggatttaca actgccttca cagggttctt cgacaatagg 2040
gagaatatgt ttagcgagga ggcaaaaagc acatccatcg cattcagatg catcaatgaa 2100
aatcttaccc ggtacatatc gaatatggac atatttgaaa aagtggatgc aatattcgat 2160
aagcacgaag tccaggagat aaaggaaaag atactgaata gcgactatga tgtcgaagat 2220
tttttcgaag gtgagttctt caactttgtc ctgactcaag aaggcattga tgtctataat 2280
gcaataattg gaggttttgt gactgagtct ggcgagaaga taaagggctt gaacgagtat 2340
atcaatctct acaaccagaa gactaagcaa aagttgccta aatttaaacc gctttacaag 2400
caagttttga gcgaccggga aagcctttcc ttttacggtg aaggatacac gagcgatgaa 2460
gaagtcctcg aagtcttccg caacacactc aacaagaact cagaaatctt ttcctcaatt 2520
aaaaaattgg agaagctttt caagaacttc gatgaatact cttcggcggg gatttttgtg 2580
aagaacggcc cggcaatttc cacaatatct aaagacattt tcggagaatg gaacgtgata 2640
agagacaagt ggaatgcgga gtatgatgac atacacctga agaagaaggc agttgtgact 2700
gaaaaatacg aagatgacag gagaaaaagc tttaaaaaga tcgggtcctt ttcactggaa 2760
cagctgcagg agtatgccga cgccgatctt tcggttgtcg aaaagctcaa agaaataatt 2820
atccagaagg tcgatgaaat ctacaaggtg tacggctcaa gcgagaagct ctttgatgct 2880
gacttcgtgt tggagaagtc tcttaaaaaa aacgacgcag tcgtcgcgat aatgaaagat 2940
ttgctggatt cagtgaaatc cttcgagaat tatatcaaag ccttcttcgg cgaggggaag 3000
gagacaaaca gggatgagtc cttctatgga gacttcgttc tggcttacga catccttctt 3060
aaggtcgacc acatctatga cgcaattcgg aactatgtga cgcagaagcc gtattcgaaa 3120
gataagttca agctctattt ccaaaaccct caatttatgg gtgggtggga taaagacaaa 3180
gagaccgatt accgggcaac aattttgcgg tacgggtcta aatattacct cgctataatg 3240
gataagaaat acgctaaatg tctccagaaa attgacaaag atgacgtcaa cggcaattat 3300
gaaaaaatca attataaact ccttcctggc ccaaataaaa tgctcccgaa ggtgtttttt 3360
tccaaaaagt ggatggccta ttataatcca tcagaggata ttcagaaaat ctataaaaat 3420

```
gggaccttta agaagggtga catgtttaac ctgaacgatt gccacaagct tatagatttt   3480
ttcaaagact ctattagccg ctatcccaaa tggtctaatg cttatgattt caacttctct   3540
gaaactgaaa agtacaaaga tattgcagga ttctaccgcg aagttgaaga acaaggttat   3600
aaggtttcct ttgagtctgc gtccaagaaa gaggtcgata agttggtcga agaagggaaa   3660
ttgtatatgt ttcaaattta caataaagac ttttccgaca agtcccatgg tacacctaat   3720
ctgcatacca tgtacttcaa actgctgttc gatgagaata atcacggtca gattcgcctg   3780
agcggagggg cggaactctt catgaggaga gcatcgttga aaaaagagga gctcgtcgtg   3840
catccggcta acagccccat tgctaacaag aatccggata atccaaagaa gactactacc   3900
ctctcctatg acgtctataa ggataagaga ttctctgagg accagtacga gttgcacatc   3960
cctattgcga taaataaatg ccctaagaac atctttaaaa tcaatactga ggtcagagtc   4020
ctgcttaagc acgacgacaa cccgtatgtg atcgggattg ataggggtga aaggaacttg   4080
ctttatattg tggttgtcga tggaaaaggt aatatagtgg aacaatactc tctgaatgaa   4140
attatcaaca acttcaatgg cattaggatc aagaccgact atcattctct gttggacaag   4200
aaagagaaag agcgcttcga ggcacggcaa aactggacgt ctattgagaa catcaaggag   4260
cttaaggctg gttacatttc tcaggttgtg cacaaaattt gcgaactggt cgagaaatat   4320
gatgccgtta tcgcacttga agatctcaac agcggattta agaattctcg ggtgaaagtc   4380
gaaaaacagg tgtatcaaaa attcgaaaag atgctgatcg acaagctcaa ttatatggtt   4440
gataaaaaga gcaacccatg cgccacgggg ggtgcgctta agggctatca gattacgaac   4500
aaatttgaat ccttcaagtc aatgtcgacg caaaatgggt ttatattcta tataccggcg   4560
tggcttacat ctaaaataga tcctagcact gggttcgtga acctgctgaa aaccaagtac   4620
acttcaatcg cagattctaa aaaatttata agcagcttcg acagaatcat gtatgtgccc   4680
gaggaagacc tcttcgagtt tgcccttgat tacaaaaatt tctcaagaac ggatgcagac   4740
tacataaaga agtggaagct gtactcttat gggaaccgga ttcggatatt cagaaatccg   4800
aaaaaaaaca atgtctttga ttgggaggaa gtttgtctta cctctgctta caaagagctg   4860
ttcaataaat atggcattaa ttaccagcaa ggtgatatcc gggcgctcct ttgcgaacag   4920
tctgacaaag ctttctattc ttcatttatg gcgctcatgt cattgatgct gcagatgagg   4980
aatagcatta cggggaggac tgatgttgac tttctgatct cgcccgtgaa aaattctgat   5040
ggaatcttct acgattccag gaattatgag gcccaggaaa atgctatcct tcccaagaac   5100
gcagacgcaa atggcgcgta caatatagct cgcaaggttt tgtgggctat aggccaattc   5160
aagaaagccg aagacgaaaa gctggacaaa gttaagattg ctatatctaa caaagagtgg   5220
cttgagtatg cgcaaacatc tgttaaacac aaacgccccg cggctacaaa gaaggctggc   5280
caggcaaaga agaagaagtg agtcgaccga tcgttcaaac atttggcaat aaagtttctt   5340
aagattgaat cctgttgccg gtcttgcgat gattatcata taatttctgt tgaattacgt   5400
taagcatgta ataattaaca tgtaatgcat gacgttattt atgagatggg tttttatgat   5460
tagagtcccg caattataca tttaatacgc gatagaaaac aaaatatagc gcgcaaacta   5520
ggataaatta tcgcgcgcgg tgtcatctat gttactagat cgatcccggg atatcgcggc   5580
cgcgtcgttc ggctgcggcg agcggtatca gctcactcaa aggcggtaat acggttatcc   5640
acagaatcag gggataacgc aggaaagaac atgtgagcaa aaggccagca aaaggccagg   5700
aaccgtaaaa aggccgcgtt gctggcgttt ttccataggc tccgcccccc tgacgagcat   5760
cacaaaaatc gacgctcaag tcagaggtgg cgaaacccga caggactata aagataccag   5820
```

```
gcgtttcccc ctggaagctc cctcgtgcgc tctcctgttc cgaccctgcc gcttaccgga   5880
tacctgtccg cctttctccc ttcgggaagc gtggcgcttt ctcatagctc acgctgtagg   5940
tatctcagtt cggtgtaggt cgttcgctcc aagctgggct gtgtgcacga accccccgtt   6000
cagcccgacc gctgcgcctt atccggtaac tatcgtcttg agtccaaccc ggtaagacac   6060
gacttatcgc cactggcagc agccactggt aacaggatta gcagagcgag gtatgtaggc   6120
ggtgctacag agttcttgaa gtggtggcct aactacggct acactagaag gacagtattt   6180
ggtatctgcg ctctgctgaa gccagttacc ttcggaaaaa gagttggtag ctcttgatcc   6240
ggcaaacaaa ccaccgctgg tagcggtggt ttttttgttt gcaagcagca gattacgcgc   6300
agaaaaaaag gatctcaaga agatcctttg atcttttcta cggggtctga cgctcagtgg   6360
aacgaaaact cacgttaagg gattttggtc atgagattat caaaaaggat cttcacctag   6420
atccttttaa attaaaaatg aagttttaaa tcaatctaaa gtatatatga gtaaacttgg   6480
tctgacagtt accaatgctt aatcagtgag gcacctatct cagcgatctg tctatttcgt   6540
tcatccatag ttgcctgact ccccgtcgtg tagataacta cgatacggga gggcttacca   6600
tctggcccca gtgctgcaat gataccgcga gacccacgct caccggctcc agatttatca   6660
gcaataaacc agccagccgg aagggccgag cgcagaagtg gtcctgcaac tttatccgcc   6720
tccatccagt ctattaattg ttgccgggaa gctagagtaa gtagttcgcc agttaatagt   6780
ttgcgcaacg ttgttgccat tgctacaggc atcgtggtgt cacgctcgtc gtttggtatg   6840
gcttcattca gctccggttc ccaacgatca aggcgagtta catgatcccc catgttgtgc   6900
aaaaaagcgg ttagctcctt cggtcctccg atcgttgtca gaagtaagtt ggccgcagtg   6960
ttatcactca tggttatggc agcactgcat aattctctta ctgtcatgcc atccgtaaga   7020
tgcttttctg tgactggtga gtactcaacc aagtcattct gagaatagtg tatgcggcga   7080
ccgagttgct cttgcccggc gtcaatacgg gataataccg cgccacatag cagaacttta   7140
aaagtgctca tcattggaaa acgttcttcg gggcgaaaac tctcaaggat cttaccgctg   7200
ttgagatcca gttcgatgta acccactcgt gcacccaact gatcttcagc atcttttact   7260
ttcaccagcg tttctgggtg agcaaaaaca ggaaggcaaa atgccgcaaa aaagggaata   7320
agggcgacac ggaaatgttg aatactcata ctcttccttt ttcaatatta ttgaagcatt   7380
tatcagggtt attgtctcat gagcggatac atatttgaat gtatttagaa aaataaacaa   7440
ataggggttc cgcgcacatt tccccgaaaa gtgccacctg acgcgccctg tagcggcacg   7500
tctaattcgg gggatctgga ttttagtact ggattttggt tttaggaatt agaaatttta   7560
ttgatagaag tattttacaa atacaaatac atactaaggg tttcttatat gctcaacaca   7620
tgagcgaaac cctataggaa ccctaattcc cttatctggg aactactcac acattattat   7680
ggagaaactc gagcttgtcg atcgacatga tcagggagct ctcaggtacc tctagacttg   7740
tacagctcgt ccatgccgta caggaacagg tggtggcggc cctcggagcg ctcgtactgt   7800
tccacgatgg tgtagtcctc gttgtgggag gtgatgtcca gcttggtgtc cacgtagtag   7860
tagccgggca gttgcacggg cttcttggcc atgtagatgg tcttgaactc caccaggtag   7920
tggccgccgt ccttcagctt cagggcctgg tggatctcgc ccttcagcac gccgtcgcgg   7980
gggtacaggc gctcggtgga ggcctcccag cccatggtct tcttctgcat tacggggccg   8040
tcggggggga agttggtgcc gcgcatcttc accttgtaga tcagcgtgcc gtcctgcagg   8100
gaggagtcct gggtcacggt caccagaccg ccgtcctcga agttcatcac gcgctcccac   8160
```

```
ttgaagccct cggggaagga cagcttcttg taatcgggga tgtcggcggg gtgcttcacg   8220
tacgccttgg agccgtacat gaactggggg gacaggatgt cccaggcgaa gggcaggggg   8280
ccgcccttgg tcaccttcag cttggcggtc tgggtgccct cgtaggggcg gccctcgccc   8340
tcgccctcga tctcgaactc gtggccgttc atggagccct ccatgcgcac cttgaagcgc   8400
atgaactctt tgatgacctc ctcgcccttg ctcaccatgg tggcgggatc gcgccctatc   8460
gttcgtaaat ggtgaaaatt ttcagaaaat tgcttttgct ttaaaagaaa tgatttaaat   8520
tgctgcaata gaagtagaat gcttgattgc ttgagattcg tttgttttgt atatgttgtg   8580
ttgagaggat cctctagagt cgacctgcag aagtaacacc aaacaacagg gtgagcatcg   8640
acaaaagaaa cagtaccaag caaataaata gcgtatgaag gcagggctaa aaaaatccac   8700
atatagctgc tgcatatgcc atcatccaag tatatcaaga tcaaaataat tataaaacat   8760
acttgtttat tataatagat aggtactcaa ggttagagca tatgaataga tgctgcatat   8820
gccatcatgt atatgcatca gtaaaaccca catcaacatg tatacctatc ctagatcgat   8880
atttccatcc atcttaaact cgtaactatg aagatgtatg acacacacat acagttccaa   8940
aattaataaa tacaccaggt agtttgaaac agtattctac tccgatctag aacgaatgaa   9000
cgaccgccca accacaccac atcatcacaa ccaagcgaac aaaagcatct ctgtatatgc   9060
atcagtaaaa cccgcatcaa catgtatacc tatcctagat cgatatttcc atccatcatc   9120
ttcaattcgt aactatgaat atgtatggca cacacataca gatccaaaat taataaatcc   9180
accaggtagt ttgaaacaga attctactcc gatctagaac gaccgcccaa ccagaccaca   9240
tcatcacaac caagacaaaa aaaagcatga aaagatgacc cgacaaacaa gtgcacggca   9300
tatattgaaa taaaggaaaa gggcaaacca aaccctatgc aacgaaacaa aaaaaatcat   9360
gaaatcgatc ccgtctgcgg aacggctaga gccatcccag gattccccaa agagaaacac   9420
tggcaagtta gcaatcagaa cgtgtctgac gtacaggtcg catccgtgta cgaacgctag   9480
cagcacggat ctaacacaaa cacggatcta acacaaacat gaacagaagt agaactaccg   9540
ggccctaacc atggaccgga acgccgatct agagaaggta gagagggggg gggaggacga   9600
gcggcgtacc ttgaagcgga ggtgccgacg ggtggatttg ggggagatcc actagttcta   9660
gagcggccgc caccgcggtg gaattctcga ggtcctctcc aaatgaaatg aacttcctta   9720
tatagaggaa gggtcttgcg aaggatagtg ggattgtgcg tcatccctta cgtcagtgga   9780
gatatcacat caatccactt gctttgaaga cgtggttgga acgtcttctt tttccacgat   9840
gctcctcgtg ggtgggggtc catctttggg accactgtcg gcagaggcat cttgaacgat   9900
agcctttcct ttatcgcaat gatggcattt gtaggtgcca ccttcctttt ctactgtcct   9960
tttgatcaag tgaccgatag ctgggcaatg gaatccgagg aggtttcccg atattaccct  10020
ttgttgaaaa gtctcaatag ccctttggtc ttctgagact gtatctttga tattcttgga  10080
gtagacgaga gtgtcgtgct ccaccatgtt atcacatcaa ttcacttgct ttgaagacgt  10140
ggttggaacg tcttcttttt ccacgatgct cctcgtgggt gggggtccat ctttgggacc  10200
actgtcggca gaggcatctt gaacgatagc ctttccttta tcgcaatgat ggcatttgta  10260
ggtgccacct tccttttcta ctgtcctttt gatcaagtga cagatagctg ggcaatggaa  10320
tccgaggagg tttcccgata ttaccctttg ttgaaaagtc tcaatagccc tttggtcttc  10380
tgagacttgc aggcaagcaa gcatgaatgc ctgggcgcgc cgatatc                10427
```

<210> SEQ ID NO 30
<211> LENGTH: 3841

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pGEP324

<400> SEQUENCE: 30

ctgacgcgcc ctgtagcggc ctgcagtgca gcgtgacccg gtcgtgcccc tctctagaga     60

taatgagcat tgcatgtcta agttataaaa aattaccaca tatttttttt gtcacacttg    120

tttgaagtgc agtttatcta tctttataca tatatttaaa ctttactcta cgaataatat    180

aatctatagt actacaataa tatcagtgtt ttagagaatc atataaatga acagttagac    240

atggtctaaa ggacaattga gtattttgac aacaggactc tacagtttta tctttttagt    300

gtgcatgtgt tctccttttt ttttgcaaat agcttcacct atataatact tcatccattt    360

tattagtaca tccatttagg gtttagggtt aatggttttt atagactaat ttttttagta    420

catctatttt attctatttt agcctctaaa ttaagaaaac taaaactcta ttttagtttt    480

tttatttaat aatttagata taaaatagaa taaaataaag tgactaaaaa ttaaacaaat    540

accctttaag aaattaaaaa aactaaggaa acatttttct tgtttcgagt agataatgcc    600

agcctgttaa acgccgtcga tcgacgagtc taacggacac caaccagcga accagcagcg    660

tcgcgtcggg ccaagcgaag cagacggcac ggcatctctg tcgctgcctc tggacccctc    720

tcgagagttc cgctccaccg ttggacttgc tccgctgtcg gcatccagaa attgcgtggc    780

ggagcggcag acgtgagccg gcacggcagg cggcctcctc ctcctctcac ggcaccggca    840

gctacggggg attcctttcc caccgctcct tcgctttccc ttcctcgccc gccgtaataa    900

atagacaccc cctccacacc ctctttcccc aacctcgtgt tgttcggagc gcacacacac    960

acaaccagat ctcccccaaa tccacccgtc ggcacctccg cttcaaggta cgccgctcgt   1020

cctccccccc ccccctctc taccttctct agatcggcgt tccggtccat ggttagggcc   1080

cggtagttct acttctgttc atgtttgtgt tagatccgtg tttgtgttag atccgtgctg   1140

ctagcgttcg tacacggatg cgacctgtac gtcagacacg ttctgattgc taacttgcca   1200

gtgtttctct ttggggaatc ctgggatggc tctagccgtt ccgcagacgg gatcgatcta   1260

ggataggtat acatgttgat gtgggtttta ctgatgcata tacatgatgg catatgcagc   1320

atctattcat atgctctaac cttgagtacc tatctattat aataaacaag tatgttttat   1380

aattattttg atcttgatat acttggatga tggcatatgc agcagctata tgtggatttt   1440

tttagccctg ccttcatacg ctatttattt gcttggtact gtttcttttg tcgatgctca   1500

ccctgttgtt tggtgttact tctgcaggga tccaaattac tgatgagtcc gtgaggacga   1560

aacgagtaag ctcgtctaat ttctactaag tgtagatctc gtcacgattc ccctctcctg   1620

gggccggcat ggtcccagcc tcctcgctgg cgccggctgg gcaacatgct tcggcatggc   1680

gaatgggacc gatcgttcaa acatttggca ataaagtttc ttaagattga atcctgttgc   1740

cggtcttgcg atgattatca tataatttct gttgaattac gttaagcatg taataattaa   1800

catgtaatgc atgacgttat ttatgagatg ggtttttatg attagagtcc cgcaattata   1860

catttaatac gcgatagaaa acaaaatata gcgcgcaaac taggataaat tatcgcgcgc   1920

ggtgtcatct atgttactag atcgatcgtc gttcggctgc ggcgagcggt atcagctcac   1980

tcaaaggcgg taatacggtt atccacagaa tcaggggata acgcaggaaa gaacatgtga   2040

gcaaaaggcc agcaaaaggc caggaaccgt aaaaaggccg cgttgctggc gtttttccat   2100
```

aggctccgcc cccctgacga gcatcacaaa aatcgacgct caagtcagag gtggcgaaac 2160
ccgacaggac tataaagata ccaggcgttt ccccctggaa gctccctcgt gcgctctcct 2220
gttccgaccc tgccgcttac cggatacctg tccgcctttc tcccttcggg aagcgtggcg 2280
ctttctcata gctcacgctg taggtatctc agttcggtgt aggtcgttcg ctccaagctg 2340
ggctgtgtgc acgaaccccc cgttcagccc gaccgctgcg ccttatccgg taactatcgt 2400
cttgagtcca acccggtaag acacgactta tcgccactgg cagcagccac tggtaacagg 2460
attagcagag cgaggtatgt aggcggtgct acagagttct tgaagtggtg gcctaactac 2520
ggctacacta gaagaacagt atttggtatc tgcgctctgc tgaagccagt taccttcgga 2580
aaaagagttg gtagctcttg atccggcaaa caaaccaccg ctggtagcgg tggttttttt 2640
gtttgcaagc agcagattac gcgcagaaaa aaaggatctc aagaagatcc tttgatcttt 2700
tctacggggt ctgacgctca gtggaacgaa aactcacgtt aagggatttt ggtcatgaga 2760
ttatcaaaaa ggatcttcac ctagatcctt ttaaattaaa aatgaagttt taaatcaatc 2820
taaagtatat atgagtaaac ttggtctgac agttaccaat gcttaatcag tgaggcacct 2880
atctcagcga tctgtctatt tcgttcatcc atagttgcct gactccccgt cgtgtagata 2940
actacgatac gggagggctt accatctggc cccagtgctg caatgatacc gcgagaccca 3000
cgctcaccgg ctccagattt atcagcaata aaccagccag ccggaagggc cgagcgcaga 3060
agtggtcctg caactttatc cgcctccatc cagtctatta attgttgccg ggaagctaga 3120
gtaagtagtt cgccagttaa tagtttgcgc aacgttgttg ccattgctac aggcatcgtg 3180
gtgtcacgct cgtcgtttgg tatggcttca ttcagctccg gttcccaacg atcaaggcga 3240
gttacatgat cccccatgtt gtgcaaaaaa gcggttagct ccttcggtcc tccgatcgtt 3300
gtcagaagta agttggccgc agtgttatca ctcatggtta tggcagcact gcataattct 3360
cttactgtca tgccatccgt aagatgcttt tctgtgactg gtgagtactc aaccaagtca 3420
ttctgagaat agtgtatgcg gcgaccgagt tgctcttgcc cggcgtcaat acgggataat 3480
accgcgccac atagcagaac tttaaaagtg ctcatcattg gaaaacgttc ttcggggcga 3540
aaactctcaa ggatcttacc gctgttgaga tccagttcga tgtaacccac tcgtgcaccc 3600
aactgatctt cagcatcttt tactttcacc agcgtttctg ggtgagcaaa aacaggaagg 3660
caaaatgccg caaaaaaggg aataagggcg acacggaaat gttgaatact catactcttc 3720
ctttttcaat attattgaag catttatcag ggttattgtc tcatgagcgg atacatattt 3780
gaatgtattt agaaaaataa acaaataggg gttccgcgca catttccccg aaaagtgcca 3840
c 3841

<210> SEQ ID NO 31
<211> LENGTH: 5611
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: pAMK-ZmWUS2-tDT-nosT

<400> SEQUENCE: 31
aggccttgaa gacaaatcca ctagtcctgc aggggatccc ttcaccgcca ttgcaaaaat 60
tgtcaataaa tatttagagt gggtggcatc agaaaaacat ctctagtgga ctctcttcct 120
atcatagcta ctcgggctgt agatagaacg agggcacaag agttgggtgg cgtaggttta 180

```
ctcgtgacct caactctttt ggctgtgtct tacgtctaag atgggtttgg catgtgagaa    240
acataggtct aagcaattca tgttagggct gttgcattgt tgttgcatca accaaatgtc    300
cagatagcag ttcatgctac atctagttga aaaccctcat cattaggcgg aacatgtgtt    360
ctttttagc atagtcaaag tcagattgcg gcactcgctc atccacggaa agaattttcc    420
ctgtgcaggc atctcgatca aaagacgcaa attaatttt gaatagcgat ataacaatat    480
ctaattaacg tttcttgttt tctgcgaaat gtctttcatc ataaaatgag tcatctcgat    540
gagcccaagt gacatagccc aacaccccac cccaccaata aaagtgaaga aaacatgttg    600
ggaaaactat accaagtaaa atacgagttg ttctaaagaa aaagtaaagt acgagttaga    660
tcgcaccctg tcctggagtg tggcttgatg atccaactcc tagcattgta tccctgtttt    720
tggatgatgt aactattatt tacaatgaat aaagaggtgt tttactagta aaaaaatctt    780
gaggggagga gaaaataatg gaggtctttt ttcaaaccga tggactatta tttttagtga    840
aagagaataa tattattgga aaaattattc tatccactta ttttatattg gcagaataca    900
aagaatggtg gggtccacgc ggaacttgcg gcccccgaaa cctatcgagg gcgcggtacc    960
caagcaagga acggaggaaa cttgcggggc ccgaaaccta gtgataaaag gcatatcatc   1020
cacacgatga agatctgacg gaccatatct cccaccacgg aaagccatca gacgaggatc   1080
agacggccag gaaggaaccc tagcgcccgc cggtgccaat ataaagcgcc actctctctc   1140
gtcttaagcc ccagcctctc cattcccctc tccctctcgc cgccgccgtc tccttctcct   1200
actcccttcg aggtgtgttg ttcatccgtc ccgaatccat ccatcccctc ttcagatgtg   1260
ttgttcatgg ctctaatagc tctagatctg cttgtttgtg ttgtttagct ctagatctac   1320
tcgcgcgcgc ttctctctcg atctcctgta gaacaatttt ggttggtttt ttgtgcatat   1380
ccatggtaat tttgtctgca atatggagga ggctttctaa gctcctacgt agcatcgatc   1440
tttagaattc cctcggtttc tgtttatttc ttcgcgaggg ctctctgtta tctgtaggag   1500
tagctgtaag cgcggttcgt tacggattaa tcgtcatgct tagttgaacc tatcggtcga   1560
aggatttgtg tgggttgtcg tgtagaattg acaccatcta cttactgtac tgatatgccg   1620
atctgtagga tactcttcat tacttttgtt tactgctagt tgtggtgtag atttagcatt   1680
ctcaaaccca tgctgtagcg tttctaatat tgttacatag atctaccggt gcctgttaat   1740
tgtattcgat cgggcgtttc tacatctgtc cgcccaccta gttttatatg tggtaatcaa   1800
aattgcgttg acttcgtgat gctgtctgtg tactgttttt aatcgctctt acttagatga   1860
tcaacatggt gatggttacg atttactgtt ttctaatccc tgttacttcg atgctgcagt   1920
ttattaatgg cggccaatgc gggcggcggt ggagcgggag gaggcagcgg cagcggcagc   1980
gtggctgcgc cggcggtgtg ccgccccagc ggctcgcggt ggacgccgac gccggagcag   2040
atcaggatgc tgaaggagct ctactacggc tgcggcatcc ggtcgcccag ctcggagcag   2100
atccagcgca tcaccgccat gctgcggcag cacggcaaga tcgagggcaa gaacgtcttc   2160
tactggttcc agaaccacaa ggcccgcgag cgccagaagc gccgcctcac cagcctcgac   2220
gtcaacgtgc ccgccgccgg cgcggccgac gccaccacca gccaactcgg cgtcctctcg   2280
ctgtcgtcgc cgccgccttc aggcgcggcg cctccctcgc ccaccctcgg cttctacgcc   2340
gccggcaatg gcggcggatc ggctgtgctg ctggacacga gttccgactg gggcagcagc   2400
ggcgctgcca tggccaccga gacatgcttc ctccaggact acatgggcgt gacggacacg   2460
ggcagctcgt cgcagtggcc acgcttctcg tcgtcggaca cgataatggc ggcggccgcg   2520
```

-continued

```
gcgcgggcgg cgacgacgcg ggcgcccgag acgctccctc tcttcccgac ctgcggcgac   2580
gacggcggca gcggtagcag cagctacttg ccgttctggg gtgccgcgtc cacaactgcc   2640
ggcgccactt cttccgttgc gatccagcag caacaccagc tgcaggagca gtacagcttt   2700
tacagcaaca gcaacagcac ccagctggcc ggcaccggca accaagacgt atcggcaaca   2760
gcagcagcag ccgccgccct ggagctgagc ctcagctcat ggtgctcccc ttaccctgct   2820
gcagggagta tgtgaattgc aaagacaagc gaatcatcag cacaaaaggt aaacaggaac   2880
acactgcaaa gggtagtaca aaactcataa ccatgtatgc cttacattcg atgttccata   2940
aaaaaattaa gtcttaatag catcacggtt tcaacgaaag taataatact tcatgaccag   3000
gcaaacattg ccatcataga ttacttgttc acgcgacaac tgcaaggatg tcaacaagac   3060
gagatatttt aagcttccac gaggtaacca acaagcaagc acagcaccag acagatagaa   3120
gatccaatgc attggtcctg caggccccgg gctatctttg tcttccggcc gccatggcca   3180
gatcgtaccc aattcgccct atagtgagtc gtattacaat tcactggccg tcgttttaca   3240
acgtcgtgac tgggaaaacc ctggcgttac ccaacttaat cgccttgcag cacatccccc   3300
tttcgccagc tgcattaaca tggtcatagc tgtttccttg cgtattgggc gctctccgct   3360
tcctcgctca ctgactcgct gcgctcggtc gttcgggtaa agcctggggt gcctaatgag   3420
caaaaggcca gcaaaaggcc aggaaccgta aaaaggccgc gttgctggcg tttttccata   3480
ggctccgccc ccctgacgag catcacaaaa atcgacgctc aagtcagagg tggcgaaacc   3540
cgacaggact ataaagatac caggcgtttc cccctggaag ctccctcgtg cgctctcctg   3600
ttccgaccct gccgcttacc ggatacctgt ccgcctttct cccttcggga agcgtggcgc   3660
tttctcatag ctcacgctgt aggtatctca gttcggtgta ggtcgttcgc tccaagctgg   3720
gctgtgtgca cgaacccccc gttcagcccg accgctgcgc cttatccggt aactatcgtc   3780
ttgagtccaa cccggtaaga cacgacttat cgccactggc agcagccact ggtaacagga   3840
ttagcagagc gaggtatgta ggcggtgcta cagagttctt gaagtggtgg cctaactacg   3900
gctacactag aagaacagta tttggtatct gcgctctgct gaagccagtt accttcggaa   3960
aaagagttgg tagctcttga tccggcaaac aaaccaccgc tggtagcggt ggtttttttg   4020
tttgcaagca gcagattacg cgcagaaaaa aaggatctca agaagatcct ttgatctttt   4080
ctacggggtc tgacgctcag tggaacgaaa actcacgtta agggattttg gtcatgagat   4140
tatcaaaaag gatcttcacc tagatccttt taaattaaaa atgaagtttt aaatcaatct   4200
aaagtatata tgagtaaact tggtctgaca gttattagaa aaattcatcc agcagacgat   4260
aaaacgcaat acgctggcta tccggtgccg caatgccata cagcaccaga aaacgatccg   4320
cccattcgcc gcccagttct tccgcaatat cacgggtggc cagcgcaata tcctgataac   4380
gatccgccac gcccagacgg ccgcaatcaa taaagccgct aaaacggcca ttttccacca   4440
taatgttcgg caggcacgca tcaccatggg tcaccaccag atcttcgcca tccggcatgc   4500
tcgctttcag acgcgcaaac agctctgccg gtgccaggcc ctgatgttct tcatccagat   4560
catcctgatc caccaggccc gcttccatac gggtacgcgc acgttcaata cgatgtttcg   4620
cctgatgatc aaacggacag gtcgccgggt ccagggtatg cagacgacgc atggcatccg   4680
ccataatgct cacttttttct gccggcgcca gatggctaga cagcagatcc tgacccggca   4740
cttcgcccag cagcagccaa tcacggcccg cttcggtcac cacatccagc accgccgcac   4800
acggaacacc ggtggtggcc agccagctca gacgcgccgc ttcatcctgc agctcgttca   4860
gcgcaccgct cagatcggtt ttcacaaaca gcaccggacg accctgcgcg ctcagacgaa   4920
```

```
acaccgccgc atcagagcag ccaatggtct gctgcgccca atcatagcca aacagacgtt   4980

ccacccacgc tgccgggcta cccgcatgca ggccatcctg ttcaatcata ctcttccttt   5040

ttcaatatta ttgaagcatt tatcagggtt attgtctcat gagcggatac atatttgaat   5100

gtatttagaa aaataaacaa ataggggttc cgcgcacatt tccccgaaaa gtgccaccta   5160

aattgtaagc gttaatattt tgttaaaatt cgcgttaaat ttttgttaaa tcagctcatt   5220

ttttaaccaa taggccgaaa tcggcaaaat cccttataaa tcaaaagaat agaccgagat   5280

agggttgagt ggccgctaca gggcgctccc attcgccatt caggctgcgc aactgttggg   5340

aagggcgttt cggtgcgggc ctcttcgcta ttacgccagc tggcacgaca ggtttcccga   5400

ctggaaagcg ggcagtgagc gcaacgcaat taatgtgagt tagctcactc attaggcacc   5460

ccaggcttta cactttatgc ttccggctcg tatgttgtgt ggaattgtga gcggataaca   5520

atttcacaca ggaaacagct atgaccatga ttacgccaag ctcgaaatta accctcacta   5580

aagggaacaa aagctggact agaggccctt a                                5611
```

<210> SEQ ID NO 32
<211> LENGTH: 3663
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: BdEF1::ZmPLT5_expression_cassette

<400> SEQUENCE: 32

```
cttcaccgcc attgcaaaaa ttgtcaataa atatttagag tgggtggcat cagaaaaaca     60

tctctagtgg actctcttcc tatcatagct actcgggctg tagatagaac gagggcacaa    120

gagttgggtg gcgtaggttt actcgtgacc tcaactcttt tggctgtgtc ttacgtctaa    180

gatgggtttg gcatgtgaga aacataggtc taagcaattc atgttagggc tgttgcattg    240

ttgttgcatc aaccaaatgt ccagatagca gttcatgcta catctagttg aaaaccctca    300

tcattaggcg gaacatgtgt tctttttag catagtcaaa gtcagattgc ggcactcgct    360

catccacgga aagaatttc cctgtgcagg catctcgatc aaaagacgca aattaatttt    420

tgaatagcga tataacaata tctaattaac gtttcttgtt ttctgcgaaa tgtctttcat    480

cataaaatga gtcatctcga tgagcccaag tgacatagcc caacacccca ccccaccaat    540

aaaagtgaag aaaacatgtt gggaaaacta taccaagtaa aatacgagtt gttctaaaga    600

aaaagtaaag tacgagttag atcgcaccct gtcctggagt gtggcttgat gatccaactc    660

ctagcattgt atccctgttt ttggatgatg taactattat ttacaatgaa taaagaggtg    720

ttttactagt aaaaaaatct tgaggggagg agaaaataat ggaggtcttt tttcaaaccg    780

atggactatt atttttagtg aaagagaata atattattgg aaaaattatt ctatccactt    840

attttatatt ggcagaatac aaagaatggt ggggtccacg cggaacttgc ggcccccgaa    900

acctatcgag ggcgcggtac ccaagcaagg aacggaggaa acttgcgggg cccgaaacct    960

agtgataaaa ggcatatcat ccacacgatg aagatctgac ggaccatatc tcccaccacg   1020

gaaagccatc agacgaggat cagacggcca ggaaggaacc ctagcgcccg ccggtgccaa   1080

tataaagcgc cactctctct cgtcttaagc cccagcctct ccattcccct ctccctctcg   1140

ccgccgccgt ctccttctcc tactcccttc gaggtgtgtt gttcatccgt cccgaatcca   1200

tccatcccct cttcagatgt gttgttcatg gctctaatag ctctagatct gcttgtttgt   1260
```

```
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttattt cttcgcgagg   1440
gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttggatcca tggacacctc gcaccactat catccatggc   1920
tcaacttctc cctcgcccac cactgtgacc tcgaggagga ggagaggggc gcggccgccg   1980
agctggccgc gatagccggc gccgcgccgc cgccgaagct ggaggacttc ctcggcggag   2040
gcgtcgccac cggtggtccg gaggcggtgg cgcccgcgga gatgtacgac tcggacctca   2100
agttcatagc cgccgccggg ttccttggcg gctcggcggc ggcggcggcg acgtcgccgc   2160
tgtcctccct cgaccaggcc ggttccaagc tggccttgcc tgcggcggcg gctgctccgg   2220
cgccggagca gaggaaggcc gtcgactcct ttgggcagcg cacgtccatc taccgcggcg   2280
tcacacggca ccggtggact ggcaggtacg aggcacatct gtgggacaac agctgccgac   2340
gcgaagggca gagccgcaag ggccgccaag tatatttggg tggctatgat aaggaggaga   2400
aggctgccag ggcgtatgat cttgcagctt tgaagtactg ggttctagc accaccacca   2460
actttccggt tgctgagtat gagaaggagg tcgaggagat gaagaacatg acgcgacaag   2520
agtttgttgc ttcccttcga aggaagagca gtggattctc tcggggtgct tccatctaca   2580
gaggtgtaac cagacatcac cagcatggac ggtggcaggc gaggatcgga agggtggccg   2640
gtaacaagga cctctacctt gggacgttca gcaccgagga ggaagctgca gaggcctacg   2700
acatagcggc catcaagttc agaggcctga acgccgtcac aaacttcgag atcagccggt   2760
acaacgtgga gaccataatg agcagcaacc ttccagtcgc gagcatgtcg tcgtcgtcgg   2820
cggcggcggc gggtggccgg agcagcaagg cgctggagtc ccctccgtcc ggctcgcttg   2880
acggcggcgg cggcatgcca gtcgtcgaag gcagcacggc accgccgctg ttcattccgg   2940
tgaagtacga ccagcagcag caggagtacc tgtcgatgct cgcgttgcag caccaccacc   3000
agcagcaaca agcagggaac ctgttgcagg ggccgctagt agggttcggc ggcctctact   3060
cctccggggt gaacctggat ttcgccaact cccacggcac ggcggctccg tcgtcgatgg   3120
cccaccactg ctacgccaat ggcaccgcgt ccgcctcgca tgagcaccag caccagcacc   3180
agatgcagca gggcggcgag aacgagacgc agccgcagcc gcagcagagc tccagcagct   3240
gctcctccct gccattcgcc accccggtcg ctttcaatgg gtcctatgaa agctccatca   3300
cggcggcagg cccctttgga tactcctacc caaatgtggc agcctttcag acgccgatct   3360
atggaatgga atgaaagctt acgcgtgtcg actcgaattt ccccgatcgt tcaaacattt   3420
ggcaataaag tttcttaaga ttgaatcctg ttgccggtct tgcgatgatt atcatataat   3480
ttctgttgaa ttacgttaag catgtaataa ttaacatgta atgcatgacg ttatttatga   3540
gatgggtttt tatgattaga gtcccgcaat tatacattta atacgcgata gaaaacaaaa   3600
```

tatagcgcgc aaactaggat aaattatcgc gcgcggtgtc atctatgtta ctagatcgct 3660
cga 3663

<210> SEQ ID NO 33
<211> LENGTH: 3648
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: BdEF1::ZmPLT7_expression_cassette

<400> SEQUENCE: 33
cttcaccgcc attgcaaaaa ttgtcaataa atatttagag tgggtggcat cagaaaaaca 60
tctctagtgg actctcttcc tatcatagct actcgggctg tagatagaac gagggcacaa 120
gagttgggtg gcgtaggttt actcgtgacc tcaactcttt tggctgtgtc ttacgtctaa 180
gatgggtttg gcatgtgaga aacataggtc taagcaattc atgttagggc tgttgcattg 240
ttgttgcatc aaccaaatgt ccagatagca gttcatgcta catctagttg aaaaccctca 300
tcattaggcg gaacatgtgt tctttttag catagtcaaa gtcagattgc ggcactcgct 360
catccacgga aagaatttc cctgtgcagg catctcgatc aaaagacgca aattaatttt 420
tgaatagcga tataacaata tctaattaac gtttcttgtt ttctgcgaaa tgtctttcat 480
cataaaatga gtcatctcga tgagcccaag tgacatagcc caacacccca ccccaccaat 540
aaaagtgaag aaaacatgtt gggaaaacta taccaagtaa aatacgagtt gttctaaaga 600
aaaagtaaag tacgagttag atcgcaccct gtcctggagt gtggcttgat gatccaactc 660
ctagcattgt atccctgttt ttggatgatg taactattat ttacaatgaa taaagaggtg 720
ttttactagt aaaaaaatct tgaggggagg agaaaataat ggaggtcttt tttcaaaccg 780
atggactatt atttttagtg aaagagaata atattattgg aaaaattatt ctatccactt 840
attttatatt ggcagaatac aaagaatggt ggggtccacg cggaacttgc ggccccgaa 900 acctatcgag ggcgcggtac ccaagcaagg aacggaggaa acttgcgggg cccgaaacct 960
agtgataaaa ggcatatcat ccacacgatg aagatctgac ggaccatatc tcccaccacg 1020
gaaagccatc agacgaggat cagacggcca ggaaggaacc ctagcgcccg ccggtgccaa 1080
tataaagcgc cactctctct cgtcttaagc cccagcctct ccattcccct ctccctctcg 1140
ccgccgccgt ctccttctcc tactcccttc gaggtgtgtt gttcatccgt cccgaatcca 1200
tccatcccct cttcagatgt gttgttcatg gctctaatag ctctagatct gcttgtttgt 1260
gttgtttagc tctagatcta ctcgcgcgcg cttctctctc gatctcctgt agaacaattt 1320
tggttggttt tttgtgcata tccatggtaa ttttgtctgc aatatggagg aggctttcta 1380
agctcctacg tagcatcgat ctttagaatt ccctcggttt ctgtttattt cttcgcgagg 1440
gctctctgtt atctgtagga gtagctgtaa gcgcggttcg ttacggatta atcgtcatgc 1500
ttagttgaac ctatcggtcg aaggatttgt gtgggttgtc gtgtagaatt gacaccatct 1560
acttactgta ctgatatgcc gatctgtagg atactcttca ttacttttgt ttactgctag 1620
ttgtggtgta gatttagcat tctcaaaccc atgctgtagc gtttctaata ttgttacata 1680
gatctaccgg tgcctgttaa ttgtattcga tcgggcgttt ctacatctgt ccgcccacct 1740
agttttatat gtggtaatca aaattgcgtt gacttcgtga tgctgtctgt gtactgtttt 1800
taatcgctct tacttagatg atcaacatgg tgatggttac gatttactgt tttctaatcc 1860

```
ctgttacttc gatgctgcag tttggatcca tggacatgga catgagctca gcttatcccc   1920

accattggct ctccttctcc ctctccaaca actaccacca tggcctactc gaggccttct   1980

ctaactcctc cggtactcct cttggagacg agccgggcgc agtggaggag tccccgagga   2040

cggtggagga cttcctcggc ggcgtcggtg gcgccggcgc cccgccgcag ccggcggctg   2100

ctgcagatca ggatcaccag cttgtgtgcg gcgagctggg cagcatcaca gccaggttct   2160

tgcgccacta cccggcggcg ccagctggga cgacggtgga gaaccccggc gcggtgaccg   2220

tggcggccat gtcgtcgacg gacgtggcgg gggcggagtc cgaccaggcg aggcggcccg   2280

ccgagacgtt cggccagcgc acatccatct accgtggcgt caccaggcac cggtggacag   2340

ggagatatga ggcgcacttg tgggacaaca gctgccgccg ggagggccaa agccgcaaag   2400

gacgccaagt ctacctagga ggctatgaca aggaggagaa ggcggctaga gcttacgacc   2460

tcgccgcgct caagtactgg gggcctacaa ccacgaccaa cttcccggtg tccaactacg   2520

agaaggagct ggaggagatg aagtccatga cgcggcagga gttcatcgcg tcgttgcgca   2580

ggaagagcag cggcttctca cgaggcgcct ccatctacag aggagtcaca aggcatcatc   2640

agcacggccg gtggcaggcg aggatcggca gggtggccgg aaacaaggac ctgtacttgg   2700

gcactttcag tactcaggaa gaggcggcgg aggcgtacga catcgctgcg atcaagttcc   2760

gcgggctcaa cgccgtcacc aacttcgaca tgagccgcta cgacgtggag agcatcctca   2820

gcagcgacct ccccgtcggg ggcggagcca ccgggcgcgc cgccaagttc ccgttggact   2880

cgctgcagcc ggggagcgct gctgcgatga tgctcgccgg ggctgctgcc gcttcgcagg   2940

ccaccatgcc gccgtccgag aaggactact ggtctctgct cgccctgcac taccagcagc   3000

agcaggagca ggagcggcag ttcccggctt ctgcttacga ggcttacggc tccggcggcg   3060

tgaacgtgga cttcacgatg ggcaccagta gcggcaacaa caacaacaac accggcagcg   3120

gcgtcatgtg gggcgccacc actggtgcag tagtagtggg acagcaagac agcagcggca   3180

agcagggcaa cggctatgcc agcaacattc cttatgctgc tgctgctgct atggtttctg   3240

gatctgctgg ctacgagggc tccaccggcg acaatggaac ctgggttact acgactatta   3300

ccagcagcaa caccggcacg gctccccact actacaacta tctcttcggg atggagtaga   3360

agcttacgcg tgtcgactcg aatttccccg atcgttcaaa catttggcaa taaagtttct   3420

taagattgaa tcctgttgcc ggtcttgcga tgattatcat ataatttctg ttgaattacg   3480

ttaagcatgt aataattaac atgtaatgca tgacgttatt tatgagatgg gtttttatga   3540

ttagagtccc gcaattatac atttaatacg cgatagaaaa caaaatatag cgcgcaaact   3600

aggataaatt atcgcgcgcg gtgtcatcta tgttactaga tcgctcga               3648
```

<210> SEQ ID NO 34
<211> LENGTH: 2961
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: BdEF1::KWS_RBP1_expression_cassette

<400> SEQUENCE: 34

```
cttcaccgcc attgcaaaaa ttgtcaataa atatttagag tgggtggcat cagaaaaaca     60

tctctagtgg actctcttcc tatcatagct actcgggctg tagatagaac gagggcacaa    120

gagttgggtg gcgtaggttt actcgtgacc tcaactcttt tggctgtgtc ttacgtctaa    180
```

```
gatgggtttg gcatgtgaga aacataggtc taagcaattc atgttagggc tgttgcattg    240
ttgttgcatc aaccaaatgt ccagatagca gttcatgcta catctagttg aaaaccctca    300
tcattaggcg gaacatgtgt tctttttag catagtcaaa gtcagattgc ggcactcgct    360
catccacgga aagaatttc cctgtgcagg catctcgatc aaaagacgca aattaatttt    420
tgaatagcga tataacaata tctaattaac gtttcttgtt ttctgcgaaa tgtctttcat    480
cataaaatga gtcatctcga tgagcccaag tgacatagcc caacacccca ccccaccaat    540
aaaagtgaag aaaacatgtt gggaaaacta taccaagtaa aatacgagtt gttctaaaga    600
aaaagtaaag tacgagttag atcgcaccct gtcctggagt gtggcttgat gatccaactc    660
ctagcattgt atccctgttt ttggatgatg taactattat ttacaatgaa taaagaggtg    720
ttttactagt aaaaaaatct tgaggggagg agaaaataat ggaggtcttt tttcaaaccg    780
atggactatt atttttagtg aaagagaata atattattgg aaaaattatt ctatccactt    840
attttatatt ggcagaatac aaagaatggt ggggtccacg cggaacttgc ggcccccgaa    900
acctatcgag ggcgcggtac ccaagcaagg aacggaggaa acttgcgggg cccgaaacct    960
agtgataaaa ggcatatcat ccacacgatg aagatctgac ggaccatatc tcccaccacg   1020
gaaagccatc agacgaggat cagacggcca ggaaggaacc ctagcgcccg ccggtgccaa   1080
tataaagcgc cactctctct cgtcttaagc cccagcctct ccattcccct ctccctctcg   1140
ccgccgccgt ctccttctcc tactcccttc gaggtgtgtt gttcatccgt cccgaatcca   1200
tccatcccct cttcagatgt gttgttcatg gctctaatag ctctagatct gcttgtttgt   1260
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttattt cttcgcgagg   1440
gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttggatcca tggagtcggg ctccgggacg gctgctggct   1920
ctggctatgt ttacagacag ccaggatcaa cgcggtggaa cccgacagct gaacaactgt   1980
ccttgcttag agaaatctac taccgcaacg gattgcggac cccgaccgcg gacgaaatca   2040
gacaaatcag ctcaaagctc tcaaggtacg gaaaaataga gggcaaaaac gtttacaact   2100
ggttccagaa tagacgcgca agagaaaagc gcaagcaacg gctctctaca atcggctgtg   2160
atccagcact gatcgagatg gggaatgtcg cttcactgga attcggtact gagagcgccc   2220
tggaatcgct gtcgtcagga ccatcctcag aactccgcga agcgccaacg agaaaatttt   2280
acgaaaaaaa gacggttgga gagaactcaa ctataataaa cccagtggaa caaaactgta   2340
ccctttcctg cggaacgtcc caagagttcc agtatgcggt cgattctcgg cgcgtcatga   2400
aagctatgga ggaaaagcag gcgacggacg atgaacccga cggaaataaa tggactgagt   2460
caaacagaca cgtcaagatt ctccagcttt tcccgctcca caataacgag gatcagacat   2520
tgataaagag cgacaaagaa atctattgtt tgggctcgtg cgagaagaaa atggatttgt   2580
```

```
caccgctggg tcattcaggc tctcagcgcg cttcggccct tgacttgtgc ctttcattgg   2640

gcaacgaatc ttgtgggctg catgataatt gaaagcttac gcgtgtcgac tcgaatttcc   2700

ccgatcgttc aaacatttgg caataaagtt tcttaagatt gaatcctgtt gccggtcttg   2760

cgatgattat catataattt ctgttgaatt acgttaagca tgtaataatt aacatgtaat   2820

gcatgacgtt atttatgaga tgggttttta tgattagagt cccgcaatta tacatttaat   2880

acgcgataga aaacaaaata tagcgcgcaa actaggataa attatcgcgc gcggtgtcat   2940

ctatgttact agatcgctcg a                                             2961
```

<210> SEQ ID NO 35
<211> LENGTH: 3282
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: BdEF1::TaRKD4_expression_cassette

<400> SEQUENCE: 35

```
cttcaccgcc attgcaaaaa ttgtcaataa atatttagag tgggtggcat cagaaaaaca     60

tctctagtgg actctcttcc tatcatagct actcgggctg tagatagaac gagggcacaa    120

gagttgggtg gcgtaggttt actcgtgacc tcaactcttt tggctgtgtc ttacgtctaa    180

gatgggtttg gcatgtgaga aacataggtc taagcaattc atgttagggc tgttgcattg    240

ttgttgcatc aaccaaatgt ccagatagca gttcatgcta catctagttg aaaaccctca    300

tcattaggcg gaacatgtgt tcttttttag catagtcaaa gtcagattgc ggcactcgct    360

catccacgga aagaatttc cctgtgcagg catctcgatc aaaagacgca aattaatttt    420

tgaatagcga tataacaata tctaattaac gtttcttgtt ttctgcgaaa tgtctttcat    480

cataaaatga gtcatctcga tgagcccaag tgacatagcc caacacccca ccccaccaat    540

aaaagtgaag aaaacatgtt gggaaaacta taccaagtaa aatacgagtt gttctaaaga    600

aaaagtaaag tacgagttag atcgcaccct gtcctggagt gtggcttgat gatccaactc    660

ctagcattgt atccctgttt ttggatgatg taactattat ttacaatgaa taaagaggtg    720

ttttactagt aaaaaaatct tgaggggagg agaaaataat ggaggtcttt tttcaaaccg    780

atggactatt atttttagtg aaagagaata atattattgg aaaaattatt ctatccactt    840

attttatatt ggcagaatac aaagaatggt ggggtccacg cggaacttgc ggccccccgaa    900

acctatcgag ggcgcggtac ccaagcaagg aacggaggaa acttgcgggg cccgaaacct    960

agtgataaaa ggcatatcat ccacacgatg aagatctgac ggaccatatc tcccaccacg   1020

gaaagccatc agacgaggat cagacggcca ggaaggaacc ctagcgcccg ccggtgccaa   1080

tataaagcgc cactctctct cgtcttaagc cccagcctct ccattcccct ctccctctcg   1140

ccgccgccgt ctccttctcc tactcccttc gaggtgtgtt gttcatccgt cccgaatcca   1200

tccatcccct cttcagatgt gttgttcatg gctctaatag ctctagatct gcttgtttgt   1260

gttgtttagc tctagatcta ctcgcgcgcg cttctctctc gatctcctgt agaacaattt   1320

tggttggttt tttgtgcata tccatggtaa ttttgtctgc aatatggagg aggctttcta   1380

agctcctacg tagcatcgat ctttagaatt ccctcggttt ctgtttattt cttcgcgagg   1440

gctctctgtt atctgtagga gtagctgtaa gcgcggttcg ttacggatta atcgtcatgc   1500

ttagttgaac ctatcggtcg aaggatttgt gtgggttgtc gtgtagaatt gacaccatct   1560
```

```
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttggatcca tggagatgca acaacaatac ttcggggggg   1920
acggcgatgc ggactggttc catcaactcg cattgcttcc cccacttcca atctcatcgt   1980
ctctcccccc actcccgatg tcagagggct catgtctccc tatggcagca gcagctgcag   2040
ctgcactccc ccttggcgat tgctcgagcg ccctcatgat acgccctgag gaacagatgt   2100
cttgccttcc aatgaacccc tctccagcgg tcgtcgacga tgtctactct tcctacgcac   2160
cgaacaatgt cgacgtgttg ccgccattcc cggcaggact tgacgacgct ctgttgatgg   2220
agtctttttc tgacatcgac ctcgaggagt ttgctgacgc atttggccac aagatcaaga   2280
cagaacccct cgacgatgcc atggtccccg cggaccacga cttcgcggct caagcccaac   2340
aggcctgccc tgtggtcatc atgaatcagc aacaactcaa cgcacccaga gacgtgcgcc   2400
tgctcattga cccggatgat gatgacagca ccgtggtggc cgggggctat gaagctgcag   2460
cggtggggtg cgccgagcag aaacaggtca ggccagcacc acgtagggtg agaaagagct   2520
caggcggcgc aagaccagcc gcgggaggaa agtccctcga tcacatcgga ttcgaggaac   2580
tcaggaccta tttctatatg ccaatcacca aggcagcgag ggaaatgaac gtggggctga   2640
cagtcctgaa gaagagatgc cgggaactgg gggtggcgcg ctggccacac agaaagatga   2700
agtctctgag aagcctgatc ctcaacattc aggagatggg gaagggcgca acatctcccg   2760
cagccgtgca gggggaactt gaagcgcttg agaggtattg cgccattatg gaggagaacc   2820
cggctataga gctcaccgag caaacgaaga agctcaggca ggcttgtttc aaagagaatt   2880
ataagcggcg tagagccgcc gcttctgtta atcttctcga tcactgctat aacgatctgg   2940
catctcatga gcagcaaatg cctctcccac aaatgggatt ctttggattt tagaagctta   3000
cgcgtgtcga ctcgaatttc cccgatcgtt caaacatttg gcaataaagt ttcttaagat   3060
tgaatcctgt tgccggtctt gcgatgatta tcatataatt tctgttgaat tacgttaagc   3120
atgtaataat taacatgtaa tgcatgacgt tatttatgag atgggttttt atgattagag   3180
tcccgcaatt atacatttaa tacgcgatag aaaacaaaat atagcgcgca aactaggata   3240
aattatcgcg cgcggtgtca tctatgttac tagatcgctc ga                      3282
```

<210> SEQ ID NO 36
<211> LENGTH: 3080
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: BdEF1::ZmWUS2_expression_cassette

<400> SEQUENCE: 36

```
cttcaccgcc attgcaaaaa ttgtcaataa atatttagag tgggtggcat cagaaaaaca     60
tctctagtgg actctcttcc tatcatagct actcgggctg tagatagaac gagggcacaa    120
gagttgggtg gcgtaggttt actcgtgacc tcaactcttt tggctgtgtc ttacgtctaa    180
gatgggtttg gcatgtgaga aacataggtc taagcaattc atgttagggc tgttgcattg    240
```

```
ttgttgcatc aaccaaatgt ccagatagca gttcatgcta catctagttg aaaaccctca    300
tcattaggcg gaacatgtgt tctttttag catagtcaaa gtcagattgc ggcactcgct    360
catccacgga aagaattttc cctgtgcagg catctcgatc aaaagacgca aattaatttt    420
tgaatagcga tataacaata tctaattaac gtttcttgtt ttctgcgaaa tgtctttcat    480
cataaaatga gtcatctcga tgagcccaag tgacatagcc caacacccca ccccaccaat    540
aaaagtgaag aaaacatgtt gggaaaacta taccaagtaa aatacgagtt gttctaaaga    600
aaaagtaaag tacgagttag atcgcaccct gtcctggagt gtggcttgat gatccaactc    660
ctagcattgt atccctgttt ttggatgatg taactattat ttacaatgaa taaagaggtg    720
ttttactagt aaaaaaatct tgaggggagg agaaaataat ggaggtcttt tttcaaaccg    780
atggactatt atttttagtg aaagagaata atattattgg aaaaattatt ctatccactt    840
attttatatt ggcagaatac aaagaatggt ggggtccacg cggaacttgc ggcccccgaa    900
acctatcgag ggcgcggtac ccaagcaagg aacggaggaa acttgcgggg cccgaaacct    960
agtgataaaa ggcatatcat ccacacgatg aagatctgac ggaccatatc tcccaccacg   1020
gaaagccatc agacgaggat cagacggcca ggaaggaacc ctagcgcccg ccggtgccaa   1080
tataaagcgc cactctctct cgtcttaagc cccagcctct ccattcccct ctccctctcg   1140
ccgccgccgt ctccttctcc tactcccttc gaggtgtgtt gttcatccgt cccgaatcca   1200
tccatcccct cttcagatgt gttgttcatg gctctaatag ctctagatct gcttgtttgt   1260
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttattt cttcgcgagg   1440
gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttattaatg gcggccaatg cgggcggcgg tggagcggga   1920
ggaggcagcg gcagcggcag cgtggctgcg ccggcggtgt gccgccccag cggctcgcgg   1980
tggacgccga cgccggagca gatcaggatg ctgaaggagc tctactacgg ctgcggcatc   2040
cggtcgccca gctcggagca gatccagcgc atcaccgcca tgctgcggca gcacggcaag   2100
atcgagggca agaacgtctt ctactggttc cagaaccaca aggcccgcga gcgccagaag   2160
cgccgcctca ccagcctcga cgtcaacgtg cccgccgccg gcgcggccga cgccaccacc   2220
agccaactcg gcgtcctctc gctgtcgtcg ccgccgcctt caggcgcggc gcctccctcg   2280
cccaccctcg gcttctacgc cgccggcaat ggcggcggat cggctgtgct gctggacacg   2340
agttccgact ggggcagcag cggcgctgcc atggccaccg agacatgctt cctccaggac   2400
tacatgggcg tgacggacac gggcagctcg tcgcagtggc cacgcttctc gtcgtcggac   2460
acgataatgg cggcggccgc ggcgcgggcg gcgacgacgc gggcgcccga gacgctccct   2520
ctcttcccga cctgcggcga cgacggcggc agcggtagca gcagctactt gccgttctgg   2580
```

```
ggtgccgcgt ccacaactgc cggcgccact tcttccgttg cgatccagca gcaacaccag   2640

ctgcaggagc agtacagctt ttacagcaac agcaacagca cccagctggc cggcaccggc   2700

aaccaagacg tatcggcaac agcagcagca gccgccgccc tggagctgag cctcagctca   2760

tggtgctccc cttaccctgc tgcagggagt atgtgaattg caaagacaag cgaatcatca   2820

gcacaaaagg taaacaggaa cacactgcaa agggtagtac aaaactcata accatgtatg   2880

ccttacattc gatgttccat aaaaaaatta agtcttaata gcatcacggt ttcaacgaaa   2940

gtaataatac ttcatgacca ggcaaacatt gccatcatag attacttgtt cacgcgacaa   3000

ctgcaaggat gtcaacaaga cgagatattt taagcttcca cgaggtaacc aacaagcaag   3060

cacagcacca gacagataga                                               3080
```

<210> SEQ ID NO 37
<211> LENGTH: 5561
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pUbi::LpCpf1_expression_cassette

<400> SEQUENCE: 37

```
ctgcagtgca gcgtgacccg gtcgtgcccc tctctagaga taatgagcat tgcatgtcta     60

agttataaaa aattaccaca tatttttttt gtcacacttg tttgaagtgc agtttatcta    120

tctttataca tatatttaaa ctttactcta cgaataatat aatctatagt actacaataa    180

tatcagtgtt ttagagaatc atataaatga acagttagac atggtctaaa ggacaattga    240

gtattttgac aacaggactc tacagtttta tctttttagt gtgcatgtgt tctccttttt    300

ttttgcaaat agcttcacct atataatact tcatccattt tattagtaca tccatttagg    360

gtttagggtt aatggttttt atagactaat ttttttagta catctatttt attctatttt    420

agcctctaaa ttaagaaaac taaaactcta ttttagtttt tttatttaat aatttagata    480

taaaatagaa taaaataaag tgactaaaaa ttaaacaaat accctttaag aaattaaaaa    540

aactaaggaa acatttttct tgtttcgagt agataatgcc agcctgttaa acgccgtcga    600

tcgacgagtc taacggacac caaccagcga accagcagcg tcgcgtcggg ccaagcgaag    660

cagacggcac ggcatctctg tcgctgcctc tggacccctc tcgagagttc cgctccaccg    720

ttggacttgc tccgctgtcg gcatccagaa attgcgtggc ggagcggcag acgtgagccg    780

gcacggcagg cggcctcctc ctcctctcac ggcaccggca gctacggggg attcctttcc    840

caccgctcct tcgctttccc ttcctcgccc gccgtaataa atagacaccc cctccacacc    900

ctctttcccc aacctcgtgt tgttcggagc gcacacacac acaaccagat ctcccccaaa    960

tccacccgtc ggcacctccg cttcaaggta cgccgctcgt cctccccccc cccccctctc   1020

taccttctct agatcggcgt tccggtccat ggttagggcc cggtagttct acttctgttc   1080

atgtttgtgt tagatccgtg tttgtgttag atccgtgctg ctagcgttcg tacacggatg   1140

cgacctgtac gtcagacacg ttctgattgc taacttgcca gtgtttctct ttggggaatc   1200

ctgggatggc tctagccgtt ccgcagacgg gatcgatcta ggataggtat acatgttgat   1260

gtgggtttta ctgatgcata tacatgatgg catatgcagc atctattcat atgctctaac   1320

cttgagtacc tatctattat aataaacaag tatgttttat aattattttg atcttgatat   1380

acttggatga tggcatatgc agcagctata tgtggatttt tttagccctg ccttcatacg   1440
```

-continued

```
ctatttattt gcttggtact gtttcttttg tcgatgctca ccctgttgtt tggtgttact   1500
tctgcaggtc gaagcttgaa gcaaacatgg catctagcat ggcaccaaag aaaaaaagga   1560
aagtttccaa acttgaaaaa tttacaaact gctactccct ttccaagacg cttaggttta   1620
aagcgatccc cgttggcaag acccaagaga atatcgataa caaaagactt ctggtcgaag   1680
atgaaaaaag ggccgaagac tacaaggggg tcaagaagtt gctcgatcgc tattatcttt   1740
cctttatcaa cgatgtgctt cattcaatca aactgaagaa cttgaataac tacattagcc   1800
ttttcagaaa gaaaacgagg actgaaaagg agaacaagga acttgagaat cttgaaataa   1860
accttcgcaa agaaattgca aaagccttca aggggaacga aggatataaa tctcttttca   1920
aaaaagacat tatagaaaca attttgcctg agtttcttga cgacaaggat gaaattgcgc   1980
tcgtcaatag ctttaacgga tttacaactg ccttcacagg gttcttcgac aatagggaga   2040
atatgtttag cgaggaggca aaaagcacat ccatcgcatt cagatgcatc aatgaaaatc   2100
ttacccggta catatcgaat atggacatat ttgaaaaagt ggatgcaata ttcgataagc   2160
acgaagtcca ggagataaag gaaaagatac tgaatagcga ctatgatgtc gaagattttt   2220
tcgaaggtga gttcttcaac tttgtcctga ctcaagaagg cattgatgtc tataatgcaa   2280
taattggagg ttttgtgact gagtctggcg agaagataaa gggcttgaac gagtatatca   2340
atctctacaa ccagaagact aagcaaaagt tgcctaaatt taaaccgctt tacaagcaag   2400
ttttgagcga ccgggaaagc ctttcctttt acggtgaagg atacacgagc gatgaagaag   2460
tcctcgaagt cttccgcaac acactcaaca agaactcaga aatcttttcc tcaattaaaa   2520
aattggagaa gcttttcaag aacttcgatg aatactcttc ggcggggatt tttgtgaaga   2580
acggcccggc aatttccaca atatctaaag acattttcgg agaatggaac gtgataagag   2640
acaagtggaa tgcggagtat gatgacatac acctgaagaa gaaggcagtt gtgactgaaa   2700
aatacgaaga tgacaggaga aaaagcttta aaaagatcgg gtccttttca ctggaacagc   2760
tgcaggagta tgccgacgcc gatctttcgg ttgtcgaaaa gctcaaagaa ataattatcc   2820
agaaggtcga tgaaatctac aaggtgtacg gctcaagcga gaagctcttt gatgctgact   2880
tcgtgttgga gaagtctctt aaaaaaaacg acgcagtcgt cgcgataatg aaagatttgc   2940
tggattcagt gaaatccttc gagaattata tcaaagcctt cttcggcgag gggaaggaga   3000
caaacaggga tgagtccttc tatggagact tcgttctggc ttacgacatc cttcttaagg   3060
tcgaccacat ctatgacgca attcggaact atgtgacgca gaagccgtat tcgaaagata   3120
agttcaagct ctatttccaa aaccctcaat ttatgggtgg gtgggataaa gacaaagaga   3180
ccgattaccg ggcaacaatt ttgcggtacg ggtctaaata ttacctcgct ataatggata   3240
agaaatacgc taaatgtctc cagaaaattg acaaagatga cgtcaacggc aattatgaaa   3300
aaatcaatta taaactcctt cctggcccaa ataaaatgct cccgaaggtg tttttttcca   3360
aaaagtggat ggcctattat aatccatcag aggatattca gaaaatctat aaaaatggga   3420
cctttaagaa gggtgacatg tttaacctga acgattgcca caagcttata gatttttca   3480
aagactctat tagccgctat cccaaatggt ctaatgctta tgatttcaac ttctctgaaa   3540
ctgaaaagta caaagatatt gcaggattct accgcgaagt tgaagaacaa ggttataagg   3600
tttcctttga gtctgcgtcc aagaaagagg tcgataagtt ggtcgaagaa gggaaattgt   3660
atatgtttca aatttacaat aaagactttt ccgacaagtc ccatggtaca cctaatctgc   3720
ataccatgta cttcaaactg ctgttcgatg agaataatca cggtcagatt cgcctgagcg   3780
gaggggcgga actcttcatg aggagagcat cgttgaaaaa agaggagctc gtcgtgcatc   3840
```

```
cggctaacag ccccattgct aacaagaatc cggataatcc aaagaagact actaccctct   3900
cctatgacgt ctataaggat aagagattct ctgaggacca gtacgagttg cacatcccta   3960
ttgcgataaa taaatgccct aagaacatct ttaaaatcaa tactgaggtc agagtcctgc   4020
ttaagcacga cgacaacccg tatgtgatcg ggattgatag ggtgaaagg aacttgcttt   4080
atattgtggt tgtcgatgga aaaggtaata tagtggaaca atactctctg aatgaaatta   4140
tcaacaactt caatggcatt aggatcaaga ccgactatca ttctctgttg gacaagaaag   4200
agaaagagcg cttcgaggca cggcaaaact ggacgtctat tgagaacatc aaggagctta   4260
aggctggtta catttctcag gttgtgcaca aaatttgcga actggtcgag aaatatgatg   4320
ccgttatcgc acttgaagat ctcaacagcg gatttaagaa ttctcgggtg aaagtcgaaa   4380
aacaggtgta tcaaaaattc gaaaagatgc tgatcgacaa gctcaattat atggttgata   4440
aaaagagcaa cccatgcgcc acgggggtg cgcttaaggg ctatcagatt acgaacaaat   4500
ttgaatcctt caagtcaatg tcgacgcaaa atgggtttat attctatata ccggcgtggc   4560
ttacatctaa aatagatcct agcactgggt tcgtgaacct gctgaaaacc aagtacactt   4620
caatcgcaga ttctaaaaaa tttataagca gcttcgacag aatcatgtat gtgcccgagg   4680
aagacctctt cgagtttgcc cttgattaca aaaatttctc aagaacggat gcagactaca   4740
taaagaagtg gaagctgtac tcttatggga accggattcg gatattcaga aatccgaaaa   4800
aaaacaatgt ctttgattgg gaggaagttt gtcttacctc tgcttacaaa gagctgttca   4860
ataaatatgg cattaattac cagcaaggtg atatccgggc gctcctttgc gaacagtctg   4920
acaaagcttt ctattcttca tttatggcgc tcatgtcatt gatgctgcag atgaggaata   4980
gcattacggg gaggactgat gttgactttc tgatctcgcc cgtgaaaaat tctgatggaa   5040
tcttctacga ttccaggaat tatgaggccc aggaaaatgc tatccttccc aagaacgcag   5100
acgcaaatgg cgcgtacaat atagctcgca aggttttgtg ggctataggc caattcaaga   5160
aagccgaaga cgaaaagctg gacaaagtta agattgctat atctaacaaa gagtggcttg   5220
agtatgcgca aacatctgtt aaacacaaac gccccgcggc tacaaagaag gctggccagg   5280
caaagaagaa gaagtgagtc gaccgatcgt tcaaacattt ggcaataaag tttcttaaga   5340
ttgaatcctg ttgccggtct tgcgatgatt atcatataat ttctgttgaa ttacgttaag   5400
catgtaataa ttaacatgta atgcatgacg ttatttatga gatgggtttt tatgattaga   5460
gtcccgcaat tatacattta atacgcgata gaaaacaaaa tatagcgcgc aaactaggat   5520
aaattatcgc gcgcggtgtc atctatgtta ctagatcgat c                        5561
```

```
<210> SEQ ID NO 38
<211> LENGTH: 1945
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pUbi::crRNA5_expression_cassette

<400> SEQUENCE: 38

gacgcgccct gtagcggcct gcagtgcagc gtgacccggt cgtgcccctc tctagagata     60
atgagcattg catgtctaag ttataaaaaa ttaccacata tttttttgt cacacttgtt    120
tgaagtgcag tttatctatc tttatacata tatttaaact ttactctacg aataatataa    180
tctatagtac tacaataata tcagtgtttt agagaatcat ataaatgaac agttagacat    240
```

```
ggtctaaagg acaattgagt attttgacaa caggactcta cagttttatc tttttagtgt    300
gcatgtgttc tccttttttt ttgcaaatag cttcacctat ataatacttc atccatttta    360
ttagtacatc catttagggt ttagggttaa tggtttttat agactaattt ttttagtaca    420
tctattttat tctattttag cctctaaatt aagaaaacta aaactctatt ttagtttttt    480
tatttaataa tttagatata aaatagaata aaataaagtg actaaaaatt aaacaaatac    540
cctttaagaa attaaaaaaa ctaaggaaac atttttcttg tttcgagtag ataatgccag    600
cctgttaaac gccgtcgatc gacgagtcta acggacacca accagcgaac cagcagcgtc    660
gcgtcgggcc aagcgaagca gacggcacgg catctctgtc gctgcctctg gacccctctc    720
gagagttccg ctccaccgtt ggacttgctc cgctgtcggc atccagaaat tgcgtggcgg    780
agcggcagac gtgagccggc acggcaggcg gcctcctcct cctctcacgg caccggcagc    840
tacgggggat tcctttccca ccgctccttc gctttccctt cctcgcccgc cgtaataaat    900
agacaccccc tccacaccct ctttccccaa cctcgtgttg ttcggagcgc acacacacac    960
aaccagatct cccccaaatc cacccgtcgg cacctccgct tcaaggtacg ccgctcgtcc   1020
tccccccccc cccctctcta ccttctctag atcggcgttc cggtccatgg ttagggcccg   1080
gtagttctac ttctgttcat gtttgtgtta gatccgtgtt tgtgttagat ccgtgctgct   1140
agcgttcgta cacggatgcg acctgtacgt cagacacgtt ctgattgcta acttgccagt   1200
gtttctcttt ggggaatcct gggatggctc tagccgttcc gcagacggga tcgatctagg   1260
ataggtatac atgttgatgt gggttttact gatgcatata catgatggca tatgcagcat   1320
ctattcatat gctctaacct tgagtaccta tctattataa taaacaagta tgttttataa   1380
ttattttgat cttgatatac ttggatgatg gcatatgcag cagctatatg tggatttttt   1440
tagccctgcc ttcatacgct atttatttgc ttggtactgt ttcttttgtc gatgctcacc   1500
ctgttgtttg gtgttacttc tgcagggatc caaattactg atgagtccgt gaggacgaaa   1560
cgagtaagct cgtctaattt ctactaagtg tagatctcgt cacgattccc ctctcctggg   1620
gccggcatgg tcccagcctc ctcgctggcg ccggctgggc aacatgcttc ggcatggcga   1680
atgggaccga tcgttcaaac atttggcaat aaagtttctt aagattgaat cctgttgccg   1740
gtcttgcgat gattatcata taatttctgt tgaattacgt taagcatgta ataattaaca   1800
tgtaatgcat gacgttattt atgagatggg tttttatgat tagagtcccg caattataca   1860
tttaatacgc gatagaaaac aaaatatagc gcgcaaacta ggataaatta tcgcgcgcgg   1920
tgtcatctat gttactagat cgatc                                         1945
```

<210> SEQ ID NO 39
<211> LENGTH: 3771
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: codon-optimized LbCpf1

<400> SEQUENCE: 39

```
atggcatcta gcatggcacc aaagaaaaaa aggaaagttt ccaaacttga aaaatttaca     60
aactgctact ccctttccaa gacgcttagg tttaaagcga tccccgttgg caagacccaa    120
gagaatatcg ataacaaaag acttctggtc gaagatgaaa aaagggccga agactacaag    180
ggggtcaaga agttgctcga tcgctattat ctttccttta tcaacgatgt gcttcattca    240
```

```
atcaaactga agaacttgaa taactacatt agccttttca gaaagaaaac gaggactgaa    300
aaggagaaca aggaacttga gaatcttgaa ataaaccttc gcaaagaaat tgcaaaagcc    360
ttcaagggga acgaaggata taaatctctt ttcaaaaaag acattataga aacaattttg    420
cctgagtttc ttgacgacaa ggatgaaatt gcgctcgtca atagctttaa cggatttaca    480
actgccttca cagggttctt cgacaatagg gagaatatgt ttagcgagga ggcaaaaagc    540
acatccatcg cattcagatg catcaatgaa aatcttaccc ggtacatatc gaatatggac    600
atatttgaaa aagtggatgc aatattcgat aagcacgaag tccaggagat aaaggaaaag    660
atactgaata gcgactatga tgtcgaagat tttttcgaag gtgagttctt caactttgtc    720
ctgactcaag aaggcattga tgtctataat gcaataattg gaggttttgt gactgagtct    780
ggcgagaaga taaagggctt gaacgagtat atcaatctct acaaccagaa gactaagcaa    840
aagttgccta aatttaaacc gctttacaag caagttttga gcgaccggga aagcctttcc    900
ttttacggtg aaggatacac gagcgatgaa gaagtcctcg aagtcttccg caacacactc    960
aacaagaact cagaaatctt ttcctcaatt aaaaaattgg agaagctttt caagaacttc   1020
gatgaatact cttcggcggg gatttttgtg aagaacggcc cggcaatttc cacaatatct   1080
aaagacattt tcggagaatg gaacgtgata agagacaagt ggaatgcgga gtatgatgac   1140
atacacctga agaagaaggc agttgtgact gaaaaatacg aagatgacag gagaaaaagc   1200
tttaaaaaga tcgggtcctt ttcactggaa cagctgcagg agtatgccga cgccgatctt   1260
tcggttgtcg aaaagctcaa agaaataatt atccagaagg tcgatgaaat ctacaaggtg   1320
tacggctcaa gcgagaagct ctttgatgct gacttcgtgt tggagaagtc tcttaaaaaa   1380
aacgacgcag tcgtcgcgat aatgaaagat ttgctggatt cagtgaaatc cttcgagaat   1440
tatatcaaag ccttcttcgg cgaggggaag gagacaaaca gggatgagtc cttctatgga   1500
gacttcgttc tggcttacga catccttctt aaggtcgacc acatctatga cgcaattcgg   1560
aactatgtga cgcagaagcc gtattcgaaa gataagttca agctctattt ccaaaaccct   1620
caatttatgg gtgggtggga taaagacaaa gagaccgatt accgggcaac aattttgcgg   1680
tacgggtcta aatattacct cgctataatg gataagaaat acgctaaatg tctccagaaa   1740
attgacaaag atgacgtcaa cggcaattat gaaaaaatca attataaact ccttcctggc   1800
ccaaataaaa tgctcccgaa ggtgtttttt tccaaaaagt ggatggccta ttataatcca   1860
tcagaggata ttcagaaaat ctataaaaat gggaccttta agaagggtga catgtttaac   1920
ctgaacgatt gccacaagct tatagatttt ttcaaagact ctattagccg ctatcccaaa   1980
tggtctaatg cttatgattt caacttctct gaaactgaaa agtacaaaga tattgcagga   2040
ttctaccgcg aagttgaaga acaaggttat aaggtttcct ttgagtctgc gtccaagaaa   2100
gaggtcgata agttggtcga agaagggaaa ttgtatatgt ttcaaattta caataaagac   2160
ttttccgaca agtcccatgg tacacctaat ctgcatacca tgtacttcaa actgctgttc   2220
gatgagaata atcacggtca gattcgcctg agcggagggg cggaactctt catgaggaga   2280
gcatcgttga aaaaagagga gctcgtcgtg catccggcta acagccccat tgctaacaag   2340
aatccggata atccaaagaa gactactacc ctctcctatg acgtctataa ggataagaga   2400
ttctctgagg accagtacga gttgcacatc cctattgcga taaataaatg ccctaagaac   2460
atctttaaaa tcaatactga ggtcagagtc ctgcttaagc acgacgacaa cccgtatgtg   2520
atcgggattg ataggggtga aaggaacttg ctttatattg tggttgtcga tggaaaaggt   2580
```

```
aatatagtgg aacaatactc tctgaatgaa attatcaaca acttcaatgg cattaggatc   2640
aagaccgact atcattctct gttggacaag aaagagaaag agcgcttcga ggcacggcaa   2700
aactggacgt ctattgagaa catcaaggag cttaaggctg gttacatttc tcaggttgtg   2760
cacaaaattt gcgaactggt cgagaaatat gatgccgtta tcgcacttga agatctcaac   2820
agcggattta agaattctcg ggtgaaagtc gaaaaacagg tgtatcaaaa attcgaaaag   2880
atgctgatcg acaagctcaa ttatatggtt gataaaaaga gcaacccatg cgccacgggg   2940
ggtgcgctta agggctatca gattacgaac aaatttgaat ccttcaagtc aatgtcgacg   3000
caaaatgggt ttatattcta tataccggcg tggcttacat ctaaaataga tcctagcact   3060
gggttcgtga acctgctgaa aaccaagtac acttcaatcg cagattctaa aaaatttata   3120
agcagcttcg acagaatcat gtatgtgccc gaggaagacc tcttcgagtt tgcccttgat   3180
tacaaaaatt tctcaagaac ggatgcagac tacataaaga agtggaagct gtactcttat   3240
gggaaccgga ttcggatatt cagaaatccg aaaaaaaaca atgtctttga ttgggaggaa   3300
gtttgtctta cctctgctta caaagagctg ttcaataaat atggcattaa ttaccagcaa   3360
ggtgatatcc gggcgctcct ttgcgaacag tctgacaaag ctttctattc ttcatttatg   3420
gcgctcatgt cattgatgct gcagatgagg aatagcatta cggggaggac tgatgttgac   3480
tttctgatct cgcccgtgaa aaattctgat ggaatcttct acgattccag gaattatgag   3540
gcccaggaaa atgctatcct tcccaagaac gcagacgcaa atggcgcgta caatatagct   3600
cgcaaggttt tgtgggctat aggccaattc aagaaagccg aagacgaaaa gctggacaaa   3660
gttaagattg ctatatctaa caaagagtgg cttgagtatg cgcaaacatc tgttaaacac   3720
aaacgccccg cggctacaaa gaaggctggc caggcaaaga agaagaagtg a            3771
```

```
<210> SEQ ID NO 40
<211> LENGTH: 1256
<212> TYPE: PRT
<213> ORGANISM: Unknown
<220> FEATURE:
<223> OTHER INFORMATION: Description of Unknown:
      Lachnospiraceae bacterium sequence

<400> SEQUENCE: 40

Met Ala Ser Ser Met Ala Pro Lys Lys Lys Arg Lys Val Ser Lys Leu
1               5                   10                  15

Glu Lys Phe Thr Asn Cys Tyr Ser Leu Ser Lys Thr Leu Arg Phe Lys
            20                  25                  30

Ala Ile Pro Val Gly Lys Thr Gln Glu Asn Ile Asp Asn Lys Arg Leu
        35                  40                  45

Leu Val Glu Asp Glu Lys Arg Ala Glu Asp Tyr Lys Gly Val Lys Lys
    50                  55                  60

Leu Leu Asp Arg Tyr Tyr Leu Ser Phe Ile Asn Asp Val Leu His Ser
65                  70                  75                  80

Ile Lys Leu Lys Asn Leu Asn Asn Tyr Ile Ser Leu Phe Arg Lys Lys
                85                  90                  95

Thr Arg Thr Glu Lys Glu Asn Lys Glu Leu Glu Asn Leu Glu Ile Asn
            100                 105                 110

Leu Arg Lys Glu Ile Ala Lys Ala Phe Lys Gly Asn Glu Gly Tyr Lys
        115                 120                 125

Ser Leu Phe Lys Lys Asp Ile Ile Glu Thr Ile Leu Pro Glu Phe Leu
    130                 135                 140

Asp Asp Lys Asp Glu Ile Ala Leu Val Asn Ser Phe Asn Gly Phe Thr
```

-continued

```
145                 150                 155                 160

Thr Ala Phe Thr Gly Phe Phe Asp Asn Arg Glu Asn Met Phe Ser Glu
                165                 170                 175

Glu Ala Lys Ser Thr Ser Ile Ala Phe Arg Cys Ile Asn Glu Asn Leu
            180                 185                 190

Thr Arg Tyr Ile Ser Asn Met Asp Ile Phe Glu Lys Val Asp Ala Ile
        195                 200                 205

Phe Asp Lys His Glu Val Gln Glu Ile Lys Glu Lys Ile Leu Asn Ser
    210                 215                 220

Asp Tyr Asp Val Glu Asp Phe Phe Glu Gly Glu Phe Phe Asn Phe Val
225                 230                 235                 240

Leu Thr Gln Glu Gly Ile Asp Val Tyr Asn Ala Ile Ile Gly Gly Phe
                245                 250                 255

Val Thr Glu Ser Gly Glu Lys Ile Lys Gly Leu Asn Glu Tyr Ile Asn
            260                 265                 270

Leu Tyr Asn Gln Lys Thr Lys Gln Lys Leu Pro Lys Phe Lys Pro Leu
        275                 280                 285

Tyr Lys Gln Val Leu Ser Asp Arg Glu Ser Leu Ser Phe Tyr Gly Glu
    290                 295                 300

Gly Tyr Thr Ser Asp Glu Glu Val Leu Glu Val Phe Arg Asn Thr Leu
305                 310                 315                 320

Asn Lys Asn Ser Glu Ile Phe Ser Ser Ile Lys Lys Leu Glu Lys Leu
                325                 330                 335

Phe Lys Asn Phe Asp Glu Tyr Ser Ser Ala Gly Ile Phe Val Lys Asn
            340                 345                 350

Gly Pro Ala Ile Ser Thr Ile Ser Lys Asp Ile Phe Gly Glu Trp Asn
        355                 360                 365

Val Ile Arg Asp Lys Trp Asn Ala Glu Tyr Asp Asp Ile His Leu Lys
    370                 375                 380

Lys Lys Ala Val Val Thr Glu Lys Tyr Glu Asp Asp Arg Arg Lys Ser
385                 390                 395                 400

Phe Lys Lys Ile Gly Ser Phe Ser Leu Glu Gln Leu Gln Glu Tyr Ala
                405                 410                 415

Asp Ala Asp Leu Ser Val Val Glu Lys Leu Lys Glu Ile Ile Ile Gln
            420                 425                 430

Lys Val Asp Glu Ile Tyr Lys Val Tyr Gly Ser Ser Glu Lys Leu Phe
        435                 440                 445

Asp Ala Asp Phe Val Leu Glu Lys Ser Leu Lys Lys Asn Asp Ala Val
    450                 455                 460

Val Ala Ile Met Lys Asp Leu Leu Asp Ser Val Lys Ser Phe Glu Asn
465                 470                 475                 480

Tyr Ile Lys Ala Phe Phe Gly Glu Gly Lys Glu Thr Asn Arg Asp Glu
                485                 490                 495

Ser Phe Tyr Gly Asp Phe Val Leu Ala Tyr Asp Ile Leu Leu Lys Val
            500                 505                 510

Asp His Ile Tyr Asp Ala Ile Arg Asn Tyr Val Thr Gln Lys Pro Tyr
        515                 520                 525

Ser Lys Asp Lys Phe Lys Leu Tyr Phe Gln Asn Pro Gln Phe Met Gly
    530                 535                 540

Gly Trp Asp Lys Asp Lys Glu Thr Asp Tyr Arg Ala Thr Ile Leu Arg
545                 550                 555                 560

Tyr Gly Ser Lys Tyr Tyr Leu Ala Ile Met Asp Lys Lys Tyr Ala Lys
                565                 570                 575
```

```
Cys Leu Gln Lys Ile Asp Lys Asp Asp Val Asn Gly Asn Tyr Glu Lys
            580                 585                 590

Ile Asn Tyr Lys Leu Leu Pro Gly Pro Asn Lys Met Leu Pro Lys Val
        595                 600                 605

Phe Phe Ser Lys Lys Trp Met Ala Tyr Tyr Asn Pro Ser Glu Asp Ile
    610                 615                 620

Gln Lys Ile Tyr Lys Asn Gly Thr Phe Lys Lys Gly Asp Met Phe Asn
625                 630                 635                 640

Leu Asn Asp Cys His Lys Leu Ile Asp Phe Phe Lys Asp Ser Ile Ser
                645                 650                 655

Arg Tyr Pro Lys Trp Ser Asn Ala Tyr Asp Phe Asn Phe Ser Glu Thr
            660                 665                 670

Glu Lys Tyr Lys Asp Ile Ala Gly Phe Tyr Arg Glu Val Glu Glu Gln
        675                 680                 685

Gly Tyr Lys Val Ser Phe Glu Ser Ala Ser Lys Lys Glu Val Asp Lys
    690                 695                 700

Leu Val Glu Glu Gly Lys Leu Tyr Met Phe Gln Ile Tyr Asn Lys Asp
705                 710                 715                 720

Phe Ser Asp Lys Ser His Gly Thr Pro Asn Leu His Thr Met Tyr Phe
                725                 730                 735

Lys Leu Leu Phe Asp Glu Asn Asn His Gly Gln Ile Arg Leu Ser Gly
            740                 745                 750

Gly Ala Glu Leu Phe Met Arg Arg Ala Ser Leu Lys Lys Glu Glu Leu
        755                 760                 765

Val Val His Pro Ala Asn Ser Pro Ile Ala Asn Lys Asn Pro Asp Asn
    770                 775                 780

Pro Lys Lys Thr Thr Thr Leu Ser Tyr Asp Val Tyr Lys Asp Lys Arg
785                 790                 795                 800

Phe Ser Glu Asp Gln Tyr Glu Leu His Ile Pro Ile Ala Ile Asn Lys
                805                 810                 815

Cys Pro Lys Asn Ile Phe Lys Ile Asn Thr Glu Val Arg Val Leu Leu
            820                 825                 830

Lys His Asp Asp Asn Pro Tyr Val Ile Gly Ile Asp Arg Gly Glu Arg
        835                 840                 845

Asn Leu Leu Tyr Ile Val Val Val Asp Gly Lys Gly Asn Ile Val Glu
    850                 855                 860

Gln Tyr Ser Leu Asn Glu Ile Ile Asn Asn Phe Asn Gly Ile Arg Ile
865                 870                 875                 880

Lys Thr Asp Tyr His Ser Leu Leu Asp Lys Lys Glu Lys Glu Arg Phe
                885                 890                 895

Glu Ala Arg Gln Asn Trp Thr Ser Ile Glu Asn Ile Lys Glu Leu Lys
            900                 905                 910

Ala Gly Tyr Ile Ser Gln Val Val His Lys Ile Cys Glu Leu Val Glu
        915                 920                 925

Lys Tyr Asp Ala Val Ile Ala Leu Glu Asp Leu Asn Ser Gly Phe Lys
    930                 935                 940

Asn Ser Arg Val Lys Val Glu Lys Gln Val Tyr Gln Lys Phe Glu Lys
945                 950                 955                 960

Met Leu Ile Asp Lys Leu Asn Tyr Met Val Asp Lys Lys Ser Asn Pro
                965                 970                 975

Cys Ala Thr Gly Gly Ala Leu Lys Gly Tyr Gln Ile Thr Asn Lys Phe
            980                 985                 990
```

```
Glu Ser Phe Lys Ser Met Ser Thr  Gln Asn Gly Phe Ile  Phe Tyr Ile
        995                 1000                 1005

Pro Ala  Trp Leu Thr Ser Lys  Ile Asp Pro Ser Thr  Gly Phe Val
    1010                 1015                 1020

Asn Leu  Leu Lys Thr Lys Tyr  Thr Ser Ile Ala Asp  Ser Lys Lys
    1025                 1030                 1035

Phe Ile  Ser Ser Phe Asp Arg  Ile Met Tyr Val Pro  Glu Glu Asp
    1040                 1045                 1050

Leu Phe  Glu Phe Ala Leu Asp  Tyr Lys Asn Phe Ser  Arg Thr Asp
    1055                 1060                 1065

Ala Asp  Tyr Ile Lys Lys Trp  Lys Leu Tyr Ser Tyr  Gly Asn Arg
    1070                 1075                 1080

Ile Arg  Ile Phe Arg Asn Pro  Lys Lys Asn Asn Val  Phe Asp Trp
    1085                 1090                 1095

Glu Glu  Val Cys Leu Thr Ser  Ala Tyr Lys Glu Leu  Phe Asn Lys
    1100                 1105                 1110

Tyr Gly  Ile Asn Tyr Gln Gln  Gly Asp Ile Arg Ala  Leu Leu Cys
    1115                 1120                 1125

Glu Gln  Ser Asp Lys Ala Phe  Tyr Ser Ser Phe Met  Ala Leu Met
    1130                 1135                 1140

Ser Leu  Met Leu Gln Met Arg  Asn Ser Ile Thr Gly  Arg Thr Asp
    1145                 1150                 1155

Val Asp  Phe Leu Ile Ser Pro  Val Lys Asn Ser Asp  Gly Ile Phe
    1160                 1165                 1170

Tyr Asp  Ser Arg Asn Tyr Glu  Ala Gln Glu Asn Ala  Ile Leu Pro
    1175                 1180                 1185

Lys Asn  Ala Asp Ala Asn Gly  Ala Tyr Asn Ile Ala  Arg Lys Val
    1190                 1195                 1200

Leu Trp  Ala Ile Gly Gln Phe  Lys Lys Ala Glu Asp  Glu Lys Leu
    1205                 1210                 1215

Asp Lys  Val Lys Ile Ala Ile  Ser Asn Lys Glu Trp  Leu Glu Tyr
    1220                 1225                 1230

Ala Gln  Thr Ser Val Lys His  Lys Arg Pro Ala Ala  Thr Lys Lys
    1235                 1240                 1245

Ala Gly  Gln Ala Lys Lys Lys  Lys
    1250                 1255
```

<210> SEQ ID NO 41
<211> LENGTH: 201
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: crRNA5_target_HMG13_referrence_A188

<400> SEQUENCE: 41

```
gaaccctgag agctgcttta tgaccggccc catattatta ctatctactt tgacttttcc     60

cttaatgacg acttattatt tgatttactc gtcacgattc cctctcctg gtcgaacttt     120

tcaggtgggg aaagctgctg gcgacaggtg gaaatccctg agcgagtcgg taagctccat     180

cttctgtact aaagtagtag t                                               201
```

<210> SEQ ID NO 42
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: crRNA5_target_sequence

<400> SEQUENCE: 42

taatttctac taagtgtaga t                                              21


<210> SEQ ID NO 43
<211> LENGTH: 4610
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: construct of pAMK-ZmWus2-tDT-nosT

<400> SEQUENCE: 43

aggccttgaa gacaaatcca ctagtggatc ccgagatttc catcgcacaa gacacgaaaa      60

aatcccgatc aatttaacga acattgtttt gcattataga ttatattgtt tacagaatga     120

agttaactaa aaccttaacc ttttgcagat aaatctctaa atagtgccgt actgtataca     180

ctcgagattt ccaccgcaca agacatgaga aaattccggt cgatttgaca aagactgggt     240

gttattaatt agaggaagca gatccagcca catgttgtct cacatctgat cccccacgta     300

tagtcgtata cgtttggccc aaacctagct cgatccatgt atgaaacacg tctcgtctcg     360

ccttctacct ccttttttcta tcacaggaga ttaaagtgag agagagaggg cgctcaatga     420

actgcggcat tgaacaatgg agctgcaaga gcaatgatgc actagctagt gtaatgcagt     480

gcatgcatgg tagattggta gcttgccttt gcagtttgca ccaggcacca gcagcagcta     540

gaagacgaca gacgacaggg gtttggctgc taggttgcgg aagggcagtt accagttgcc     600

acaaggggag cctggccctc tgcatcctcc tcatgatagc tctgtctctc tctctcacag     660

acacacacac agagactctt ccaaattccg aagcggccaa tgcaatgcaa gagccagccc     720

ccggccgtgt gtcaacttca cttgtctctc tccaaaagat atcgtatcac ccatggccat     780

gaccccccctc ccccagcccc aacctatatc acctagcgca gctacgctct cttctcccgc     840

tctcgctctc tgcatgctag ctaccttcta gctatctagc ctctaggtcc aatgcactcc     900

ctccttataa acaaggaacc ctccttcgcc tctcttgcca tagaccggac accggagagg     960

tcactgcaca ggagcgctca ggaaggccgc tgcgctgaga tagaggcatt atctcaacac    1020

aacatataca aaacaaacga atctcaagca atcaagcatt ctacttctat tgcagcaatt    1080

taaatcattt cttttaaagc aaaagcaatt ttctgaaaat tttcaccatt tacgaacgat    1140

agggcgcgat cccgccacca tggtgagcaa gggcgaggag gtcatcaaag agttcatgcg    1200

cttcaaggtg cgcatggagg gctccatgaa cggccacgag ttcgagatcg agggcgaggg    1260

cgagggccgc ccctacgagg gcacccagac cgccaagctg aaggtgacca agggcggccc    1320

cctgcccttc gcctgggaca tcctgtcccc ccagttcatg tacggctcca aggcgtacgt    1380

gaagcacccc gccgacatcc ccgattacaa gaagctgtcc ttccccgagg gcttcaagtg    1440

ggagcgcgtg atgaacttcg aggacggcgg tctggtgacc gtgacccagg actcctccct    1500

gcaggacggc acgctgatct acaaggtgaa gatgcgcggc accaacttcc cccccgacgg    1560

ccccgtaatg cagaagaaga ccatgggctg ggaggcctcc accgagcgcc tgtacccccg    1620

cgacggcgtg ctgaagggcg agatccacca ggccctgaag ctgaaggacg gcggccacta    1680
```

```
cctggtggag ttcaagacca tctacatggc caagaagccc gtgcaactgc ccggctacta   1740
ctacgtggac accaagctgg acatcacctc ccacaacgag gactacacca tcgtggaaca   1800
gtacgagcgc tccgagggcc gccaccacct gttcctgtac ggcatggacg agctgtacaa   1860
gtaaatgccg aatttccccg atcgttcaaa catttggcaa taaagtttct taagattgaa   1920
tcctgttgcc ggtcttgcga tgattatcat ataatttctg ttgaattacg ttaagcatgt   1980
aataattaac atgtaatgca tgacgttatt tatgagatgg gtttttatga ttagagtccc   2040
gcaattatac atttaatacg cgatagaaaa caaaatatag cgcgcaaact aggataaatt   2100
atcgcgcgcg gtgtcatcta tgttactaga tcgctcgaag atcccccggg ctatctttgt   2160
cttccggccg ccatggccag atcgtaccca attcgcccta tagtgagtcg tattacaatt   2220
cactggccgt cgttttacaa cgtcgtgact gggaaaaccc tggcgttacc caacttaatc   2280
gccttgcagc acatccccct ttcgccagct gcattaacat ggtcatagct gtttccttgc   2340
gtattgggcg ctctccgctt cctcgctcac tgactcgctg cgctcggtcg ttcgggtaaa   2400
gcctggggtg cctaatgagc aaaaggccag caaaaggcca ggaaccgtaa aaaggccgcg   2460
ttgctggcgt ttttccatag gctccgcccc cctgacgagc atcacaaaaa tcgacgctca   2520
agtcagaggt ggcgaaaccc gacaggacta taaagatacc aggcgtttcc ccctggaagc   2580
tccctcgtgc gctctcctgt tccgaccctg ccgcttaccg gatacctgtc cgcctttctc   2640
ccttcgggaa gcgtggcgct ttctcatagc tcacgctgta ggtatctcag ttcggtgtag   2700
gtcgttcgct ccaagctggg ctgtgtgcac gaaccccccg ttcagcccga ccgctgcgcc   2760
ttatccggta actatcgtct tgagtccaac ccggtaagac acgacttatc gccactggca   2820
gcagccactg gtaacaggat tagcagagcg aggtatgtag gcggtgctac agagttcttg   2880
aagtggtggc ctaactacgg ctacactaga agaacagtat ttggtatctg cgctctgctg   2940
aagccagtta ccttcggaaa aagagttggt agctcttgat ccggcaaaca aaccaccgct   3000
ggtagcggtg gtttttttgt ttgcaagcag cagattacgc gcagaaaaaa aggatctcaa   3060
gaagatcctt tgatcttttc tacggggtct gacgctcagt ggaacgaaaa ctcacgttaa   3120
gggattttgg tcatgagatt atcaaaaagg atcttcacct agatcctttt aaattaaaaa   3180
tgaagtttta aatcaatcta aagtatatat gagtaaactt ggtctgacag ttattagaaa   3240
aattcatcca gcagacgata aaacgcaata cgctggctat ccggtgccgc aatgccatac   3300
agcaccagaa aacgatccgc ccattcgccg cccagttctt ccgcaatatc acgggtggcc   3360
agcgcaatat cctgataacg atccgccacg cccagacggc cgcaatcaat aaagccgcta   3420
aaacggccat tttccaccat aatgttcggc aggcacgcat caccatgggt caccaccaga   3480
tcttcgccat ccggcatgct cgctttcaga cgcgcaaaca gctctgccgg tgccaggccc   3540
tgatgttctt catccagatc atcctgatcc accaggcccg cttccatacg ggtacgcgca   3600
cgttcaatac gatgtttcgc ctgatgatca aacggacagg tcgccgggtc cagggtatgc   3660
agacgacgca tggcatccgc cataatgctc actttttctg ccggcgccag atggctagac   3720
agcagatcct gacccggcac ttcgcccagc agcagccaat cacggcccgc ttcggtcacc   3780
acatccagca ccgccgcaca cggaacaccg gtggtggcca gccagctcag acgcgccgct   3840
tcatcctgca gctcgttcag cgcaccgctc agatcggttt tcacaaacag caccggacga   3900
ccctgcgcgc tcagacgaaa caccgccgca tcagagcagc caatggtctg ctgcgcccaa   3960
tcatagccaa acagacgttc cacccacgct gccgggctac ccgcatgcag gccatcctgt   4020
```

```
tcaatcatac tcttcctttt tcaatattat tgaagcattt atcagggtta ttgtctcatg   4080

agcggataca tatttgaatg tatttagaaa aataaacaaa taggggttcc gcgcacattt   4140

ccccgaaaag tgccacctaa attgtaagcg ttaatatttt gttaaaattc gcgttaaatt   4200

tttgttaaat cagctcattt tttaaccaat aggccgaaat cggcaaaatc ccttataaat   4260

caaaagaata gaccgagata gggttgagtg gccgctacag ggcgctccca ttcgccattc   4320

aggctgcgca actgttggga agggcgtttc ggtgcgggcc tcttcgctat tacgccagct   4380

ggcacgacag gtttcccgac tggaaagcgg gcagtgagcg caacgcaatt aatgtgagtt   4440

agctcactca ttaggcaccc caggctttac actttatgct tccggctcgt atgttgtgtg   4500

gaattgtgag cggataacaa tttcacacag gaaacagcta tgaccatgat tacgccaagc   4560

tcgaaattaa ccctcactaa agggaacaaa agctggacta gaggccctta              4610


<210> SEQ ID NO 44
<211> LENGTH: 1458
<212> TYPE: DNA
<213> ORGANISM: Zea mays

<400> SEQUENCE: 44

atggacatgg acatgagctc agcttatccc caccattggc tctccttctc cctctccaac     60

aactaccacc atggcctact cgaagccttc tctaactcct ccggtactcc tcttggagac    120

gagcagggcg cagtggagga gtccccgagg acggtggagg acttcctcgg cggcgtcggt    180

ggcgccggcg ccccgccgca gccggcggcg gctgcagatc aggatcacca gcttgtgtgc    240

ggcgagctgg gcagcatcac agccaggttc ttgcgccact acccggcggc gccagctggg    300

acgacggtgg agaaccccgg cgcggtgacc gtggcggcca tgtcgtcgac ggacgtggcc    360

ggggcggagt ccgaccaggc gaggcggccc gccgagacgt tcggccagcg cacatccatc    420

taccgtggcg tcaccaggca ccggtggacg gggagatatg aggcgcacct gtgggacaac    480

agctgccgcc gggagggcca aagccgcaaa ggacggcaag gaggctatga caaggaggag    540

aaggcggcta gagcttacga cctcgccgcg ctcaagtact gggggcctac aaccacgacc    600

aacttcccgg tgtccaacta cgagaaggag ctggaggaga tgaagtccat gacgcggcag    660

gagttcatcg cgtcgttgcg caggaagagc agcggcttct cacgaggcgc ctccatctac    720

agaggagtca caaggcatca tcagcacggc cggtggcagg cgaggatcgg cagggtggcc    780

ggaaacaagg acctgtactt gggcactttc agtactcagg aagaggcggc ggaggcgtac    840

gacatcgctg cgatcaagtt ccgcgggctc aacgccgtca ccaactttga catgagccgc    900

tacgacgtgg agagcatcct cagcagcgac ctccccgtcg gggcggagc tagcggtcgc    960

gcccccgcca agttcccgtt ggactcgctg cagccgggga gcgctgccgc catgatgctc   1020

gccggggctg ctgccgcttc gcaggccacc atgccgccgt ccgagaagga ctactggtct   1080

ctgctcgccc tgcactacca gcagcagcag gagcaggagc ggcagttccc ggcttctgct   1140

tacgaggctt acggctccgg cggcgtgaac gtggacttca cgatgggcac cagtagcggc   1200

aacaacaaca acaacaccgg cagcggcgtc atgtggggcg ccaccactgg tgcagtagta   1260

gtgggacagc aagacagcag cggcaagcag ggcaacggct atgccagcaa cattccttat   1320

gctgctgctg ctatggtttc tggatctgct ggctacgagg gctccaccgg cgacaatgga   1380

acctgggtta ctacgactac cagcagcaac accggcacgg ctccccacta ctacaactat   1440

ctcttcggga tggagtag                                                 1458
```

<210> SEQ ID NO 45
<211> LENGTH: 485
<212> TYPE: PRT
<213> ORGANISM: Zea mays

<400> SEQUENCE: 45

```
Met Asp Met Asp Met Ser Ser Ala Tyr Pro His His Trp Leu Ser Phe
1               5                   10                  15

Ser Leu Ser Asn Asn Tyr His His Gly Leu Leu Glu Ala Phe Ser Asn
            20                  25                  30

Ser Ser Gly Thr Pro Leu Gly Asp Glu Gln Gly Ala Val Glu Glu Ser
        35                  40                  45

Pro Arg Thr Val Glu Asp Phe Leu Gly Gly Val Gly Gly Ala Gly Ala
    50                  55                  60

Pro Pro Gln Pro Ala Ala Ala Ala Asp Gln Asp His Gln Leu Val Cys
65                  70                  75                  80

Gly Glu Leu Gly Ser Ile Thr Ala Arg Phe Leu Arg His Tyr Pro Ala
                85                  90                  95

Ala Pro Ala Gly Thr Thr Val Glu Asn Pro Gly Ala Val Thr Val Ala
            100                 105                 110

Ala Met Ser Ser Thr Asp Val Ala Gly Ala Glu Ser Asp Gln Ala Arg
        115                 120                 125

Arg Pro Ala Glu Thr Phe Gly Gln Arg Thr Ser Ile Tyr Arg Gly Val
    130                 135                 140

Thr Arg His Arg Trp Thr Gly Arg Tyr Glu Ala His Leu Trp Asp Asn
145                 150                 155                 160

Ser Cys Arg Arg Glu Gly Gln Ser Arg Lys Gly Arg Gln Gly Gly Tyr
                165                 170                 175

Asp Lys Glu Glu Lys Ala Ala Arg Ala Tyr Asp Leu Ala Ala Leu Lys
            180                 185                 190

Tyr Trp Gly Pro Thr Thr Thr Thr Asn Phe Pro Val Ser Asn Tyr Glu
        195                 200                 205

Lys Glu Leu Glu Glu Met Lys Ser Met Thr Arg Gln Glu Phe Ile Ala
    210                 215                 220

Ser Leu Arg Arg Lys Ser Ser Gly Phe Ser Arg Gly Ala Ser Ile Tyr
225                 230                 235                 240

Arg Gly Val Thr Arg His His Gln His Gly Arg Trp Gln Ala Arg Ile
                245                 250                 255

Gly Arg Val Ala Gly Asn Lys Asp Leu Tyr Leu Gly Thr Phe Ser Thr
            260                 265                 270

Gln Glu Glu Ala Ala Glu Ala Tyr Asp Ile Ala Ala Ile Lys Phe Arg
        275                 280                 285

Gly Leu Asn Ala Val Thr Asn Phe Asp Met Ser Arg Tyr Asp Val Glu
    290                 295                 300

Ser Ile Leu Ser Ser Asp Leu Pro Val Gly Gly Gly Ala Ser Gly Arg
305                 310                 315                 320

Ala Pro Ala Lys Phe Pro Leu Asp Ser Leu Gln Pro Gly Ser Ala Ala
                325                 330                 335

Ala Met Met Leu Ala Gly Ala Ala Ala Ala Ser Gln Ala Thr Met Pro
            340                 345                 350

Pro Ser Glu Lys Asp Tyr Trp Ser Leu Leu Ala Leu His Tyr Gln Gln
        355                 360                 365

Gln Gln Glu Gln Glu Arg Gln Phe Pro Ala Ser Ala Tyr Glu Ala Tyr
    370                 375                 380
```

```
Gly Ser Gly Gly Val Asn Val Asp Phe Thr Met Gly Thr Ser Ser Gly
385                 390                 395                 400

Asn Asn Asn Asn Asn Thr Gly Ser Gly Val Met Trp Gly Ala Thr Thr
                405                 410                 415

Gly Ala Val Val Val Gly Gln Gln Asp Ser Ser Gly Lys Gln Gly Asn
            420                 425                 430

Gly Tyr Ala Ser Asn Ile Pro Tyr Ala Ala Ala Ala Met Val Ser Gly
        435                 440                 445

Ser Ala Gly Tyr Glu Gly Ser Thr Gly Asp Asn Gly Thr Trp Val Thr
    450                 455                 460

Thr Thr Thr Ser Ser Asn Thr Gly Thr Ala Pro His Tyr Tyr Asn Tyr
465                 470                 475                 480

Leu Phe Gly Met Glu
                485


<210> SEQ ID NO 46
<211> LENGTH: 2107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pZmWUS2::tDT-nosT_expression_cassette

<400> SEQUENCE: 46

cgagatttcc atcgcacaag acacgaaaaa atcccgatca atttaacgaa cattgttttg     60

cattatagat tatattgttt acagaatgaa gttaactaaa accttaacct tttgcagata    120

aatctctaaa tagtgccgta ctgtatacac tcgagatttc caccgcacaa gacatgagaa    180

aattccggtc gatttgacaa agactgggtg ttattaatta gaggaagcag atccagccac    240

atgttgtctc acatctgatc ccccacgtat agtcgtatac gtttggccca aacctagctc    300

gatccatgta tgaaacacgt ctcgtctcgc cttctacctc ctttttctat cacaggagat    360

taaagtgaga gagagagggc gctcaatgaa ctgcggcatt gaacaatgga gctgcaagag    420

caatgatgca ctagctagtg taatgcagtg catgcatggt agattggtag cttgcctttg    480

cagtttgcac caggcaccag cagcagctag aagacgacag acgacagggg tttggctgct    540

aggttgcgga agggcagtta ccagttgcca caaggggagc ctggccctct gcatcctcct    600

catgatagct ctgtctctct ctctcacaga cacacacaca gagactcttc caaattccga    660

agcggccaat gcaatgcaag agccagcccc cggccgtgtg tcaacttcac ttgtctctct    720

ccaaaagata tcgtatcacc catggccatg acccccctcc cccagcccca acctatatca    780

cctagcgcag ctacgctctc ttctcccgct ctcgctctct gcatgctagc taccttctag    840

ctatctagcc tctaggtcca atgcactccc tccttataaa caaggaaccc tccttcgcct    900

ctcttgccat agaccggaca ccggagaggt cactgcacag gagcgctcag gaaggccgct    960

gcgctgagat agaggcatta tctcaacaca acatatacaa aacaaacgaa tctcaagcaa   1020

tcaagcattc tacttctatt gcagcaattt aaatcatttc ttttaaagca aaagcaattt   1080

tctgaaaatt ttcaccattt acgaacgata gggcgcgatc ccgccaccat ggtgagcaag   1140

ggcgaggagg tcatcaaaga gttcatgcgc ttcaaggtgc gcatggaggg ctccatgaac   1200

ggccacgagt tcgagatcga gggcgagggc gagggccgcc cctacgaggg cacccagacc   1260

gccaagctga aggtgaccaa gggcggcccc ctgcccttcg cctgggacat cctgtccccc   1320

cagttcatgt acggctccaa ggcgtacgtg aagcaccccg ccgacatccc cgattacaag   1380
```

```
aagctgtcct tccccgaggg cttcaagtgg gagcgcgtga tgaacttcga ggacggcggt   1440

ctggtgaccg tgacccagga ctcctccctg caggacggca cgctgatcta caaggtgaag   1500

atgcgcggca ccaacttccc ccccgacggc cccgtaatgc agaagaagac catgggctgg   1560

gaggcctcca ccgagcgcct gtacccccgc gacggcgtgc tgaagggcga gatccaccag   1620

gccctgaagc tgaaggacgg cggccactac ctggtggagt tcaagaccat ctacatggcc   1680

aagaagcccg tgcaactgcc cggctactac tacgtggaca ccaagctgga catcacctcc   1740

cacaacgagg actacaccat cgtggaacag tacgagcgct ccgagggccg ccaccacctg   1800

ttcctgtacg gcatggacga gctgtacaag taaatgccga atttccccga tcgttcaaac   1860

atttggcaat aaagtttctt aagattgaat cctgttgccg gtcttgcgat gattatcata   1920

taatttctgt tgaattacgt taagcatgta ataattaaca tgtaatgcat gacgttattt   1980

atgagatggg tttttatgat tagagtcccg caattataca tttaatacgc gatagaaaac   2040

aaaatatagc gcgcaaacta ggataaatta tcgcgcgcgg tgtcatctat gttactagat   2100

cgctcga                                                             2107
```

<210> SEQ ID NO 47
<211> LENGTH: 783
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA of KWS-RBP2

<400> SEQUENCE: 47

```
atggaatcgg gctccggcac ggcggcaggg tctggttatg tctatcggca gagcggaagc     60

acccggtgga atccaacagc agaacagttg tcgctgctca aggaacttta ttaccggaat    120

ggaattcgga caccgtcggc agatcaaatt aggcaaattt cggcccggct gtccagatac    180

ggcaaaatag aagggaaaaa cgtcttttac tggtttcaaa atcataaagc acgggaacgg    240

cagaagaaaa gactttccac ggtcggctgc gaccctgctc tcatagaaat gggtaacgtc    300

gcgagcttgg aatttgggac cgaaagcgct cttgaatctc tcagctcagg cccgtccagc    360

gagttgcgcg aggctcctac ccgcaagttt tatgagaaga aaaccgttgg tgagaacagc    420

accataatca atcctgttga gcagaactgc acactttctt gcggtacttc gcaggaattt    480

cagtatgctg ttgatagccg ccgggtgatg aaggcaatgg aagagaagca agcaacggat    540

gatgaaccgg acggaaacaa atggacggag tcgaacaggc atgtgaagac cctccctctt    600

ttccccttgc ataataatga agatcagacc ttgatcaagt cggacaagga aatttattgc    660

cttgggagct gtgaaaaaaa aatggatctg tccccattgg gacactcggg ctctcagagg    720

gcgtcggcac tggatttgtg cctgtctttg ggtaatgaat cttgtggcct ccacgacaat    780

tga                                                                  783
```

<210> SEQ ID NO 48
<211> LENGTH: 260
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: protein of KWS-RBP2

<400> SEQUENCE: 48

Met Glu Ser Gly Ser Gly Thr Ala Ala Gly Ser Gly Tyr Val Tyr Arg
1               5                   10                  15

Gln Ser Gly Ser Thr Arg Trp Asn Pro Thr Ala Glu Gln Leu Ser Leu
            20                  25                  30

Leu Lys Glu Leu Tyr Tyr Arg Asn Gly Ile Arg Thr Pro Ser Ala Asp
        35                  40                  45

Gln Ile Arg Gln Ile Ser Ala Arg Leu Ser Arg Tyr Gly Lys Ile Glu
    50                  55                  60

Gly Lys Asn Val Phe Tyr Trp Phe Gln Asn His Lys Ala Arg Glu Arg
65                  70                  75                  80

Gln Lys Lys Arg Leu Ser Thr Val Gly Cys Asp Pro Ala Leu Ile Glu
                85                  90                  95

Met Gly Asn Val Ala Ser Leu Glu Phe Gly Thr Glu Ser Ala Leu Glu
            100                 105                 110

Ser Leu Ser Ser Gly Pro Ser Ser Glu Leu Arg Glu Ala Pro Thr Arg
        115                 120                 125

Lys Phe Tyr Glu Lys Lys Thr Val Gly Glu Asn Ser Thr Ile Ile Asn
    130                 135                 140

Pro Val Glu Gln Asn Cys Thr Leu Ser Cys Gly Thr Ser Gln Glu Phe
145                 150                 155                 160

Gln Tyr Ala Val Asp Ser Arg Arg Val Met Lys Ala Met Glu Glu Lys
                165                 170                 175

Gln Ala Thr Asp Asp Glu Pro Asp Gly Asn Lys Trp Thr Glu Ser Asn
            180                 185                 190

Arg His Val Lys Thr Leu Pro Leu Phe Pro Leu His Asn Asn Glu Asp
        195                 200                 205

Gln Thr Leu Ile Lys Ser Asp Lys Glu Ile Tyr Cys Leu Gly Ser Cys
    210                 215                 220

Glu Lys Lys Met Asp Leu Ser Pro Leu Gly His Ser Gly Ser Gln Arg
225                 230                 235                 240

Ala Ser Ala Leu Asp Leu Cys Leu Ser Leu Gly Asn Glu Ser Cys Gly
                245                 250                 255

Leu His Asp Asn
            260

<210> SEQ ID NO 49
<211> LENGTH: 5865
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pABM-BdEF1_KWS-RBP2

<400> SEQUENCE: 49
agcttacgcg tgtcgactcg aatttccccg atcgttcaaa catttggcaa taaagtttct 60
taagattgaa tcctgttgcc ggtcttgcga tgattatcat ataatttctg ttgaattacg 120
ttaagcatgt aataattaac atgtaatgca tgacgttatt tatgagatgg gtttttatga 180
ttagagtccc gcaattatac atttaatacg cgatagaaaa caaaatatag cgcgcaaact 240
aggataaatt atcgcgcgcg gtgtcatcta tgttactaga tcgctcgacg cggccgccat 300
ggccagatcg tacccaattc gccctatagt gagtcgtatt acaattcact ggccgtcgtt 360
ttacaacgtc gtgactggga aaaccctggc gttacccaac ttaatcgcct tgcagcacat 420

```
cccccctttcg ccagctggcg taatagcgaa gaggcccgca ccgatcgccc ttcccaacag    480
ttgcgcagcc tgaatggcga atggaaattg taagcgttaa tattttgtta aaattcgcgt    540
taaatttttg ttaaatcagc tcatttttta accaataggc cgaaatcggc aaaatccctt    600
ataaatcaaa agaatagacc gagatagggt tgagtgttgt tccagtttgg aacaagagtc    660
cactattaaa gaacgtggac tccaacgtca aagggcgaaa aaccgtctat cagggcgatg    720
gcccactacg tgaaccatca ccctaatcaa gtttttttggg gtcgaggtgc cgtaaagcac    780
taaatcggaa ccctaaaggg agcccccgat ttagagcttg acggggaaag ccggcgaacg    840
tggcgagaaa ggaagggaag aaagcgaaag gagcgggcgc tagggcgctg gcaagtgtag    900
cggtcacgct gcgcgtaacc accacacccg ccgcgcttaa tgcgccgcta cagggcgcgt    960
caggtggcac ttttcgggga aatgtgcgcg gaacccctat ttgtttattt ttctaaatac   1020
attcaaatat gtatccgctc atgagacaat aaccctgata aatgcttcaa taatattgaa   1080
aaaggaagag tatgagtatt caacatttcc gtgtcgccct tattcccttt tttgcggcat   1140
tttgccttcc tgtttttgct cacccagaaa cgctggtgaa agtaaaagat gctgaagatc   1200
agttgggtgc acgagtgggt tacatcgaac tggatctcaa cagcggtaag atccttgaga   1260
gttttcgccc cgaagaacgt tttccaatga tgagcacttt taaagttctg ctatgtggcg   1320
cggtattatc ccgtattgac gccgggcaag agcaactcgg tcgccgcata cactattctc   1380
agaatgactt ggttgagtac tcaccagtca cagaaaagca tcttacggat ggcatgacag   1440
taagagaatt atgcagtgct gccataacca tgagtgataa cactgcggcc aacttacttc   1500
tgacaacgat cggaggaccg aaggagctaa ccgctttttt gcacaacatg ggggatcatg   1560
taactcgcct tgatcgttgg gaaccggagc tgaatgaagc cataccaaac gacgagcgtg   1620
acaccacgat gcctgtagca atggcaacaa cgttgcgcaa actattaact ggcgaactac   1680
ttactctagc ttcccggcaa caattaatag actggatgga ggcggataaa gttgcaggac   1740
cacttctgcg ctcggccctt ccggctggct ggtttattgc tgataaatct ggagccggtg   1800
agcgtgggtc tcgcggtatc attgcagcac tggggccaga tggtaagccc tcccgtatcg   1860
tagttatcta cacgacgggg agtcaggcaa ctatggatga acgaaataga cagatcgctg   1920
agataggtgc ctcactgatt aagcattggt aactgtcaga ccaagtttac tcatatatac   1980
tttagattga tttaaaactt catttttaat ttaaaaggat ctaggtgaag atcctttttg   2040
ataatctcat gaccaaaatc ccttaacgtg agttttcgtt ccactgagcg tcagaccccg   2100
tagaaaagat caaaggatct tcttgagatc cttttttttct gcgcgtaatc tgctgcttgc   2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca ggggggcgga   2700
gcctatggaa aaacgccagc aacgcggcct ttttacggtt cctggccttt tgctggcctt   2760
```

```
ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
caccccacca ataaaagtga agaaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgttttacta gtaaaaaaat cttgaggga ggagaaaata atggaggtct   3960
tttttcaaac cgatggacta ttatttttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
cgccggtgcc aatataaagc gccactctct ctcgtcttaa gccccagcct ctccattccc   4320
ctctccctct cgccgccgcc gtctccttct cctactccct tcgaggtgtg ttgttcatcc   4380
gtcccgaatc catccatccc ctcttcagat gtgttgttca tggctctaat agctctagat   4440
ctgcttgttt gtgttgttta gctctagatc tactcgcgcg cgcttctctc tcgatctcct   4500
gtagaacaat tttggttggt tttttgtgca tatccatggt aattttgtct gcaatatgga   4560
ggaggctttc taagctccta cgtagcatcg atctttagaa ttccctcggt ttctgtttat   4620
ttcttcgcga gggctctctg ttatctgtag gagtagctgt aagcgcggtt cgttacggat   4680
taatcgtcat gcttagttga acctatcggt cgaaggattt gtgtgggttg tcgtgtagaa   4740
ttgacaccat ctacttactg tactgatatg ccgatctgta ggatactctt cattactttt   4800
gtttactgct agttgtggtg tagatttagc attctcaaac ccatgctgta gcgtttctaa   4860
tattgttaca tagatctacc ggtgcctgtt aattgtattc gatcgggcgt ttctacatct   4920
gtccgcccac ctagttttat atgtggtaat caaaattgcg ttgacttcgt gatgctgtct   4980
gtgtactgtt tttaatcgct cttacttaga tgatcaacat ggtgatggtt acgatttact   5040
gttttctaat ccctgttact tcgatgctgc agtttggatc catggaatcg ggctccggca   5100
cggcggcagg gtctggttat gtctatcggc agagcggaag cacccggtgg aatccaacag   5160
```

```
cagaacagtt gtcgctgctc aaggaacttt attaccggaa tggaattcgg acaccgtcgg   5220

cagatcaaat taggcaaatt tcggcccggc tgtccagata cggcaaaata gaagggaaaa   5280

acgtctttta ctggtttcaa aatcataaag cacgggaacg gcagaagaaa agactttcca   5340

cggtcggctg cgaccctgct ctcatagaaa tgggtaacgt cgcgagcttg gaatttggga   5400

ccgaaagcgc tcttgaatct ctcagctcag gcccgtccag cgagttgcgc gaggctccta   5460

cccgcaagtt ttatgagaag aaaaccgttg gtgagaacag caccataatc aatcctgttg   5520

agcagaactg cacactttct tgcggtactt cgcaggaatt tcagtatgct gttgatagcc   5580

gccgggtgat gaaggcaatg gaagagaagc aagcaacgga tgatgaaccg gacggaaaca   5640

aatggacgga gtcgaacagg catgtgaaga ccctccctct tttccccttg cataataatg   5700

aagatcagac cttgatcaag tcggacaagg aaatttattg ccttgggagc tgtgaaaaaa   5760

aaatggatct gtccccattg ggacactcgg gctctcagag ggcgtcggca ctggatttgt   5820

gcctgtcttt gggtaatgaa tcttgtggcc tccacgacaa ttgaa                   5865
```

<210> SEQ ID NO 50
<211> LENGTH: 2961
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: BdEF1::KWS-RBP2_expression_cassette

<400> SEQUENCE: 50

```
cttcaccgcc attgcaaaaa ttgtcaataa atatttagag tgggtggcat cagaaaaaca     60

tctctagtgg actctcttcc tatcatagct actcgggctg tagatagaac gagggcacaa    120

gagttgggtg gcgtaggttt actcgtgacc tcaactcttt tggctgtgtc ttacgtctaa    180

gatgggtttg gcatgtgaga aacataggtc taagcaattc atgttagggc tgttgcattg    240

ttgttgcatc aaccaaatgt ccagatagca gttcatgcta catctagttg aaaaccctca    300

tcattaggcg gaacatgtgt tcttttttag catagtcaaa gtcagattgc ggcactcgct    360

catccacgga aagaatttc cctgtgcagg catctcgatc aaaagacgca aattaatttt    420

tgaatagcga tataacaata tctaattaac gtttcttgtt ttctgcgaaa tgtctttcat    480

cataaaatga gtcatctcga tgagcccaag tgacatagcc caacacccca ccccaccaat    540

aaaagtgaag aaaacatgtt gggaaaacta taccaagtaa aatacgagtt gttctaaaga    600

aaaagtaaag tacgagttag atcgcaccct gtcctggagt gtggcttgat gatccaactc    660

ctagcattgt atccctgttt ttggatgatg taactattat ttacaatgaa taaagaggtg    720

ttttactagt aaaaaaatct tgaggggagg agaaaataat ggaggtcttt tttcaaaccg    780

atggactatt atttttagtg aaagagaata atattattgg aaaaattatt ctatccactt    840

attttatatt ggcagaatac aaagaatggt ggggtccacg cggaacttgc ggcccccgaa    900

acctatcgag ggcgcggtac ccaagcaagg aacggaggaa acttgcgggg cccgaaacct    960

agtgataaaa ggcatatcat ccacacgatg aagatctgac ggaccatatc tcccaccacg   1020

gaaagccatc agacgaggat cagacggcca ggaaggaacc ctagcgcccg ccggtgccaa   1080

tataaagcgc cactctctct cgtcttaagc cccagcctct ccattcccct ctccctctcg   1140

ccgccgccgt ctccttctcc tactcccttc gaggtgtgtt gttcatccgt cccgaatcca   1200

tccatcccct cttcagatgt gttgttcatg gctctaatag ctctagatct gcttgtttgt   1260
```

```
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttattt cttcgcgagg   1440
gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttggatcca tggaatcggg ctccggcacg gcggcagggt   1920
ctggttatgt ctatcggcag agcggaagca cccggtggaa tccaacagca gaacagttgt   1980
cgctgctcaa ggaactttat taccggaatg gaattcggac accgtcggca gatcaaatta   2040
ggcaaatttc ggcccggctg tccagatacg gcaaaataga agggaaaaac gtcttttact   2100
ggtttcaaaa tcataaagca cgggaacggc agaagaaaag actttccacg gtcggctgcg   2160
accctgctct catagaaatg ggtaacgtcg cgagcttgga atttgggacc gaaagcgctc   2220
ttgaatctct cagctcaggc ccgtccagcg agttgcgcga ggctcctacc cgcaagtttt   2280
atgagaagaa aaccgttggt gagaacagca ccataatcaa tcctgttgag cagaactgca   2340
cactttcttg cggtacttcg caggaatttc agtatgctgt tgatagccgc cgggtgatga   2400
aggcaatgga agagaagcaa gcaacggatg atgaaccgga cggaaacaaa tggacggagt   2460
cgaacaggca tgtgaagacc ctccctcttt tccccttgca taataatgaa gatcagacct   2520
tgatcaagtc ggacaaggaa atttattgcc ttgggagctg tgaaaaaaaa atggatctgt   2580
ccccattggg acactcgggc tctcagaggg cgtcggcact ggatttgtgc ctgtctttgg   2640
gtaatgaatc ttgtggcctc cacgacaatt gaaagcttac gcgtgtcgac tcgaatttcc   2700
ccgatcgttc aaacatttgg caataaagtt tcttaagatt gaatcctgtt gccggtcttg   2760
cgatgattat catataattt ctgttgaatt acgttaagca tgtaataatt aacatgtaat   2820
gcatgacgtt atttatgaga tgggttttta tgattagagt cccgcaatta tacatttaat   2880
acgcgataga aaacaaaata tagcgcgcaa actaggataa attatcgcgc gcggtgtcat   2940
ctatgttact agatcgctcg a                                              2961
```

<210> SEQ ID NO 51
<211> LENGTH: 70
<212> TYPE: DNA
<213> ORGANISM: Zea mays

<400> SEQUENCE: 51

```
acgacttatt atttgattta ctcgtcacga ttcccctctc ctggtcgaac ttttcaggtg     60
gggaaagctg                                                             70
```

<210> SEQ ID NO 52
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: target region from edited T0 plant (genotype A188) with a 5 bp deletion aligned to reference sequence of SEQ ID NO: 51 as shown in Fig. 21A

<400> SEQUENCE: 52
acgacttatt atttgattta ctcgtcacga ttctcctggt cgaacttttc aggtggggaa 60
agctg 65

<210> SEQ ID NO 53
<211> LENGTH: 68
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: target region from edited T0 plant (genotype B73) with a 2 bp deletion aligned to reference sequence of SEQ ID NO: 51 as shown in Fig. 21A

<400> SEQUENCE: 53
acgacttatt atttaattta ctcgtcacga ttcccctcct ggtcgaactt ttcaggtggg 60
gaaagctg 68

<210> SEQ ID NO 54
<211> LENGTH: 70
<212> TYPE: DNA
<213> ORGANISM: Zea mays

<400> SEQUENCE: 54
cttattattt gatttactcg tcacgattcc cctctcctgg tcgaactttt caggtgggga 60
aagctgctgg 70

<210> SEQ ID NO 55
<211> LENGTH: 64
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: target region from edited T0 plant (genotype A188) with a 6 bp deletion aligned to reference sequence of SEQ ID NO: 54 as shown in Fig. 21B

<400> SEQUENCE: 55
cttattattt gatttactcg tcacgattcc ctggtcgaac ttttcaggtg gggaaagctg 60
ctgg 64

<210> SEQ ID NO 56
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: target region from edited T0 plant (genotype B73) with a 5 bp deletion aligned to reference sequence of SEQ ID NO: 54 as shown in Fig. 21B

<400> SEQUENCE: 56
cttattattt aatttactcg tcacgattcc cctggtcgaa cttttcaggt ggggaaagct 60
gctgg 65

```
<210> SEQ ID NO 57
<211> LENGTH: 70
<212> TYPE: DNA
<213> ORGANISM: Zea mays

<400> SEQUENCE: 57

cgacttatta tttgatttac tcgtcacgat tcccctctcc tggtcgaact tttcaggtgg     60

ggaaagctgc                                                            70


<210> SEQ ID NO 58
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: target region from edited T0 plant (genotype
      A188) with a 8 bp deletion aligned to reference sequence of SEQ ID
      NO: 57 as shown in Fig. 21C

<400> SEQUENCE: 58

cgacttatta tttgatttac tcgtcacgat tcccctcgaa cttttcaggt ggggaaagct     60

gc                                                                    62


<210> SEQ ID NO 59
<211> LENGTH: 70
<212> TYPE: DNA
<213> ORGANISM: Zea mays

<400> SEQUENCE: 59

cgacttatta tttaatttac tcgtcacgat tcccctctcc tggtcgaact tttcaggtgg     60

ggaaagctgc                                                            70
```